United States Patent
Zhou et al.

(10) Patent No.: US 12,152,246 B2
(45) Date of Patent: Nov. 26, 2024

(54) NUCLEOTIDE SEQUENCES AND CORRESPONDING POLYPEPTIDES CONFERRING MODULATED GROWTH RATE AND BIOMASS IN PLANTS GROWN IN SALINE CONDITIONS

(71) Applicant: CERES, INC., Thousand Oaks, CA (US)

(72) Inventors: Fasong Zhou, Oxnard, CA (US); Kenneth A. Feldmann, Tucson, AZ (US); Julissa Sosa, Northridge, CA (US)

(73) Assignee: Ceres, Inc., Thousand Oaks, CA (US)

( * ) Notice: Subject to any disclaimer, the term of this patent is extended or adjusted under 35 U.S.C. 154(b) by 0 days.

(21) Appl. No.: 18/483,428

(22) Filed: Oct. 9, 2023

(65) Prior Publication Data

US 2024/0102040 A1      Mar. 28, 2024

Related U.S. Application Data

(62) Division of application No. 17/831,146, filed on Jun. 2, 2022, now Pat. No. 11,814,636, which is a division of application No. 16/859,573, filed on Apr. 27, 2020, now Pat. No. 11,421,244, which is a division of application No. 16/275,595, filed on Feb. 14, 2019, now Pat. No. 10,696,978, which is a division of application No. 15/487,287, filed on Apr. 13, 2017, now Pat. No. 10,233,460, which is a division of application No. 13/663,204, filed on Oct. 29, 2012, now Pat. No. 9,637,756, which is a division of application No. 12/282,342, filed as application No. PCT/US2007/006544 on Mar. 14, 2007, now Pat. No. 8,324,454.

(60) Provisional application No. 60/782,735, filed on Mar. 14, 2006.

(51) Int. Cl.
| | |
|---|---|
| *C12N 15/82* | (2006.01) |
| *A23K 10/30* | (2016.01) |
| *A23L 19/00* | (2016.01) |
| *C07K 14/415* | (2006.01) |
| *C12N 9/88* | (2006.01) |

(52) U.S. Cl.
CPC .......... *C12N 15/8273* (2013.01); *A23K 10/30* (2016.05); *A23L 19/00* (2016.08); *C07K 14/415* (2013.01); *C12N 9/88* (2013.01); *C12N 15/8261* (2013.01); *C12Y 208/02015* (2013.01); *A23V 2002/00* (2013.01); *Y02A 40/146* (2018.01)

(58) Field of Classification Search
None
See application file for complete search history.

(56) References Cited

U.S. PATENT DOCUMENTS

| | | |
|---|---|---|
| 6,281,411 B1 | 6/2001 | Adams et al. |
| 8,222,482 B2 | 7/2012 | Bobzin et al. |
| 8,324,454 B2 | 12/2012 | Zhou et al. |
| 9,637,756 B2 | 5/2017 | Zhou et al. |
| 10,233,460 B2 | 3/2019 | Zhou et al. |
| 10,428,346 B2 | 10/2019 | Zhou et al. |
| 10,696,978 B2 | 6/2020 | Zhou et al. |
| 10,968,461 B2 | 4/2021 | Zhou et al. |
| 11,421,244 B2 | 8/2022 | Zhou et al. |
| 11,421,245 B2 | 8/2022 | Zhou et al. |
| 11,466,284 B2 | 10/2022 | Zhou et al. |
| 11,655,479 B2 | 5/2023 | Zhou et al. |
| 11,814,636 B2 | 11/2023 | Zhou et al. |
| 11,840,699 B2 | 12/2023 | Zhou et al. |
| 2002/0016980 A1 | 2/2002 | Alberte et al. |
| 2007/0039067 A1 | 2/2007 | Feldmann et al. |
| 2009/0324797 A1 | 12/2009 | Bobzin et al. |
| 2015/0259699 A1 | 9/2015 | Nadzan et al. |
| 2016/0369294 A9 | 12/2016 | Nadzan et al. |
| 2017/0037426 A1* | 2/2017 | Alexandrov ....... C12N 15/8271 |
| 2019/0225981 A1 | 7/2019 | Zhou et al. |
| 2020/0056200 A1 | 2/2020 | Zhou et al. |
| 2020/0299715 A1 | 9/2020 | Zhou et al. |
| 2021/0062212 A1 | 3/2021 | Zhou et al. |
| 2021/0254089 A1 | 8/2021 | Zhou et al. |
| 2022/0372505 A1 | 11/2022 | Zhou et al. |
| 2024/0102041 A1 | 3/2024 | Zhou et al. |

FOREIGN PATENT DOCUMENTS

| | | | |
|---|---|---|---|
| EP | 1033405 A2 * | 9/2000 | ............. C07H 21/04 |
| WO | WO 99/61616 A2 | 12/1999 | |
| WO | WO 2004/092326 A2 | 10/2004 | |
| WO | WO 2004/092326 A3 | 10/2004 | |

OTHER PUBLICATIONS

Wells (Biochemistry 29:8509-8517, 1990).*

(Continued)

*Primary Examiner* — Vinod Kumar

(74) *Attorney, Agent, or Firm* — Dentons US LLP

(57) ABSTRACT

The present invention relates to isolated nucleic acid molecules and their corresponding encoded polypeptides able confer the trait of improved plant size, vegetative growth, growth rate, seedling vigor and/or biomass in plants challenged with saline conditions. The present invention further relates to the use of these nucleic acid molecules and polypeptides in making transgenic plants, plant cells, plant materials or seeds of a plant having plant size, vegetative growth, growth rate, seedling vigor and/or biomass that are improved in saline conditions with respect to wild-type plants grown under similar conditions.

8 Claims, 16 Drawing Sheets

Specification includes a Sequence Listing.

(56) References Cited

OTHER PUBLICATIONS

Guo et al. (PNAS, 101: 9205-9210, 2004 ).*
Ngo et al., (The Protein Folding Problem and Tertiary Structure Prediction, K. Merz., and S. Le Grand (eds.) pp. 492-495, 1994).*
Thornton et al. (Nature structural Biology, structural genomics supplement, Nov. 2000).*
Keskin et al. (Protein Science, 13:1043-1055, 2004).*
U.S. Appl. No. 18/495,560, filed Oct. 26, 2023, Zhou, et al.
U.S. Appl. No. 16/859,564, filed Apr. 27, 2020, Zhou et al.
U.S. Appl. No. 17/170,347, filed Feb. 8, 2021, Zhou et al.
U.S. Appl. No. 17/831,156, filed Jun. 2, 2022, Zhou et al.
Bustos et al. "Regulation of beta-glucuronidase expression in transgenic tobacco plants by an A/T-rich, cis-acting sequence ," *Plant Cell*; 1(9);839-853;1989.
Guo et al., "Protein tolerance to random amino acid change," PNAS 101:9205-9210; 2004.
Keskin et al. A new, structurally nonredundant, diverse data set of protein-protein interfaces and its implications; *Protein Sci*; 13:1043-1055; 2004.
Klein et al., The multi-protein family of *Arabidopsis sulphotransferases* and their relatives in other plant species; *J of Experimental Botarny*; vol. 55; No. 404; 2004.
Maniatis et al.; Molecular Cloning: A laboratory manual, Cold Spring Harbor Laboratory; 1982.
Ngo et al., "Computational Complexity, Protein Structure Prediction, and the Levinthal Paradox," *The Protein Folding Problem and Tertiary Structure Prediction*; pp. 492-495; 1994.
Rabbani et al., "Monitoring Expression Profiles of Rice Genes under Cold, Drought, and High-Salinity Stresses and Abscisic Acid Application Using cDNA Microarray and RNA Gel-Blot Analyses," *Plant Physio*; vol. 133; pp. 1755-1767; 2003.
Thornton et al.; "From structure to function: Approaches and limitations," Nature Structural Biology, Structural Genomics supplement; Nov. 2000.
Wells, "Additivity of Mutational Effects in Proteins," *Biochemistry* 29:8509-8517; 1990.
Yamamoto et al., "The Promoter of a Pine Photosynthetic Gene Allows Expression of a β-Glucuronidase Reporter Gene in Transgenic Rice Plants in a Light-Independent but Tissue-Specific Manner, " *Plant Cell Physiol* 35: 773-778; 1995.
NCBI GenBank Accession No. NP_179785; Aug. 21, 2001.
NCBI GenBank Accession No. NP_565906; Jan. 29, 2002.
NCBI GenBank Accession No. NP_565305; Jan. 29, 2002.
NCBI GenBank Accession No. NP_567957; Jan. 30, 2002.
NCBI GenBank Accession No. NP_566785; Jan. 29, 2002.
NCBI GenBank Accession No. NP_567754; Jan. 29, 2002.
NCBI GenBank Accession No. NM_129505; Aug. 21, 2001.
NCBI GenBank Accession No. NM_119581; Jan. 30, 2002.
NCBI GenBank Accession No. BT018295; Oct. 27, 2004.
NCBI GenBank Accession No. NM_127763; Nov. 4, 2005.
NCBI GenBank Accession No. BT003928; Feb. 14, 2003.
NCBI GenBank Accession No. AY086786; Jan. 27, 2006.
NCBI GenBank Accession No. AY092961; Apr. 21, 2002.
NCBI GenBank Accession No. AF410323; Aug. 27, 2001.
Notice of Publication regarding U.S. Appl. No. 15/275,537, dated Jul. 25, 2019.
Notice of Allowance regarding U.S. Appl. No. 15/275,537, dated May 21, 2019.
Hirschmann et al., (Front Plant Sci., 5:1-13, 2014).
Wang et al., (Nature Communications, DOI: 10:1038/ncomms5768, pp. 1-8).
Smith et al., (Nature Biotechnology, 15:1222-1223, 1997).
Bork et al., (TIG, 12:425-427, 1996).
Doerks et al., (TIG, 14:248-250, 1998).
GenBank Accession No. AY099809.1, dated May 6, 2002.
Kang et al. (Cell death and differentiation, 13:84-95, 2006).
Rhoads et al. (The FASEB Journal, 11:331-340, 1997).

* cited by examiner

Figure 1

| | | | | |
|---|---|---|---|---|
| SEQ-ID-NO-90-CLONE-554272 | ---MNCYWWHAL | MSGCVLGLC | VGIGGCVCVV | ---------- | 29 |
| SEQ-ID-NO-92-CLONE-881632 | ---MAPP----- | LLLLLLVPLV | AATAPCAHPA | HPSQ---PAS | 41 |
| SEQ-ID-NO-93-GI-50944095 | ---MAHLAPLFL | LLLLLLLPLH | AAATPSAHPA | YPNE---PPS | 45 |
| SEQ-ID-NO-80-CLONE-8686 | ---MTRSVSFPL | FLAVVLSLS | SSLLA----- | ---------- | 30 |
| SEQ-ID-NO-84-CLONE-954851 | ---MTSS----- | ---------- | ---------- | ---DDPKPI | 10 |
| SEQ-ID-NO-85-CLONE-1064137 | ---MAVPPLLLL | TLLSPSLL | HAAISDAYPT | IPGT--APID | 47 |
| SEQ-ID-NO-95-ANNOT-1494052 | MSTTKTMIPL | LLLLSPLS | TASTAAYPT | IPGTIDTSVS | 50 |

| | | | | |
|---|---|---|---|---|
| SEQ-ID-NO-90-CLONE-554272 | ---ENENGRI | IDISHRYHPD | MPAWESKDSL | GQ--FLWLRS | 76 |
| SEQ-ID-NO-92-CLONE-881632 | RREAHGCGRI | LDITHYYRED | MPSWESGAGV | GQ--FLWLPAS | 90 |
| SEQ-ID-NO-93-GI-50944095 | RREAHGCGRI | LDITHYYRED | MPSWESDGGV | GQ--FLWLPAS | 94 |
| SEQ-ID-NO-80-CLONE-8686 | RREVYEGGKI | YDISHRYTPE | IPAWESSEGL | GKIT-FLRLAAS | 80 |
| SEQ-ID-NO-84-CLONE-954851 | ROEVYGERKI | FDITHRYTQD | MPVWESTEGV | KP--FLRLTTS | 59 |
| SEQ-ID-NO-85-CLONE-1064137 | RREVYGEGKI | FDISHRYTPE | MPAWESKEGI | GR--FLWLAAS | 96 |
| SEQ-ID-NO-95-ANNOT-1494052 | RNEIYGNGKI | FDISHRYND | MPVWDSKDGL | GK--FLSLPAS | 99 |

| | | | | |
|---|---|---|---|---|
| SEQ-ID-NO-90-CLONE-554272 | QFKLPAHSGT | HVDAPGHVFD | HYFSGFDVD | SLDLLLNGP | 126 |
| SEQ-ID-NO-92-CLONE-881632 | EMRMPTHTGT | HIDASGHVFQ | HYFDAGFDVD | TLDLDVLNGP | 140 |
| SEQ-ID-NO-93-GI-50944095 | EMRLPTHTGT | HVDAPGHVFD | HYFDAGFDVD | SLDLEVLNGL | 144 |
| SEQ-ID-NO-80-CLONE-8686 | EMKLSVHSGT | HVDAPGHFWD | NYYDAGFDTD | SLDQVLHGP | 130 |
| SEQ-ID-NO-84-CLONE-954851 | ROKLSVHTGT | HLDAPGHFHD | KYYDAGFDSD | SLDLQVLHGP | 109 |
| SEQ-ID-NO-85-CLONE-1064137 | EMKIPTHTGT | HVDSPGHVYD | EYYDAGFDVD | SLDLEVLNGP | 146 |
| SEQ-ID-NO-95-ANNOT-1494052 | EMKLPTHTGT | HVDSPGHVFD | HYFDSGFDVD | TLDLEVLNGP | 149 |

| | | | | |
|---|---|---|---|---|
| SEQ-ID-NO-90-CLONE-554272 | NISAGVMKSL | NIPRGVRRVL | FRTLNTMYRRL | MYQKEFDTSY | 176 |
| SEQ-ID-NO-92-CLONE-881632 | NITAKTMESL | HIPKGVQRVL | FRTLNTDRNL | MWKKEFDTSY | 190 |
| SEQ-ID-NO-93-GI-50944095 | NITAKMMESL | HIPKGIQRVL | FRTLNTDROL | MWKKEFDTSY | 194 |
| SEQ-ID-NO-80-CLONE-8686 | NITAEVMESL | HIORGVRRVL | FRTINTDKRL | MFKKEFDSSF | 180 |
| SEQ-ID-NO-84-CLONE-954851 | NIX-XVMKSL | HIPKGVRRVL | FRTLNXDRRL | MFKKEFDSSF | 158 |
| SEQ-ID-NO-85-CLONE-1064137 | NITAEVMKSL | NIPRGVRRVL | FRTLNTDRRL | MFKREFDTSY | 196 |
| SEQ-ID-NO-95-ANNOT-1494052 | NITAEVMKSL | HIPKGVRRVL | FRTLNTDRRL | MFKREFDRSY | 199 |

Figure 1 - continued

| | | | | | |
|---|---|---|---|---|---|
| SEQ-ID-NO-90-CLONE-554272 | VENTDI KLV | GI DYLSVAAY | DHLI PAHLVF | LKGREII LVE | GLKLDDVAAG | 226 |
| SEQ-ID-NO-92-CLONE-881632 | VDNTDI KLV | GI DYLSVAAF | DDLI PSHLVL | ENRDI I LVE | GLKLENVI PG | 240 |
| SEQ-ID-NO-93-GI-50944095 | VDNTDI KLV | GI DYLSVAAF | DDLI PSHLVL | KNRDI I LVE | GLKLENI MPG | 244 |
| SEQ-ID-NO-80-CLONE-8686 | VENTDI KLI | GLDYLSFAAF | EESPAT HRVI | KGRDI I PVE | ALKLDGVEVG | 230 |
| SEQ-ID-NO-84-CLONE-954851 | VENTDI KLV | GLDYLSFAAY | EEAPET HKFI | GERDI I PVE | ALKLDGVEVG | 208 |
| SEQ-ID-NO-85-CLONE-1064137 | VDNTDI KLV | GVDYLSVAAY | DDLI PSHLVF | KGREII LVE | GLKLDDVKAG | 246 |
| SEQ-ID-NO-95-ANNOT-1494052 | VDNTDI KLV | GI DYLSVAAW | SDLI PSHLVF | EGREII LVE | ALKLDDI QPG | 249 |

| | | | | |
|---|---|---|---|---|
| SEQ-ID-NO-90-CLONE-554272 | YTVHCLPLR | LAGAEGSPI R | CI LI K | 251 |
| SEQ-ID-NO-92-CLONE-881632 | YSLHCLPLR | LRGAEGSPI R | CI LI K | 265 |
| SEQ-ID-NO-93-GI-50944095 | YSLHCLPLR | LRGAEGSPI R | CI LI K | 269 |
| SEQ-ID-NO-80-CLONE-8686 | TYSLHCLPLR | LVGAEGAPTR | CI LI K | 255 |
| SEQ-ID-NO-84-CLONE-954851 | VYSLHCLPLR | LPGAEGAPTR | CI LI K | 233 |
| SEQ-ID-NO-85-CLONE-1064137 | VYSVHCLPLR | LVGAEGSPI R | CI LI G | 271 |
| SEQ-ID-NO-95-ANNOT-1494052 | VYSVHCLPLR | LFGAEGSPI R | CVLI K | 274 |

Figure 2

```
SEQ-ID-252:                    MGKRGKWFSA VKKVFSSSDP DGKEA AQKA  DKSKSKRRWP FGKSKHSEPS    50
SEQ-ID-NO-301-CLONE-228069     MGKKCKWFGA VKKVFSPESK EKKEERL           RR  KSAASNPA      37
SEQ-ID-NO-302-CLONE-335348     MGKKGKWFGA VKKVFSPESK EKKEE                               25
SEQ-ID-NO-100-GI-56202321      MGKKGNFSA  VKKVFSSSDP DGREAKI EKA  DKSRSRR  KWPFGKSK      45
SEQ-ID-NO-303-GI-54306075      MGKKGKWFGA VKKVFSPESK EKKEERL           RR  KLAASNPN      37
SEQ-ID-NO-312-CLONE-1727738    MGKKGKWFGA VKKVFSPESK EKKEERL           RR  KSAASNPT      37
SEQ-ID-NO-298-CLONE-1792902    MGKKGKWFGA VKKVFSPESK EKKEERQ           RR  KSAASNPT      37

SEQ-ID-252:                    -ISTVPGTAP AVA-PLPSPP A----T    -QPHSLEIKD VNPVEIDSEQ    89
SEQ-ID-NO-301-CLONE-228069     PVDLTPSTSL EVNVSVPPPP A----P    -PPVPROFDE VRVPEAEQEQ    78
SEQ-ID-NO-302-CLONE-335348                                                               25
SEQ-ID-NO-100-GI-56202321      KSDPWTSTV  APTSTAPPPP QPPPPPTHP                           94
SEQ-ID-NO-303-GI-54306075      PPDLTPSASL EVNVSVPPPP P----P    PPQPEEIKD  VKAVEIDSEQ    77
SEQ-ID-NO-312-CLONE-1727738    PRDLTPSTSL EVNVSVPPPP A----P    PPVQQIEE   VKVPEVEQEQ    77
SEQ-ID-NO-298-CLONE-1792902    PLDLTPSTSL EVNVSVPPPP A----P    PALHQIEE   RAPEAEQEQ     77
                                                                PALHQIKE   VRPEAEQEQ    77

SEQ-ID-252:                    NKHAYSVALA SA---VAAEA AVAAQAAAE  VVRLTAVTTA APKMPVSSRE   136
SEQ-ID-NO-301-CLONE-228069     SKHVT-LEEA PAAAAPAQA                          PPGAPTE   107
SEQ-ID-NO-302-CLONE-335348                                                                25
SEQ-ID-NO-100-GI-56202321      NKHAYSVALA SA---VAAEA AVAAQAAAE  VVRLTTATTA VPKSPVSSKD   141
SEQ-ID-NO-303-GI-54306075      SKHVT-VEAV PEAVPVPAQT -APAQA               SS PPGVSRE    106
SEQ-ID-NO-312-CLONE-1727738    SKHVT-VEEA PA---APAQA                       SV PPGVPSE   103
SEQ-ID-NO-298-CLONE-1792902    SKHIT-VEEA PA---APAQA                       SV PPGVPSE   103

SEQ-ID-252:                    ELAAIKIQTA FRGYLARRAL RALRGLVRLK SLVDGNAVKR QTAHTLQCIQ   186
SEQ-ID-NO-301-CLONE-228069     ELAAIKIQTA FRGYLARRAL RALRGLVRLK SLVEGNSVKR QSASTLRCMQ   157
SEQ-ID-NO-302-CLONE-335348                                                                25
SEQ-ID-NO-100-GI-56202321      EDAIKIQTA  FRGYLARRAL RALRGLVRLK SLVDGNAVKR QTAHTLHCIQ   191
SEQ-ID-NO-303-GI-54306075      ELAAIKIQTA FRGYLARRAL RALRGLVRLK SLVEGNSVKR QAASTLRCMQ   156
SEQ-ID-NO-312-CLONE-1727738    ELAAIKIQTA FRGYLARRAL RALRGLVRLK SLVEGDSVRR QSASTLRCMQ   153
SEQ-ID-NO-298-CLONE-1792902    ELAAIKIQTA FRGYLARRAL RALRGLVRLK SLVEGDSVRR QSASTLRCMQ   153
```

Figure 2 - continued

```
SEQ·ID·252                   AMTRVQTQIY SRRVKLEEEK QALQRQLQLK          HQRELEKMKI DEDWDHSHQS  236
SEQ·ID·NO·301·CLONE·228069   TLSRVQSQIR SRRAKMSEEN QALQRQLLLK          -QELENFRM GENWDDSTQS  205
SEQ·ID·NO·302·CLONE·335348                                                                    25
SEQ·ID·NO·100·GI·56202321    TMTRVQTQIY SRRVKMEEEK QALQRQLLLK          HQRELEKMKI DEDWDHSHQS  241
SEQ·ID·NO·303·GI·54306075    TLARVQSQIR SRRLKMSEEN QALQRQLLLK          -QELESLRM GEQWDDSTQS  204
SEQ·ID·NO·312·CLONE·1727738  TLSRVQSQIR SRRAKMSEEN QALQRQLLLK          -QELENFRM GENWDDSTQS  201
SEQ·ID·NO·298·CLONE·1792902  TLSRVQSQIR SRRAKMSEEN QALQRQLLLK          -QELENFRM GENWDDSTQS  201

SEQ·ID·252                   KEQIEANLMM KQEAALRRER ALAYAFSHQW          RNSGRTITPT FLEPGNPNWG  286
SEQ·ID·NO·301·CLONE·228069   KEQIEASLIS RQEAAIRRER ALAYAFSHQW          KSTSRSANPM FVDPNNLQWG  255
SEQ·ID·NO·302·CLONE·335348                                                                    25
SEQ·ID·NO·100·GI·56202321    KEQVEISLMM KQEAALRRER ALAYAFSHQW          KNSGRTITPT FLDQGNPNWG  291
SEQ·ID·NO·303·GI·54306075    KEQIEASLIS RQEAAVRRER ALAYAFSHQW          KSTSRSVNPM FVDPNNPQWG  254
SEQ·ID·NO·312·CLONE·1727738  KEQIEASLIS RQEAAIRRER ALAYAFSHQW          KSTSRSVNPM FVDPNNLQWG  251
SEQ·ID·NO·298·CLONE·1792902  KEQIEASLIS RQEAAIRRER ALAYAFSHQW          KSTSRSVNPM FVDPNNLQWG  251

SEQ·ID·252                   WSWMERWMIA RPWESRL-AAA SDKDP-KERA         VTKNASTSA- -VRVPVSRAI  333
SEQ·ID·NO·301·CLONE·228069   WSWLERWMAA KPWEGRNG--- TDKESNIDRA         SVKNMSLNL- VGEGEITKAF  303
SEQ·ID·NO·302·CLONE·335348                                     SNIDRG  SVKSMSLNL- -GEGEITKAF  49
SEQ·ID·NO·100·GI·56202321    WSWMERWMIS RPWESRVI--- SDKDP-KDHY         STKNPSTSA- -SRTYVPRAI  336
SEQ·ID·NO·303·GI·54306075    WSWLERWMAA KPWEGRAG--- TDKESNLDRA         SAKSASLNL- -GEGEITKAF  300
SEQ·ID·NO·312·CLONE·1727738  WSWLERWMAA KPWEGCNG--- ADKESNIDRG         SVKSMSLNL- -GEGEITKAF  297
SEQ·ID·NO·298·CLONE·1792902  WSWLERWMAA KPWEGRNG--- TDKESNVDRG         SVKSMSLNL- -GEGEITKAF  297

SEQ·ID·252                   ---SIQRP-- ATPN-KSSRP PSRQSLSTPP         SKTPSASGKA RPASPRNSWL  377
SEQ·ID·NO·301·CLONE·228069   NRRDSKPEKP SPPTPKPARP ASRQSPSTPS         ARVAPIPARR KSSTPKNGLS  353
SEQ·ID·NO·302·CLONE·335348   ---SIQRP-- SPTTPKL-TRP TSRHSPLTPS         ARVAPIPARR KSVTPKNGLS  99
SEQ·ID·NO·100·GI·56202321    NRRGSKPDKS SPITPKL-TRP PSRQSPSTPP         SRVPSVTGKI RPASPRDSWL  380
SEQ·ID·NO·303·GI·54306075    NRRDSKPEKP SPPTPKL-TRP ASRQSPSTPS         AKVSPIFAKK KSATPKNGLS  350
SEQ·ID·NO·312·CLONE·1727738  NRRDSKPEKP SPPTPKL-TRP ASRQSPSTPS         AKVAPIPARR KSATPENGLS  347
SEQ·ID·NO·298·CLONE·1792902  NRRDSKPEKP SPPTPKL-TRP ASRQSPSTPS         AKVAPIPVRR KSVTPKNGLS  347
```

Figure 2 - continued

| SEQ ID | | | | | |
|---|---|---|---|---|---|
| SEQ-ID-NO-252 | TKEDDLRSI T | SI RSERPRRQ | ST GG-GSVRD | DI SLI STPP L | PSYMQSI TESA | 426 |
| SEQ-ID-NO-301-CLONE-228069 | QVDDDVRSVL | SVQSERPRRH | SI AT STMRD | DESLASSPSL | PSYMVPTESA | 403 |
| SEQ-ID-NO-302-CLONE-335348 | QVDDDARSVL | SVQSERPRRH | SI AT STVRD | DESLI SSPSL | PSYMVPTESA | 148 |
| SEQ-ID-NO-100-GI-56202321 | TKEDDLRSI T | SI RSERPRRQ | ST GG-ASVRD | DASLI STPAL | PSYMQSI TESA | 429 |
| SEQ-ID-NO-303-GI-54306075 | QVDDDAKSVF | SVQSERPRRH | SI AT STVRD | DESLASSPSV | PSYMAPTKSA | 399 |
| SEQ-ID-NO-312-CLONE-1727738 | HVDDDARSVF | SVQSERPRRH | SI AT STVQD | NESLASSPSL | PSYMVPTESA | 396 |
| SEQ-ID-NO-298-CLONE-1792902 | HVDDDARSVF | SVQSERPRRH | SI AT STVRD | DESLASSPSL | PSYMVPTESA | 396 |

| SEQ ID | | | | | |
|---|---|---|---|---|---|
| SEQ-ID-NO-252 | RAKSRYRSLL | LTEKLEWP E | RAPLAHSVVK | KRLSFPVVEK | PSVVPTEKPR | 475 |
| SEQ-ID-NO-301-CLONE-228069 | RAKSRI A | TANGAETP E | KGGSA GPVK | KRLSFQGGA A | A | 440 |
| SEQ-ID-NO-302-CLONE-335348 | RAKSRLQGSA | MANGAETP E | KGGSI GPAK | KRLSFQGGI A | A | 188 |
| SEQ-ID-NO-100-GI-56202321 | RAKLRYRSL | LTDRFEVP E | RVPLVHSSI K | KRLSFPVADK | PNGEHADKLM | 477 |
| SEQ-ID-NO-303-GI-54306075 | RAKLRLQGSA | VTDGAETPPE | KVASV GSVK | KKLSFQAGMA | P | 440 |
| SEQ-ID-NO-312-CLONE-1727738 | RAKSRLQGSA | LTNGAETP E | KGSSA GPVK | KRLSFQGGT A | A | 436 |
| SEQ-ID-NO-298-CLONE-1792902 | RAKSRLQGSA | LNNGAETP E | KGSSA GPVK | KRLSFQGGT A | A | 436 |

| SEQ ID | | | | |
|---|---|---|---|---|
| SEQ-ID-NO-252 | ERVRRHSDPP | KVDPAT KDA | PAA | | 498 |
| SEQ-ID-NO-301-CLONE-228069 | SPMRRHSGPP | KVESA VKDI | ANGG GSK | A | 476 |
| SEQ-ID-NO-302-CLONE-335348 | SPMRRHSGPP | KVE | APPQPEALV | VNG GSK | 217 |
| SEQ-ID-NO-100-GI-56202321 | ERGRRHSDPP | KVDPASL KDV | | PVS | 500 |
| SEQ-ID-NO-303-GI-54306075 | SPMRRHSGPP | KVEV VKDI | AEPPQPEALV | NG GSK | 474 |
| SEQ-ID-NO-312-CLONE-1727738 | SPMRRHSGPP | KVDSA VKDI | VAPPQPEALV | NG GSK | 471 |
| SEQ-ID-NO-298-CLONE-1792902 | SPMRRHSGPP | KVGSA VKDI | VAPPQPEALV | NG GSK | 471 |

```
SEQ-ID-NO-106-CLONE-105319  GEAYTNANAR VSLENI AAKR GYKNVSDLTP TEI CI EAFEQ VLSFLE KEET  295
SEQ-ID-NO-107-CLONE-463638  GEAYANANAR VSLKNI ALKL GKRDVSELSP TDI AI EALEQ DNFL-KGEG  243
SEQ-ID-NO-115-GI-76782196   SEAYANANAR VSLEDVAAKL CHRDVSNLTP TAI AI EALEQ EGFL-KEEN  297
SEQ-ID-NO-113-GI-56805577   GDAYANADVR VSLEEI ASKQ GHDDVSKLTP TDI AI ESFHK ENFV--EHI  288
SEQ-ID-NO-112-CLONE-749796  MDSYANADAR VSLENI ALKQ GHNDVNVLTP STI AI EALLK MESFL-TEKA  291
SEQ-ID-NO-114-CLONE-294723  MDSYANADAR VSLEHI ALKQ GHNDVTI LTP STI AI EALLK MESFL-TEKT  185

SEQ-ID-NO-106-CLONE-105319  ME PDGDL----------                    303
SEQ-ID-NO-107-CLONE-463638  GRYAEC-----------                     249
SEQ-ID-NO-115-GI-76782196   GDFAL------------                     302
SEQ-ID-NO-113-GI-56805577   VDNPVGDSQA DSRAQRI QTL                308
SEQ-ID-NO-112-CLONE-749796  MVRN-------------                     295
SEQ-ID-NO-114-CLONE-294723  MVRN-------------                     189
```

```
SEQ-ID-NO-143-CLONE:1272732  METAAVAASS AGRRMVAVD EGEESLHALN WCLANVSPA- GGDTLVLH A  50
SEQ-ID-NO-139-CLONE:684584   MAAQAPPPPP PEQKMMVAID ESEGSHYALE WALRNL---- APRRLILFTV  46
SEQ-ID-NO-142-CLONE:1059727  ---------- ---MVAID  DSDCSKHALR MTLSYLKDS- ADSDILFTA   35
SEQ-ID-NO-134-ANNOT:1486744  ---------- ---MVILD   ESEYSHSFM  WVDNLKEF-- TESPLVIAA   35
SEQ-ID-NO-132-CLONE:2767     ---------- -MKNWMLID  ESNASYDLLI WALENQKDT- ESSKVMFAK   39

SEQ-ID-NO-143-CLONE:1272732  RRPRPV---Y AAMDSAG--- -----YMMTSD VLASVERHAN AVSAAADKA   90
SEQ-ID-NO-139-CLONE:684584   QPFSPLSY-L PVGSPLG--- -DSVASPE-- LIRSVTEHQR QLAQALVDKA  89
SEQ-ID-NO-142-CLONE:1059727  QPQLDLS--S VYASSYG--- ---AAPIE-- LINSMQQNYK NAALNREEG   75
SEQ-ID-NO-134-ANNOT:1486744  LPAPNCK--F FYGAQFGTAA LCCFVSPTLD LICAIQEKNK KILLGLLEKA  83
SEQ-ID-NO-132-CLONE:2767     QPQNSFTPPT VLSSSWGFAQ IFYPFSPNSE LIRLAQEKNM KIALGLLEKA  89

SEQ-ID-NO-143-CLONE:1272732  KRVCADHPHV KVETIVESGD PRDVICDAAAN KMAADLLVMG SHG-YGFIQR  139
SEQ-ID-NO-139-CLONE:684584   KAI CAEH-GV DAETVIEVSGD PKEII CEAAE KLNVDLLILG SHS-RGDVQR  137
SEQ-ID-NO-142-CLONE:1059727  TKI CAES-GV TPKKVMEFGN PKEAI CDAVE KLGVDLLIVG SHG-KGALER  123
SEQ-ID-NO-134-ANNOT:1486744  VNI CASR-GV KAETI LEAGE PYELTCNAVQ KNNI NLLVIG NTSI NGTLKR  132
SEQ-ID-NO-132-CLONE:2767     KKI CINH-GI KAETFTNVGD PKDLIRKILQ ERNINLIVTS DQQ---SLKK  135

SEQ-ID-NO-143-CLONE:1272732  ---AFLGS-- VSNHCAQNCK CPYLIVKR-- ---------- ---------   162
SEQ-ID-NO-139-CLONE:684584   ---FFLGS-- VSNYCSHHAK CPYLVVKK-- ---------- ---------   160
SEQ-ID-NO-142-CLONE:1059727  ---TFLGS-- VSNYCVNKAK CPYLVVRT-- ---------- ---------   146
SEQ-ID-NO-134-ANNOT:1486744  LGNFFVTSKI SFALESRIN  CMNLIQNELF QELEHAGMVV NPINSCNKLH  182
SEQ-ID-NO-132-CLONE:2767     ---------- CTQNTD    CSLLVVKK-- ---------- --------R   150

SEQ-ID-NO-143-CLONE:1272732  --PKE  165
SEQ-ID-NO-139-CLONE:684584   --KE   162
SEQ-ID-NO-142-CLONE:1059727  --KA   148
SEQ-ID-NO-134-ANNOT:1486744  YQKH   186
SEQ-ID-NO-132-CLONE:2767     LRKD   154
```

Figure 6

```
SEQ-ID-NO-151-GI-50944591      MAT HSI S APA  APAFSA F PLA  AAVRF P CASA  TSN T CAFSLA  EH L T REGMF F     50
SEQ-ID-NO-152-CLONE:1551032    MAT-AVPAAC     LRA P CSSPA A  VARR L GA---  -GGPS E RKRH  CAVAPVAAA C      45
SEQ-ID-NO-146-CLONE:16403      MAVSSLSTRC     --GGFSPT L S   HK T EI L C-  -PNPS L -KAC  CL S SGGKA D     43
SEQ-ID-NO-147-CLONE:611156     M V VSS C SL-- ---SW I SPCLS  HK N NL P H-- -N--C L PRNI  ATS I SSNFVF C   41
SEQ-ID-NO-149-ANNOT-1464944    MA I SSLSL---  --SWAS T TLS   QKLSVP G ---   -SNE I L PRVA  AFSGNNSV T C    42

SEQ-ID-NO-151-GI-50944591      DLQ---S KR     E AEER-SRRR   M LL A A G AAMF  LSW P NPAAYA   A E AKKGFL PV   96
SEQ-ID-NO-152-CLONE:1551032    GPAPPRL L DN   EEAV C I-SVRR  RVL V AGAAAF    LSRPNPAAFA    A E AKKGFL PV   94
SEQ-ID-NO-146-CLONE:16403      SSE S --TYQK   GSG N N WKRRQ   A L VGVG T LVA  T S I PATL L L A EE I PKSYSPF I 91
SEQ-ID-NO-147-CLONE:611156     ELD---T PSI    GE S HC--RRRP  LLGI GALI A    NL Q PI T NLVFA QEK P DRY RAF  87
SEQ-ID-NO-149-ANNOT-1464944    TAE----AT FN   EESNC--KRR L   LLLGVGAL I T   SL VPANF L FA   EE L PKN Y TSF  88

SEQ-ID-NO-151-GI-50944591      I DKKDGYSFL    Y PFGW Q EVVV  QGQ D KV Y KDV  I E PL ESVSV N   T I PT SKQDI R  146
SEQ-ID-NO-152-CLONE:1551032    V DKKAGYSFL    Y PFGWEEVAV    QGQ D KV Y KDV  I E PL ESVSV N   S I PT SKEDI R  144
SEQ-ID-NO-146-CLONE:16403      V DREDGYSY L   YP S DWRE F DF  RA H DSAFKDR   YL Q L QNVRVR    F I PT EKKDI R  141
SEQ-ID-NO-147-CLONE:611156     VD Y EDGYSY I  YP I DWKE F DF  RAH DSAFKDR    YL Q L QNVRVR    F I PT EKKDI R  137
SEQ-ID-NO-149-ANNOT-1464944    VD F EDGYSY Y  YP S DW I D F DF  RGH DSAFKDR    TK Q L QNVRVR    F I PT EKKDI H  138

SEQ-ID-NO-151-GI-50944591      ELGPPDQVAE     A LI RKVLAAP   TQKTKL I EAK    ENDVDGRI YY     T FEFT AQAPN    196
SEQ-ID-NO-152-CLONE:1551032    DLGPPDKVAE     A LI KKVLA P S  TQKTKL I -EAK   ENDVDGRA YY     T FEFT AQAPN    194
SEQ-ID-NO-146-CLONE:16403      EVGPMEEVV Y    DLVK H K F AAP  NQ V AT I YDMK   ERVEDGKNYY      T FEYG L RTP I   191
SEQ-ID-NO-147-CLONE:611156     DLGPMEEV I L   DLVK H RY AAP  NQRPT I NDMQ    EKT I DGKHYY    T FEY L LT SPN   187
SEQ-ID-NO-149-ANNOT-1464944    ELGPMEE---Y    D SHMQ QE I MN   VK L S N FL E-N   QK T I VEGKNYY   T FEYE L T SPN   185

SEQ-ID-NO-151-GI-50944591      F T RHA L GA I A  I ANGKFYTL T  T GANERRWE K   KDRLHT V D      S FKI E AREVR   246
SEQ-ID-NO-152-CLONE:1551032    Y T RHA L GA I     I ANGKFYTL T  T GANERRWE K   MKDRLHT V D     S FKI E NRI--   242
SEQ-ID-NO-146-CLONE:16403      Y A T T I SFATVA   VG N N RYYTLI  VGANERRWRK     VK K QLQVVAD    SI KI LQ---    238
SEQ-ID-NO-147-CLONE:611156     YSS A SFAT I A    G N GRYYTLI   VGANERRWKR     FRDQLKVVAD     SFRLLD I ----   234
SEQ-ID-NO-149-ANNOT-1464944    YSSVSFAT I V     A NGRFYTL I   VGANERRWRR     YR S QLKVVAD    SFKVLD I ----   232

SEQ-ID-NO-151-GI-50944591      FNGKCREHGS Y   257
SEQ-ID-NO-152-CLONE:1551032    ------------   242
SEQ-ID-NO-146-CLONE:16403      ------------   238
SEQ-ID-NO-147-CLONE:611156     ------------   234
SEQ-ID-NO-149-ANNOT-1464944    ------------   232
```

Figure 7

| | | | | | |
|---|---|---|---|---|---|
| SEQ:ID:NO:168-CLONE-1064128 | | | | M ATVFPRDAGV | STPEADEA------KKIYDEAR | 27 |
| SEQ:ID:NO:161-CLONE-703785 | | | | -MASSPQSSS | SAPKADDKAA SHKEIYDQLL | 29 |
| SEQ:ID:NO:169-GI-77552975 | | | | | | 0 |
| SEQ:ID:NO:160-GI-68067679 | | | | | ------ME | 2 |
| SEQ:ID:NO:163-GI-1706738 | | | | | ------ME | 2 |
| SEQ:ID:NO:154-CLONE-3964 | MFTFFTILSL | CFKSWEQIIT | | PNYMKDDN-- | ----VSQETK | 44 |
| SEQ:ID:NO:164-GI-342004 | | | | | ----TQEITR | 20 |
| SEQ:ID:NO:157-ANNOT-1448303 | | | | MVLNHF | MEASKEAHHL -----MESSSV TKNQANDNGE DLERTNECK | 26 |

| SEQ:ID:NO:168-CLONE-1064128 | RVVSTYEMVP | SPSGTLDYC | RHPSGWCITL | PIMVSSMWAE | QHFEARGTDV | 77 |
| SEQ:ID:NO:161-CLONE-703785 | EVVSTYPTAP | SGIG---RPYT | HHPDCMYAFT | PAVVNAMIK | RHLKACDTDV | 77 |
| SEQ:ID:NO:169-GI-77552975 | | | | MVVK | SHLTARATDI | 14 |
| SEQ:ID:NO:160-GI-68067679 | DITKTLPQHT | CSFLKHRFTL | YKYKDAWNHQ | EFLEGRILSE | QIKFKAHPNDV | 52 |
| SEQ:ID:NO:163-GI-1706738 | DIIKTLPQHT | CSFLKQRFTL | YKYQDVWNHQ | EFLEGRMLSE | QIFKAHPNDV | 52 |
| SEQ:ID:NO:154-CLONE-3964 | NLITSLPSDK | DFMG-----YGL | YNYKGCWYYP | NTLQAVLDVQ | KHFKPRDTDI | 91 |
| SEQ:ID:NO:164-GI-342004 | DLLSSLPSEK | GWLV-----SQM | YQFEG-MQTQ | ALVQGIVNCQ | KHFEANDSDV | 67 |
| SEQ:ID:NO:157-ANNOT-1448303 | ELLSLPREK | GWRT-----ACL | YKYKGFWCQP | KELQAILSFQ | KHFEPRDTDV | 73 |

| SEQ:ID:NO:168-CLONE-1064128 | LMTMPKSGT | TWIKALLYAA | AHRTDDTSSS | ILRQLASHNS | HQLVPFFLEAQ | 127 |
| SEQ:ID:NO:161-CLONE-703785 | FLSTFPKSGT | TWLKALLFAT | LRRI----ADGP | AIAALAAHSP | HQIPFLEVQ | 125 |
| SEQ:ID:NO:169-GI-77552975 | FLVTFPKSGT | TWIKALPYSA | LHRR----AD-- | -----ELLAHSP | HQLISFLESQ | 57 |
| SEQ:ID:NO:160-GI-68067679 | LASYPKSGT | TWLKALAFAI | TREKFDDST | S--PLLTTMP | HDCIPLLEKD | 100 |
| SEQ:ID:NO:163-GI-1706738 | LASYPKSGT | TWLKALAFAI | TREKFDDST | S--PLLTTMP | HDLPLLEKD | 100 |
| SEQ:ID:NO:154-CLONE-3964 | LASPKGGT | TWLKSLIFAV | VHREKYRGTP | QTHPLLQNP | HDLVPFLEVE | 141 |
| SEQ:ID:NO:164-GI-342004 | LATLAKSGT | TWLKALLFAL | HRIKFPVSG | K--HPLLVFNP | HSLVPYLEGD | 116 |
| SEQ:ID:NO:157-ANNOT-1448303 | LASIPKSGT | TWLKALSFAI | LNRKKFAISS | NDHPLLVSNP | HDLAPFFEYK | 123 |

| SEQ:ID:NO:168-CLONE-1064128 | VYIKDQIPDL | SSLPAPRLFA | THIPAESLPP | SVVASGCKVV | YLCRDPKDCF | 177 |
| SEQ:ID:NO:161-CLONE-703785 | VFSNGRIPDL | SSLPAPRLLM | THIPSRSLPE | SVAASGCKVV | YLCRDPKDCF | 175 |
| SEQ:ID:NO:169-GI-77552975 | VFVKDRIPDL | SSLPEPMLLM | THIPSDSLPD | SVAASGCKVV | YLCRDPKDCF | 107 |
| SEQ:ID:NO:160-GI-68067679 | ---EKIQEN | QRNSLYTPS | HFHYKSLPE | SARTSNCKIV | YIRNMKDVI | 147 |
| SEQ:ID:NO:163-GI-1706738 | ---EKIQEN | QRNSLYTPS | HFHYKSLPE | SARTSNCKIV | YIRNMKDVI | 147 |
| SEQ:ID:NO:154-CLONE-3964 | YANSQIPDL | AKYSSPMFS | THMHLQALRE | AT-TKACKIV | YVCRGIKDTF | 190 |
| SEQ:ID:NO:164-GI-342004 | YCSSPEVNE | AELPSPRLMQ | THLTHSLPV | SIKSSSCKII | CCRNPKDMF | 165 |
| SEQ:ID:NO:157-ANNOT-1448303 | YADKQVPDL | SKLPDPRLFA | THIPFASLQD | SIKKSNCRII | YICRNPFDTF | 173 |

Figure 7 - continued

| SEQ ID | Sequence | Position |
|---|---|---|
| SEQ-ID-NO-168-CLONE-1064128 | VSLWHFMNKF T———PWD DEAHGRFCEG VSLYGPFWEH VLSYWRWHVD | 222 |
| SEQ-ID-NO-161-CLONE-703785 | VSLWHFWNRF AP——SPWDL GEALQQFCDG VSLFGPFWEH VLGYWRWHVE | 222 |
| SEQ-ID-NO-169-GI-77552975 | VSLWHFWNRF M———PWN DDAHROFCNG VSLFGLYWEH VLSYWNWHVE | 152 |
| SEQ-ID-NO-160-GI-68067679 | VSTYHFLRQI VKLSVEEAPF EEAFDEFCQG SSCGPYWEH KGYWKASLE | 197 |
| SEQ-ID-NO-163-GI-1706738 | VSMYHFLRQI VKLSVEEAPF EEAVDEFCQG SSCGPYWEH GYWKASLE | 197 |
| SEQ-ID-NO-154-CLONE-3964 | VSGWHYRNML HRTKMDQATF ELMFDAYCRC VLLYGPYWEH VLSYWKGSLE | 240 |
| SEQ-ID-NO-164-GI-342004 | VSLWHFGRKL APEKTAEYPL ETAVAAFCKG KFLGGPFWDH VLEYWYESLK | 215 |
| SEQ-ID-NO-157-ANNOT-1448303 | SSMTFSNKL RSETVPLLL EETFKMYCEG VVGFGPFWDH MLGYWKFSLE | 223 |
| SEQ-ID-NO-168-CLONE-1064128 | RPGQVLFLTY EELSADPLGQ LRRLAEFIGR PFTPGEQEAG VDREIAEACA | 272 |
| SEQ-ID-NO-161-CLONE-703785 | RPEQVLFLTY EELAADLGQ KRLAAFLGR PFTSEEREAR VDREIVEACA | 272 |
| SEQ-ID-NO-169-GI-77552975 | RPSEVLFLTY EELAADILGH LRRLAEFVGR PFTTEEQDAR VDRKIVETCA | 202 |
| SEQ-ID-NO-160-GI-68067679 | KPEIFLFLKY EDMKKDPVPS VKKLADFIGH PFTPKEEEAG VIEDIVKLCS | 247 |
| SEQ-ID-NO-163-GI-1706738 | KPEIFLFLKY EDMKKDPVPS VKKLADFIGH PFTPKEEEAG VIENIKLCS | 247 |
| SEQ-ID-NO-154-CLONE-3964 | AKENVLFMKY EEIEEPRVQ VKRLAEFLEC PFTKEEEESG SVEEILKLCS | 290 |
| SEQ-ID-NO-164-GI-342004 | NPNKVLFVTY EELKKQTEVE VKRIAEFIGC GFTAEEE VSEIVKLCS | 261 |
| SEQ-ID-NO-157-ANNOT-1448303 | RQDKVLFLKY EDMKADVTFY LKKIAKFLGC PFSMEEKEG VVEKIASLCS | 273 |
| SEQ-ID-NO-168-CLONE-1064128 | MKSMVNQEVN QSRTTEIVEL MPIPNGIFFR RGMVGDWNY LTPEMAGRID | 321 |
| SEQ-ID-NO-161-CLONE-703785 | MESLAGLEVN RSGKTDMTE SSVANNIFFR RGVVGDWKNH LTPEMARRID | 321 |
| SEQ-ID-NO-169-GI-77552975 | MESLSGLEVN RSGMINFTK KDVPNNISFR RGVVGDWRNH LTPEMARRID | 251 |
| SEQ-ID-NO-160-GI-68067679 | FEKLSSLEVN KSGMHRPEEA HSIENRLYFR KGKDGDWKNY FTDEMTQKID | 297 |
| SEQ-ID-NO-163-GI-1706738 | FEKLSSLEVN KSGMHRPEEA HSIENRLYFR KGKDGDWKNY FTDEMLEKID | 297 |
| SEQ-ID-NO-154-CLONE-3964 | LRNLSNLEVN KNGITR IGVDSQVFFR KGEVGDWKNH LTPOMAKTFD | 336 |
| SEQ-ID-NO-164-GI-342004 | FESLSSLEVN ROCKLP NGIESNAFFR KGEGGWRDE SESLADVID | 307 |
| SEQ-ID-NO-157-ANNOT-1448303 | EEKMKNLEVN KSGRSI TNFENKHLFR KAEVGDWNYS LSPSMVKQLS | 319 |
| SEQ-ID-NO-168-CLONE-1064128 | EITKSKFEGS GLMLPKTISE ISKI | 345 |
| SEQ-ID-NO-161-CLONE-703785 | EITDSKFRGS GLALTPATAD QN | 343 |
| SEQ-ID-NO-169-GI-77552975 | EITEVKFKGS GLLLHPPFLQ VKRELNEL | 279 |
| SEQ-ID-NO-160-GI-68067679 | KLIDEKLGAT GLVLK | 312 |
| SEQ-ID-NO-163-GI-1706738 | KLIDEKLGAT GLVLK | 312 |
| SEQ-ID-NO-154-CLONE-3964 | EIIDYRLGDS GLIFQ | 351 |
| SEQ-ID-NO-164-GI-342004 | RTTEQKFGGS GLKFSS | 323 |
| SEQ-ID-NO-157-ANNOT-1448303 | QLIEEKLGGS GGVQAAAAAA SSSSSVIKKK FELQRYGENK NTNVN | 364 |

FIGURE 8

| | | | | | |
|---|---|---|---|---|---|
| SEQ-ID-NO-172-CLONE-965405 | MSADDSSNAT | DVDGKLGSDL | NVNSDGEDAA | DNDSSKTLT- | PAPAVCLVR | 49 |
| SEQ-ID-NO-173-CLONE-5367 | MAANDSSNAI | DIDGNLDSDS | NLNTDGDEAT | DNDSSSKALVT | PAPAVCLVR | 50 |
| SEQ-ID-NO-174-GI-79537394 | MAAENSSNAI | NVDTSLDSDS | KPNRDANDMT | DHDSSSKALV | PAPAVCLVR | 50 |
| SEQ-ID-NO-175-GI-9758183 | MAAENSSNAI | NVDTSLDSDS | KPNRDANDMT | DHDSSSKALV | PAPAVCLVR | 50 |
| SEQ-ID-NO-176-CLONE-1060894 | MAAENPSNGV | DVDTSLASDS | NDNRKASDLT | NHDSS-MALT | VPSTAVCLGR | 49 |
| SEQ-ID-NO-179-ANNOT-1494390 | MATANSPNTS | NNSDSDVEDP | NPNPSSN--N | NNASTTPSAE | SSTPSVCLIR | 48 |
| SEQ-ID-NO-177-CLONE-639280 | MAAR-SENES | DGDVG----- | NPAEGGS | SLSLPPL | AAGPAVCVLR | 39 |
| | | | | | |
| SEQ-ID-NO-172-CLONE-965405 | FAGDAAGGAV | MGSIFGYGSG | LFKKGFKGS | FADAGQSAKT | FAVLSGVHSL | 99 |
| SEQ-ID-NO-173-CLONE-5367 | FAGDAAGGAV | MGSIFGYGSG | LFKKGFKGS | FADAGQSAKT | FAVLSGVHSL | 100 |
| SEQ-ID-NO-174-GI-79537394 | FAGDAASGAF | MGSVFGYGSG | LFKKGFKGS | FVDAGQSAKT | FAVLSGVHSL | 100 |
| SEQ-ID-NO-175-GI-9758183 | FAGDAAGGAF | MGSVFGYG-- | LFKKGFKGS | FVDAGQSAKT | FAVLSGVHSL | 98 |
| SEQ-ID-NO-176-CLONE-1060894 | FAGDAAGGAV | MGSIFGYGSG | LFKKGFKGS | FADAGQSAKN | FAILSGVHSL | 99 |
| SEQ-ID-NO-179-ANNOT-1494390 | FAGDSAAGAF | MGSIFGYGSG | LTKKGFKGS | FGEAGSCAKT | FAVLSGVHSL | 98 |
| SEQ-ID-NO-177-CLONE-639280 | SAGDFAGGAF | VGSIFGYGQE | LLSKKGLKGS | LGNAGSSAKS | FAVLSGYQSL | 89 |
| | | | | | |
| SEQ-ID-NO-172-CLONE-965405 | VVCLLKQLRG | KDDAINVGVA | GCCTGLALSF | PGAPQALLQS | CLTFGAFSFI | 149 |
| SEQ-ID-NO-173-CLONE-5367 | VVCLLKQIRG | KDDAINVGVA | GCCTGLALSF | PGAPQALLQS | CLTFGAFSFI | 150 |
| SEQ-ID-NO-174-GI-79537394 | VVCLLKQIRG | KDDAINVGVA | GCCTGLALSF | PGAPQAMLQS | CLTFGAFSFI | 150 |
| SEQ-ID-NO-175-GI-9758183 | VVCLLKQIRG | KDDAINVGVA | GCCTGLALSF | PGAPQAMLQS | CLTFGAFSFI | 148 |
| SEQ-ID-NO-176-CLONE-1060894 | VVCLLKKLRG | KDDAINVGIA | GCCTGLALSY | PGAPQAMLQS | CVTFGAFSFI | 149 |
| SEQ-ID-NO-179-ANNOT-1494390 | VVCFLKRLRG | KDDVINAGVA | GCCTGLALSF | PGAPQALLQS | CLTFGAFSFI | 148 |
| SEQ-ID-NO-177-CLONE-639280 | VLCLLRKLRG | KDDIINSGIA | GCCTGLALSF | PGTPQALLQN | CATFAAFSCI | 139 |
| | | | | | |
| SEQ-ID-NO-172-CLONE-965405 | EGLNKROTA | LAHSVSLR-H | QTGNFGDHQQ | RPLQLSLALP | HEEIKGLFS | 197 |
| SEQ-ID-NO-173-CLONE-5367 | EGLNKROTA | LAHSVSLR-H | QTGLFQDHH- | RALPLSLALP | PEEIKGAFS | 198 |
| SEQ-ID-NO-174-GI-79537394 | EGLNKROTA | LAHSVSFR-Q | QTRSP---QH | DLPLLSLAIP | HDEIKGAFS | 196 |
| SEQ-ID-NO-175-GI-9758183 | EGLNKROTA | LAHSVSFR-Q | QTRSP---QH | DLPLLSLAIP | HDEIKGAFS | 194 |
| SEQ-ID-NO-176-CLONE-1060894 | EGLNKROTA | LAHSVSSRHD | QTRSL---KD | DLP-LSLALP | HEEIKGAFS | 195 |
| SEQ-ID-NO-179-ANNOT-1494390 | EGLNKKQTA | LAHSISSR-N | KCDYHS---KP | CPLALPLSVP | LPDELKGAFS | 195 |
| SEQ-ID-NO-177-CLONE-639280 | MEGLNKQQTA | MAHTLTGN-A | LTFAH---DN | GAGVLPPSLS | PQSSMLPMLS | 185 |

Figure 8 - continued

| | | |
|---|---|---|
| SEQ-ID-NO-172-CLONE-965405 | SFCKSLTKPK | KI------ | 209 |
| SEQ-ID-NO-173-CLONE-5367 | SFCKSLAKPR | KF------ | 210 |
| SEQ-ID-NO-174-GI-795373944 | SFCNSLTKPK | KLKFPHAR- | 214 |
| SEQ-ID-NO-175-GI-9758183 | SFCNSLTKPK | KLKFPHAR- | 212 |
| SEQ-ID-NO-176-CLONE-1060894 | SFCKSLTKPK | KLAFPSSR- | 213 |
| SEQ-ID-NO-179-ANNOT-1494390 | FFCKSLRKPK | SANFPAAAP | 214 |
| SEQ-ID-NO-177-CLONE-639280 | PHAARPWSPS | LRSTRQQH- | 203 |

Figure 9

| SEQ ID | 1-47 | 48-97 | 98-145 | 146-187 |
|---|---|---|---|---|
| SEQ-ID-NO-304-CLONE-335348-T | —ESNIDRGSV KSMSLNL—G EGEITKAFNR RDSKLEKPSP PTPRPARPLS | RHSPLTPSAR VAPIPARRKS VTPKNGLSQV DDDARSVLSV QSERPRRHSI | AT—STVRDDE SLTSSPSLPS YMVPTESARA KSRLQGSAMA NGAETP—EKG | GST—GPAKKR LSFQGGTAA— ————————— MRRHSGPPKV ASP———EL—AP |
| SEQ-ID-NO-305-CLONE-228069-T | —ESNIDRGSV KNMSLNLGVG EGEITKAFNR RDSKPEKPSP PTPKPARPAS | RQSPSTPSAR VAPIPARRKS STPKNGLSQY DDDVRSVLSV QSERPRRHSI | ATT—STMRDDE SLASSPSLPS YMVPTESARA KSR——TATA NGAETP—EKG | GSA—GPVKKR LSFQGGAAA— ————————— MRRHSGPPKV ASP———ESAVKDIAAP |
| SEQ-ID-NO-306-CLONE-375578-T | —DP—KERAVT KNASTSA—V RVPVSRAI—— ——SIQRPAI PN—KSSRPPS | RQSL—STPSK TPSASGKARP ASPRNSWLYK EDDLRSITSI RSERPRRQST | GG—GSVRDDT SLTSTPPLPS YMQSTESARA KSRYRSLLLT EKLEMP—ERA | PLAHSVVKKR LSFPVVEKPS VVPTEKPRER VRRHSDPPKV RER———DPA—AP |
| SEQ-ID-NO-307-CLONE-229668-T | —ESNLDRASA KSASLNL—G EGEITKAFNR RGSKPDKSSP PTPKLTRPAS | RQSPSTPSAK VAPIPARRKS VTPKNGLSQV DDDAKSVFSV QSERPRRHSI | AT—STVRDDE SLASSPSVPS YMAPTKSARA KLRLQGSAVT DGAETPPEKV | GST—GPAKKR LSFQAGMAP— ————————— MRRHSGPPKV ASP———EL—AP |
| SEQ-ID-NO-308-GI-54306075-T | —DP—KDHYST KNPSSA—V RTYVPRA—— ——SIQRPAI TTPKLTRPAS | RQSPSTPPSR VSPIFAKKKS ASPRDSWLYK EDDLRSITSI RSERPRROQST | GG—ASVRDDA SLTSTPALPS YMVPTESARA KSRYR—SLT DRFEVP—EKV | ASV—GSVKKKI LSFQAGMAP— ————————— GRRHSGPPKV PSP———EV—VKDIAEP |
| SEQ-ID-NO-309-GI-56202321-T | —DP—KDHYST KNPSSA—V RTYVPRA—— ——SIQRPAI TTPKLTRPAS | RQSPSTPPSR VPSVTGKIRP ASPRDSWLYK EDDLRSITSI RSERPRROQST | GG—ASVRDDA SLTSTPALPS YMVPTESARA KSRYR—SLT DRFEVP—EKV | PLVHSSIKKR LSFPVADKPN GEHADKLMER GRRHSGPPKV P5P———DPA—AP |
| SEQ-ID-NO-310-CLONE-1792902-T | —ESNVDRGSV KSMSLNL—G EGEITKAFNR RDSKPEKPSP PTPKPARPAS | RQSPSTPSAK VAPIPARRKS VTPKNGLSHV DDDARSVFSV QSERPRRHSI | AT—STVRDDE SLASSPSLPS YMVPTESARA KSRLQGSALN NGAETP—EKG | SSA—GPVKKR LSFQGGTAA— ————————— MRRHSGPPKV ASP———GSAVKDIVAP |
| SEQ-ID-NO-311-CLONE-1727738-T | KESNIDRGSV KSMSLNL—G EGEITKAFNR RDSKPEKPSP PTPKLTRPAS | RQSPSTPSAK VAPIPARRKS ATPENGLSHV DDDARSVFSV QSERPRRHSI | AT—STVODNE SLASSPSLPS YMVPTESARA KSRLQGSALT NGAETP—EKG | SSA—GPVKKR LSFQGGTAA— ————————— MRRHSGPPKV ASP———DSAVKDIVAP |

Figure 9 - continued

| | | | |
|---|---|---|---|
| SEQ-ID-NO-304-CLONE-335348-T | PQPEALVVNG | -GSK | 193 |
| SEQ-ID-NO-305-CLONE-228069-T | PQPEALVANG | GGSK | 200 |
| SEQ-ID-NO-306-CLONE-375578-T | ----TLKDA | -PIAA | 189 |
| SEQ-ID-NO-307-CLONE-229668-T | PQPEALVVNG | -GSK | 193 |
| SEQ-ID-NO-308-GI-54306075-T | PQPEALVING | -GSK | 199 |
| SEQ-ID-NO-309-GI-56202321-T | ----SLKDV | -PVS | 188 |
| SEQ-ID-NO-310-CLONE-1792902-T | PQPEALVING | -GSK | 199 |
| SEQ-ID-NO-311-CLONE-1727738-T | PQPEALVING | -GSK | 200 |

NUCLEOTIDE SEQUENCES AND CORRESPONDING POLYPEPTIDES CONFERRING MODULATED GROWTH RATE AND BIOMASS IN PLANTS GROWN IN SALINE CONDITIONS

This application is a is a Divisional of U.S. patent application Ser. No. 17/831,146, filed Jun. 2, 2022, which is a Divisional of application Ser. No. 16/859,573, filed Apr. 27, 2020, patented as U.S. Pat. No. 11,421,244, which is a Divisional of application Ser. No. 16/275,595, filed Feb. 14, 2019, patented as U.S. Pat. No. 10,696,978, which is a Divisional of application Ser. No. 15/487,287, filed Apr. 13, 2017, patented as U.S. Pat. No. 10,233,460, which is a Divisional of application Ser. No. 13/663,204, filed Oct. 29, 2012, patented as U.S. Pat. No. 9,637,756, which is a Divisional of application Ser. No. 12/282,342, filed on Nov. 17, 2008, patented as U.S. Pat. No. 8,324,454, and for which priority is claimed under 35 U.S.C. § 120. application Ser. No. 12/282,342 is a National Phase under 35 U.S.C. § 371 of PCT International Application No. PCT/US2007/006544, which has the International filing date of Mar. 14, 2007, which designated the United States of America, and which claims priority under 35 U.S.C. § 119(e) of U.S. Provisional Application No. 60/782,735, filed Mar. 14, 2006, the entire contents of each of which are hereby incorporated by reference.

INCORPORATION OF SEQUENCE LISTING

The sequence listing that is contained in the XML file named "CRES002USD13_ST26," which is 788 kilobytes as measured in Microsoft Windows operating system and was created on Sep. 29, 2023, is filed electronically herewith and incorporated herein by reference.

FIELD OF THE INVENTION

The present invention relates to isolated nucleic acid molecules and their corresponding encoded polypeptides able to enhance plant growth under saline conditions. The present invention further relates to using the nucleic acid molecules and polypeptides to make transgenic plants, plant cells, plant materials or seeds of a plant having improved growth rate, vegetative growth, seedling vigor and/or biomass under saline conditions as compared to wild-type plants grown under similar conditions.

BACKGROUND OF THE INVENTION

Plants specifically improved for agriculture, horticulture, biomass conversion, and other industries (e.g. paper industry, plants as production factories for proteins or other compounds) can be obtained using molecular technologies. As an example, great agronomic value can result from enhancing plant growth in saline conditions.

A wide variety agriculturally important plant species demonstrate significant sensitivity to saline water and/or soil. Upon salt concentration exceeding a relatively low threshold, many plants suffer from stunted growth, necrosis, and death that results in an overall stunted appearance and reduced yields of plant material, seeds, fruit and other valuable products. Physiologically, plants challenged with salinity experience disruption in ion and water homeostasis, inhibition of metabolism, and damage to cellular membranes that result in developmental arrest and cell death (Huh et al. (2002) *Plant J,* 29(5): 649-59).

In many of the world's most productive agricultural regions, agricultural activities themselves lead to increased water and soil salinity, which threatens their sustained productivity. One example is crop irrigation in arid regions that have abundant sunlight. After irrigation water is applied to cropland, it is removed by the processes of evaporation and evapotranspiration. While these processes remove water from the soil, they leave behind dissolved salts carried in irrigation water. Consequently, soil and groundwater salt concentrations build over time, rendering the land and shallow groundwater saline and thus damaging to crops.

In addition to human activities, natural geological processes have created vast tracts of saline land that would be highly productive if not saline. In total, approximately 20% of the irrigated lands in are negatively affected by salinity. (Yamaguchi and Blumwald, 2005, *Trends in Plant Science*, 10: 615-620). For these and other reasons, it is of great interest and importance to identify genes that confer improved salt tolerance characteristics to thereby enable one to create transgenic plants (such as crop plants) with enhanced growth and/or productivity characteristics in saline conditions.

The availability and sustainability of a stream of food and feed for people and domesticated animals has been a high priority throughout the history of human civilization and lies at the origin of agriculture. Specialists and researchers in the fields of agronomy science, agriculture, crop science, horticulture, and forest science are even today constantly striving to find and produce plants with an increased growth potential to feed an increasing world population and to guarantee a supply of reproducible raw materials. The robust level of research in these fields of science indicates the level of importance leaders in every geographic environment and climate around the world place on providing sustainable sources of food, feed and energy.

Manipulation of crop performance has been accomplished conventionally for centuries through selection and plant breeding. The breeding process is, however, both time-consuming and labor-intensive. Furthermore, appropriate breeding programs must be specially designed for each relevant plant species.

On the other hand, great progress has been made in using molecular genetic approaches to manipulate plants to provide better crops. Through the introduction and expression of recombinant nucleic acid molecules in plants, researchers are now poised to provide the community with plant species tailored to grow more efficiently and yield more product despite suboptimal geographic and/or climatic environments. These new approaches have the additional advantage of not being limited to one plant species, but instead being applicable to multiple different plant species (Zhang et al. (2004) *Plant Physiol.* 135:615; Zhang et al. (2001) *Proc. Natl. Acad. Sci. USA* 98:12832).

Despite this progress, today there continues to be a great need for generally applicable processes that improve forest or agricultural plant growth to suit particular needs depending on specific environmental conditions. To this end, the present invention is directed to advantageously manipulating plant tolerance to salinity in order to maximize the benefits of various crops depending on the benefit sought, and is characterized by expression of recombinant DNA molecules in plants. These molecules may be from the plant itself, and simply expressed at a higher or lower level, or the molecules may be from different plant species.

SUMMARY OF THE INVENTION

The present invention, therefore, relates to isolated nucleic acid molecules and polypeptides and their use in making transgenic plants, plant cells, plant materials or seeds of plants having improved growth characteristics in saline conditions compared to wild-type plants under similar or identical conditions.

The present invention also relates to processes for increasing the growth potential of plants challenged with saline conditions due to salt tolerance derived from recombinant nucleic acid molecules and polypeptides. The phrase "increasing growth potential" refers to continued growth in saline conditions, better yield after exposure to saline conditions and/or increased vigor in saline conditions.

Unless otherwise defined, all technical and scientific terms used herein have the same meaning as commonly understood by one of ordinary skill in the art to which this invention belongs.

BRIEF DESCRIPTION OF THE FIGURES

FIG. 1 Amino acid sequence alignment of homologues of Ceres clone 8686 (SEQ ID NO: 80). Conserved regions are enclosed in a box.

FIG. 2. Amino acid sequence alignment of homologues of Ceres clone 375578 (SEQ ID NO: 252). Conserved regions are enclosed in a box.

FIG. 3 Amino acid sequence alignment of homologues of Ceres clone 105319 (SEQ ID NO: 106). Conserved regions are enclosed in a box.

FIG. 4 Amino acid sequence alignment of homologues of Ceres clone 29658 (SEQ ID NO: 123). Conserved regions are enclosed in a box.

FIG. 5 Amino acid sequence alignment of homologues of Ceres clone 2767 (SEQ ID NO: 132). Conserved regions are enclosed in a box.

FIG. 6 Amino acid sequence alignment of homologues of Ceres clone 16403 (SEQ ID NO: 146). Conserved regions are enclosed in a box.

FIG. 7 Amino acid sequence alignment of homologues of Ceres clone 3964 (SEQ ID NO: 154). Conserved regions are enclosed in a box.

FIG. 8 Amino acid sequence alignment of homologues of Ceres clone 965405 (SEQ ID NO: 172). Conserved regions are enclosed in a box.

FIG. 9 Amino acid sequence alignment of a conserved region of Ceres clones 375578 (SEQ ID NO: 306) and 335348 (SEQ ID NO: 304) and homologues. Conserved regions are enclosed in a box.

DETAILED DESCRIPTION OF THE INVENTION

1. The Invention

The present invention discloses novel isolated nucleic acid molecules, nucleic acid molecules that interfere with these nucleic acid molecules, nucleic acid molecules that hybridize to these nucleic acid molecules, and isolated nucleic acid molecules that encode the same protein due to the degeneracy of the DNA code. Additional embodiments of the present application further include the polypeptides encoded by the isolated nucleic acid molecules of the present invention.

Figure 3:
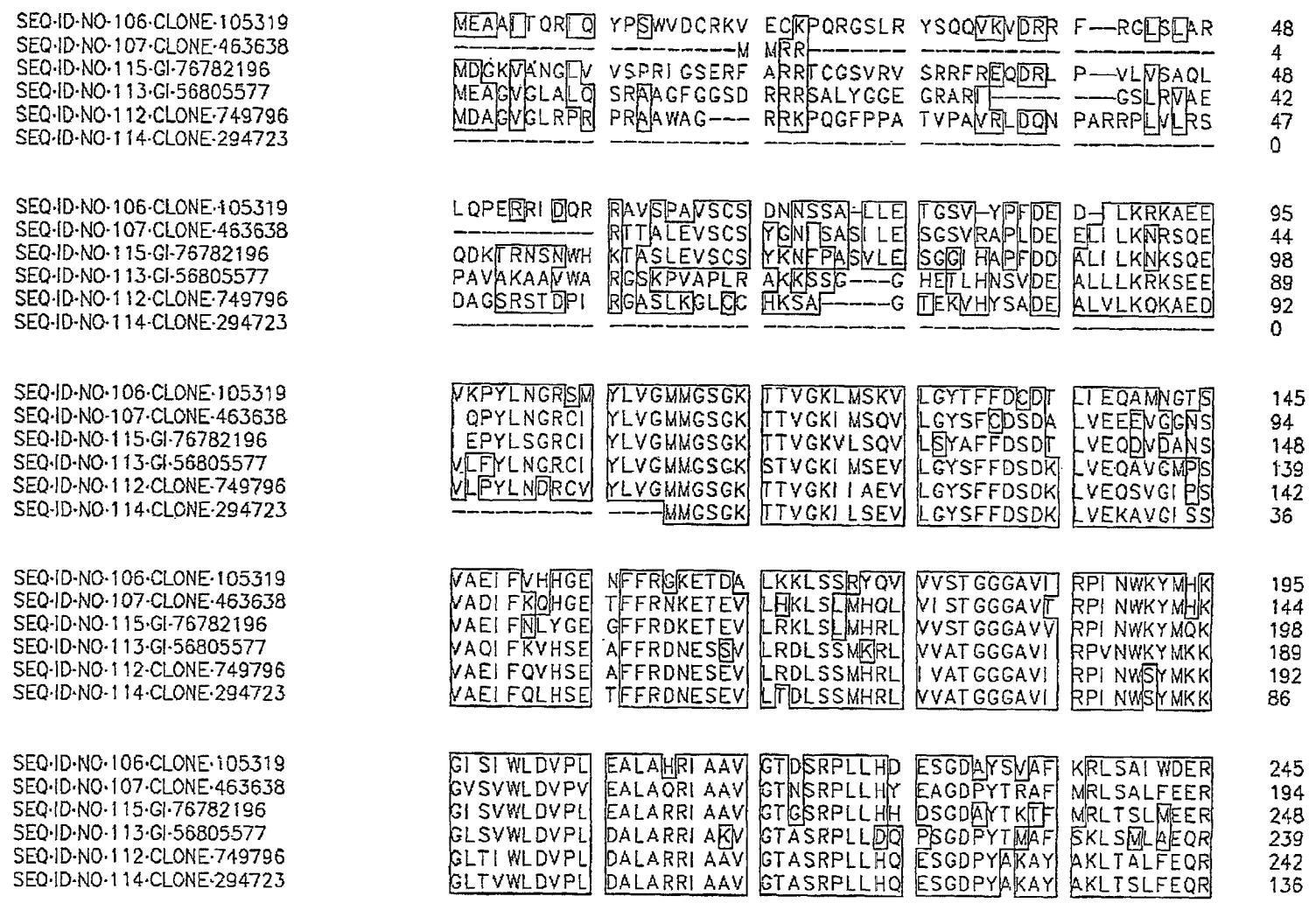

More particularly, the nucleic acid molecules of the present invention comprise: (a) a nucleotide sequence that encodes an amino acid sequence and that is at least 85% identical to any one of SEQ ID Nos. 80, 99, 106, 123, 132, 146, 154 and 172 respectively, (b) a nucleotide sequence that is complementary to any one of the nucleotide sequences according to (a), (c) a nucleotide sequence according to any one of SEQ ID NOs. 79, 98, 105, 122, 131, 145, 153 and 171, (d) a nucleotide sequence able to interfere with any one of the nucleotide sequences according to (a), (e) a nucleotide sequence able to form a hybridized nucleic acid duplex with the nucleic acid according to any one of paragraphs (a)-(d) at a temperature from about 5° C. to about 10° C. below a melting temperature of the hybridized nucleic acid duplex, (f) a nucleotide sequence encoding any one of amino acid sequences of SEQ ID NOS. 80, 99, 106, 123, 132, 146, 154 and 172, (g) a nucleotide sequence encoding any one of the amino acid sequences with an HMM bit score greater than 20 that fits an HMM based on the sequences aligned in any one of FIGS. 1-8, and (h) a nucleotide sequence encoding an amino acid sequence having a fragment that fits an HMM based on the sequences aligned in FIG. 9 and which has an HMM bit score greater than 400.

Additional embodiments of the present invention include those polypeptide and nucleic acid molecule sequences disclosed in SEQ ID NOs: 81-97, 100-104, 107-121, 124-130, 133-144, 147-152, 155-170, 173-252 and 269-315.

The present invention further embodies a vector comprising a first nucleic acid having a nucleotide sequence encoding a plant transcription and/or translation signal, and a second nucleic acid having a nucleotide sequence according to the isolated nucleic acid molecules of the present invention. More particularly, the first and second nucleic acids may be operably linked. Even more particularly, the second nucleic acid may be endogenous to a first organism, and any other nucleic acid in the vector may be endogenous to a second organism. Most particularly, the first and second organisms may be different species.

In a further embodiment of the present invention, a host cell may comprise an isolated nucleic acid molecule according to the present invention. More particularly, the isolated nucleic acid molecule of the present invention found in the host cell of the present invention may be endogenous to a first organism and may be flanked by nucleotide sequences endogenous to a second organism. Further, the first and second organisms may be different species. Even more particularly, the host cell of the present invention may comprise a vector according to the present invention, which itself comprises nucleic acid molecules according to those of the present invention.

In another embodiment of the present invention, the isolated polypeptides of the present invention may additionally comprise amino acid sequences that are at least 85% identical to any one of SEQ ID Nos. 80, 99, 106, 123, 132, 146, 154 and 172.

Other embodiments of the present invention include methods of introducing an isolated nucleic acid of the present invention into a host cell. More particularly, an isolated nucleic acid molecule of the present invention may be contacted to a host cell under conditions allowing transport of the isolated nucleic acid into the host cell. Even more particularly, a vector as described in a previous embodiment of the present invention may be introduced into a host cell by the same method.

Methods of detection are also available as embodiments of the present invention. Particularly, methods for detecting a nucleic acid molecule according to the present invention in a sample. More particularly, the isolated nucleic acid molecule according to the present invention may be contacted with a sample under conditions that permit a comparison of the nucleotide sequence of the isolated nucleic acid molecule with a nucleotide sequence of nucleic acid in the sample. The results of such an analysis may then be considered to determine whether the isolated nucleic acid molecule of the present invention is detectable and therefore present within the sample.

A further embodiment of the present invention comprises a plant, plant cell, plant material or seeds of plants comprising an isolated nucleic acid molecule and/or vector of the present invention. More particularly, the isolated nucleic acid molecule of the present invention may be exogenous to the plant, plant cell, plant material or seed of a plant.

A further embodiment of the present invention includes a plant regenerated from a plant cell or seed according to the present invention. More particularly, the plant, or plants derived from the plant, plant cell, plant material or seeds of a plant of the present invention preferably has increased size (in whole or in part), increased vegetative growth and/or increased biomass (sometimes hereinafter collectively referred to as increased biomass) in saline conditions, as compared to a wild-type plant cultivated under identical conditions. Furthermore, the transgenic plant may comprise a first isolated nucleic acid molecule of the present invention, which encodes a protein involved in improving growth and phenotype characteristics in saline conditions, and a second isolated nucleic acid molecule which encodes a promoter capable of driving expression in plants, wherein the growth and phenotype improving component and the promoter are operably linked. More preferably, the first isolated nucleic acid may be mis-expressed in the transgenic plant of the present invention, and the transgenic plant exhibits improved characteristics as compared to a progenitor plant devoid of the polynucleotide, when the transgenic plant and the progenitor plant are cultivated under identical, saline conditions. In another embodiment of the present invention the improved growth and phenotype characteristics may be due to the inactivation of a particular sequence, using for example an interfering RNA.

A further embodiment consists of a plant, plant cell, plant material or seed of a plant according to the present invention which comprises an isolated nucleic acid molecule of the present invention, wherein the plant, or plants derived from the plant, plant cell, plant material or seed of a plant, has the improved growth and phenotype characteristics in saline conditions as compared to a wild-type plant cultivated under identical conditions.

The polynucleotide conferring increased biomass or vigor in saline conditions may be mis-expressed in the transgenic plant of the present invention, and the transgenic plant exhibits an increased biomass or vigor as compared to a progenitor plant devoid of the polynucleotide, when the transgenic plant and the progenitor plant are cultivated under identical saline conditions. In another embodiment of the present invention increased biomass or vigor phenotype may be due to the inactivation of a particular sequence, using for example an interfering RNA.

Another embodiment consists of a plant, plant cell, plant material or seed of a plant according to the present invention which comprises an isolated nucleic acid molecule of the present invention, wherein the plant, or plants derived from the plant, plant cell, plant material or seed of a plant, has increased biomass or vigor in saline conditions as compared to a wild-type plant cultivated under identical conditions.

Another embodiment of the present invention includes methods of enhancing biomass or vigor in plants challenged with saline conditions. More particularly, these methods comprise transforming a plant with an isolated nucleic acid molecule according to the present invention. Preferably, the method is a method of enhancing biomass or vigor in the transgenic plant, whereby the plant is transformed with a nucleic acid molecule encoding the polypeptide of the present invention.

Polypeptides of the present invention include sequences belonging to the consensus sequence families shown in FIGS. 1-9 as delineated by Hidden Markov Models (HMMs).

2. Definitions

The following terms are utilized throughout this application:

Functionally Comparable Proteins or Functional Homologs: This phrase describes a set of proteins that perform similar functions within an organism. By definition, perturbation of an individual protein within that set (through misexpression or mutation, for example) is expected to confer a similar phenotype as compared to perturbation of any other individual protein. Such proteins typically share sequence similarity resulting in similar biochemical activity. Within this definition, homologs, orthologs and paralogs are considered to be functionally comparable.

Functionally comparable proteins will give rise to the same characteristic to a similar, but not necessarily the same, degree. Typically, comparable proteins give the same characteristics where the quantitative measurement due to one of the comparables is at least 20% of the other; more typically, between 30 to 40%; even more typically, between 50-60%; even more typically between 70 to 80%; even more typically between 90 to 100% of the other.

Heterologous sequences: "Heterologous sequences" are those that are not operatively linked or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence, are considered heterologous to said coding sequence. Elements operatively linked in nature and contiguous to each other are not heterologous to each other. On the other hand, these same elements remain operatively linked but become heterologous if other filler sequence is placed between them. Thus, the promoter and coding sequences of a corn gene expressing an amino acid transporter are not heterologous to each other, but the promoter and coding sequence of a corn gene operatively linked in a novel manner are heterologous.

Hidden Markov Model (HMM): HMM is a statistical description of a sequence family's consensus. The model is indicative of similarity of a polypeptide sequence to a group of structurally and functionally related polypeptides (Durbin, R., Eddy, S. R., Krogh, A. & Mitchison, G. J. *Biological Sequence Analysis: Probabilistic Models of Proteins and Nucleic Acids* Cambridge University Press, Cambridge UK, 1998).

HMM based on specified sequences: An HMM profile based on specified sequences is the output model generated by the program HMMER 2.3.2 (released Oct. 3, 2003 under a GNU general public license, and available from various sources, such as the HMMER website on the internet) configured with default parameters, the model being built by the program using as input the specified sequences. The program outputs the model as a text file.

HMM bit score: An HMM bit score is a probabilistic indication of confidence that a sequence fits the model. The bit score reflects whether the sequence is a better fit to an HMM of interest than to a null model of nonhomologous sequences. A significant HMM bit score is greater than zero, but is typically greater than 20. The HMM bit score of a polypeptide sequence fitted to an HMM profile can be determined by fitting the polypeptide to the HMM with program HMMER 2.3.2 configured for glocal alignments.

Misexpression: The term "misexpression" refers to an increase or a decrease in the transcription of a coding region into a complementary RNA sequence as compared to the wild-type. This term also encompasses expression and/or translation of a gene or coding region or inhibition of such transcription and/or translation for a different time period as compared to the wild-type and/or from a non-natural location within the plant genome, including a gene or coding region from a different plant species or from a non-plant organism.

Percentage of sequence identity: As used herein, the term "percent sequence identity" refers to the degree of identity between any given query sequence and a subject sequence. A subject sequence typically has a length that is from about 80 percent to 250 percent of the length of the query sequence, e.g., 82, 85, 87, 89, 90, 93, 95, 97, 99, 100, 105, 110, 115, or 120, 130, 140, 150, 160, 170, 180, 190, 200, 210, 220, 230, 240, or 250 percent of the length of the query sequence. A query nucleic acid or amino acid sequence is aligned to one or more subject nucleic acid or amino acid sequences using the computer program ClustalW (version 1.83, default parameters), which allows alignments of nucleic acid or protein sequences to be carried out across their entire length (global alignment). Chenna et al. (2003) *Nucleic Acids Res.* 31(13):3497-500.

ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For an alignment of multiple nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The output is a sequence alignment that reflects the relationship between sequences. ClustalW can be run, for example, at the Baylor College of Medicine Search Launcher website and at the European Bioinformatics Institute website on the World Wide Web.

To determine a percent identity for polypeptide or nucleic acid sequences between a query and a subject sequence, the sequences are aligned using Clustal W and the number of identical matches in the alignment is divided by the query length, and the result is multiplied by 100. The output is the percent identity of the subject sequence with respect to the query sequence. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

Photosynthetic efficiency: photosynthetic efficiency, or electron transport via photosystem II, is estimated by the relationship between Fm, the maximum fluorescence signal and the variable fluorescence, Fv. Here, a reduction in the optimum quantum yield (Fv/Fm) indicates stress and can be used to monitor the performance of transgenic plants compared to non-transgenic plants under salt stress conditions.

Regulatory Regions: The term "regulatory region" refers to nucleotide sequences that, when operably linked to a sequence, influence transcription initiation or translation initiation or transcription termination of said sequence and the rate of said processes, and/or stability and/or mobility of a transcription or translation product. As used herein, the term "operably linked" refers to positioning of a regulatory region and said sequence to enable said influence. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns. Regulatory regions can be classified in two categories, promoters and other regulatory regions.

Salt tolerance: Plant species vary in their capacity to tolerate salinity. "Salinity" can be defined as the set of environmental conditions under which a plant will begin to suffer the effects of elevated salt concentration, such as ion imbalance, decreased stomatal conductance, decreased photosynthesis, decreased growth rate, increased cell death, loss of turgor (wilting), or ovule abortion. For these reasons, plants experiencing salinity stress typically exhibit a significant reduction in biomass and/or yield.

Elevated salinity may be caused by natural, geological processes and by human activities, such as irrigation. Since plant species vary in their capacity to tolerate water deficit, the precise environmental salt conditions that cause stress cannot be generalized. However, under saline conditions, salt tolerant plants produce higher biomass, yield and survivorship than plants that are not salt tolerant. Differences in physical appearance, recovery and yield can be quantified and statistically analyzed using well known measurement and analysis methods.

Seedling area: The total leaf area of a young plant about 2 weeks old.

Seedling vigor: As used herein, "seedling vigor" refers to the plant characteristic whereby the plant emerges from soil faster, has an increased germination rate (i.e., germinates faster), has faster and larger seedling growth and/or germinates faster under salt conditions as compared to the wild-type or control under similar conditions. Seedling vigor has often been defined to comprise the seed properties that determine "the potential for rapid, uniform emergence and development of normal seedlings under a wide range of field conditions".

Stringency: "Stringency," as used herein is a function of nucleic acid molecule probe length, nucleic acid molecule probe composition (G+C content), salt concentration, organic solvent concentration and temperature of hybridization and/or wash conditions. Stringency is typically measured by the parameter T m, which is the temperature at which 50% of the complementary nucleic acid molecules in the hybridization assay are hybridized, in terms of a temperature differential from $T_m$. High stringency conditions are those providing a condition of $T_m-5°$ C. to $T_m-10°$ C. Medium or moderate stringency conditions are those providing $T_m-20°$ C. to $T_m-29°$ C. Low stringency conditions are those providing a condition of $T_m-40°$ C. to $T_m-48°$ C. The relationship between hybridization conditions and $T_m$ (in ° C.) is expressed in the mathematical equation:

$$T_m = 81.5 - 16.6(\log_{10}[Na^+]) + 0.41(\% \ G+C) - (600/N) \quad (I)$$

where N is the number of nucleotides of the nucleic acid molecule probe. This equation works well for probes 14 to 70 nucleotides in length that are identical to the target sequence. The equation below, for $T_m$ of DNA-DNA hybrids, is useful for probes having lengths in the range of 50 to greater than 500 nucleotides, and for conditions that include an organic solvent (formamide):

$$T_m = 81.5 + 16.6 \log\{[Na^+]/(1+0.7[Na^+])\} + 0.41(\%\ G+C) - 500/L\ 0.63(\%\ \text{formamide}) \quad (II)$$

where L represents the number of nucleotides in the probe in the hybrid (Bonner et al. (1973) *J. Mol. Biol.* 81:123). The $T_m$ of Equation II is affected by the nature of the hybrid: for DNA-RNA hybrids, $T_m$ is 10-15° C. higher than calculated; for RNA-RNA hybrids, $T_m$ is 20-25° C. higher. Because the $T_m$ decreases about 1° C. for each 1% decrease in homology when a long probe is used (Frischauf et al. (1983) *J. Mol Biol,* 170: 827-842), stringency conditions can be adjusted to favor detection of identical genes or related family members.

Equation II is derived assuming the reaction is at equilibrium. Therefore, hybridizations according to the present invention are most preferably performed under conditions of probe excess and allowing sufficient time to achieve equilibrium. The time required to reach equilibrium can be shortened by using a hybridization buffer that includes a hybridization accelerator such as dextran sulfate or another high volume polymer.

Stringency can be controlled during the hybridization reaction, or after hybridization has occurred, by altering the salt and temperature conditions of the wash solutions. The formulas shown above are equally valid when used to compute the stringency of a wash solution. Preferred wash solution stringencies lie within the ranges stated above; high stringency is 5-8° C. below $T_m$, medium or moderate stringency is 26-29° C. below $T_m$ and low stringency is 45-48° C. below $T_m$.

For example, the hybridization step may be performed in aqueous hybridization solution at a temperature between 63° C. and 70° C., more preferably at a temperature between 65° C. and 68° C. and most preferably at a temperature of 65° C. Alternatively, the high stringency hybridization step may be performed in formamide hybridization solution at a temperature between 40° C. and 46° C., at a temperature between 41° C. and 44° C. and most preferably at a temperature of 42° C.

A wash step follows hybridization, and an initial wash is performed with wash solution 1 at 25° C. or 37° C. Following the initial wash, additional washes are performed with wash solution 1 at a temperature between 63° C. and 70° C., more preferably at a temperature between 65° C. and 68° C. and most preferably at a temperature of 65° C. The number of additional wash steps can be 1, 2, 3, 4, 5 or more. The time of both the initial and additional wash steps may be 5 minutes, 10 minutes, 15 minutes, 20 minutes, 25 minutes, 30 minutes, 45 minutes, 1 hour, 1.5 hours, 2 hours or more.

Set forth below are the composition of the hybridization and wash solutions and their components. A person of ordinary skill in the art will recognize that these solutions are typical and exemplary of high stringency hybridization solutions.

Aqueous Hybridization Solution: 6×SSC or 6×SSPE
    0.05% Blotto or 5×Denhardt's Reagent
    100 µg/ml denatured salmon sperm DNA
    0.05% SDS
Formamide Hybridization Solution: 50% Formamide
    6×SSC or 6×SSPE
    0.05% Blotto or 5×Denhardt's Reagent
    100 µg/ml denatured salmon sperm DNA
    0.05% SDS
Wash Solution 1: 2×SSC or SSPE
    0.1% SDS
Wash Solution 2: 0.1×SSC or SSPE
    0.5% SDS
20×SSC: 175.3 g NaCl
    88.2 g Sodium Citrate
    Bring to 800 ml with $H_2O$
    Adjust to pH 7 with 10 n NaOH
    Bring to 1 L with $H_2O$
20×SSPE: 175.3 g NaCl
    27.6 g $NaH_2PO_4$
    Bring to 800 ml with $H_2OH_2O$
    7.4 g EDTA
    Adjust to pH 7.4 with 10 n NaOH
    Bring to 1 L with $H_2O$
1× BLOTTO: 5% Non-fat dry milk
    0.02% Sodium azide
50×Denhardts's Reagent: 5 g Ficoll
    5 g Polyvinylpyrrolidone
    5 g BSA
    Adjust to 500 ml with $H_2O$ Superpool: As used in the context of the current invention, a "superpool" contains an equal amount of seed from 500 different events, representing 100 distinct exogenous nucleotide sequences. An event is a plant carrying a unique insertion of a distinct exogenous sequence which misexpresses that sequence. Transformation of a single polynucleotide sequence can result in multiple events because the sequence can insert in a different part of the genome with each transformation.

$T_0$: The term "$T_0$" refers to the whole plant, explant or callus tissue, inoculated with the transformation medium.

$T_1$: The term $T_1$ refers to either the progeny of the $T_0$ plant, in the case of whole-plant transformation, or the regenerated seedling in the case of explant or callous tissue transformation.

$T_2$: The term $T_2$ refers to the progeny of the $T_1$ plant. $T_2$ progeny are the result of self-fertilization or cross-pollination of a $T_1$ plant.

$T_3$: The term $T_3$ refers to second generation progeny of the plant that is the direct result of a transformation experiment. $T_3$ progeny are the result of self-fertilization or cross-pollination of a $T_2$ plant.

$T_4$: As used in the current application, the term $T_4$ refers to third generation progeny of the plant that is the direct result of a transformation experiment. $T_4$ progeny are the result of self-fertilization or cross pollination of a $T_3$ plant.

Transformation: Examples of means by which this can be accomplished are described below and include *Agrobacterium*-mediated transformation (of dicots (Needleman and Wunsch (1970) *J. Mol. Biol.* 48:443; Pearson and Lipman (1988) *Proc. Natl. Acad. Sci.* (USA) 85: 2444), of monocots (Yamauchi et al. (1996) *Plant Mol Biol.* 30:321-9; Xu et al. (1995) *Plant Mol. Biol.* 27:237; Yamamoto et al. (1991) *Plant Cell* 3:371), and biolistic methods (P. Tijessen, "Hybridization with Nucleic Acid Probes" In Laboratory Techniques in Biochemistry and Molecular Biology, P. C. vand der Vliet, ed., c. 1993 by Elsevier, Amsterdam), electroporation, in planta techniques and the like. Such a plant containing the exogenous nucleic acid is referred to here as a $T_0$ for the primary transgenic plant and $T_1$ for the first generation.

3. Important Characteristics of the Polynucleotides and Polypeptides of the Invention The nucleic acid molecules and polypeptides of the present invention are of interest because when the nucleic acid molecules are mis-expressed (i.e., when expressed at a non-natural location or in an increased or decreased amount relative to wild-type) they produce plants that exhibit improved salt tolerance as compared to wild-type plants, as evidenced by the results of various experiments disclosed below. In particular, plants transformed with at least one of the nucleic acid molecules and polypeptides of the present invention have increased salt growth index values as compared to wild-type plants. For example, plants transformed with the sequences of the present invention can exhibit increases in SGI values of at least 25%, at least 50%, at least 75%, at least 100%, at least 200%, at least 300%, at least 400%, or even at least 500%. This trait can be used to exploit or maximize plant products. For example, the nucleic acid molecules and polypeptides of the present invention are used to increase the expression of genes that cause the plant to have improved biomass, growth rate and/or seedling vigor in saline conditions.

Because the disclosed sequences and methods increase vegetative growth and growth rate in saline conditions, the disclosed methods can be used to enhance plant growth in plants irrigated with saline water and/or grown in saline soil. For example, plants of the invention show, under saline conditions, increased photosynthetic efficiency and increased seedling area as compared to a plant of the same species that is not genetically modified for substantial vegetative growth. Examples of increases in biomass production include increases of at least 5%, at least 20%, or even at least 50%, when compared to an amount of biomass production by a wild-type plant of the same species under identical conditions.

Seed or seedling vigor is an important characteristic that can greatly influence successful growth of a plant, such as crop plants. Adverse environmental conditions, such as saline conditions, can affect a plant growth cycle, germination of seeds and seedling vigor (i.e. vitality and strength under such conditions can differentiate between successful and failed crop growth). Seedling vigor has often been defined to comprise the seed properties that determine "the potential for rapid, uniform emergence and development of normal seedlings under a wide range of field conditions". Hence, it would be advantageous to develop plant seeds with increased vigor, particularly in elevated salinity.

For example, increased seedling vigor would be advantageous for cereal plants such as rice, maize, wheat, etc. production. For these crops, germination and growth can often be slowed or stopped by salination. Genes associated with increased seed vigor and/or salination tolerance have therefore been sought for producing improved crop varieties. (Walia et al. (2005) *Plant Physiology* 139:822-835).

4. The Polypeptides/Polynucleotides of the Invention

The polynucleotides of the present invention and the proteins expressed via translation of these polynucleotides are set forth in the Sequence Listing, specifically SEQ ID NOs. 79-253 and 269-315. The Sequence Listing also consists of functionally comparable proteins. Polypeptides comprised of a sequence belonging to the consensus sequence families shown in FIGS. 1 to 9 as delineated by HMMs can be utilized for the purposes of the invention, namely to make transgenic plants with improved biomass, growth rate and/or seedling vigor in saline conditions.

5. Use of the Polypeptides to Make Transgenic Plants

To use the sequences of the present invention or a combination of them or parts and/or mutants and/or fusions and/or variants of them, recombinant DNA constructs are prepared that comprise the polynucleotide sequences of the invention inserted into a vector and that are suitable for transformation of plant cells. The construct can be made using standard recombinant DNA techniques (see, Sambrook et al., Molecular Cloning: A Laboratory Manual, Second Edition, Cold Spring Harbor Laboratory Press, 1989, New York.) and can be introduced into the plant species of interest by, for example, *Agrobacterium*-mediated transformation, or by other means of transformation, for example, as disclosed below.

The vector backbone may be any of those typically used in the field such as plasmids, viruses, artificial chromosomes, BACs, YACs, PACs and vectors such as, for instance, bacteria-yeast shuttle vectors, lambda phage vectors, T-DNA fusion vectors and plasmid vectors (see, Shizuya et al. (1992) *Proc. Natl. Acad. Sci. USA* 89: 8794-8797; Hamilton et al. (1996) *Proc. Natl. Acad. Sci. USA* 93: 9975-9979; Burke et al. (1987) *Science* 236:806-812; Sternberg N. et al. (1990) *Proc Natl Acad Sci USA*. 87:103-7; Bradshaw et al. (1995) *Nucl Acids Res* 23: 4850-4856; Frischauf et al. (1983) *J. Mol Biol* 170: 827-842; Huynh et al., Glover N M (ed) *DNA Cloning: A practical Approach*, Vol. 1 Oxford: IRL Press (1985); Walden et al. (1990) *Mol Cell Biol* 1: 175-194).

Typically, the construct comprises a vector containing a nucleic acid molecule of the present invention with any desired transcriptional and/or translational regulatory sequences such as, for example, promoters, UTRs, and 3' end termination sequences. Vectors may also include, for example, origins of replication, scaffold attachment regions (SARs), markers, homologous sequences, and introns. The vector may also comprise a marker gene that confers a selectable phenotype on plant cells. The marker may preferably encode a biocide resistance trait, particularly antibiotic resistance, such as resistance to, for example, kanamycin, bleomycin, or hygromycin, or herbicide resistance, such as resistance to, for example, glyphosate, chlorosulfuron or phosphinotricin.

It will be understood that more than one regulatory region may be present in a recombinant polynucleotide, e.g., introns, enhancers, upstream activation regions, transcription terminators, and inducible elements. Thus, more than one regulatory region can be operably linked to said sequence.

To "operably link" a promoter sequence to a sequence, the translation initiation site of the translational reading frame of said sequence is typically positioned between one and about fifty nucleotides downstream of the promoter. A promoter can, however, be positioned as much as about 5,000 nucleotides upstream of the translation initiation site, or about 2,000 nucleotides upstream of the transcription start site. A promoter typically comprises at least a core (basal) promoter. A promoter also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al. (1989) *Plant Cell* 1:977-984.

Some suitable promoters initiate transcription only, or predominantly, in certain cell types. For example, a promoter that is active predominantly in a reproductive tissue (e.g., fruit, ovule, pollen, pistils, female gametophyte, egg cell, central cell, nucellus, suspensor, synergid cell, flowers, embryonic tissue, embryo sac, embryo, zygote, endosperm, integument, or seed coat) can be used. Thus, as used herein a cell type- or tissue-preferential promoter is one that drives expression preferentially in the target tissue, but may also lead to some expression in other cell types or tissues as well. Methods for identifying and characterizing promoter regions in plant genomic DNA include, for example, those described in the following references: Jordano, et al. (1989) *Plant Cell* 1:855-866; Bustos et al. (1989) *Plant Cell* 1:839-854; Green et al. (1988) *EMBO J.* 7: 4035-4044; Meier et al. (1991) *Plant Cell* 3: 309-316; and Zhang et al. (1996) *Plant Physiology* 110: 1069-1079.

Examples of various classes of promoters are described below. Some of the promoters indicated below are described in more detail in U.S. Patent Application Ser. Nos. 60/505, 689; 60/518,075; 60/544,771; 60/558,869; 60/583,691; 60/619,181; 60/637,140; 10/950,321; 10/957,569; 11/058, 689; 11/172,703; 11/208,308; and PCT/US05/23639. It will be appreciated that a promoter may meet criteria for one classification based on its activity in one plant species, and yet meet criteria for a different classification based on its activity in another plant species.

Other Regulatory Regions: A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

Various promoters can be used to drive expression of the polynucleotides of the present invention. Nucleotide sequences of such promoters are set forth in SEQ ID NOS: 1-78. Some of them can be broadly expressing promoters, others may be more tissue preferential.

A promoter can be said to be "broadly expressing" when it promotes transcription in many, but not necessarily all, plant tissues or plant cells. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid constructs provided herein include the p326 (SEQ ID NO: 76), YP0144 (SEQ ID NO: 55), YP0190 (SEQ ID NO: 59), p13879 (SEQ ID NO: 75), YP0050 (SEQ ID NO: 35), p32449 (SEQ ID NO: 77), 21876 (SEQ ID NO: 1), YP0158 (SEQ ID NO: 57), YP0214 (SEQ ID NO: 61), YP0380 (SEQ ID NO: 70), PT0848 (SEQ ID NO: 26), and PT0633 (SEQ ID NO: 7). Additional examples include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter, and ubiquitin promoters such as the maize ubiquitin-1 promoter. In some cases, the CaMV 35S promoter is excluded from the category of broadly expressing promoters.

Root-active promoters drive transcription in root tissue, e.g., root endodermis, root epidermis, or root vascular tissues. In some embodiments, root-active promoters are root-preferential promoters, i.e., drive transcription only or predominantly in root tissue. Root-preferential promoters include the YP0128 (SEQ ID NO: 52), YP0275 (SEQ ID NO: 63), PT0625 (SEQ ID NO: 6), PT0660 (SEQ ID NO: 9), PT0683 (SEQ ID NO: 14), and PT0758 (SEQ ID NO: 22). Other root-preferential promoters include the PT0613 (SEQ ID NO: 5), PT0672 (SEQ ID NO: 11), PT0688 (SEQ ID NO: 15), and PT0837 (SEQ ID NO: 24), which drive transcription primarily in root tissue and to a lesser extent in ovules and/or seeds. Other examples of root-preferential promoters include the root-specific subdomains of the CaMV 35S promoter (Lam et al. (1989) *Proc. Natl. Acad. Sci. USA* 86:7890-7894), root cell specific promoters reported by Conkling et al. (1990) *Plant Physiol.* 93:1203-1211 and the tobacco RD2 gene promoter.

In some embodiments, promoters that drive transcription in maturing endosperm can be useful. Transcription from a maturing endosperm promoter typically begins after fertilization and occurs primarily in endosperm tissue during seed development and is typically highest during the cellularization phase. Most suitable are promoters that are active predominantly in maturing endosperm, although promoters that are also active in other tissues can sometimes be used. Non-limiting examples of maturing endosperm promoters that can be included in the nucleic acid constructs provided herein include the napin promoter, the Arcelin-5 promoter, the phaseolin gene promoter (Bustos et al. (1989) *Plant Cell* 1(9):839-853), the soybean trypsin inhibitor promoter (Riggs et al. (1989) *Plant Cell* 1(6):609-621), the ACP promoter (Baerson et al. (1993) *Plant Mol Biol,* 22(2):255-267), the stearoyl-ACP desaturase gene (Slocombe et al. (1994) *Plant Physiol* 104(4):167-176), the soybean α' subunit of β-conglycinin promoter (Chen et al. (1986) *Proc Natl Acad Sci USA* 83:8560-8564), the oleosin promoter (Hong et al. (1997) *Plant Mol Biol* 34(3):549-555), and zein promoters, such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al. (1993) *Mol. Cell Biol.* 13:5829-5842), the beta-amylase gene promoter, and the barley hordein gene promoter. Other maturing endosperm promoters include the YP0092 (SEQ ID NO: 38), PT0676 (SEQ ID NO: 12), and PT0708 (SEQ ID NO: 17).

Promoters that drive transcription in ovary tissues such as the ovule wall and mesocarp can also be useful, e.g., a polygalacturonidase promoter, the banana TRX promoter, and the melon actin promoter. Other such promoters that drive gene expression preferentially in ovules are YP0007 (SEQ ID NO: 30), YP0111 (SEQ ID NO: 46), YP0092 (SEQ ID NO: 38), YP0103 (SEQ ID NO: 43), YP0028 (SEQ ID NO: 33), YP0121 (SEQ ID NO: 51), YP0008 (SEQ ID NO: 31), YP0039 (SEQ ID NO: 34), YP0115 (SEQ ID NO: 47), YP0119 (SEQ ID NO: 49), YP0120 (SEQ ID NO: 50) and YP0374 (SEQ ID NO: 68).

In some other embodiments of the present invention, embryo sac/early endosperm promoters can be used in order drive transcription of the sequence of interest in polar nuclei and/or the central cell, or in precursors to polar nuclei, but not in egg cells or precursors to egg cells. Most suitable are promoters that drive expression only or predominantly in polar nuclei or precursors thereto and/or the central cell. A pattern of transcription that extends from polar nuclei into early endosperm development can also be found with embryo sac/early endosperm-preferential promoters, although transcription typically decreases significantly in later endosperm development during and after the cellularization phase. Expression in the zygote or developing embryo typically is not present with embryo sac/early endosperm promoters.

Promoters that may be suitable include those derived from the following genes: *Arabidopsis* viviparous-1 (see, GenBank No. U93215); *Arabidopsis* atmyc1 (see Urao (1996) *Plant Mol. Biol.*, 32:571-57; Conceicao (1994) *Plant,* 5:493-505); *Arabidopsis* FIE (GenBank No. AF129516); *Arabidopsis* MEA; *Arabidopsis* FIS2 (GenBank No. AF096096); and FIE 1.1 (U.S. Pat. No. 6,906,244). Other promoters that may be suitable include those derived from the following genes: maize MAC1 (see, Sheridan (1996) Genetics, 142: 1009-1020); maize Cat3 (see, GenBank No. L05934; Abler (1993) *Plant Mol. Biol.*, 22:10131-1038). Other promoters include the following *Arabidopsis* promoters: YP0039 (SEQ ID NO: 34), YP0101 (SEQ ID NO: 41), YP0102 (SEQ ID NO: 42), YP0110 (SEQ ID NO: 45), YP0117 (SEQ ID NO: 48), YP0119 (SEQ ID NO: 49), YP0137 (SEQ ID NO: 53), DME, YP0285 (SEQ ID NO: 64), and YP0212 (SEQ ID NO: 60). Other promoters that may be useful include the following rice promoters: p530c10, pOsFIE2-2, pOsMEA, pOsYp102, and pOsYp285.

Promoters that preferentially drive transcription in zygotic cells following fertilization can provide embryo-preferential expression and may be useful for the present invention. Most suitable are promoters that preferentially drive transcription in early stage embryos prior to the heart stage, but expression in late stage and maturing embryos is also suitable. Embryo-preferential promoters include the barley lipid transfer protein (Ltp1) promoter (*Plant Cell Rep* (2001) 20:647-654, YP0097 (SEQ ID NO: 40), YP0107 (SEQ ID NO: 44), YP0088 (SEQ ID NO: 37), YP0143 (SEQ ID NO: 54), YP0156 (SEQ ID NO: 56), PT0650 (SEQ ID NO: 8), PT0695 (SEQ ID NO: 16), PT0723 (SEQ ID NO: 19), PT0838 (SEQ ID NO: 25), PT0879 (SEQ ID NO: 28) and PT0740 (SEQ ID NO: 20).

Promoters active in photosynthetic tissue in order to drive transcription in green tissues such as leaves and stems are of particular interest for the present invention. Most suitable are promoters that drive expression only or predominantly such tissues. Examples of such promoters include the ribulose-1,5-bisphosphate carboxylase (RbcS) promoters such as the RbcS promoter from eastern larch (*Larix laricina*), the pine cab6 promoter (Yamamoto et al. (1994) *Plant Cell Physiol.* 35:773-778), the Cab-1 gene promoter from wheat (Fejes et al. (1990) *Plant Mol. Biol.* 15:921-932), the CAB-1 promoter from spinach (Lubberstedt et al. (1994) *Plant Physiol.* 104:997-1006), the cab1R promoter from rice (Luan et al. (1992) *Plant Cell* 4:971-981), the pyruvate orthophosphate dikinase (PPDK) promoter from corn (Matsuoka et al. (1993) *Proc Natl Acad. Sci USA* 90:9586-9590), the tobacco Lhcb1*2 promoter (Cerdan et al. (1997) *Plant Mol. Biol.* 33:245-255), the *Arabidopsis thaliana* SUC2 sucrose-H+ symporter promoter (Truernit et al. (1995) *Planta* 196:564-570), and thylakoid membrane protein promoters from spinach (psaD, psaF, psaE, PC, FNR, atpC, atpD, cab, rbcS. Other promoters that drive transcription in stems, leafs and green tissue are PT0535 (SEQ ID NO: 3), PT0668 (SEQ ID NO: 2), PT0886 (SEQ ID NO: 29), PR0924 (SEQ ID NO: 265), YP0144 (SEQ ID NO: 55), YP0380 (SEQ ID NO: 70) and PT0585 (SEQ ID NO: 4).

In some other embodiments of the present invention, inducible promoters may be desired. Inducible promoters drive transcription in response to external stimuli such as chemical agents or environmental stimuli. For example, inducible promoters can confer transcription in response to hormones such as giberellic acid or ethylene, or in response to light or drought. Examples of drought inducible promoters are YP0380 (SEQ ID NO: 70), PT0848 (SEQ ID NO: 26), YP0381 (SEQ ID NO: 71), YP0337 (SEQ ID NO: 66), PT0633 (SEQ ID NO: 7), YP0374 (SEQ ID NO: 68), PT0710 (SEQ ID NO: 18), YP0356 (SEQ ID NO: 67), YP0385 (SEQ ID NO: 73), YP0396 (SEQ ID NO: 74), YP0384 (SEQ ID NO: 72), PT0688 (SEQ ID NO: 15), YP0286 (SEQ ID NO: 65), YP0377 (SEQ ID NO: 69), and PD1367 (SEQ ID NO: 78). Examples of promoters induced by nitrogen are PT0863 (SEQ ID NO: 27), PT0829 (SEQ ID NO: 23), PT0665 (SEQ ID NO: 10) and PT0886 (SEQ ID NO: 29). An example of a promoter induced by salt is rd29A (Kasuga et al. (1999) *Nature Biotech* 17: 287-291).

Other Promoters: Other classes of promoters include, but are not limited to, leaf-preferential, stem/shoot-preferential, callus-preferential, guard cell-preferential, such as PT0678 (SEQ ID NO: 13), and senescence-preferential promoters. Promoters designated YP0086 (SEQ ID NO: 36), YP0188 (SEQ ID NO: 58), YP0263 (SEQ ID NO: 62), PT0758 (SEQ ID NO: 22), PT0743 (SEQ ID NO: 21), PT0829 (SEQ ID NO: 23), YP0119 (SEQ ID NO: 49), and YP0096 (SEQ ID NO: 39), as described in the above-referenced patent applications, may also be useful.

Alternatively, misexpression can be accomplished using a two component system, whereby the first component consists of a transgenic plant comprising a transcriptional activator operatively linked to a promoter and the second component consists of a transgenic plant that comprise a nucleic acid molecule of the invention operatively linked to the target-binding sequence/region of the transcriptional activator. The two transgenic plants are crossed and the nucleic acid molecule of the invention is expressed in the progeny of the plant. In another alternative embodiment of the present invention, the misexpression can be accomplished by having the sequences of the two component system transformed in one transgenic plant line.

Another alternative consists in inhibiting expression of a biomass or vigor-modulating polypeptide in a plant species of interest under saline conditions. The term "expression" refers to the process of converting genetic information encoded in a polynucleotide into RNA through transcription of the polynucleotide (i.e., via the enzymatic action of an RNA polymerase), and into protein through translation of mRNA. "Up-regulation" or "activation" refers to regulation that increases the production of expression products relative to basal or native states, while "down-regulation" or "repression" refers to regulation that decreases production relative to basal or native states.

A number of nucleic-acid based methods, including antisense RNA, ribozyme directed RNA cleavage, and interfering RNA (RNAi) can be used to inhibit protein expression in plants. Antisense technology is one well-known method. In this method, a nucleic acid segment from the endogenous gene is cloned and operably linked to a promoter so that the antisense strand of RNA is transcribed. The recombinant vector is then transformed into plants, as described above, and the antisense strand of RNA is produced. The nucleic acid segment need not be the entire sequence of the endogenous gene to be repressed, but typically will be substantially identical to at least a portion of the endogenous gene to be repressed. Generally, higher homology can be used to compensate for the use of a shorter sequence. Typically, a sequence of at least 30 nucleotides is used (e.g., at least 40, 50, 80, 100, 200, 500 nucleotides or more).

Thus, for example, an isolated nucleic acid provided herein can be an antisense nucleic acid to one of the aforementioned nucleic acids encoding a polypeptide modulates biomass under saline conditions. A nucleic acid that decreases the level of a transcription or translation product of a gene encoding a biomass-modulating polypeptide is transcribed into an antisense nucleic acid similar or identical to the sense coding sequence of the biomass- or growth rate-modulating polypeptide. Alternatively, the transcription product of an isolated nucleic acid can be similar or identical to the sense coding sequence of a biomass growth rate-modulating polypeptide, but is an RNA that is unpolyadenylated, lacks a 5' cap structure, or contains an unsplicable intron.

In another method, a nucleic acid can be transcribed into a ribozyme, or catalytic RNA, that affects expression of an mRNA. (See, U.S. Pat. No. 6,423,885). Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman, et al. (1995) *Proc. Natl. Acad. Sci. USA*, 92(13):6175-6179; de Feyter and Gaudron, Methods in Molecular Biology, Vol. 74, Chapter 43, "Expressing Ribozymes in Plants", Edited by Turner, P. C, Humana Press Inc., Totowa, NJ. RNA endoribonucleases such as the one that occurs naturally in *Tetrahymena thermophila*, and which have been described extensively by Cech and collaborators can be useful. See, for example, U.S. Pat. No. 4,987,071.

Methods based on RNA interference (RNAi) can be used. RNA interference is a cellular mechanism to regulate the expression of genes and the replication of viruses. This mechanism is thought to be mediated by double-stranded small interfering RNA molecules. A cell responds to such a double-stranded RNA by destroying endogenous mRNA having the same sequence as the double-stranded RNA. Methods for designing and preparing interfering RNAs are known to those of skill in the art; see, e.g., WO 99/32619 and WO 01/75164. For example, a construct can be prepared that includes a sequence that is transcribed into an interfering RNA. Such an RNA can be one that can anneal to itself, e.g., a double stranded RNA having a stem-loop structure. One strand of the stem portion of a double stranded RNA comprises a sequence that is similar or identical to the sense coding sequence of the polypeptide of interest, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises an antisense sequence of the biomass-modulating polypeptide of interest, and can have a length that is shorter, the same as, or longer than the corresponding length of the sense sequence. The loop portion of a double stranded RNA can be from 10 nucleotides to 5,000 nucleotides, e.g., from 15 nucleotides to 1,000 nucleotides, from 20 nucleotides to 500 nucleotides, or from 25 nucleotides to 200 nucleotides. The loop portion of the RNA can include an intron. See, e.g., WO 99/53050.

Transcriptional silencing of the target gene can also be achieved via the promoter through expression of an RNAi construct. This results in the synthesis of double stranded RNA molecules of which the nucleotides sequence is identical to a part of the promoter region of the target gene.

Another alternative method for suppression of the target gene may be achieved through a methodology generally referred to as Virus Induced Gene Silencing or VIGS (Ratcliff et al (2001) Plant J. 25, 237-245). Here, effective and specific gene silencing is achieved by infection of a plant with a plant virus carrying an insert which is homologous to the target gene. The advantage of the VIGS system is that there is no need to develop a plant transformation protocol for the plant species in which the target gene resides.

In all of these silencing methods, the silencing construct (antisense RNA, co-suppression, RNAi or hairpin construct or VIGs vector) preferably contains a DNA fragment that is identical to the target sequence (gene or promoter) that needs to be silenced. The percentage of identity may, however, range between 50-100%, preferably between 60-100%, more preferably between 70-100%, even more preferably between 80-100% and most preferably between 90-100%.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller, 1997, *Antisense Nucleic Acid Drug Dev.*, 7:187-195; Hyrup et al., 1996, *Bioorgan. Med. Chem.*, 4: 5-23. In addition, the deoxyphosphate backbone can be replaced with, for example, a phosphorothioate or phosphorodithioate backbone, a phosphoroamidite, or an alkyl phosphotriester backbone.

Transformation

Nucleic acid molecules of the present invention may be introduced into the genome or the cell of the appropriate host plant by a variety of techniques. These techniques, able to transform a wide variety of higher plant species, are well known and described in the technical and scientific literature (see, e.g., Weising et al. (1988) *Ann. Rev. Genet.*, 22:421 and Christou (1995) *Euphytica*, 85:13-27).

A variety of techniques known in the art are available for the introduction of DNA into a plant host cell. These techniques include transformation of plant cells by injection (Newell (2000) *Mol Biotech* 16:53-65), microinjection (Griesbach (1987) *Plant Sci.* 50:69-77), electroporation of DNA (Fromm et al. (1985) *Proc. Natl. Acad. Sci. USA* 82:5824), PEG (Paszkowski et al. (1984) *EMBO J.* 3:2717), use of biolistics (Klein et al. (1987) *Nature* 327:773), fusion of cells or protoplasts (Willmitzer, L. (1993) Transgenic Plants. In: Iotechnology, A Multi-Volume Comprehensive treatise (H. J. Rehm, G. Reed, A. Puler, P. Stadler, eds., Vol. 2, 627-659, VCH Weinheim-New York-Basel-Cambridge), and via T-DNA using *Agrobacterium tumefaciens* (*Crit. Rev. Plant. Sci.* 4:1-46; Fromm et al. (1990) *Biotechnology* 8:833-844) or *Agrobacterium rhizogenes* (Cho et al. (2000) *Planta* 210:195-204) or other bacterial hosts (Brootghaerts et al. (2005) *Nature* 433:629-633), for example.

In addition, a number of non-stable transformation methods that are well known to those skilled in the art may be desirable for the present invention. Such methods include, but are not limited to, transient expression (Lincoln et al. (1998) *Plant Mol. Biol. Rep.* 16:1-4) and viral transfection (Lacomme et al. (2001), "Genetically Engineered Viruses" (C. J. A. Ring and E. D. Blair, Eds). Pp. 59-99, BIOS Scientific Publishers, Ltd. Oxford, UK).

Seeds are obtained from the transformed plants and used for testing stability and inheritance. Generally, two or more generations are cultivated to ensure that the phenotypic feature is stably maintained and transmitted.

A person of ordinary skill in the art recognizes that after the expression cassette is stably incorporated in transgenic plants and confirmed to be operable, it can be introduced into other plants by sexual crossing. Any of a number of standard breeding techniques can be used, depending upon the species to be crossed.

In aspects related to making transgenic plants, a typical step involves selection or screening of transformed plants, e.g., for the presence of a functional vector as evidenced by expression of a selectable marker. Selection or screening can be carried out among a population of recipient cells to identify transformants using selectable marker genes such as herbicide resistance genes. Physical and biochemical methods can be used to identify transformants. These include Southern analysis or PCR amplification for detection of a polynucleotide; Northern blots, 51 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.

A population of transgenic plants can be screened and/or selected for those members of the population that have a desired trait or phenotype conferred by expression of the transgene. For example, a population of progeny of a single transformation event can be screened for those plants having a desired level of expression of a heterologous salt tolerance polypeptide or nucleic acid. As an alternative, a population of plants comprising independent transformation events can be screened for those plants having a desired trait, such as salt tolerance. Selection and/or screening can be carried out over one or more generations, which can be useful to identify those plants that have a statistically significant difference in a protein level as compared to a corresponding level in a control plant. Selection and/or screening can also be carried out in more than one geographic location. In some cases, transgenic plants can be grown and selected under conditions which induce a desired phenotype or are otherwise necessary to produce a desired phenotype in a transgenic plant. In addition, selection and/or screening can be carried out during a particular developmental stage in which the phenotype is expected to be exhibited by the plant. Selection and/or screening can be carried out to choose those transgenic plants having a statistically significant difference in salt tolerance relative to a control plant that lacks the transgene. Selected or screened transgenic plants have an altered phenotype as compared to a corresponding control plant, as described elsewhere in this specification.

The nucleic acid molecules of the present invention may be used to confer the trait of improved tolerance to saline conditions. The invention has utility in improving important agronomic characteristics of crop plants, for example enabling plants to be productively cultivated in saline conditions. As noted above, transgenic plants that exhibit overexpression of the polynucleotides of the invention grow well under high salt conditions.

The nucleic acid molecules of the present invention encode appropriate proteins from any organism, but are preferably found in plants, fungi, bacteria or animals.

Transgenic Plant Phenotypes

Information that the polypeptides disclosed herein can modulate salt tolerance is useful in breeding of crop plants. Based on the effect of the disclosed polypeptides on salt tolerance, one can search for and identify polymorphisms linked to genetic loci for such polypeptides. Polymorphisms that can be identified include simple sequence repeats (SSRs), amplified fragment length polymorphisms (AFLPs) and restriction fragment length polymorphisms (RFLPs).

If a polymorphism is identified, its presence and frequency in populations is analyzed to determine if it is statistically significantly correlated to an increase in salt tolerance. Those polymorphisms that are correlated with an increase in salt tolerance can be incorporated into a marker assisted breeding program to facilitate the development of lines that have a desired increase in salt tolerance. Typically, a polymorphism identified in such a manner is used with polymorphisms at other loci that are also correlated with a desired increase in salt tolerance or other desired trait.

The methods according to the present invention can be applied to any plant, preferably higher plants, pertaining to the classes of Angiospermae and Gymnospermae. Plants of the subclasses of the Dicotylodenae and the Monocotyledonae are particularly suitable. Dicotyledonous plants belonging to the orders of the Magniolales, Illiciales, Laurales, Piperales Aristochiales, Nymphaeales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, Santales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales, for example, are also suitable. Monocotyledonous plants belonging to the orders of the Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchidales also may be useful in embodiments of the present invention. Further examples include, but are not limited to, plants belonging to the class of the Gymnospermae are Pinales, Ginkgoales, Cycadales and Gnetales.

The methods of the present invention are preferably used in plants that are important or interesting for agriculture, horticulture, biomass for bioconversion and/or forestry.

Non-limiting examples include, for instance, tobacco, oilseed rape, sugar beet, potatoes, tomatoes, cucumbers, peppers, beans, peas, citrus fruits, avocados, peaches, apples, pears, berries, plumbs, melons, eggplants, cotton, soybean, sunflowers, roses, poinsettia, petunia, guayule, cabbages, spinach, alfalfa, artichokes, sugarcane, mimosa, Servicea lespedera, corn, wheat, rice, rye, barley, sorghum and grasses such as switch grass, giant reed, Bermuda grass, Johnson grasses or turf grass, millet, hemp, bananas, poplars, eucalyptus trees and conifers. Of interest are plants grown for energy production, so called energy crops, such as broadleaf plants like alfalfa, hemp, Jerusalem artichoke and grasses such as sorghum, switchgrass, Johnson grass and the likes. Thus, the described materials and methods are useful for modifying biomass characteristics, such as characteristics of biomass renewable energy source plants. A biomass renewable energy source plant is a plant having or producing material (either raw or processed) that comprises stored solar energy that can be converted to fuel. In general terms, such plants comprise dedicated energy crops as well as agricultural and woody plants. Examples of biomass renewable energy source plants include: switchgrass, elephant grass, giant chinese silver grass, energycane, giant reed (also known as wild cane), tall fescue, bermuda grass, sorghum, napier grass, also known as uganda grass, triticale, rye, winter wheat, shrub poplar, shrub willow, big bluestem, reed canary grass and corn.

Homologues Encompassed by the Invention

It is known in the art that one or more amino acids in a sequence can be substituted with other amino acid(s), the charge and polarity of which are similar to that of the substituted amino acid, i.e. a conservative amino acid substitution, resulting in a biologically/functionally silent change. Conservative substitutes for an amino acid within the polypeptide sequence can be selected from other members of the class to which the amino acid belongs. Amino acids can be divided into the following four groups: (1) acidic (negatively charged) amino acids, such as aspartic acid and glutamic acid; (2) basic (positively charged) amino acids, such as arginine, histidine, and lysine; (3) neutral polar amino acids, such as serine, threonine, tyrosine, asparagine, and glutamine; and (4) neutral nonpolar (hydrophobic) amino acids such as glycine, alanine, leucine, isoleucine, valine, proline, phenylalanine, tryptophan, cysteine, and methionine.

Nucleic acid molecules of the present invention can comprise sequences that differ from those encoding a protein or fragment thereof selected from the group consisting of SEQ ID NOs. 80, 99, 106, 123, 132, 146, 154 and 172, respectively, due to the fact that the different nucleic acid sequence encodes a protein having one or more conservative amino acid changes.

Biologically functional equivalents of the polypeptides, or fragments thereof, of the present invention can have about 10 or fewer conservative amino acid changes, more preferably about 7 or fewer conservative amino acid changes, and most preferably about 5 or fewer conservative amino acid changes. In a preferred embodiment of the present invention, the polypeptide has between about 5 and about 500 conservative changes, more preferably between about 10 and about 300 conservative changes, even more preferably between about 25 and about 150 conservative changes, and most preferably between about 5 and about 25 conservative changes or between 1 and about 5 conservative changes.

Identification of Useful Nucleic Acid Molecules and Their Corresponding Nucleotide Sequences The nucleic acid molecules, and nucleotide sequences thereof, of the present invention were identified by use of a variety of screens that are predictive of nucleotide sequences that provide plants with improved vegetative growth, growth rate, and/or biomass under saline conditions. One or more of the following screens were, therefore, utilized to identify the nucleotide (and amino acid) sequences of the present invention.

The present invention is further exemplified by the following examples. The examples are not intended to in any way limit the scope of the present application and its uses.

6. Experiments Confirming the Usefulness of the Polynucleotides and Polypeptides of the Invention General Protocols

*Agrobacterium*-Mediated Transformation of *Arabidopsis*

Host Plants and Transgenes: Wild-type *Arabidopsis thaliana* Wassilewskija (WS) plants are transformed with Ti plasmids containing nucleic acid sequences to be expressed, as noted in the respective examples, in the sense orientation relative to the 35S promoter in a Ti plasmid. A Ti plasmid vector useful for these constructs, CRS 338, contains the Ceres-constructed, plant selectable marker gene phosphinothricin acetyltransferase (PAT), which confers herbicide resistance to transformed plants.

Ten independently transformed events are typically selected and evaluated for their qualitative phenotype in the $T_1$ generation.

Preparation of Soil Mixture: 24 L Sunshine Mix #5 soil (Sun Gro Horticulture, Ltd., Bellevue, WA) is mixed with 16 L Therm-O-Rock vermiculite (Therm-O-Rock West, Inc., Chandler, AZ) in a cement mixer to make a 60:40 soil mixture. To the soil mixture is added 2 Tbsp Marathon 1% granules (Hummert, Earth City, MO), 3 Tbsp OSMO-COTE® 14-14-14 (Hummert, Earth City, MO) and 1 Tbsp Peters fertilizer 20-20-20 (J. R. Peters, Inc., Allentown, PA), which are first added to 3 gallons of water and then added to the soil and mixed thoroughly. Generally, 4-inch diameter pots are filled with soil mixture. Pots are then covered with 8-inch squares of nylon netting.

Planting: Using a 60 mL syringe, 35 mL of the seed mixture is aspirated. 25 drops are added to each pot. Clear propagation domes are placed on top of the pots that are then placed under 55% shade cloth and subirrigated by adding 1 inch of water.

Plant Maintenance: 3 to 4 days after planting, lids and shade cloth are removed. Plants are watered as needed. After 7-10 days, pots are thinned to 20 plants per pot using forceps. After 2 weeks, all plants are subirrigated with Peters fertilizer at a rate of 1 Tsp per gallon of water. When bolts are about 5-10 cm long, they are clipped between the first node and the base of stem to induce secondary bolts. Dipping infiltration is performed 6 to 7 days after clipping.

Preparation of *Agrobacterium*: To 150 mL fresh YEB is added 0.1 mL each of carbenicillin, spectinomycin and rifampicin (each at 100 mg/ml stock concentration). *Agrobacterium* starter blocks are obtained (96-well block with *Agrobacterium* cultures grown to an OD 600 of approximately 1.0) and inoculated one culture vessel per construct by transferring 1 mL from appropriate well in the starter block. Cultures are then incubated with shaking at 27° C. Cultures are spun down after attaining an $OD_{600}$ of approximately 1.0 (about 24 hours). 200 mL infiltration media is added to resuspend *Agrobacterium* pellets. Infiltration media is prepared by adding 2.2 g MS salts, 50 g sucrose, and 5 μL 2 mg/ml benzylaminopurine to 900 ml water.

Dipping Infiltration: The pots are inverted and submerged for 5 minutes so that the aerial portion of the plant is in the *Agrobacterium* suspension. Plants are allowed to grow normally and seed is collected.

High-throughput Phenotypic Screening of Misexpression Mutants: Seed is evenly dispersed into water-saturated soil in pots and placed into a dark 4° C. cooler for two nights to promote uniform germination. Pots are then removed from the cooler and covered with 55% shade cloth for 4-5 days. Cotyledons are fully expanded at this stage. FINALE® (Sanofi Aventis, Paris, France) is sprayed on plants (3 ml FINALE® diluted into 48 oz. water) and repeated every 3-4 days until only transformants remain.

Screening: Screening is routinely performed by high-salt agar plate assay and also by high-salt soil assay. Traits assessed in high-salt conditions include: seedling area, photosynthesis efficiency, salt growth index, and regeneration ability.

Seedling area: the total leaf area of a young plant about 2 weeks old.

Photosynthesis efficiency (Fv/Fm): Seedling photosynthetic efficiency, or electron transport via photosystem II, is estimated by the relationship between Fm, the maximum fluorescence signal and the variable fluorescence, Fv. Here, a reduction in the optimum quantum yield (Fv/Fm) indicates stress, and so can be used to monitor the performance of transgenic plants compared to non-transgenic plants under salt stress conditions.

Salt growth index=seedling area×photosynthesis efficiency (Fv/Fm).

PCR was used to amplify the DNA insert in one randomly chosen $T_2$ plant. This PCR product was then sequenced to confirm the sequence in the plants.

Assessing Tolerance to Salt Stress: Initially, independently transformed plant lines are selected and qualitatively evaluated for their tolerance to salt stress in the $T_1$ generation. The transformed lines that qualitatively show the strongest tolerance to salt stress in the $T_1$ generation are selected for further evaluation in the $T_2$ and $T_3$ generations. This evaluation involves sowing seeds from the selected transformed plant lines on MS agar plates containing either 100 mM or 150 mM NaCl and incubating the seeds for 5 to 14 days to allow for germination and growth.

Calculating SGI: After germination and growth, seedling area and photosynthesis efficiency of transformed lines and a wild-type control are determined. From these measurements, the Salt Growth Index (SGI) is calculated and compared between wild-type and transformed seedlings. The SGI calculation is made by averaging seedling area and photosynthesis efficiency measurements taken from two replicates of 36 seedlings for each transformed line and a wild-type control and performing a t-test.

Determining Transgene Copy Number: $T_2$ generation transformed plants are tested on BASTA™ plates in order to determine the transgene copy number of each transformed line. A BASTA™ resistant:BASTA™ sensitive segregation ratio of 3:1 generally indicates one copy of the transgene.

Results:

The following Examples provide information for polynucleotides and their encoded polypeptides useful for increasing tolerance to salt stress Enhanced salt tolerance gives the opportunity to grow crops in saline conditions without stunted growth and diminished yields due to salt-induced ion imbalance, disruption of water homeostasis, inhibition of metabolism, damage to membranes, and/or cell death. The ability to grow crops in saline conditions would result in an overall expansion of arable land and increased output of land currently marginally productive due to elevated salinity Example 1: ME03807 (Ceres Clone 8686; SEQ ID No. 79)

Wild-type *Arabidopsis thaliana* Wassilewskija was transformed with a Ti plasmid carrying the 35S promoter operatively linked to Ceres Clone 8686. Two transformed lines, ME03807-02 and ME03807-03, showed the strongest qualitative tolerance to salt stress in a prevalidation assay (Table 1-1). Their tolerance to 150 mM NaCl was further evaluated in a validation assay for two generations. Segregation ratios (BASTA™ resistant: BASTA™ sensitive) indicated that ME03807-02 contains two copies of the transgene and that ME03807-03 carries one copy of the transgene.

TABLE 1-1

Prevalidation assay of ME03807 salt tolerance as compared to wild-type Ws

|  | WS Wild-type | ME03807-02 | ME03807-03 |
|---|---|---|---|
| Mean* | 0.0268 | 0.0397 | 0.0506 |
| Standard Error | 0.0006 | 0.0041 | 0.0038 |

*Average seedling area of 36 plants grown on MS agar plates containing 150 mM NaCl for 14 days When grown on MS agar plates containing 150 mM NaCl, ME03807-02 and ME03807-03 transgenic plants showed significantly increased seedling area and SGI relative to non-transgenic plants. As shown in Table 1-2, the T2-generation SGI value for ME03807-02 seedlings increased by 74.4% while ME03807-03 seedlings increased by 87.6% compared to non-transgenic control seedlings. In the $T_3$ generation, the SGI increase was 134.2% for ME03807-02 and 141.8% for ME03807-03. The differences between transgenic and non-transgenic seedlings are statistically significant under the t-test, and clearly demonstrate that the enhanced tolerance to salt stress is a result of the ectopic expression of Ceres Clone 8686 in the ME03807 transformant lines.

TABLE 1-2

Validation assay of ME03807 salt stress tolerance in two generations

| ME Events | SGI* of transgenics | | | SGI of pooled non-transgenics | | | t-Test | | % of SGI |
|---|---|---|---|---|---|---|---|---|---|
| | Avg | SE | N | Avg | SE | N | t-value | $t_{0.05}$ | increase |
| ME03807-02T$_2$ | 0.952 | 0.126 | 32 | 0.546 | 0.087 | 24 | 2.66 | 1.68 | 74.4 |
| ME03807-03T$_2$ | 0.604 | 0.047 | 24 | 0.322 | 0.065 | 13 | 3.51 | 1.70 | 87.6 |
| ME03807-02T$_3$ | 0.965 | 0.111 | 19 | 0.412 | 0.031 | 11 | 5.95 | 1.70 | 134.2 |
| ME03807-03T$_3$ | 1.064 | 0.104 | 42 | 0.440 | 0.028 | 16 | 9.60 | 1.68 | 141.8 |

*SGI (Salt Growth Index) = seedling area × Fv/Fm (photosynthesis efficiency)

Summary of Results:

Ectopic expression of Ceres Clone 8686 under the control of the 35S promoter enhances tolerance to salt stress that causes necrotic lesions and stunted growth in wild-type WS seedlings.

The protein encoded by Ceres Clone 8686 is a 255-amino-acid putative cyclase (Susstrunk et al. (1998) *Mol Microbiol,* 30(1):33-46 and Kang et al. (1999) *Microbiology,* 145:1161-72. Cyclase is a large gene family that includes adenylyl cyclase, which converts ATP to cAMP. cAMP is an important signal molecule that is involved in signal transduction which conveys signals from a plasma membrane receptor to cytosol cascades. The ME03807 transgene is more closely related to cyclase enzymes that are involved in antibiotic synthesis.

Example 2: ME00774 (Ceres Clone 2767; SEQ ID No. 131)

Wild-type *Arabidopsis thaliana* Wassilewskija was transformed with a Ti plasmid carrying the 32449 promoter (SEQ ID No. 77) and Ceres Clone 2767. Two transformed lines, ME00774-03 and ME00774-04, showed the strongest qualitative tolerance to salt stress in a prevalidation assay (Table 2-1). Their tolerance to 150 mM NaCl was further evaluated in a validation assay for two generations. Segregation ratios (BASTA™ resistant:BASTA™ sensitive) indicated that ME00774-03 contains two copies of the transgene and that ME00774-04 carries one copy of the transgene.

TABLE 2-1

Prevalidation assay of ME00774 salt tolerance as compared to wild-type Ws

|  | Ws wild-type | ME00774-01 | ME00774-02 | ME00774-03 | ME00774-04 | ME00774-05 |
|---|---|---|---|---|---|---|
| Mean* | 0.0286 | 0.0313 | 0.0333 | 0.0468 | 0.0384 | 0.0343 |
| Std Error | 0.0006 | 0.0015 | 0.0019 | 0.0037 | 0.0026 | 0.0024 |

*Average seedling area of 36 plants grown on MS agar plates containing 150 mM NaCl for 14 days When grown on MS agar plates containing 150 mM NaCl, ME00774-03 and ME00774-04 transgenic plants showed significantly greater seedling area and SGI relative to non-transgenic plants. As shown in Table 2-2, the T2-generation SGI value for ME00774-03 seedlings increased by 41.8% while ME00774-04 seedlings increased by 379.4% compared to non-transgenic control seedlings. In the $T_3$ generation, the SGI increase was 315.1% for ME00774-03 and 551.8% for ME00774-04. The differences between transgenic and non-transgenic seedlings are statistically significant under the t-test, and clearly demonstrate that the enhanced tolerance to salt stress was a result of the ectopic expression of Ceres Clone 2767 in the ME00774 transformant lines.

Summary of Results:

Ectopic expression of Clone 2767 under the control of the 32449 promoter enhances tolerance to salt stress.

Ceres Clone 2767 encodes a 154-amino-acid protein that belongs to a universal stress protein family (Kerk et al. (2003) *Plant Physiol.* 131 (3):1209-19). The USP superfamily has its members conserved in bacteria, archaea, and eukaryotes. The expression of USP genes in *E. coli* is induced by a large variety of environmental insults. The uspA gene plays an important role for *E. coli* to survive in cellular growth arrest, but the molecular mechanism of the gene function is not known yet (Nachin et al. (2005) *J Bacteriol* 187(18):6265-72). In *Arabidopsis,* there are 44 family members of USP. However, their function has not been characterized yet (Kerk et al. 2003). A rice homolog, OsUsp1, has been found to be induced by submergence and ethylene (Sauter et al. (2002) *J Exp Bot* 53(379):2325-31).

The identification of an AtUsp gene in a salt screen suggests that the *Arabidopsis USP family members may play a similar role in stress tolerance as observed in E. coli.*

Example 3: ME0146 (Ceres Clone 16403: SEQ ID No. 145)

Wild-type *Arabidopsis thaliana* Wassilewskija was transformed with a Ti plasmid carrying the 35S promoter and Ceres Clone 16403. Two transformed lines, ME01468-01 and ME01468-04, showed the strongest qualitative tolerance to salt stress in a prevalidation assay (Table 3-1). Their tolerance to 100 mM NaCl was further evaluated in a validation assay for two generations. Segregation ratios (BASTA™ resistant: BASTA™ sensitive) indicated ME01468-01 and ME01468-04 transformed lines each carry one copy of the transgene.

TABLE 2-2

Validation assay of ME00774 on salt tolerance in two generations

|  | SGI* of transgenics | | | SGI of pooled non-transgenics | | | t-Test | | % of SGI |
|---|---|---|---|---|---|---|---|---|---|
| ME Events | Avg | SE | N | Avg | SE | N | t-value | $t_{0.05}$ | increase |
| ME00774-03$T_2$ | 1.462 | 0.122 | 51 | 1.031 | 0.127 | 18 | 2.45 | 1.67 | 41.8 |
| ME00774-04$T_2$ | 0.954 | 0.072 | 20 | 0.199 | 0.03 | 10 | 9.78 | 1.70 | 379.4 |
| ME00774-03$T_3$ | 1.598 | 0.081 | 48 | 0.385 | 0.05 | 23 | 12.79 | 1.67 | 315.1 |
| ME00774-04$T_3$ | 1.082 | 0.091 | 20 | 0.166 | 0.032 | 16 | 9.52 | 1.70 | 551.8 |

*SGI (Salt Growth Index) = seedling area × Fv/Fm (photosynthesis efficiency)

TABLE 3-1

Prevalidation assay of ME00774 salt tolerance as compared to wild-type Ws

|  | Ws Wild-type | ME01468-01 | ME01468-02 | ME01468-03 | ME01468-04 |
|---|---|---|---|---|---|
| Mean* | 0.0268 | 0.0424 | 0.0312 | 0.0215 | 0.0395 |
| Standard Error | 0.0006 | 0.0032 | 0.0018 | 0.0027 | 0.0031 |

*Average seedling area of 36 plants grown on VIS agar plates containing 150 mM NaCl for 14 days When grown on MS agar plates containing 100 mM NaCl, ME01468-01 and ME01468-04 transgenic plants showed significantly greater seedling area and SGI relative to non-transgenic plants. As shown in Table 3-1, the T2-generation SGI value for ME01468-01 seedlings increased by 23.7% while ME01468-04 seedlings increased by 39.3% compared to non-transgenic control seedlings. In the $T_3$ generation, the SGI increase was 83.7% for ME01468-01 and 79.4% for ME01468-04. The differences between transgenic and non-transgenic seedlings are statistically significant under the t-test, and clearly demonstrate that the enhanced tolerance to salt stress was a result of the ectopic expression of Ceres Clone 16403 in the ME01468 transformant lines.

TABLE 3-2

Validation assay of ME01468 on salt tolerance in two generations

| | SGI* of transgenics | | | SGI of pooled non-transgenics | | | t-Test | | % of SGI |
|---|---|---|---|---|---|---|---|---|---|
| ME Events | Avg | SE | N | Avg | SE | N | t-value | $t_{0.05}$ | increase |
| ME01468-01T$_2$ | 3.842 | 0.146 | 39 | 3.105 | 0.307 | 29 | 2.162 | 1.67 | 23.7 |
| ME01468-04T$_2$ | 3.143 | 0.179 | 35 | 2.256 | 0.261 | 32 | 2.795 | 1.67 | 39.3 |
| ME01468-01T$_3$ | 5.939 | 0.416 | 33 | 3.233 | 0.296 | 37 | 5.293 | 1.67 | 83.7 |
| ME01468-04T$_3$ | 7.508 | 0.524 | 13 | 4.186 | 0.469 | 21 | 4.719 | 1.70 | 79.4 |

*SGI (Salt Growth Index) = seedling area × Fv/Fm (photosynthesis efficiency)

Summary of Results:
  Ectopic expression of Ceres Clone 16403 under the control of the 35S promoter enhances tolerance to high salt stress.
  Ceres Clone 16403 encodes a 238-amino-acid calcium-binding protein that also shows similarity to an oxygen evolving complex from rice (Sanchez-Barrena et al. (2005) *J Mol Biol*. 345(5):1253-64). It is worth noting that SOS3, an important gene involved in salt tolerance, has been molecularly characterized as a $Ca^{++}$ binding protein.

Example 4: ME02064 (Ceres Clone 375578; SEQ ID No. 98)

Wild-type *Arabidopsis thaliana* Wassilewskija was transformed with a Ti plasmid carrying the 35S promoter and Ceres Clone 375578. Three transformed lines, ME02064-01 and ME02064-03, ME02064-04, showed the strongest qualitative tolerance to salt stress in a prevalidation assay (Table 4-1). Their tolerance to 150 mM NaCl was further evaluated in a validation assay for two generations. Segregation ratios (BASTA™ resistant: BASTA™ sensitive) indicated ME02064-01 and ME02064-03, ME02064-04 transformed lines each carry one copy of the transgene.

TABLE 4-1

Prevalidation assay of ME02064 salt tolerance as compared to wild-type Ws

|  | Ws Wild-type | ME02064-01 | ME02064-02 | ME02064-03 | ME02064-04 | ME02064-05 |
|---|---|---|---|---|---|---|
| Mean* | 0.0359 | 0.0435 | 0.0346 | 0.0441 | 0.0438 | 0.0305 |
| Standard Error | 0.0016 | 0.0048 | 0.004 | 0.0041 | 0.0035 | 0.0019 |

*Average seedling area of 36 plants grown on MS agar plates containing 150 mM NaCl for 14 days When grown on MS agar plates containing 150 mM NaCl, ME02064-01 and ME02064-03, ME02064-04 transgenic plants showed significantly greater seedling area and SGI relative to non-transgenic plants. As shown in Table 4-2, the T2-generation SGI value for ME02064-01 seedlings increased by 110% while ME02064-03 seedlings increased by 131% and ME02064-04 seedlings increased by 72% compared to non-transgenic control seedlings. In the $T_3$ generation, the SGI increase was 43% for ME02064-01, 47% for ME02064-03, and 64% for ME02064-04. The differences between transgenic and non-transgenic seedlings are statistically significant, and clearly demonstrate that the enhanced tolerance to salt stress was a result of the ectopic expression of Ceres Clone 375578 in the ME02064 transformant lines.

TABLE 4-2

Validation assay of ME02064 on salt tolerance in two generations

| ME Events | SGI* of transgenics | | | SGI of pooled non-transgenics | | | t-Test | | % of SGI increase |
|---|---|---|---|---|---|---|---|---|---|
| | Avg | SE | N | Avg | SE | N | t-value | $t_{0.05}$ | |
| ME02064-01-$T_2$ | 2.057 | 0.249 | 12 | 0.977 | 0.205 | 17 | 3.35 | 1.70 | 110.5 |
| ME02064-03-$T_2$ | 2.237 | 0.371 | 5 | 0.968 | 0.140 | 24 | 3.20 | 1.70 | 131.1 |
| ME02064-04-$T_2$ | 1.810 | 0.146 | 14 | 1.055 | 0.135 | 13 | 3.81 | 1.70 | 71.6 |
| ME02064-01-$T_3$ | 2.438 | 0.170 | 21 | 1.708 | 0.289 | 9 | 2.18 | 1.70 | 42.7 |
| ME02064-03-$T_3$ | 2.837 | 0.257 | 20 | 1.927 | 0.271 | 14 | 2.43 | 1.70 | 47.2 |
| ME02064-04-$T_3$ | 2.770 | 0.318 | 16 | 1.688 | 0.188 | 19 | 2.93 | 1.70 | 64.1 |

*SGI (Salt Growth Index) = seedling area × Fv/Fm (photosynthesis efficiency)

Summary of Results:
Ectopic expression of Ceres Clone 375578 under the control of the 35S promoter enhances tolerance to salt stress that causes necrotic lesions and stunted growth in wild-type Ws seedlings.

Ceres Clone 375578 encodes a 311-amino-acid protein that belongs to the calmodulin binding family (Sanchez-Barrena et al. (2005) *J Mol Biol.* 345(5):1253-64). $Ca^{++}$ homeostasis is an important signaling cascade in abiotic and biotic resistance. A critical gene, SOS3, involved in salt tolerance has been previously identified to be a $Ca^{++}$ binding protein. Understanding the connection between SOS3 and the transgene in ME02064 will help to better engineer resistance to salt stress.

Example 5: ME04074 (Ceres Clone 105319; SEQ ID No. 105)

Wild-type *Arabidopsis thaliana* Wassilewskija was transformed with a Ti plasmid carrying the 35S promoter and Ceres Clone 105319. Two transformed lines, ME04074-02 and ME04074-05, showed the strongest qualitative tolerance to salt stress in a prevalidation assay (Table 5-1). Their tolerance to 150 mM NaCl was further evaluated in a validation assay for two generations. Segregation ratios (BASTA™ resistant: BASTA™ sensitive) indicate ME04074-02 and ME04074-05 transformed lines each carry one copy of the transgene.

TABLE 5-1

Prevalidation assay of ME04074 salt tolerance as compared to wild-type Ws

| | Ws Wild-type | ME04074-01 | ME04074-02 | ME04074-03 | ME04074-04 | ME04074-05 |
|---|---|---|---|---|---|---|
| Mean* | 0.0301 | 0.0332 | 0.0423 | 0.0351 | 0.039 | 0.0448 |
| Standard Error | 0.0032 | 0.0027 | 0.0033 | 0.0026 | 0.0025 | 0.0027 |

*Average seedling area of 36 plants grown on MS agar plates containing 150 mM NaCl for 14 days When grown on MS agar plates containing 150 mM NaCl, ME04074-02 and ME04074-05 transgenic plants showed significantly greater seedling area and SGI relative to non-transgenic plants. As shown in Table 5-2, the T2-generation SGI value for ME04074-02 seedlings increased by 40.6% while ME04074-05 seedlings increased by 52.2% compared to non-transgenic control seedlings. In the $T_3$ generation, the SGI increase was 18.5% for ME04074-02 and 60.6% for ME04074-05. The differences between transgenic and non-transgenic seedlings are statistically significant under the t-test, and clearly demonstrate that the enhanced tolerance to salt stress was a result of the ectopic expression of Ceres Clone 105319 in the ME04074 transformant lines.

TABLE 5-2

Validation assay of ME04074 on salt tolerance in two generations

| ME Events | SGI* of transgenics | | | SGI of pooled non-transgenics | | | t-Test | | % of SGI increase |
|---|---|---|---|---|---|---|---|---|---|
| | Avg | SE | N | Avg | SE | N | t-value | $t_{0.05}$ | |
| ME04074-$0_2$-$T_2$ | 2.432 | 0.212 | 23 | 1.730 | 0.155 | 40 | 2.68 | 1.67 | 40.6 |
| ME04074-$0_5$-$T_2$ | 2.707 | 0.212 | 26 | 1.778 | 0.171 | 38 | 3.41 | 1.67 | 52.2 |
| ME04074-$0_2$-$T_3$ | 2.257 | 0.156 | 34 | 1.905 | 0.190 | 34 | 1.43 | 1.67 | 18.5 |
| ME04074-$0_5$-$T_3$ | 2.851 | 0.158 | 32 | 1.775 | 0.147 | 52 | 4.98 | 1.67 | 60.6 |

*SGI (Salt Growth Index) = seedling area × Fv/Fm (photosynthesis efficiency)

Summary of Results:
  Ectopic expression of Ceres Clone 105319 under the control of the 35S promoter enhances tolerance to salt stress that causes necrotic lesions and stunted growth in wild-type Ws seedlings.
  The protein encoded by Ceres Clone 105319 encodes a putative shikimate cyclase (Griffen et al. (1995) *DNA Seq* 5(3):195-197). The enzyme has ATP binding activity and catalyzes the fifth step in the biosynthesis of aromatic amino acids from chorismate. The protein is found in bacteria, fungi and plants. How this protein is involved in stress response is not yet known. However, aromatic acids, such as L-phenylalanine, are important substrates for the phenylpropanoid biosynthesis pathway, which produces many compounds related to stress responses.

Example 6: ME02907 (Ceres Clone 29658; SEQ ID No. 122)

Wild-type *Arabidopsis thaliana* Wassilewskija was transformed with a Ti plasmid carrying the 35S promoter and Ceres Clone 29658. Three transformed lines, ME02907-01, ME02907-03 and ME02907-05, showed the strongest qualitative tolerance to salt stress in a prevalidation assay (Table 6-1). Their tolerance to 150 mM NaCl was further evaluated in a validation assay using ME02907-03 and ME02907-05 for two generations. Segregation ratios (BASTA™ resistant: BASTA™ sensitive) indicated ME02907-03 and ME02907-05 transformed lines each carry one copy of the transgene.

TABLE 6-1

Prevalidation assay of ME02907 salt tolerance as compared to wild-type Ws

| | Ws Wild-type | ME02907-01 | ME02907-03 | ME02907-04 | ME02907-05 |
|---|---|---|---|---|---|
| Mean* | 0.0268 | 0.034483 | 0.0315 | 0.0224 | 0.0368 |
| Standard Error | 0.0006 | 0.002016 | 0.0029 | 0.0031 | 0.0039 |

*Average seedling area of 36 plants grown on MS agar plates containing 150 mM NaCl for 14 days When grown on MS agar plates containing 150 mM NaCl, ME02907-03 and ME02907-05 transgenic plants showed significantly greater seedling area and SGI relative to non-transgenic plants. As shown in Table 6-2, the T2-generation SGI value for ME02907-03 seedlings increased by 59% while ME02907-05 seedlings increased by 67% as compared to non-transgenic control seedlings. In the $T_3$ generation, the SGI increase was 110% for ME02907-03 and 99% for ME02907-05. The differences between transgenic and non-transgenic seedlings are statistically significant under the t-test, and clearly demonstrate that the enhanced tolerance to salt stress was a result of the ectopic expression of Ceres Clone 29658 in the ME02907 transformant lines.

TABLE 6-2

Validation assay of ME02907 on salt tolerance in two generations

| ME Events | SGI* of transgenics | | | SGI of pooled non-transgenics | | | t-Test | | % of SGI increase |
|---|---|---|---|---|---|---|---|---|---|
| | Avg | SE | N | Avg | SE | N | t-value | $t_{0.05}$ | |
| ME02907-03-$T_2$ | 1.252 | 0.115 | 31 | 0.787 | 0.121 | 18 | 2.79 | 1.68 | 59.1 |
| ME02907-05-$T_2$ | 1.235 | 0.120 | 34 | 0.738 | 0.100 | 28 | 3.18 | 1.67 | 67.3 |
| ME02907-03-$T_3$ | 1.039 | 0.100 | 26 | 0.495 | 0.023 | 15 | 7.40 | 1.69 | 109.9 |
| ME02907-05-$T_3$ | 1.157 | 0.064 | 37 | 0.582 | 0.070 | 17 | 7.53 | 1.70 | 98.8 |

*SGI (Salt Growth Index) = seedling area × Fv/Fm (photosynthesis efficiency)

Summary of Results:
Ectopic expression of Ceres Clone 29658 under the control of the 35S promoter enhances tolerance to salt stress that causes necrotic lesions and stunted growth in wild-type Ws seedlings.

The protein encoded by Ceres Clone 29658 is a putative calmodulin. Sanchez-Barrena et al. *J Mol Biol.* 345(5): 1253-64. $Ca^{++}$-mediated signaling is critical in salt tolerance. SOS3 has been demonstrated to confer salt tolerance in *Arabidopsis* and it has $Ca^{++}$-binding activity.

Example 7: ME00199 (Ceres Clone 3964; SEQ ID No. 153)

Wild-type *Arabidopsis thaliana* Wassilewskija was transformed with a Ti plasmid carrying the 32499 promoter and Ceres Clone 3964. Two transformed lines, ME00199-02 and ME00199-03, showed the strongest qualitative tolerance to salt stress in a prevalidation assay (Table 7-1). Their tolerance to 100 mM NaCl was further evaluated in a validation assay for two generations. Segregation ratios (BASTA™ resistant: BASTA™ sensitive) indicated ME00199-02 and ME00199-03 transformed lines each carry one copy of the transgene.

TABLE 7-1

Prevalidation assay of ME00199 salt tolerance as compared to wild-type Ws

| | Ws wild-type | ME00199-01-01 | ME00199-02-01 | ME00199-03-01 |
|---|---|---|---|---|
| Mean* | 0.0268 | 0.0244 | 0.0401 | 0.0307 |
| Standard Error | 0.0006 | 0.0025 | 0.0052 | 0.0037 |

*Average seedling area of 36 plants grown on MS agar plates containing 150 mM NaCl for 14 days When grown on MS agar plate containing 100 mM NaCl, ME00199-02 and ME00199-03 transgenic plants showed significantly greater seedling area and SGI relative to non-transgenic plants. As shown in Table 7-2, the SGI value of T2-generation ME00199-02 seedlings increased by 106.6% and the SGI value of $T_2$-generation ME00199-03 seedlings increased by 48.2% as compared to non-transgenic control seedlings. In the $T_3$ generation, the SGI increase was 174.3% for ME00199-02 and 205.9% for ME00199-03. The differences between transgenic and non-transgenic seedlings are statistically significant under the t-test, and clearly demonstrate that the enhanced tolerance to salt stress was a result of the ectopic expression of Ceres Clone 3964 in the ME00199 transformant lines.

TABLE 7-2

Validation assay of ME00199 on salt tolerance in two generations

| ME Events | SGI* of transgenics | | | SGI of pooled non-transgenics | | | t-Test | | % of SGI increase |
|---|---|---|---|---|---|---|---|---|---|
| | Avg | SE | N | Avg | SE | N | t-value | $t_{0.05}$ | |
| ME00199-02$T_3$ | 4.6025 | 0.3400 | 43 | 2.2277 | 0.2159 | 28 | 5.90 | 1.67 | 106.6 |
| ME00199-03$T_3$ | 3.8795 | 0.3444 | 40 | 2.6182 | 0.3855 | 28 | 2.44 | 1.67 | 48.2 |
| ME00199-02$T_4$ | 6.8743 | 0.5132 | 45 | 2.5058 | 0.5904 | 12 | 5.58 | 1.68 | 174.3 |
| ME00199-03$T_4$ | 7.4472 | 0.7392 | 30 | 2.4343 | 0.5283 | 15 | 5.52 | 1.68 | 205.9 |

*SGI (Salt Growth Index) = seedling area × Fv/Fm (photosynthesis efficiency)

Summary of Results:
Ectopic expression of Ceres Clone 3964 under the control of the 32499 promoter enhances tolerance to salt stress that causes necrotic lesions and stunted growth in wild-type Ws seedlings.

The protein encoded by Ceres Clone 3964 is a putative steroid sulfotransferase (351 AA).

Example 8: ME09814 (Ceres Clone 965405; SEQ ID No. 171)

Wild-type *Arabidopsis thaliana* Wassilewskija was transformed with a Ti plasmid carrying the 35S promoter and Ceres Clone 965405. Two transformed lines, ME09814-01 and ME09814-02, showed the strongest qualitative tolerance to salt stress in a prevalidation assay. Their tolerance to 100 mM NaCl was further evaluated in a validation assay for two generations. Segregation ratios (BASTA™ resistant: BASTA™ sensitive) indicated ME09814-01 and ME09814-02 transformed lines each carry one copy of the transgene originated from *Brassica napus* subsp. *napus* (canola).

Grown on MS agar plates containing 100 mM NaCl, ME09814-01 and ME09814-02 transgenic plants showed significantly greater seedling area and SGI relative to non-transgenic plants. As shown in Table 8-1, the SGI value of T2-generation ME09814-01 seedlings increased by 29% and the SGI value of T2-generation ME09814-02 seedlings increased by 69% as compared to non-transgenic control seedlings. In the $T_3$ generation, the SGI increase was 80% for ME09814-01 and 49% for ME09814-02. The differences between transgenic and non-transgenic seedlings are statistically significant under the t-test, and clearly demonstrate that the enhanced tolerance to salt stress was a result of the ectopic expression of Ceres Clone 965405 in the ME09814 transgenic lines.

TABLE 8-1

Validation assay of ME09814 on salt tolerance in two generations

| ME Events | SGI* of transgenics | | | SGI of pooled non-transgenics | | | t-Test | | % of SGI |
|---|---|---|---|---|---|---|---|---|---|
| | Avg | SE | N | Avg | SE | N | t-value | $t_{0.05}$ | increase |
| ME09814-01$T_2$ | 2.6841 | 0.2346 | 37 | 2.0812 | 0.1830 | 34 | 2.03 | 1.67 | 29.0 |
| ME09814-02$T_2$ | 2.6985 | 0.2438 | 32 | 1.5942 | 0.1909 | 38 | 3.57 | 1.67 | 69.3 |
| ME09814-01$T_3$ | 3.0664 | 0.2934 | 29 | 1.6996 | 0.1724 | 42 | 4.02 | 1.67 | 80.4 |
| ME09814-02$T_3$ | 2.6878 | 0.2350 | 36 | 1.8087 | 0.1743 | 34 | 3.00 | 1.67 | 48.6 |

*SGI (Salt Growth Index) = seedling area × Fv/Fm (photosynthesis efficiency)

Summary of Results:
  Ectopic expression of Ceres Clone 965405 under the control of the 35S promoter enhances tolerance to salt stress that causes necrotic lesions and stunted growth in wild-type Ws seedlings.
  The protein encoded by Ceres Clone 965405 is an unknown protein.

Example 9— ME07361 (Ceres Clone 5367; SEQ ID NO: 245)

Wild-type *Arabidopsis thaliana* Wassilewskija was transformed with a Ti plasmid carrying the 35S promoter and Ceres Clone 5367. Ceres Clone 5367 is a functional homolog of Ceres clone 965405.

Grown on MS agar plates containing 100 mM NaCl, ME07361-04 transgenic plants showed significantly greater seedling area and SGI relative to non-transgenic plants. As shown in Table 9-1, the SGI value of T2-generation ME07361-03 seedlings increased by 30.34% and the SGI value of T2-generation ME07361-04 seedlings increased by 52% as compared to non-transgenic control seedlings. The differences between transgenic and non-transgenic seedlings are statistically significant under the t-test, and clearly demonstrate that the enhanced tolerance to salt stress was a result of the ectopic expression of Ceres Clone 5367 in the ME07361 transgenic lines.

TABLE 9-1

Results of ME07361 on salt tolerance assay in T2 generations

| ME Events | SGI* of transgenics | | | SGI of pooled non-transgenics | | | t-Test | SGI |
|---|---|---|---|---|---|---|---|---|
| | Avg | SE | N | Avg | SE | N | p-value | increase |
| ME07361-01 | 0.89 | 0.103 | 16 | 0.89 | 0.105 | 20 | 0.489 | −0.45% |
| ME07361-02 | 1.30 | 0.160 | 17 | 1.22 | 0.132 | 18 | 0.357 | 06.29% |
| ME07361-03 | 1.58 | 0.195 | 21 | 1.21 | 0.151 | 15 | 0.073 | 30.34% |
| ME07361-04 | 1.98 | 0.369 | 15 | 1.30 | 0.145 | 21 | 0.049 | 52.00% |

*SGI (Salt Growth Index) = seedling area × Fv/Fm (photosynthesis efficiency)

Transgenic plants of ME07361-04 showed significant better tolerance to high salt than pooled non-transgenics.
Summary of Results:
Ectopic expression of Ceres Clone 5367 under the control of the 35S promoter enhances tolerance to salt stress that causes necrotic lesions and stunted growth in wild-type Ws seedlings.

Example 10—ME09594 (Annot ID 566551; SEO ID NO: 290)

Wild-type *Arabidopsis thaliana* Wassilewskija was transformed with a Ti plasmid carrying the 35S promoter and Annot ID 566551. Annot ID 566551 is a functional homolog of Ceres clone 965405.

Grown on MS agar plates containing 100 mM NaCl, ME09594-03 transgenic plants showed significantly greater seedling area and SGI relative to non-transgenic plants. As shown in Table 10-1, the SGI value of T2-generation ME09594-03 seedlings increased by 60.09% as compared to non-transgenic control seedlings. The differences between transgenic and non-transgenic seedlings are statistically significant under the t-test, and clearly demonstrate that the enhanced tolerance to salt stress was a result of the ectopic expression of Annot ID 566551 in the ME09594 transgenic lines.

TABLE 10-1

Results of ME09594 on salt tolerance assay in T2/T3 generation

| ME Events | SGI* of transgenics | | | SGI of pooled non-transgenics | | | t-Test | SGI increase |
|---|---|---|---|---|---|---|---|---|
| | Avg | SE | N | Avg | SE | N | p-value | |
| ME09594-01 | 2.17 | 0.357 | 19 | 2.36 | 0.352 | 16 | 0.357 | −7.87% |
| ME09594-02-99 | 1.83 | 1.109 | 4 | 1.72 | 0.252 | 24 | 0.463 | 6.20% |
| ME09594-03 | 2.32 | 0.380 | 24 | 1.45 | 0.280 | 9 | 0.038 | 60.09% |
| ME09594-04-99 | 0.71 | 0.110 | 16 | 0.79 | 0.082 | 17 | 0.288 | −9.82% |
| ME09594-05 | 2.38 | 0.465 | 13 | 2.69 | 0.392 | 21 | 0.305 | −11.66% |

*SGI (Salt Growth Index) = seedling area × Fv/Fm (photosynthesis efficiency)

Transgenic plants of ME09594-03 showed significant better tolerance to high salt than pooled non-transgenics.
Summary of Results:
Ectopic expression of Annot ID 566551 under the control of the 35S promoter enhances tolerance to salt stress that causes necrotic lesions and stunted growth in wild-type Ws seedlings.

Example 11—ME23428 (Annot ID 842118; SEO ID NO: 289)

Wild-type *Arabidopsis thaliana* Wassilewskija was transformed with a Ti plasmid carrying the 35S promoter and Annot ID 842118. Annot ID 842118 is a functional homolog of Ceres clone 29658.

Grown on MS agar plates containing 100 mM NaCl, ME23428-02 transgenic plants showed significantly greater seedling area and SGI relative to non-transgenic plants. As shown in Table 11-1, the SGI value of T2-generation ME23428-02 seedlings increased by 81.77% as compared to non-transgenic control seedlings. The differences between transgenic and non-transgenic seedlings are statistically significant under the t-test, and clearly demonstrate that the enhanced tolerance to salt stress was a result of the ectopic expression of Annot ID 842118 in the ME23428 transgenic lines.

TABLE 11-1

Results of ME23428 on salt tolerance assay in T2 generation

| ME Events | SGI* of transgenics | | | SGI of pooled non-transgenics | | | t-Test | SGI increase |
|---|---|---|---|---|---|---|---|---|
| | Avg | SE | N | Avg | SE | N | p-value | |
| ME23428-01 | 1.26 | 0.166 | 9 | 1.76 | 0.283 | 26 | 0.069 | −28.36% |
| ME23428-02 | 1.17 | 0.134 | 18 | 0.65 | 0.139 | 11 | 0.005 | 81.77% |
| ME23428-03 | 0.63 | 0.036 | 13 | 0.64 | 0.039 | 19 | 0.386 | −2.43% |
| ME23428-04 | 0.93 | 0.108 | 18 | 0.84 | 0.222 | 13 | 0.371 | 9.72% |
| ME23428-05 | 0.99 | 0.144 | 19 | 0.97 | 0.166 | 14 | 0.466 | 1.96% |

*SGI (Salt Growth Index) = seedling area × Fv/Fm (photosynthesis efficiency)

Transgenic plants of ME23428-02 showed significant better tolerance to high salt than pooled non-transgenics.

Summary of Results:

Ectopic expression of Annot ID 842118 under the control of the 35S promoter enhances tolerance to salt stress that causes necrotic lesions and stunted growth in wild-type Ws seedlings.

Example 12—ME24903 (Clone 295570; SEO ID NO: 275)

Wild-type *Arabidopsis thaliana* Wassilewskija was transformed with a Ti plasmid carrying the 35S promoter and Ceres clone 295570. Ceres clone 295570 is a functional homolog of Ceres clone 8686.

Grown on MS agar plates containing 100 mM NaCl, ME24903-04, ME24903-05 ME24903-07 and ME24903-09 transgenic plants showed significantly greater seedling area and SGI relative to non-transgenic plants. As shown in Table 12-1, the SGI value of T2-generation ME24903-04 seedlings increased by 68.42%, the SGI value of T2-generation ME24903-05 seedlings increased by 55.99%, the SGI value of T2-generation ME24903-07 seedlings increased by 140.73% and the SGI value of T2-generation ME24903-09 seedlings increased by 121.46% as compared to non-transgenic control seedlings. The differences between transgenic and non-transgenic seedlings are statistically significant under the t-test, and clearly demonstrate that the enhanced tolerance to salt stress was a result of the ectopic expression of Ceres clone 295570 in the ME24903 transgenic lines.

TABLE 12-1

Results of ME24903 on salt tolerance assay in T2 generation

| ME Events | SGI* of transgenics | | | SGI of pooled non-transgenics | | | t-Test | SGI |
|---|---|---|---|---|---|---|---|---|
| | Avg | SE | N | Avg | SE | N | p-value | increase |
| ME24903-04 | 0.97 | 0.141 | 19 | 0.58 | 0.091 | 15 | 0.0123 | 68.42% |
| ME24903-05 | 1.72 | 0.221 | 18 | 1.10 | 0.160 | 17 | 0.0153 | 55.99% |
| ME24903-07 | 1.51 | 0.229 | 21 | 0.63 | 0.112 | 12 | 0.0008 | 140.73% |
| ME24903-08 | 0.89 | 0.087 | 18 | 0.79 | 0.208 | 12 | 0.3241 | 13.22% |
| ME24903-09 | 1.86 | 0.303 | 14 | 0.84 | 0.104 | 20 | 0.0016 | 121.46% |

*SGI (Salt Growth Index) = seedling area × Fv/Fm (photosynthesis efficiency)

Transgenic plants of ME24903-04, -5, -7 and -09 showed significant better tolerance to high salt than pooled non-transgenics.

Summary of Results:

Ectopic expression of Ceres clone 295570 under the control of the 35S promoter enhances tolerance to salt stress that causes necrotic lesions and stunted growth in wild-type Ws seedlings.

Example 13—ME10681 (Clone 335348; SEO ID NO: 314)

Wild-type *Arabidopsis thaliana* Wassilewskija was transformed with a Ti plasmid carrying the 35S promoter and Ceres clone 335348. Ceres clone 335348 is a functional homolog of Ceres clone 375578.

Grown on MS agar plates containing 100 mM NaCl, ME10681-02, ME10681-04, and ME10681-05 transgenic plants showed significantly greater seedling area and SGI relative to non-transgenic plants. As shown in Table 13-1, the SGI value of T2-generation, the SGI value of T2-generation ME10681-02 seedlings increased by 119.17%, the SGI value of T2-generation ME10681-04 seedlings increased by 113.51% and the SGI value of T2-generation ME10681-05 seedlings increased by 103.98% as compared to non-transgenic control seedlings. The differences between transgenic and non-transgenic seedlings are statistically significant under the t-test, and clearly demonstrate that the enhanced tolerance to salt stress was a result of the ectopic expression of Ceres clone 335348 in the ME10681 transgenic lines.

TABLE 13-1

Results of ME10681 on salt tolerance assay in T2 generation

| ME Events | SGI* of transgenics | | | SGI of pooled non-transgenics | | | t-Test | SGI |
|---|---|---|---|---|---|---|---|---|
| | Avg | SE | N | Avg | SE | N | p-value | increase |
| ME10681-01 | 3.87 | 0.6837 | 9 | 2.78 | 0.4324 | 24 | 0.0940 | 39.17% |
| ME10681-02 | 4.13 | 0.3354 | 25 | 1.89 | 0.5752 | 11 | 0.0009 | 119.17% |
| ME10681-04 | 6.22 | 0.4787 | 12 | 2.91 | 0.5671 | 15 | 7.66E−05 | 113.51% |
| ME10681-05 | 5.25 | 0.3916 | 20 | 2.57 | 0.6140 | 15 | 0.0004 | 103.98% |

*SGI (Salt Growth Index) = seedling area × Fv/Fm (photosynthesis efficiency)

Transgenic plants of ME10681-02, -04 and -05 showed significant better tolerance to high salt than pooled non-transgenics.

Summary of Results:

Ectopic expression of Ceres clone 335348 under the control of the 35S promoter enhances tolerance to salt stress that causes necrotic lesions and stunted growth in wild-type Ws seedlings.

Example 14—Determination of Functional Homolog Sequences

The sequences described in the above Examples are utilized as query sequences to identify functional homologs of the query sequences and, together with those sequences, are utilized to define consensus sequences for a given group of query and functional homolog sequences. Query sequences and their corresponding functional homolog sequences are aligned to illustrate conserved amino acids consensus sequences that contain frequently occurring amino acid residues at particular positions in the aligned sequences, as shown in FIGS. 1-9.

A subject sequence is considered a functional homolog of a query sequence if the subject and query sequences encode proteins having a similar function and/or activity. A process known as Reciprocal BLAST (Rivera et al. (1998) *Proc. Natl. Acad. Sci. USA* 95:6239-6244) is used to identify potential functional homolog sequences from databases consisting of all available public and proprietary peptide sequences, including NR from NCBI and peptide translations from Ceres clones.

Before starting a Reciprocal BLAST process, a specific query polypeptide is searched against all peptides from its source species using BLAST in order to identify polypeptides having sequence identity of 80% or greater to the query polypeptide and an alignment length of 85% or greater along the shorter sequence in the alignment. The query polypeptide and any of the aforementioned identified polypeptides are designated as a cluster.

The main Reciprocal BLAST process consists of two rounds of BLAST searches; forward search and reverse search. In the forward search step, a query polypeptide sequence, "polypeptide A," from source species S A is BLASTed against all protein sequences from a species of interest. Top hits are determined using an E-value cutoff of $10^{-5}$ and an identity cutoff of 35%. Among the top hits, the sequence having the lowest E-value is designated as the best hit, and considered a potential functional homolog. Any other top hit that had a sequence identity of 80% or greater to the best hit or to the original query polypeptide is considered a potential functional homolog as well. This process is repeated for all species of interest.

In the reverse search round, the top hits identified in the forward search from all species are used to perform a BLAST search against all protein or polypeptide sequences from the source species S A. A top hit from the forward search that returned a polypeptide from the aforementioned cluster as its best hit is also considered as a potential functional homolog.

Functional homologs are identified by manual inspection of potential functional homolog sequences. Representative functional homologs are shown in FIGS. 1-9. The Figures represents a grouping of a query sequence aligned with the corresponding identified functional homolog subject sequences. Query sequences and their corresponding functional homolog sequences are aligned to identify conserved amino acids and to determine a consensus sequence that contains a frequently occurring amino acid residue at particular positions in the aligned sequences, as shown in FIGS. 1-9.

An HMM was made based on SEQ ID NOs: 80, 84, 85, 90, 92, 93 and 95, aligned in FIG. 1. When fit to the HMM, SEQ ID NOs: 80, 81, 82, 83, 84, 85, 86, 87, 89, 90, 91, 92, 93, 95, 97, 182, 184, 186, 188, 190, 191, and 192 gave HMM bit scores of 576.8, 394.8, 231.4, 382.2, 523.7, 632.7, 39.3, 409.6, 386.4, 569.7, 551.4, 621.4, 635.3, 633.5, 573.9, 543.4, 594.6546.7, 493.1, 613.4, and 635.3, respectively.

An HMM was made based on SEQ ID NOs: 100, 252, 298, 301, 302, 303 and 312 aligned in FIG. 2. When fit to the HMM, SEQ ID NOs: 100, 102, 103, 104, 252, 298, 300, 301, 302, 303 and 312 gave HMM bit scores of 1315.8, 208.1, 118.5, 173.9, 1272.1, 1235.9, 635.2, 1206.4, 225.6, 1212.9 and 1233.4, respectively.

An HMM was made based on SEQ ID NOs: 106, 107, 112, 113, 114 and 115, aligned in FIG. 3. When fit to the HMM, SEQ ID NOs: 106, 107, 109, 110, 111, 112, 113, 114, 115, 116, 117, 118, 119, 121, 194, 196, 197, 198 and 200 gave HMM bit scores of 593.7, 487.6, 238.4, 113.8, 492.6, 536.1, 524.8, 289.4, 624.9, 288.2, 476.4, 282.4, 489.3, 588.8, 545.8, 503.3, 491.5, 486, 504.9, respectively.

Figure 4:
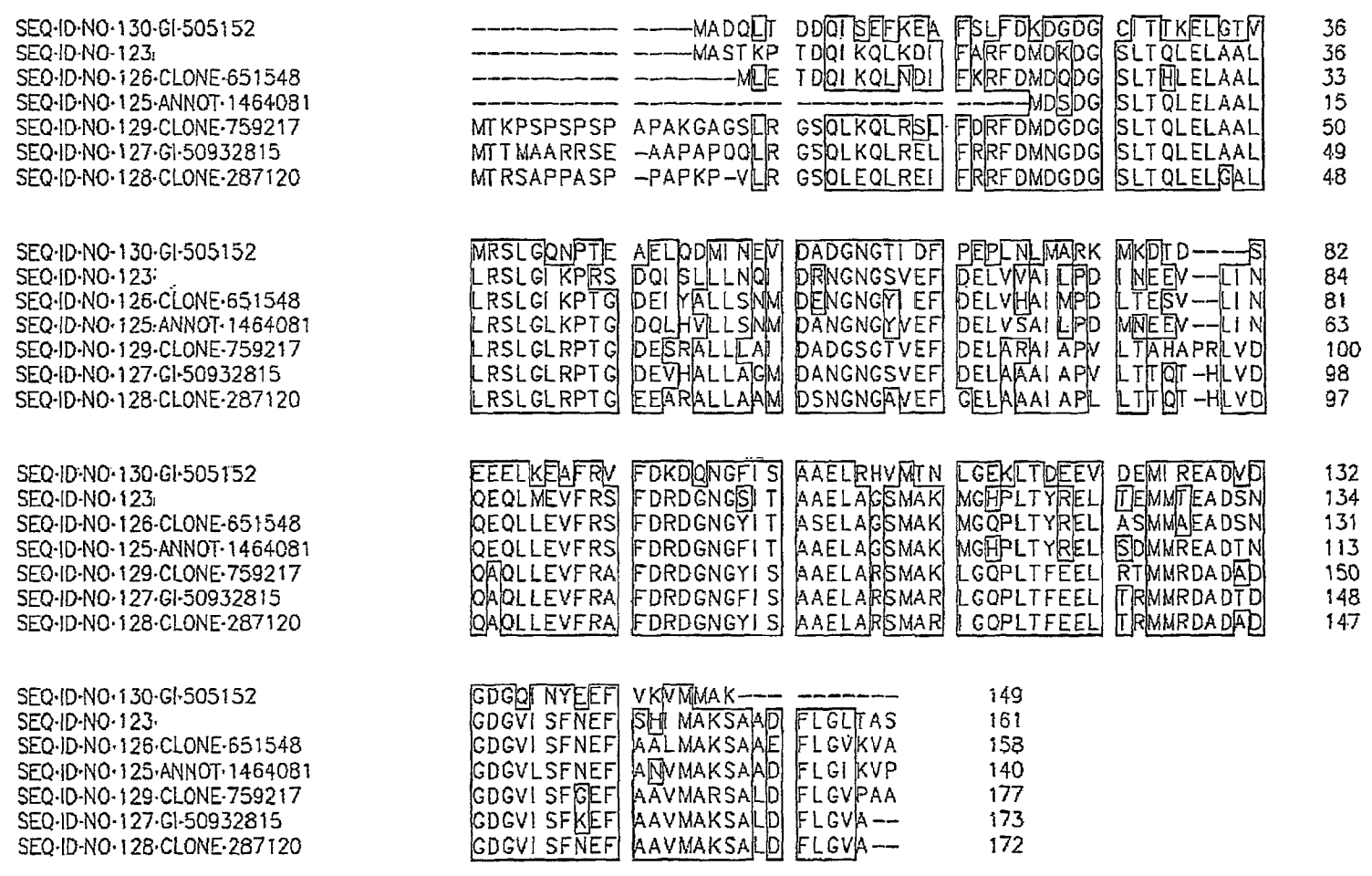

An HMM was made based on SEQ ID NOs: 123, 125, 126, 127, 128, 129 and 130, aligned in FIG. 4. When fit to the HMM, SEQ ID NOs: 123, 125, 126, 127, 128, 129. 130, 270 and 284 gave HMM bit scores of 390.1, 327.9, 392.3, 396.5, 394.8, 393.7, 323.8, 330.6 and 235.5, respectively.

An HMM was made based on SEQ ID NOs: 132, 134, 139, 142 and 143, aligned in FIG. 5. When fit to the HMM, SEQ ID NOs: 132, 134, 136, 138, 139, 141, 142, 143 and 144 gave HMM bit scores of 343.8, 454.5, 208, 197, 388.2, 144.1, 319.9, 375.2 and 295.2, respectively.

An HMM was made based on SEQ ID NOs: 146, 147, 149, 151 and 152, aligned in FIG. 6. When fit to the HMM, SEQ ID NOs: 146, 147, 149, 150, 151, 152, 202, 204 and 206 gave HMM bit scores of 593.1, 602.9, 570.8, 355.3, 633.9, 570.8, 369.3, 474.7 and 357.4, respectively.

An HMM was made based on SEQ ID NOs: 154, 157, 160, 161, 163, 164, 168, and 169, aligned in FIG. 7. When fit to the HMM, SEQ ID NOs: 154, 155, 157, 159, 160, 161, 162, 163, 164, 165, 166, 167, 168, 169, 170, 274, 278, 282, 286 and 288 gave HMM bit scores of 894.1, 719.9, 901.3, 801.4, 747, 810.2, 692.7, 748.7, 779.9, 656.3, 603.6, 485.1, 816.9, 634.5, 149, 498, 510, 584.3, 455.2 and 670.6, respectively.

An HMM was made based on SEQ ID NOs: 172, 173, 174, 175, 176, 177 and 179, aligned in FIG. 8. When fit to the HMM, SEQ ID NOs: 172, 173, 174, 175, 176, 177, 179, 208, 210, 212 and 213 gave HMM bit scores of 533.9, 542, 570.8, 559.9, 547.5, 474.8, 531.3, 414.3, 447.1, 358.5 and 344, respectively.

An HMM was made based on SEQ ID NOs: 304, 305, 306, 307, 308, 309, 310 and 311, aligned in FIG. 9. When fit to the HMM, SEQ ID NOs: 100, 102, 103, 104, 252, 298, 300, 301, 302, 303, 304, 305, 306, 307, 308, 309, 310, 311 and 312 gave HMM bit scores of 418.9, 208.1, 118.5, 173.9, 407.6, 490.5, 156.9, 461, 462, 469.6, 462, 461, 406.7, 462, 469.6, 418.9, 490.5 and 493.3, 493.3 respectively.

Useful polypeptides of the invention include each of the sequences and corresponding functional homolog sequences shown in the Figures and/or the Sequence Listing, as well as polypeptides belonging to the corresponding consensus sequence families as delineated by HMMs. In different embodiments, consensus sequence families have HMM bit score lower limits as about 50%, 60%, 70%, 80%, 90%, or 95% of any of the HMM bit scores of the family members presented in this application. In some embodiments the lower HMM bit score limits correspond approximately to the HMM bit score of any of the family members disclosed in this application. A sequence that has an HMM bit score of 20 means that it has a 95% likelihood of belonging to the consensus sequence defined by a particular HMM. Alternative HMM bit scores that are useful for the current invention are 50, 75, 100, 125, 150, 200, 250, 300, 350, 400, 450 and 500.

The present invention further encompasses nucleotides that encode the above described polypeptides, as well as the complements thereof, and including alternatives thereof based upon the degeneracy of the genetic code.

The invention being thus described, it will be apparent to one of ordinary skill in the art that various modifications of the materials and methods for practicing the invention can be made. Such modifications are to be considered within the scope of the invention as defined by the following claims.

The following references are cited in the Specification. Each of the references from the patent and periodical literature cited herein is hereby expressly incorporated in its entirety by such citation.

REFERENCES (1) Zhang et al. (2004) *Plant Physiol.* 135:615.
(2) Salomon et al. (1984) *EMBO J.* 3:141.
(3) Herrera-Estrella et al. (1983) *EMBO J.* 2:987.
(4) Escudero et al. (1996) *Plant J.* 10:355.
(5) Ishida et al. (1996) *Nature Biotechnology* 14:745.
(6) May et al. (1995) *Bio/Technology* 13:486)
(7) Armaleo et al. (1990) *Current Genetics* 17:97.
(8) Smith. T. F. and Waterman, M. S. (1981) *Adv. App. Math.* 2:482.
(9) Needleman and Wunsch (1970) *J. Mol. Biol.* 48:443.
(10) Pearson and Lipman (1988) *Proc. Natl. Acad. Sci.* (USA) 85: 2444.
(11) Yamauchi et al. (1996) *Plant Mol Biol.* 30:321-9.
(12) Xu et al. (1995) *Plant Mol. Biol.* 27:237.
(13) Yamamoto et al. (1991) *Plant Cell* 3:371.
(14) P. Tijessen, "Hybridization with Nucleic Acid Probes" In Laboratory Techniques in Biochemistry and Molecular Biology, P. C. vand der Vliet, ed., c. 1993 by Elsevier, Amsterdam.
(15) Bonner et al., (1973) *J. Mol. Biol.* 81:123.
(16) Sambrook et al., Molecular Cloning: A Laboratory Manual, Second Edition, Cold Spring Harbor Laboratory Press, 1989, New York.
(17) Shizuya et al. (1992) *Proc. Natl. Acad. Sci. USA,* 89: 8794-8797.
(18) Hamilton et al. (1996) *Proc. Natl. Acad. Sci. USA,* 93: 9975-9979.
(19) Burke et al. (1987) *Science,* 236:806-812.
(20) Sternberg N. et al. (1990) *Proc Natl Acad Sci USA.,* 87:103-7.
(21) Bradshaw et al. (1995) *Nucl Acids Res,* 23: 4850-4856.
(22) Frischauf et al. (1983) *J. Mol Biol,* 170: 827-842.
(23) Huynh et al., Glover N M (ed) DNA Cloning: A practical Approach, Vol. 1 Oxford: IRL Press (1985).
(24) Walden et al. (1990) *Mol Cell Biol* 1: 175-194.
(25) Vissenberg et al. (2005) *Plant Cell Physiol* 46:192.
(26) Husebye et al. (2002) *Plant Physiol* 128:1180.
(27) Plesch et al. (2001) *Plant J* 28:455.
(28) Weising et al. (1988) *Ann. Rev. Genet.,* 22:421.
(29) Christou (1995) *Euphytica,* v. 85, n. 1-3:13-27.
(30) Newell (2000)
(31) Griesbach (1987) *Plant Sci.* 50:69-77.
(32) Fromm et al. (1985) *Proc. Natl. Acad. Sci. USA* 82:5824.
(33) Paszkowski et al. (1984) *EMBO J.* 3:2717.
(34) Klein et al. (1987) *Nature* 327:773.
(35) Willmitzer, L. (1993) Transgenic Plants. In: iotechnology, A Multi-Volume Comprehensive treatise (H. J. Rehm, G. Reed, A. Puler, P. Stadler, eds., Vol. 2, 627-659, VCH Weinheim-New York-Basel-Cambridge).
(36) *Crit. Rev. Plant. Sci.* 4:1-46.
(37) Fromm et al. (1990) *Biotechnology* 8:833-844.
(38) Cho et al. (2000) *Planta* 210:195-204.
(39) Brootghaerts et al. (2005) *Nature* 433:629-633.
(40) Lincoln et al. (1998) *Plant Mol. Biol. Rep.* 16:1-4.
(41) Lacomme et al. (2001), "Genetically Engineered Viruses" (C. J. A. Ring and E. D. Blair, Eds). Pp. 59-99, BIOS Scientific Publishers, Ltd. Oxford, UK.
(42) Huh G H, Damsz B, Matsumoto T K, Reddy M P, Rus A M, Ibeas J I, Narasimhan M L, Bressan R A, Hasegawa P M, 2002, Salt causes ion disequilibrium-induced programmed cell death in yeast and plants. *Plant J* 29(5): 649-59.
(43) Kang D K, Li X M, Ochi K, Horinouchi S, 1999, Possible involvement of cAMP in aerial mycelium formation and secondary metabolism in *Streptomyces griseus. Microbiology,* 145 (Pt 5):1161-72.
(44) Kerk D, Bulgrien J, Smith D W, Gribskov M, 2003, *Arabidopsis* proteins containing similarity to the universal stress protein domain of bacteria. *Plant Physiol.* 131(3): 1209-19.
(45) Zhu J K, 2001, Cell signaling under salt, water and cold stresses. *Curr Opin* Plant Biol. 4(5):401-6.
(46) Susstrunk U, Pidoux J, Taubert S, Ullmann A, Thompson C J, 1998, Pleiotropic effects of cAMP on germination, antibiotic biosynthesis and morphological development in *Streptomyces coelicolor. Mol Microbiol* 30(1):33-46.
(47) Davletova S, Schlauch K, Coutu J, Mittler R., 2005, The zinc-finger protein Zat12 plays a central role in reactive oxygen and abiotic stress signaling in *Arabidopsis. Plant Physiol* 139(2):847-56.

(48) Fowler S G, Cook D, Thomashow M F., 2005, Low temperature induction of *Arabidopsis* CBF1, 2, and 3 is gated by the circadian clock. *Plant Physiol* 137(3):961-8.
(49) Nachin L, Nannmark U, Nystom T (2005) Differential roles of the universal stress proteins of *Escherichia coli* in oxidative stress resistance, adhesion and motility *J Bacteriol* 187(18):6265-72.
(50) Rizhsky L, Davletova S, Liang H, Mittler R, 2004, The zinc finger protein Zat12 is required for cytosolic ascorbate peroxidase 1 expression during oxidative stress in *Arabidopsis*. *J Biol Chem*. 19; 279(12):11736-43.
(51) Vogel J T, Zarka D G, Van Buskirk H A, Fowler S G, Thomashow M F, 2005, Roles of the CBF2 and ZAT12 transcription factors in configuring the low temperature transcriptome of *Arabidopsis*. *Plant J.* 41(2):195-211.
(52) Sanchez-Barrena M J, Martinez-Ripoll M, Zhu J K, Albert A., 2005, The structure of the *Arabidopsis thaliana* SOS3: molecular mechanism of sensing calcium for salt stress response *J Mol Biol*. 345(5):1253-64.
(53) Griffen, H. G, and Gasson, M. J. (1995) The Gene (aroK) Encoding Shikimate Kinase I from *E. Coli. DNA Seq.*, 5(3):195-197.
(54) Susstrunk et al. (1998) *Mol Microbiol,* 30(1):33-46
(55) Kang et al. (1999) *Microbiology,* 145:1161-72.
(56) Sauter M, Rzewuski G, Marwedel T, Lorbiecke R (2002) The novel ethylene-regulated gene OsUsp1 from rice encodes a member of a plant protein family related to prokaryotic universal stress proteins. *J Exp Bot* 53 (379): 2325-31.
(57) Kasuga et al. (1999) *Nature Biotech* 17: 287-291.
(58) Rus et al. (2001) *PNAS* 98:14150-14155.
(60) Shi et al. (2000) *PNAS* 97:6896-6901.
(61) Apse et al. (1999) *Science* 285:1256-1258.
(62) Zhang et al. (2001) *PNAS* 98:12832-12836.
(63) Berthomieu et al. (2003) *EMBO J* 22:2004-2014.
(64) Ren et al. (2005) *Nat Genet.* 37:1029-30
(65) Davletova et al (2005) *Plant Physiol*. 139:847-56

SEQUENCE LISTING

```
Sequence total quantity: 315
SEQ ID NO: 1              moltype = DNA  length = 1823
FEATURE                   Location/Qualifiers
misc_feature              1..1823
                          note = Ceres Promoter 21876
source                    1..1823
                          mol_type = unassigned DNA
                          organism = Arabidopsis thaliana
SEQUENCE: 1
gtctcttaaa aaggatgaac aaacacgaaa ctggtggatt atacaaatgt cgccttatac   60
atatatcggt tattggccaa aagagctatt ttaccttatg gataatggtg ctactatggt  120
tggagttgga ggtgtagttc aggcttcacc ttctggttta agccctccaa tgggtaatgg  180
taaatttccg gcaaaaggtc ctttgagatc agccatgttt tccaatgttg aggtcttata  240
ttccaagtat gagaaaggta aaataaatgc gtttcctata gtggagttgc tagatagtag  300
tagatgttat gggctacgaa ttggtaagag agttcgattt tggactagtc cactcggata  360
cttttcaat tatggtggtc ctggaggaat ctcttgtgga gtttgatatt tgcgagtata  420
atctttgaac ttgtgtagat tgtacccaaa accgaaaaca tatcctatat aaatttcatt  480
atgagagtaa aattgtttgt tttatgtatc atttctcaac tgtgattgag ttgactattg  540
aaaacatatc ttagataagt ttcgttatga gagttaatga tgattgatga catacacact  600
cctttatgat ggtgattcaa cgttttggag aaaatttatt tataatctct cataaattct  660
ccgttattag ttgaataaaa tcttaaatgt ctccttttaac catagcaaac caacttaaaa  720
atttagattt taaagttaag atggatattg tgattcaacg attaattatc gtaatgcata  780
ttgattatgt aaaataaaat ctaactaccg gaatttattc aataactcca ttgtgtgact  840
gcatttaaat atatgttta tgtcccatta attaggctgt aatttcgatt tatcaattta  900
tatactagta ttaatttaat tccatagatt tatcaaagcc aactcatgac ggctagggtt  960
ttccgtcacc ttttcgatca tcaagagagt ttttttataa aaaaatttat acaattatac 1020
aatttcttaa ccaaacaaca cataattata agctatttaa catttcaaat tgaaaaaaaa 1080
aatgtatgag aattttgtgg atccatttt gtaattcttt gttgggtaaa ttcacaacca 1140
aaaaaataga aaggcccaaa acgcgtaagg gcaaattagt aaaagtagaa ccacaaagag 1200
aaagcgaaaa ccctagacac ctcgtagcta taagtaccct cgagtcgacc aggattaggg 1260
tgcgctctca tatttctcac attttcgtag ccgcaagact cctttcagat tcttacttgc 1320
aggttagata ttttctctct ttagtgtctc cgatcttcat cttcttatga ttattgtagc 1380
tgtttagggt ttagattctt agttttagct ctatattgac tgtgattatc gcttattctt 1440
tgctgttgtt atactgcttt tgattctcta gctttagatc cgtttactcg tcgatcaata 1500
ttgttcctat tgagtctgat gtataatcct ctgattaatt gatagcgttt agttttgata 1560
tcgtcttcgc atgttttta tcatgtcgat ctgtatctgc tctggttata gttgattctg 1620
atgtatttgg ttggtgatgt tccttagatt tgatatacct gttgtctcgt ggtttgatat 1680
gatagctcaa ctggtgatat gtggttttgt ttcagtggat ctgtgtttga ttatattgtt 1740
gacgttttgg ttgttgtatg gttgatggtt gatgtatttt tgttgattct gatgtttcga 1800
tttttgtttt tgttttgaca gct                                         1823

SEQ ID NO: 2              moltype = DNA  length = 1000
FEATURE                   Location/Qualifiers
misc_feature              1..1000
                          note = Ceres Promoter PT0668
source                    1..1000
                          mol_type = unassigned DNA
                          organism = Arabidopsis thaliana
SEQUENCE: 2
atagagtttt actatgcttt tggaatcttt cttctaatgt gccaactaca gagaaataca   60
tgtattacca ctaggaatcg gaccatatca tagatatcag gattagataa ctagttctcg  120
tcgctatcac ttcgcattaa gttctagtaa ttgttaaaga ttctaatttt ttactaaaca  180
aaaactaaat caacatcaaa tatgcaaagt gtgtgttgtc cacacaagtg actcaaagta  240
tacgcaggtg ggattggacc atattattgc aaatcgtttc cgaaccactc atatttcttt  300
```

```
ttttctctcc tttttttatc cggagaatta tggaaccact tcatttcaac ttcaaaacta    360
atttttggt  tcagtgatca aatacaaaaa aaaaaaaaaa gttatagata ttaaatagaa    420
aactattcca atcttaaaaa tacaaatgaa accataattt taatttatac aaaactattt    480
aattagctaa gggttgtctt aacgtttaga aaataaaaaa ttatgattgt ctgtttaaaa    540
ttacaatgaa tgaataaaaa aaatatgcaa tgaatgaaaa aataaatttt gtacatccga    600
tagaatgaga aaatgaattt tgtacaaacc actcaagaat tcaaaacaat tgtcaaagtt    660
ttcttctcag ccgtgtgtcc tcctctccta gccgccacat ctcacacact aatgctaacc    720
acgcgatgta accgtaagcg ctgagttttt gcatttcaga tttcacttcc accaaacaaa    780
actcgccacg tcatcaatac gaatcattcc gtataaacgt ctagattctt tacagcctac    840
aatgttctct tctttggtcg gccattattt aacgcttga  acctaaatct agcccagcca    900
acgaagaaga cgaagcaaat ccaaaccaaa gttctccatt ttcgtagctt ctttaagctt    960
tttcagtatc atagagacac tttttttttt ttgattagaa                        1000

SEQ ID NO: 3            moltype = DNA  length = 1000
FEATURE                 Location/Qualifiers
misc_feature            1..1000
                        note = Ceres Promoter PT0535
source                  1..1000
                        mol_type = unassigned DNA
                        organism = Arabidopsis thaliana
SEQUENCE: 3
ttagtgaaat tatgacatta agtaaggttt tcttagttag ctaatgtatg gctattcaat     60
tgttatgtta ggctatttta gttagtatat gaatttaggc agtctatgca aatgatttcg    120
ttttcatttt ttcatatgta aacatcaaga tcaagtaacg ccattcgagt tgatatttt    180
tttttaaatt agtgtgtgta aattttggac cgcttatttg agtttgctaa tgaagttgca    240
tatatattac gttaaaccat aggcaaacta atttgaaata tccgattcga tttcctgtaa    300
ttttttcttgg ttaattgacc aaaatcaaga tcttcagaaa taaaataaaa gacgaaagaa    360
agctgtcgca aagcagattg tgttaaaaaa aagtggattg ggctcaaacg caacttgtcc    420
agcccgtgac aattacccta tacgcaagta agagtaacgt atcactggca aaagttgta    480
ttagttacga tatctttgtc atgggggcat gcatggcgat gcttaagag ttaagccta    540
agaagagtcc cacactcgtg actctcatga tcacttgttg tttcttacgg gcaaatacat    600
ttaacttat tctccattta ttcacctata ttctttgga taataacttt tctctatata    660
aaataacaaa catcgtacgt ttcatttatt tacaacaagc gatgagaatt aaaaggagac    720
cttaattgat gatactcttc ttttctctcg gttacaacgg attattaca gataatgata    780
atctatatgg atgctgacgt ggaaaaacaa aatttggtga aacacgtcaa ttaagcacga    840
cttttccatg gctagtggct aagatcgttt catcacatgg ctatatcata taatacttgg    900
atgaattcaa aataaacgac tgagaaaatg tccacgtcac ggcgcaccgc tttggactta    960
agtctcctat aataaataca acaccaaaca ttgcattcca                        1000

SEQ ID NO: 4            moltype = DNA  length = 999
FEATURE                 Location/Qualifiers
misc_feature            1..999
                        note = Ceres Promoter PT0585
source                  1..999
                        mol_type = unassigned DNA
                        organism = Arabidopsis thaliana
SEQUENCE: 4
tgaagtcatt taatatgagt ttgacattag gtaaacctaa tctatgagat tatagaatgt     60
agcaaaacta tcaatgtttc ttttccaaaa tattttgtgg tttttctttt tggttcatta    120
tgttttgtta tttgtgaatt attttaatat gaagtaatta tattgatttt atgatata    180
catattattt tgatataaaa tttaacactt atccattaaa atagcatggg cataatcaaa    240
atcgggacta ttacgatgaa aaagatagtt aaattgtatg ataaaataaa atgtgtaaga    300
ttaaaatttt gggttttaga aaattactaa acaaaatata gacaaagtat gttgactatt    360
atttaaaatt taaatatcat caataagata tagttaaagt cattaagtgt atagcaaaat    420
gaaaattcta agattaaaat tcgattaaaa tttttttttac taaattaaat attaaaaat    480
agggattatc atttactatt tacaattcta atatcatggg taaaaattga taacttttt    540
taaacccgcc tatctaggtg ggcctaacct agtttactaa ttactatatg attaacttat    600
taccactttt acttcttctt ttttggtcaa attactttat tgttttttat aaagtcaaat    660
tactctttgc attgtaaata atagtagtaa ctaaaatctt aaaacaaaat attcaacctt    720
tcccattatt ggaatggtaa tgtcttcaac accattgacc aacgttaagg aatgtctttt    780
aatatttttg gaacctaaat gctaatactg tataccacaa tcacttatga gtattgaagt    840
tgagatagag gaggtacaag gagaccttat ctgcagaaga caaaaagcca ttttttagcaa    900
aactaaagaa agaaaaaaga ttgaaacaca aatatgcgcc actcgtagtc caccccctatc    960
tctttggcaa aagccacttc actcttttc ccttttat                            999

SEQ ID NO: 5            moltype = DNA  length = 1000
FEATURE                 Location/Qualifiers
misc_feature            1..1000
                        note = Ceres Promoter PT0613
source                  1..1000
                        mol_type = unassigned DNA
                        organism = Arabidopsis thaliana
SEQUENCE: 5
ttaatactaa cattgtagaa agccacaaaa aagaaattga aatgtgagta gatgctgagt     60
cagaggtttg gtcaatacac aacagctaat tgagataata ttatacacgt cacgatgact    120
tgtttttttct cctcccaact tgttaatttc tttattctta aaattaaacc atcgcaaaaa    180
cagaagaaca cagctgtttt tctcgactcc caatttctat tttgctgcta aggacatttc    240
atttcattat ttcccaattc aggactcctt agatttttcct aaatttgttt tcctaacttg    300
ctctctctca ttctaacatt ttctcatttt tttagattat cttgtacttt ttagtagatt    360
```

```
atttatcag gtttacaaa catacattga cattctaaaa agggcttcta aaaattcagt    420
gtggaatgct gatatactaa aaaaaggtca tgcaaaatta tctacgattt atctaaaatt    480
agataatttg ccatatataa ctattaacta ataatcgatc ctttgatttt ttgtttagat    540
aaaacgaaac agctatatct ttttttttg ttatcggatt ttaatcgaat aaaagctgaa    600
aaataacagt tatatcttct tcttttttaa ctaatgaaac agttatatct taaacaaaca    660
acagaaacag taaatatta atgcaaatcc gcgtcaagag ataaatttta acaaactaat    720
aacaattgag ataagattag cgcaaaagaa actctaattt tagagcgtgt aaacacaaac    780
acgtcttgaa agtaaacgtg aattacacgc ttctaaaacg agcgtgagtt ttggttataa    840
cgaagatacg gtgaagtgtg acacctttct acgttaattt cagtttgagg acacaactca    900
agttatgttt gatatctaag gacttgcact gtctccaaat ctgcaggaag gacttttga    960
ttggatcaat ataaatacca tctccattct cgtctcctc                          1000

SEQ ID NO: 6            moltype = DNA    length = 351
FEATURE                 Location/Qualifiers
misc_feature            1..351
                        note = Ceres Promoter PT0625
source                  1..351
                        mol_type = unassigned DNA
                        organism = Arabidopsis thaliana
SEQUENCE: 6
gatcatgatc agtttcaact cgctgtgccc acgtgtcgag agatcggcac gtgcctgagc     60
tctcagccgc tcataaatac acttgtttag tagcaacagt atactatagt agtcctctcc    120
tgtttggctt ttagcttgca tcgatggatg gatggatgga tcgcatgaga gggcttcgcg    180
aaggtacgga accttacaca acgcgtgtcc tttctacgtg gccatcgtgt aggcgtctcg    240
ccatgctacg tgtcccggag gatgtctcga tgccaaccct tataaatact gttccattcc    300
aatcccatcg ccacagccag tgcaaatctg atcgatcaag ataatcgagc a             351

SEQ ID NO: 7            moltype = DNA    length = 1022
FEATURE                 Location/Qualifiers
misc_feature            1..1022
                        note = Ceres Promoter PT0633
source                  1..1022
                        mol_type = unassigned DNA
                        organism = Arabidopsis thaliana
SEQUENCE: 7
cccgatcggc cttaatctga gtcctaaaaa ctgttatact taacagttaa cgcatgattt     60
gatggaggag ccatagatgc aattcaatca aactgaaatt tctgcaagaa tctcaaacac    120
ggagatctca aagtttgaaa gaaaatttat ttcttcgact caaaacaaac ttacgaaatt    180
taggtagaac ttatatacat tatattgtaa tttttttgaa caaaatgttt ttattattat    240
tatagaattt tactggttaa attaaaaatg aatagaaaag gtgaattaag aggagagagg    300
aggtaaacat tttcttctat tttttcatat tttcaggata aattattgta aaagtttaca    360
agatttccat ttgactagtg taaatgagga atattctcta gtaagatcat tatttcatct    420
acttcttta tcttctacca gtagaggaat aaacaatatt tagctccttt tgtaaatacaa    480
attaatttc gttcttgaca tcattcaatt ttaattttac gtataaaata aaagatcata    540
cctattagaa cgattaagga gaaatacaat tcgaatgaga aggatgtgcc gtttgttata    600
ataaacagcc acacgacgta aacgtaaaat gaccacatga tgggccaata gacatggacc    660
gactactaat aatagtaagt tacattttag gatggaataa atatcatacc gacatcagtt    720
tgaaagaaaa gggaaaaaaa gaaaaataa ataaaagata tactaccgac atgagttcca    780
aaaagcaaaa aaaagatca agccgacaca gacacgcgta gagagcaaaa tgactttgac    840
gtcacaccac gaaaacagac gcttcatacg tgtccctta tctctctcag tctctctata    900
aacttagtga gaccctcctc tgttttactc acaaatatgc aaactagaaa acaatcatca    960
ggaataaagg gtttgattac ttctattgga aagaaaaaaa tcttggaaa aggcctgcag    1020
gg                                                                  1022

SEQ ID NO: 8            moltype = DNA    length = 1000
FEATURE                 Location/Qualifiers
misc_feature            1..1000
                        note = Ceres Promoter PT0650
source                  1..1000
                        mol_type = unassigned DNA
                        organism = Arabidopsis thaliana
SEQUENCE: 8
catacttaat tctaaaaaaa caacacttat agtttataag cagctcttat gataaaaatc     60
tttctgagtt atagctctgt taaacttgta ttcaccccaa aaacggatgt ttcatttctt    120
atttttact tggagtattt tattgtaatt tgtaaaaaaa aatgtaaagt gggggatatc    180
atgaaaaaca acgtcacttt gtttggtcac aatatacatt tgataaaata atggtcgtcg    240
cgtgatttag ttgattttg ttttatcaac cacgtgtttc acttgatgag tagtttatat    300
agttaacatg attcggccac ttcagatttg ggtttgccca catatgacat accgacatag    360
aaggttaaat ccacgtggga aatgccaata ttcaatgtt ggttttcaaa agagaatcat    420
ttctttatat gatctcaaaa gtatggaatt gaaatgacta atgagcacat gcaattggtg    480
ctatcttaaa aaccgaacgt ctttgaattt aatttgtttt tcaccaaagg tacctaatga    540
aacccctttca ttaaaaata aaggtaacaa acaaatttt gtattggaaa aacattttt    600
tggaatatat aatttggtaa tagaattatg agcaaaaaag aaaagaaaa gaagaataa    660
tgagcataat aaaagccttt cagtattact aattgggccg agcagttttg ggctcttgat    720
catgtctagt aatcttaaac agacgataaa gttaactgca atttagttgg tcaggtgag    780
ctaccaaatc caaaaatacg cagattaggt tcacgtacc ggaacaaacc ggatttatca    840
aaatccttaa gttatacgaa atcacgcttt tccttcgatt tctccgctct tctccactct    900
tcttctctgt tctatcgcag acattttgt ttatatgcat acataataat aatacactct    960
tgtcaggatt tttgattctc tctttggttt tctcggaaaa                         1000
```

| SEQ ID NO: 9 | moltype = DNA length = 998 |
| --- | --- |
| FEATURE | Location/Qualifiers |
| misc_feature | 1..998 |
| | note = Ceres Promoter PT0660 |
| source | 1..998 |
| | mol_type = unassigned DNA |
| | organism = Arabidopsis thaliana |

SEQUENCE: 9

```
caagtcaagt tccaatattc taaggagaaa taatagtata ctaaacatac attagagagg   60
ttaaacttct ttttggattt aagtgtgtat gcataggcta tttattctta agtataacta  120
ttaactgtag ctagatttat acaagaaata cataaaactt tatgcatgtg aggtagccat  180
gaatatacgt acatgttgca atcgattata catgttgtat ttggatttct ctatacatgt  240
tttaacttgt cattctctaa gtatatacat accattaata ctgtgggcat gagtttatga  300
taagactttt cttttggaga ccagttttgt tttccttcc acctatattt gtctataggc  360
ttcacggtac actagtttac aagtgttttt atatgttcta aataaaattg agattttccg  420
gaacggtatg atctgtttgc aaataaggac gtatatataa cagtatcaaa tatatttgtt  480
gttataaggc aataatatat tttctgagat attgcgtgtt acaaaaaaga aatatttgtt  540
aagaaaaaaa aagatggtcg aaaaggggga gtaggtgggg gcggtcggct tttgattagt  600
aataaaagaa accacacgag tgacctaccg attcgactca acgagtctac cgagctaaca  660
cagattcaac tcgctcgagc ttcgttttat gacaagttgg tttttttttt tttttttaat  720
tttttcatct tcttcgggtt ggttgggtca ctcttcaggt cagtgtgta aaaaagaaag  780
aaagaaaaga gagattgttg tgttgtaacc cctttgacta aaatctaatg aacttttta  840
acacaacaaa actccttcag atctgaaagg gttcttcttc tctcttagtc tcttcgtcct  900
tttattctcc gtcgtcgttt catgatctga ctctctggtc ttctcttctt cttcttcttc  960
ttctattttt tcttacttcg tcactgttgt gtctgaac                         998
```

| SEQ ID NO: 10 | moltype = DNA length = 1000 |
| --- | --- |
| FEATURE | Location/Qualifiers |
| misc_feature | 1..1000 |
| | note = Ceres Promoter PT0665 |
| source | 1..1000 |
| | mol_type = unassigned DNA |
| | organism = Arabidopsis thaliana |

SEQUENCE: 10

```
aaaaaggatg ggtaatggga cctatttttcc ccaacatccc acatgcacac ttccctctcc   60
attctctcac atttatttct ttcattctaa tttatccatt ccgtgtgtaa catattcact  120
aataatctca tctcactaac tcattcattg attgtgatat gtttatctag aattagtgtt  180
ttaacactgt gtctatacat gatttccttt tcattgtatg tgaacatgtt aactcactaa  240
tcatttttgta ttttcgagtt aacatgagtc tccacttcgg tagactaaag taaagatagg  300
tttgagtata ataagttta aaatttgctt taaaatcaat atttataaat aagtttttat  360
cataagtgat ttttgtatgt tatattggac cttgtataaa cagactacag aagaaaatta  420
tttatgagaa cttgtaatgt tagagtggac ctcgtataaa ctaattatgt gggctttac  480
cataaactat ttatgaaat tattatggcc cacaccacta taactaaagc ccacataatt  540
agcagcccag tttcattgta agagacatgt tcgctctgga actagaattt tctggttttt  600
gggtatttgt ttttcttatgt gtagagaaat gatggtaacg attaaatgtt gtgtattaca  660
atttacaatg gtaagacgat taatatattt acacacaatt ttgttgttgc tgtaacacgt  720
tagtgtgtgt gatgatagaa tttcataaag ctttaactac gagggcaaa atgttaattc  780
taaatagttg acagcagaaa aagatatgta tacataatat aaggattaaa acgtaaataa  840
taataaaata ggcgagttaa attaaaaccc tgttaaaacc ctagcttgaa acacatgtat  900
aaaaacactt gcgagcgcag cttcatcgcc atcgccattc tctctctcat caaaagcttt  960
tctccttgat tttcgcattc tttagagtct taacgcaaag                       1000
```

| SEQ ID NO: 11 | moltype = DNA length = 999 |
| --- | --- |
| FEATURE | Location/Qualifiers |
| misc_feature | 1..999 |
| | note = Ceres Promoter PT0672 |
| source | 1..999 |
| | mol_type = unassigned DNA |
| | organism = Arabidopsis thaliana |

SEQUENCE: 11

```
cagccgtaaa tcctccataa atttattttg caagttttgc tcattatata atgagcggaa   60
tttatgatat aatcgtttgt aataatgtta tgttttgatc aaaatttgaa attaaaagta  120
ggtgagaact tgttatacag tgtagataag gtggatcttg aaataaaaa taaaatttat  180
aagatgtatt taaagcagaa aagcataaaa ctttagataa aataatgtaa aaatgtgtta  240
gcatcaatgt tgggatattg gccgacccga acttaatcaa tgtcggaagc cattacttct  300
ctcccaaaag accttttttcc ttcggagaac taggaacttc ctcactacct ttcgcttaac  360
gtgaaagcca taaatttcat atattcataa aaatcagaaa atctaaaact gtttagtatc  420
acctgttttt ggtatagact attggttttg tgttacttcc taaactatat gatttcgtac  480
ttcattggat cttatagaga tgaatattcg taaaaagata agttatctgg tgaaacgtta  540
cttcagtcat gttgggtcta gatttacata ctactatgaa acatttttaag ataattaatta  600
tcctagccaa ctatatgttc tatattatgg gccaagaaga tatagaacta aaagttcaga  660
atttaacgat ataaattact agtatattct aatacttgaa tgattactgt tttagttgtt  720
tagaataaat agtagcgtgt tggttaagat accatctatc cacatctata tttgtgtggt  780
ttacataaaa tgtacataat attatataca tatatatgta tattttgat aaagccatat  840
attactcctt gacctctgcc cccattttcct tttactataa ataggaatac tcatgatcct  900
ctaattcagc aatcaacacc aacgaacaca accttttcca aagccaataa taaaagaaca  960
aaagctttta gttctcatcaa agacgaagct gccttagaa                       999
```

-continued

```
SEQ ID NO: 12            moltype = DNA   length = 1000
FEATURE                  Location/Qualifiers
misc_feature             1..1000
                         note = Ceres Promoter PT0676
source                   1..1000
                         mol_type = unassigned DNA
                         organism = Arabidopsis thaliana
SEQUENCE: 12
aagatagtac agtttcagtg ttttgagaaa aaaagctgaa ctaaaactaa aatgtttaag    60
gacacaatat ttagtttcaa ttagataatt caacagtttg aacaattttt ttttttttt   120
tttgaagtca tttatttata caatgtttta aaacgcatta agcatttagg cagccgacaa   180
acgcctattg tctaactgta aataggcgct tccacttagg ttcatattgc atatttacta   240
tatgtgtata gtgacaaaaa ccaatatttc tcttattttg gatgaaggta tagtagttgt   300
taaatgttca atataattaa gcattaatga caaataaaat aaaattaatt tagttgataa   360
aaagataatc ttataaaaag atcgatgaat agatataatg gtttactgaa ttctatagct   420
cttaccttgc acgactatgt cccaaggaga ggaagtaccg taactataat tctgaacata   480
attttgtcta tcttggtgag tattatatga cctaaaccct ttaataagaa aaagtataat   540
actggcgtaa cgtaataaat taacacaatc ataagttgtt gacaagcaaa aaaacataca   600
taatttgttt aatgagatat attagttata gttcttatgt caaagtacaa ttatgcctac   660
caaaattaat taatgatttc aacaggaagt ctgagatgat gggccgacgt gtagttacgt   720
ttcttgaatt gtgagagatg gtatttatta tactgaagaa aacattattt actaaataaa   780
ttttcatttc acatcttctg taatcaatgc gggtagatga agaagttgtt aatacgatgg   840
ccaaccatat ggatctcttt tttggcgttt ctatatatag taacctcgac tccaaaggca   900
ttacgtgact caataaaatc aagtcttttg tttccttttta tccaaaaaaa aaaaaaagtc   960
ttgtgttctt cttaggttgg ttgagaatca tttcatttca                       1000

SEQ ID NO: 13            moltype = DNA   length = 998
FEATURE                  Location/Qualifiers
misc_feature             1..998
                         note = Ceres Promoter PT0678
source                   1..998
                         mol_type = unassigned DNA
                         organism = Arabidopsis thaliana
SEQUENCE: 13
aattaaatga aaccgcccct aaattaggag ggatttgggt aagtggtaac acattcactg    60
gaaacatgtg aagaaggag gatgtcaagt agctgaaaac tcagtatagt aaccaacggc   120
ttctcaccaa cctttcatta ataattggt catccctata ttttattca acattttgtt   180
tttcaatagc ttagagcacc ttaataccct tcagtgtttt tttataaaaa aaacaaaat   240
tgggattaat catcaatccc caaatgtaac gtttacttag attatgttca tttttctata   300
cacacaaatc atattctttt gttttaatct tcgaaaaacg agaggacatt aaatacccct   360
aaaaaaggag gggacattac taccaacgta cattaacatg tttgatagca aacgatttat   420
tttgttcgtt ttgaaaaggg gaaagtaatg tgtaaattat gtaaagatta ataaactttt   480
atggtatagt aacattttcg aataataaga gagggaaaac actcgccatt gtcggcaatt   540
tagaaccaat attagaaggg tttttttaga gaaaaaggac ttaaaagttt agagacctta   600
acaacaactt atttagaaat agacatgctt aagttgacaa cagcgagttt atttttctata   660
tcgaagaaaa atacgaactt tttccttaatt agatttcgaa tgcatgcact atcgagaatc   720
gaccgtcaca agaaaaaact aatatacata ctgtacatat ctatattcaa tattggtggg   780
gatgggttta atgtgtatt ataattcatg gataaattca cacaataagg tccatgaaac   840
tagaaggtac caaaaataag cattaatgac tctttgccac ttatatatat gattctctca   900
tagtaccatt ttattctccc aaacctatct tcttcttcct ctcttgtctc tctcgctctc   960
tctcttctac attgtttctt gaggtcaatc tattaaaa                          998

SEQ ID NO: 14            moltype = DNA   length = 1000
FEATURE                  Location/Qualifiers
misc_feature             1..1000
                         note = Ceres Promoter PT0683
source                   1..1000
                         mol_type = unassigned DNA
                         organism = Arabidopsis thaliana
SEQUENCE: 14
gattgaatga tgagtgtgca cccttgtatt actaataaaa aatttagcaa cagttataag    60
ctaacgtcat ccatgagtca ttcattagat tcactatttg cgttctcaaa aatcgaattg   120
ttaaaatttg agaagctcta atatacgagt caatgagatg tggcaaaagc atgtccttga   180
ccataaaatt tcgaggggtc aactcattag ataaggacaa actcaacca attgaaggcg   240
tcttctataa caagtttctt tattactaat attaaagtcc aatggggtga ggggagaag   300
aacttaaata aaaggaaata attggtaagt gaataaaatc taaatacgat actagatgat   360
tgatttgtgc tagtgcatgg tattagatca gatatgtgtt actattcgaa ttcaaattgg   420
catattccat gttgttgata agaaaattgt agaagtgtaa aagctgagtt actatattca   480
aactagtagt ttacataaag tgagacaaca actgtttcac aaaaatgact ataaaatagt   540
aagtagtatt aggtcaattg atttttaaat tttaatcaaa ttcaaatttg tgatataatc   600
aaatttgttt atagaaaatg ttaagaaatc aattttggca gaactaattc agtgagaaac   660
aatcatttac aaaacaatt ttaacattat ttaacagtaa gatttgacat ttaacccgtt   720
cgtgtgaacc catcatatct aacatggctc tacccatgac gcctccatgc catggacaat   780
tttgacagat ggaagttct gaacgtggac gaggtaagaa caccatgatg atacgattgg   840
agttagttat gtcgccaccg acatcactgc caatctcatt aataaagtg gtactaaatc   900
tctaatctct attaactata aatataacaa agaaccaaaa gaaagtttct tatctctctt   960
atctttcata atttccaaga aacacaaacc ttttctacta                       1000

SEQ ID NO: 15            moltype = DNA   length = 1000
```

```
FEATURE                 Location/Qualifiers
misc_feature            1..1000
                        note = Ceres Promoter PT0688
source                  1..1000
                        mol_type = unassigned DNA
                        organism = Arabidopsis thaliana
SEQUENCE: 15
acgttcagag gcatcgcttt tgtacaaatt gaagcgggtt tgttcaatat ttaaaataac    60
acaggaaaca ttcaaatgta ttattgatgt tgcttaggtt tgtgaaatga tatgaaccat   120
atcgtatata ttactagatt ttttcttatat gttttaaggg tagtggggct gacctatcat   180
tctgtttggc attaccaatc agactatcag agtattcacc attcaggatt ccataactag   240
aaaaagaagg ggtttacatt ttctcatact gtataatttt ctactatcag agattttatc   300
gattacatta atctcataat gattattctg atttataaaa aagttgacaa aataattaaa   360
accagtattt tataacaaga ttgtctctct cccatggcca ttattttgac ctctgactta   420
tttaaatctt aattaacagc ataatactgt attaagcgta tttaaatgaa acaaaataaa   480
agaaaaaaag aacaaaacga aagagtggac cacatgcgtg tcaagaaagg ccggtcgtta   540
ccgttaaggt gtgtcgaact gtgattgggc cacgttaacg gcgtatccaa aagaaagaaa   600
gggcacgtgt atagatctag gaaaaaagaa agaatggacg gtttagattg tatctaggta   660
ccaggaaatg gaacgtcaca ccaaacggta cgtgtcggat cctgcccgtt gatgctgacg   720
gtcagcaact tcccccttatt catgcccccc tgccgttaa ttacgtgtaa cccttccatg   780
cgaaaatcaa acccttttttt tttttgcgt tcttcttcaa ctttttcttttt taaatcaaac   840
cttttctttt taaaatcaca ttgcatttcc taacgctcaa caaaatctct ctctactaat   900
atctctctct ctctctctct attgttgaag aagactcata atcggagatt gtttgttttt   960
ggtttgctct gtaaattgga gaagtttttgt tagagatcaa                        1000

SEQ ID NO: 16           moltype = DNA   length = 1000
FEATURE                 Location/Qualifiers
misc_feature            1..1000
                        note = Ceres Promoter PT0695
source                  1..1000
                        mol_type = unassigned DNA
                        organism = Arabidopsis thaliana
SEQUENCE: 16
aacattttct ttaacttact cttaaatttt aatagtaagt tgatgcatgt tatgttgatc    60
cgtcttgatc acaaatattg ttttatggac gaattcttg acagtaaatg gctatagtga   120
ctcagcttgg agcatcccga tatgaaaaca aagtgcagta ttgtgtcgtg gtcatcacta   180
acgcactttc ctagaactat cgcgcgtgtt tgacctatgc aacacaccag atgtcatgaa   240
cgtatactta aatagaaaca atgatataga caattggcta tattctgtca tggaacgcaa   300
accggataac atgtctatta gattcatcgg acttgatcat ggttatgtct taatagacga   360
attctttgtt aacgattggt taaaacggct cacgttagag catcctacta tgacttcaaa   420
attgataaat attacatgga aatcacttta attttagtta gaaggtagtt aatttagata   480
ttcttatta ataaatttaaa aaatagaaga aaaaagatg agaagagttt ttgttttaaa    540
aataagaaat atcttttatt gtaatttaaa aattaaacaa atttaattta tattaaaatt   600
atctttgttt tattgttaag gcaataatta tttttttggt gggaattgtt aaaacaataa   660
ttagtatact gttaagtggt cctttaataa taagataacg tgatttaaaa aagaacgaga   720
caggctaata tagtagagag gaaaaatac aatttaggcc caataaagcc caatatagag    780
ttgtgctcaa acacaggtct tcgccagatt tcctatgacg cgtcgtgtca atcatgacgc   840
caagtgtcat tcaagaccgt cacgtggcgt tgtttctaca cataggcgat ccatacaaat   900
cagtaacaaa cacgaaaaga gcattcatat gtacgaaagt agaaaagaag agactctttg   960
tgataaaact aagtaagaaa tagcataaaa gtaaaaggga                         1000

SEQ ID NO: 17           moltype = DNA   length = 1000
FEATURE                 Location/Qualifiers
misc_feature            1..1000
                        note = Ceres Promoter PT0708
source                  1..1000
                        mol_type = unassigned DNA
                        organism = Arabidopsis thaliana
SEQUENCE: 17
gtttccaaaa ctagtattct ttatttgctc tattcattat attttttatat ttgtaacgtc    60
ccgaccgtct ttattaggtt tcgacaatca cttctcggaa ggtcgtccat cctgaaatta   120
ctctatccta aacatgttta actataaaat tctctcgaaa cttttgtaac gtatataacc   180
acataaattc tcttaaactt atttgcatac accattatat ttctgaaatc gatatgttac   240
aatattattt aatatttaga ttacttttac tgaatcgaat taaatatcaa atcgaaacaa   300
atctaatcta ccaaaaataa ttttgttata aacatttctt gcctagttct acctcatata   360
cattttagtt aaagaaagaa atcacaacaa ttcccataat tcaataatta aatccacaaa   420
atcttggagt aagtaagaga aataaaaaga tagtatctta acataaacaa ttcaaagatg   480
ctctctcaca caattcacac acacttacaa aacaaaagac aaaacaatg ttttcattca   540
aatcaaaaga agttataaca ctagtacaaa aaaagcaa attcaatag taactctttt      600
tatttcccaa ttacccaaag attctctctc acttcacaaa actagctttg agagtcgtgt   660
tccacaaaat ccattaaagc tgaaacggtt ttgctcacca ttcaaacaaa tacaaaattg   720
caaaccccca aattataaca aaataatata aaaattaaac cgctaaaaag agtgaaccaa   780
caaaaatcgc cgaatgtgtg tgtaatgaga aaccgaccc atcatcccaa tcatctcttc   840
ccgtgtcact cctctctct cccacgtttc ttctctctc tcctttatgg ttttaacttc   900
tccttcttct tcttcttcaa tcttcagttt tcaaattcaa caacaattca catttgatt   960
tcttcatcat ctctctctct ctcgcttctc tctcaaatcg                         1000

SEQ ID NO: 18           moltype = DNA   length = 1000
FEATURE                 Location/Qualifiers
```

| misc_feature | 1..1000 |
| | note = Ceres Promoter PT0710 |
| source | 1..1000 |
| | mol_type = unassigned DNA |
| | organism = Arabidopsis thaliana |

SEQUENCE: 18

```
tagtgcgcgt ggggagaggg aatggtgaaa ccttagtggt taagttatga ggaaaatgat   60
aaaaggataa aacaatcaaa tgcagcttga aacggccata acataaagta ccttatggtg  120
gtgcgaatat ttttgtgttt ctttcactct tttattgctg aaagctacga cacttgtctt  180
aatatattgt ttccgcaagt cacatgatct acttttttatt taacgtctag aaacgccgag  240
atatatgatg attagtatat cacgtctatg caaattgtta gttcgtgttt ggccaaaaga  300
tatcgagaca tgtctgaaga accgagtctg gttttgagat atttcttcaa gcattactat  360
acaatagaaa aaggagacac gcgaatatga taatagcaaa aggcataaaa aggcgaaaat  420
taaagaaaaa cgtaaagtga tttggcctca atcaacggga acgtatctta attttagagg  480
ttcttctttt actttgagaa cgagagagtt tgcgtctttg cgagctgctt tggttgacta  540
aacattatca tattgaaaac caaaatacaa cggaggaata tttgtcacag tttcactttc  600
acattgtttc cttaacgttt aatcaacctt gttcaaaatt tctatagttg taatcatcat  660
tgtttacaaa attttcgttc aaagatgatt ttaaataaat ttgtgaaaga aaaccttttc  720
tgaaataagg attggatgat agtgttaaaa gaaaaatatg aactgaggca aaaagaggag  780
tggtccccgg aagattgtga aatgtgtcat ctaaaccagc cagacgtagt cacgtgttct  840
ctctagcttt atgaacttcc ttagccagca ccatcattgt gattgtagta tatatgtaac  900
cctaccttca tctctcccat tttccattct ccatatagac tcctttacaa tatacaaaac  960
ctatccaaaa gcgaagaagc caagcaaaca tattataaaa                        1000
```

| SEQ ID NO: 19 | moltype = DNA length = 1002 |
| FEATURE | Location/Qualifiers |
| misc_feature | 1..1002 |
| | note = Ceres Promoter PT0723 |
| source | 1..1002 |
| | mol_type = unassigned DNA |
| | organism = Arabidopsis thaliana |

SEQUENCE: 19

```
gtcatatctt atcaacacgt caacgatcaa aacctttagc ctattaaatt caacggctta   60
gatcaaaacg aaactaggtg ggtcccactt ttaatatcgt ggctgcataa catttcctcg  120
ataactgaag ccgttgtggt ctttctcaga atctggtgct taaacactct ggtgagttct  180
agtacttctg ctatgatcga tctcattacc atttcttaaa tttctctccc taaatattcc  240
gagttcttga ttttttgataa cttcaggttt tctcttttttg ataaatctgg tctttccatt  300
tttttttttt tgtggttaat ttagtttcct atgttcttcg attgtattat gcatgatctg  360
tgtttggatt ctgttagatt atgttattgg tgaatatgta tgtgttttttg catgtctggt  420
tttggtctta aaaatgttca aatctgatga tttgattgaa gcttttttag tgttggtttg  480
attcttctca aaactactgt taatttacta tcatgttttc caactttgat tcatgatgac  540
acttttgttc tgctttgtta taaaattttg gttggtttga ttttgtaatt atagtgtaat  600
tttgttagga atgaacatgt tttaatactc tgttttcgca ttgtcacac attcgaatta  660
ttaatcgata atttaactga aaattcatgg ttctagatct tgttgtcatc agattatttg  720
tttcgataat tcatcaaata tgtagtcctt ttgctgattt gcgactgttt cattttttct  780
caaaattgtt ttttgttaag tttatctaac agttatcgtt gtcaaaagtc tctttcattt  840
tgcaaaatct tctttttttt tttgtttgta acttgtttta ttaagctaca catttagtct  900
gtaaaatagc atcgaggaac agttgtctta gtagacttgc atgttctttgt aacttctatt  960
tgtttcagtt tgttgatgac tgctttgatt ttgtaggtca aa                      1002
```

| SEQ ID NO: 20 | moltype = DNA length = 1001 |
| FEATURE | Location/Qualifiers |
| misc_feature | 1..1001 |
| | note = Ceres Promoter PT0740 |
| source | 1..1001 |
| | mol_type = unassigned DNA |
| | organism = Arabidopsis thaliana |

SEQUENCE: 20

```
tgtggccact aaagatttac ccttaaccgg gcccatataa gcccacgtca agtggcgctt   60
atacgctctc cgtaagagag ccaacatttg gtatgtaatg ttgcaaatta ttccttcaaga  120
caataaattc aaatataatt caatattgtc caaatatagt gatgtacttc agttgtgcac  180
atagaaactc cactaaacca actttttgat agatgcattc acaaattttc aacaatgtcg  240
cgaaagtcta atccatcacc agattctaac attttaatta ttatatttaa ctatacatac  300
tctaatcagc atgagtcaaa cgtgtacaat agcccaagca tacataataa ccaaagtcaa  360
actcaaataa atgtctccaa actcaaaact tgaaaaagac ctaattatta catggtagat  420
atgactttgt cgacaagtaa accaactaat cctcgaagct accttctctt cccagttatt  480
atgtgtgatc gatttataaa tctcttcttc taataacacc tatattttc ttatgatgtg  540
aataaatata aaacttttaa cttttaaaaca tatttatccg aaatattgca cttagatttc  600
aaatagataa ataatagtac tatctaactg atattgaaaa gacctaacac ggaaaacagt  660
tttataaaaa atcccaaatg tgggtaatta tcttgatttc ttgggggaaa cagaaaatgg  720
attaagatta atcggagtcg tgtcaagcag ctcgttaata actgtagcaa gttgactgag  780
taagcatcaa cgtgtcatct ccgtaaagcc cattatttct agtctcgccg cgtcttctct  840
tccacgtagc acttcacttt ttctctcctt tgtttcctt tggaacacaa acgtttctat  900
ttataggaat aattacgtcg tccgtatctg tgtcggaaca tagatccaaa ttaaaagcga  960
cttacttaat tacacatcgt tcgtgtttttt tcttccaaaa a                     1001
```

| SEQ ID NO: 21 | moltype = DNA length = 1024 |
| FEATURE | Location/Qualifiers |
| misc_feature | 1..1024 |

|  | note = Ceres Promoter PT0743 |  |
| --- | --- | --- |
| source | 1..1024 |  |
|  | mol_type = unassigned DNA |  |
|  | organism = Arabidopsis thaliana |  |

SEQUENCE: 21
```
tcgattggcc cgatcggccc caaaatcaag ctgagccgct tcaaacttca gcttttgaaa    60
tcaccccaa  actcatgtcc tcttatcatt ataactaaag gatctttcat tttatttaac   120
tcatcgtctt gcactaccca acccaaaggt tccaactata cccgaagctt tctaaaggtc   180
caaagacttt tttttcgag  ccagactatt caagccaaga aaagccaaac cccacaagcc   240
agtacttttc aattccatat tataaaactta tctgtcttgt tttagtccca ctaaaaacaa   300
cagaatttaa tttaggttga gctaaaaccc ttgacaaaag tgtatagtcg tcgattcagt   360
agcacactca tcactcatca gatttgtatag ttgacctaaa gtatgactac tccatttcaa   420
ctaacaaatg aaaataaaag agacctaagg gttagaggat tgaaactata ctctcaagtc   480
ttttatcact aggctactac cagctagtta acttgatgga tttaagcaag aaaacgtgaa   540
atttatattc gagcagattg tttagctaaa aaagctgggg tttgaaattg cctttttctcc   600
catataagca cgtcggttcc taaataactc tttctagcgg agagtgtctt tccaataatt   660
taataaaaat ggtgtttgta tatcaaaaaa aaagaaaaa agaaactgat cgagatagaa   720
cgtttgcagt tttataaaca atttaaaaaa caaaaaaat taaactcaat gtattttta   780
ttaattcaca aacaataata aatcatagga tcgaatattt acacggtatc aaaacctact   840
cgccgctact atataaaaat tgaagtcaaa tatcaaccgc aattattaaa ccagcaagac   900
aataattcat aaacttaata taaacataaa taaattaatg ttacacaacg atatatggtg   960
agggttatta ctatcttctt cctctcaaaa cacatctcct aaccttaagc tttagacggc  1020
ctgc                                                                1024
```

|  |  |  |
| --- | --- | --- |
| SEQ ID NO: 22 | moltype = DNA  length = 1000 |  |
| FEATURE | Location/Qualifiers |  |
| misc_feature | 1..1000 |  |
|  | note = Ceres Promoter PT0758 |  |
| source | 1..1000 |  |
|  | mol_type = unassigned DNA |  |
|  | organism = Arabidopsis thaliana |  |

SEQUENCE: 22
```
agctagccac atcagtgacc aaaaaagata ttaacaaac  caaataaaat aacaaatttt    60
gatcatttgg aataaaattt ataaaaggaa cgaaagcgtc ttctcacggg tcccatccat   120
tgaaatatat tctctctttt tgctctatat aataataacg cgtactaatt tgtagtatat   180
attattacaa agtcgatatt tgattgtttt gtgaacgttg atatattaat tttcttggat   240
gatgacaaaa aaagtcatag aaagtaacgt gtgaacatag cattaacaaa atacaaacat   300
aatatataac caaatatatg aaaataggat aaaatctcat tgaatagatc ttcttctatt   360
caaatatata aatatttgtt tgtctataaa attaacagag cattcacatt atctaaaata   420
atagtaaaat caaaataaaa ctaaataaaa ataactctgg ttttataacg attgatttta   480
aatattagtt tttgttgtaa agagatcatt atatatgtct gtaatatttt tatactgagt   540
tacatgatat ttagttatta tagcgtaatt aactaagata agaaattaac taaagtgata   600
ttctgattat tattattttt gttaggacac gtacgtgaa  aactaaaca ctataggtta   660
caaaacggta taataaactc accattactg gaaaatgttt gcatttgact caataagtaa   720
cttattataa gttactgata taatgcatag ttttgaaatt cttaaataaa ttattttggt   780
ttcgcatgaa aatatgaaag gagagaaatt tattattgtc acttatatat atacatcg    840
taatcatttt ttcgtgaata atttctctctc ccattccatt aatttctcagt atctctcttt   900
cttccctta  ctttattgtt gcttttaaac cttcaattgg ctcataaacc aaatatataa   960
tatcaaaaca aacaaacaaa aaatcagaat tccctaata                          1000
```

|  |  |  |
| --- | --- | --- |
| SEQ ID NO: 23 | moltype = DNA  length = 921 |  |
| FEATURE | Location/Qualifiers |  |
| misc_feature | 1..921 |  |
|  | note = Ceres Promoter PT0829 |  |
| source | 1..921 |  |
|  | mol_type = unassigned DNA |  |
|  | organism = Arabidopsis thaliana |  |

SEQUENCE: 23
```
aaagttttga attattggga atcaatttcg aagttttgta attctttggg ggctaatagg    60
atattttatt ttcttggttt cgtctattgt tgttttcta tttatggttg ggcttttaga   120
actctggaca ggcccatgtc atatgttttc ccttctcctt atatttttca ttttttcattt   180
tgttaaatta atgcataata tccaaaaaca atttaaattt tgaaggaac ccttttagtta   240
cggctccgaa gctttcacaa gtgagaatgt gagatcaaag aaggcaaatg gaggatttta   300
aaagttaaaa tcatctttta tctgcaaaag ttgacaattt tttgtatca aatctaaatc   360
atcaaactct cttaaactac aagagcataa caacctctat gtaatccatg aaataatctg   420
cttgaaggac ataacataaa tcattatggc tagagtgact aacttcaatc aaatcctctt   480
aactctagct cccttacaat ggtatcgtaa aacattatgc attagggatt gttgtcctag   540
gaaataaaa taaaaatccc cacagaccaa ctaccatttt aacttaaaaa taagcttcgt   600
ccgcgacgaa ttgtttttcca tcctaaaaat agaatggtgt aatctgctaa tggtttagtt   660
ccattaactt gcaagttcta ttgaaagcct aaatgtcaat aaagatatta aaattcggag   720
tcaaaagaca aatgaatcaa aagcaacaag acaagtcagc tccattcttc actacccatc   780
ttttacaata aatcatctct cttttcacaa atttcaaact actctcattg cccttttagct   840
ttgttataga gccaacacta cagagagact cacacacttg tttcaataat taaatctgaa   900
tttggctctt cttataaact a                                             921
```

|  |  |  |
| --- | --- | --- |
| SEQ ID NO: 24 | moltype = DNA  length = 763 |  |
| FEATURE | Location/Qualifiers |  |
| misc_feature | 1..763 |  |
|  | note = Ceres Promoter PT0837 |  |

| source | 1..763 |
| --- | --- |
| | mol_type = unassigned DNA |
| | organism = Arabidopsis thaliana |
| SEQUENCE: 24 | |

```
aactacaagg gagacataat atcaccatct ggttcctgtt atcatctgaa gatttcttgt   60
tttaccttcc agtgataaaa tgatcccttat aatacatata gatatattaa attgctgtat  120
tttaagatta tagatatata aggtacatga gagtgtttat ttaaaaaaat tcacttggaa   180
ttcatgtttt gtgatacgtt agattggaat ccatttggga aaagaagaat catctgttct  240
tatgtctcaa attttgactt cattcacttt tcttcctgtc ttttaagaaa gcttccacaa   300
tctaactgtt cgatgtgaaa actgagattc gagtaagaaa atgtgaactg tgttatactg   360
tttttaatt agataattta gattgcactc agataaatta ataacattcc tcgaatactt   420
ttatgtgatt ggatatatta ggtatatctg ccaaccaacc aataaactgc tatgtttaaa  480
caaattaaat aaattagtat atgttttactc aagaataaag aagatagaaa agaaaattct  540
atatgagcta aatttgctgg aggaggcatc ggacgtgggt accagaccttt tccaagcaca  600
cgagtagtgc ttagccatgt catgctaaca tacaccatttt ggttcataca aaatccaaat  660
caaaatctat ttttaaaatc ttttgcacac gtctttgaaa aacacctctc atactatagc  720
tacgggaagct tcaatttcaa ggtttgtcta aaagctaacg att                    763
```

| SEQ ID NO: 25 | moltype = DNA length = 751 |
| --- | --- |
| FEATURE | Location/Qualifiers |
| misc_feature | 1..751 |
| | note = Ceres Promoter PT0838 |
| source | 1..751 |
| | mol_type = unassigned DNA |
| | organism = Arabidopsis thaliana |
| SEQUENCE: 25 | |

```
atactggtat gcttaaggtt gaagccaaga tctctgtctt acccaagtaa ccactttcta   60
ttagaaggga tcaacactaa gaatatggag atttaagcct aagggctaag gcggttctca  120
acaatacatg atgtgaatac aatcacagac gatttactga ggtttgttga taagatcttg  180
atcagtctct gcatcatctg ttcaacaatc tcaatctttg actgtttgct ttcggagcca  240
taaacagagg aatccccttat tccctgttat aggagcaata caccaagtat tatttccatg  300
gctgaaattc tcttatggaa acctaattgt tccattgaag ctgtaaaatc gaatctggtg  360
aatattctcg agcaaagccg catgctaatt atgtcaattc agaagagttt gattaggaga  420
ctcgaagcga gtttgatgat cttttcttgat gttcaactcc gattgtaagg gtataattga  480
cttttcatgt attacggctc caccacctga cactaaggca ctctttgtcc atctcgttga  540
tatcatcgga ttcggatggt aaaaataaaa agagcagagg aaacttgtta ctcatgcaag  600
cttctcaggt gccacgtcac tccattacgt gtcatcttca cacaccatct cgctcaaaac  660
cgatctcatt tttcaaacct taaaggcaga agcaactgat taagttaaca ctcttgagaa  720
gctctcgatt aagcttgaac ttggaggatc a                                  751
```

| SEQ ID NO: 26 | moltype = DNA length = 669 |
| --- | --- |
| FEATURE | Location/Qualifiers |
| misc_feature | 1..669 |
| | note = Ceres Promoter PT0848 |
| source | 1..669 |
| | mol_type = unassigned DNA |
| | organism = Arabidopsis thaliana |
| SEQUENCE: 26 | |

```
tctctttaaa tcagttaact aaccgtttat atatttacga taaggtttga agagattatt   60
gataaaataa tacatttcat aatcccgcgt tcaaccgttt aaagtaacat ttaagttgac  120
tatatctaat tttttttcca ttaaatatgg agctggtaaa cttatcaac ttctaaaaag   180
tgtaacaaca aaaattaggt caatcacaat tctgtttttt ttattatttt ggattggactt  240
ccaattgcaa atagtcttag tgatcaccat tatcatacat atatacatca gtaggtttc   300
atcatgatat accacaaagt atttgacaag ccatatggtt ttggatcaaa aagtcggtcc  360
aaaattaatg ttttatgtgc aagaaccgac ccattgtaca cacgtgttaa catcttcaag  420
actttcatct ctatttttct tttggtcatt aagatacca ttgatccgaa tctgttacat   480
tcccacctac ttttttaatt tttactatcc actccaaatt aaacacaacc gatgattta   540
ataattggaa gcttttaaaa atatttcaaa acaagcctct ttgtgtttgt ctatatat    600
acacgtaata agaaggtgaa tgaatctcac agcttacttg ttctaaggct tccaataacg  660
aaaacagta                                                          669
```

| SEQ ID NO: 27 | moltype = DNA length = 702 |
| --- | --- |
| FEATURE | Location/Qualifiers |
| misc_feature | 1..702 |
| | note = Ceres Promoter PT0863 |
| source | 1..702 |
| | mol_type = unassigned DNA |
| | organism = Arabidopsis thaliana |
| SEQUENCE: 27 | |

```
cgggaaacga caatctgatc tctagtccag tcgattggcc cgatcggccg attataaact   60
tacatgagac aagtataaat aattattata aactttattaa gttaagatc aaggcttttg   120
tgcaatgtat caatgaatgt tagatgtgat atgatgaaag caatgttttta aacacataca  180
tagtcattga tcggaatgtg tgttattaga aatgcatgcc taagccgata gggttatcta  240
tgtttggtct tggacattat agccaaattt cgaatctaat tcttccaata tatattttt    300
ttttttttgct tagggccact actagtattg cttatcaatt ttaagagctc atgaaaatgc  360
aacaatatag tagttgcaaa tccttgtttc aagagaaatc aaagggccac ttgtgaattg  420
aataataata atatttgcaa ataaccttttc actaaaccat accaacaaaa ccacacagat  480
ttggcaaaga cataaccttt gggagacgtg aaaaggctca aatttgaca attgtcctta  540
caaattcgct cattagtgca attgtgagat ttgtttgcat ccaaatccaa ttcataactc  600
```

```
acactcgtct caaattcgaa aaggcctgca gggccagtgc actgggatcc aacaatgtcc    660
tccgactcgt ccaagatcaa gaggaagcgg aaccgcaccg cg                       702

SEQ ID NO: 28            moltype = DNA   length = 435
FEATURE                  Location/Qualifiers
misc_feature             1..435
                         note = Ceres Promoter PT0879
source                   1..435
                         mol_type = unassigned DNA
                         organism = Arabidopsis thaliana
SEQUENCE: 28
ttctaggaag actggtcaag ctaagctgtt tctgtttttt gttttgtac ttactttt       60
gtttgctagt gggaactggg tttattgggc cttgaagttg ataaaagatg aataaaagac    120
atatcgccta aagcccatat gagaagcaga agacaaaaac ctccaacttt gggcataaat    180
tttgattata gttaaaagtc cagacccaat ttggcacctg gctagttac gattctaagg    240
catgacacct gcctaatatg tttattacag aaaataaaga gaatcagcta ggtgtccctt    300
attgaacaca ttaacaaact ccaacgacac tacgtgtctt cgtgactctt actatatcca    360
aaaacctata gctaaagctg aattttccat gattagtata gtcccaacca aaaaaatact    420
gaagaaggca taagc                                                     435

SEQ ID NO: 29            moltype = DNA   length = 397
FEATURE                  Location/Qualifiers
misc_feature             1..397
                         note = Ceres Promoter PT0886
source                   1..397
                         mol_type = unassigned DNA
                         organism = Arabidopsis thaliana
SEQUENCE: 29
agtgtatttg aaaacgacat tgaagaatta atatattttt ttttaatttt agttttttat    60
agtacaaata ttaaaacaaa caatcctacc atatcataaa atttgtaaat aacattttaa    120
gttttgtttt gagttttaat taattttcta tgcaaaaaaa atgaagtcaa tagactaagt    180
gaatcatata gtataaataa acacaattta aatagtttca aataaattta gaaagaataa    240
aacaaatagaa aatcagaagg tgtctgtttc ctcctcgcaa catacgatca aagagaaaca    300
acttgaccct ttacattgct caagagctca tctcttccct ctacaaaaat ggccgcacgt    360
ctccaacctt ctcccaactc cttcttccgc catcatc                             397

SEQ ID NO: 30            moltype = DNA   length = 1024
FEATURE                  Location/Qualifiers
misc_feature             1..1024
                         note = Ceres Promoter YP0007
source                   1..1024
                         mol_type = unassigned DNA
                         organism = Arabidopsis thaliana
SEQUENCE: 30
agcagaacaa ctatatttat tgtgtcacat aaatctgaga tcatttataa ccaccaaaga    60
acctatacac agtaaatgac aaatgtatct ccctctatct ctattgccca tatgtagatg    120
ctaaagtaag atttctcttt tttttaatgt acttttttt gtataaagta tattccataa    180
gaaaaaggaa aagcttgttt atggatcaat tgaccccaaa aaaagttttt agatcaaagc    240
ccaatataaa aaaaaacac agtagtgaca caaaggaact taaataaacc atgaattgat    300
ctataaacag tagagatcga taaggcgaac attttccatg tgaagtgtct tctttcatct    360
ataatttttt tgcatccaa taatttcctc tataatatca ttcacataat tgatagaaac    420
attatgttag aattgtccac atcatttgag ctgtaatata ttctgttta caaaattata    480
tggtagttgc ttaatcttat gtccatcttc ttctatgcat cgttttgcgc cctagttgtc    540
cagtccattt caactaccta cctctaattc ttatcttaaa acaacatttt ttaatttaag    600
tattgctc aaagactaac tagatagaaa accgttatta aacattaaaa gaattaaaag    660
tcttacatgg aaaatgtagg tttataaacc acgagttatg attgacaata aaaaaaatgc    720
aaatcatcaa tcaaaagaga cttgagtgcg actctatatc aaccattgca attaaaatta    780
tctatcacaa aaattttaga cagattaagt taatttagtc taaattcact aatttatttt    840
ctataattag taattaacta tatttattta tttacacatt ttctgataat ttagaaattt    900
gcatgaataa caaatataag attttggaaa ttagtagcaa atttaattaa taatttttt    960
tgcctaaatg aaccaaacta taaaacctcc acatacacca gtcatcaaat ttacagagac    1020
aaca                                                                 1024

SEQ ID NO: 31            moltype = DNA   length = 1000
FEATURE                  Location/Qualifiers
misc_feature             1..1000
                         note = Ceres Promoter YP0008
source                   1..1000
                         mol_type = unassigned DNA
                         organism = Arabidopsis thaliana
SEQUENCE: 31
ctcgagagat gaagtcttag taatgtttga acaaacaata atcacgtttt ccatcaaatt    60
cgagcattta aagtttatat tactacatgc cccaagatga taccgtccat ctcatccgaa    120
aatatttctg aaattgcgct aagacaacaa tgtttgctca aattcgatca tttaaagttt    180
acaaatctct catcaatctt acaaacttct cacactaaac agaggtacat atttttctat    240
aaagacaaaa ggttcgaaca gctgcttct caactcgagt tgtttgtcag ggcctctctt    300
cactaactac aagttggtac ttcaaatatt ggtggctagc ttcacgtgat attgtctaca    360
aattaaaccc atgaaaaagc tgcattaatt gttccaagtg aaccctgagg agtgtcaata    420
gtctttgctt tagtgtgatc attaaaccaa atctctaaat tcctaatttg tactaacatt    480
```

```
tggaacgtat ttcctactct tctccctgct ccaactccca aaaataagat tagtttagatt    540
tctataacta atatacatgt atactcccaa aaacagtaaa accatattaa taaagctaat    600
tttgcataga tttatttcgg taaaccggcg gttcaagttg gggaaaaaaa agacaaacgg    660
tctaaagtca tccaaagaca aaaaaccaaa gacaagttga gagagacgag accaatcaca    720
acattgcttc gtagattgcg tgacatcatc cttgacggct actttcattt gtgtcttatt    780
tggataaaac gcacgtgttt aattcacgaa ccttcatagc aataagaaat ttccattact    840
ttcatatttt caactttttt tattacccat tacatgctta aaatattaat tcacaagtct    900
ttgtcaaaat tcaatatttt ccaggttcat gaaccctttt tatctcaatc tactctataa    960
tatctcccta taaattacaa caaaacctct ttatttttca                         1000

SEQ ID NO: 32           moltype = DNA   length = 999
FEATURE                 Location/Qualifiers
misc_feature            1..999
                        note = Ceres Promoter YP0019
source                  1..999
                        mol_type = unassigned DNA
                        organism = Arabidopsis thaliana
SEQUENCE: 32
gatataagta gaatcatttt ttgccgccgt ttctcgctaa cacaccgaaa actgaatcaa     60
atctcctagc tcttctacgc aaaatcgagt gcatcgacaa tggcggaacg tggtgtcgaa    120
cgtggtggag atcgcggcga tttcggacgt ggattcggtg gtcgcggcgg tggaagaggt    180
ggtccggaga gtcgtggtcg ccgtgcaggt cgtgctccag aggaggagaa atgggtgcca    240
gtgactaagc ttggtcgtct cgtaaaggaa ggtaagatca caaagattga gcagatctac    300
ctccattctc tcccagtcaa ggagtaccag atcatagatt tactcgtcgg tccttcattg    360
aaagacgaag tgatgaaaat catgccggtt caaaaacaaa ccagagccgg tcagagaacg    420
agattcaagg ccttcatcgt cgtcggagat agtaacgctc agtcggatt aggagtcaaa    480
tgctccaagg aagttgcgac ggcgatcaga ggcgcgatca ttctcgcgaa attgtctgtg    540
gttccgatac gaagaggtta ttggggtaac aagattggaa aaccacatac ggttccgtgt    600
aaggtaaccg ggaaatgtgg atctgttact gtacgtatgg ttccagctcc gagaggttct    660
ggtattgtgg cggctagagt tcctaagaag gttcttcaat tcgctggatt tgatgatgtc    720
tttacttctt ctagaggatc caccaaaact cttggaaact tcgtcaaggt atgtactttc    780
acaatggctg ttttggtttg atgaactctg aattaggcag tgaaaagta atcattacca    840
gttaagtgaa tttatattga agattaggat ttagctgatt gtattggttt gagcatgtga    900
gtttgtgttt aagattgctt gaattgaaat gctttaggtt gtttgattac gctaaattct    960
gactaatgta attcaaattg ttgttgtttt ttttggtc                            999

SEQ ID NO: 33           moltype = DNA   length = 1024
FEATURE                 Location/Qualifiers
misc_feature            1..1024
                        note = Ceres Promoter YP0028
source                  1..1024
                        mol_type = unassigned DNA
                        organism = Arabidopsis thaliana
SEQUENCE: 33
gtcagtgaag tcgattggta gtacttgaaa cacttggttg gtttcatgta tttggcctat     60
atataaacaa acatcgtaat tatatacgga ttttttttcgg aattttacgc catatctgta   120
agtatatata acatgcatgt cgttttcaaa ttcatatgat gaacgatcca cgtaagtgct   180
actactccta caatattgca tgagagagat atgtatttat aaattttatt ttgaagaaga   240
aataagaggg aaggttactt gggtggatcg atgtgaaaac aaaagaagaa aaagcgaaac   300
ccactaagcc attacatgat atcgaccttc ttatcttttt cctctttatt ttattttct    360
catcttcttt ttgtcaggac ttttttctac ttaatgaaca ctccaaacta tctaactaat   420
acactcccat gtagaataaa gaaaattata taagatattg ttgatatttt gtaactagaa   480
aatatatttg ctctgtaatt tttcgtaagt taaatcaaca ttttaaagta gaacaaata    540
ttactgcaaa aagtaggatc attatttttg tccaaaatct cagttagcta tagggttgta   600
gtaaaaacaa aacacattct tgatttgccc caaaaaataa agagagagaa gaatattgtt   660
caaaagtggt ctcttctctc tctaattatg ttttcactaa acccaattag attcaaacag   720
tctacaaagt ccaaaagata aacatgggac aacaattcga tgcaaaaaat cctcttttca   780
tgctcttttt ttattctcta gtctttttaaa ttactaataa aaactcacaa atccaccaaa   840
cccattctct acaactcacc ttcatctaga tttacccact cccaccgaga aacacaagaa   900
aaaaaatata catatataaa tatacaagac aacacatgat gctgatgcaa tatacacaac   960
aaagtattaa atcttagata ttgtgggtct ccctttcttc tattcatttt cttattcatt  1020
aaaa                                                                 1024

SEQ ID NO: 34           moltype = DNA   length = 1024
FEATURE                 Location/Qualifiers
misc_feature            1..1024
                        note = Ceres Promoter YP0039
source                  1..1024
                        mol_type = unassigned DNA
                        organism = Arabidopsis thaliana
SEQUENCE: 34
ccgttcgagt atttgaaaat ttcgggtaca cccgcctaaa taggcggacc ttatctagta     60
tatatataca tttgaactat attgttact ttttagttga tttaggctat gtcatgacat    120
tgacataaat ctacctgtta ttatcacgt gtaattcgta taaagtgtaa actagaaagt   180
tcaaatacgt atttgttttt gttctgttat ataggattgt catagttgta aatctacaat   240
ttattacaac atgaataagt acacaagcaa tgtaattgga tttaattgct aaactcttta   300
catggtcaat ctaaatttga taagaaatac gtcacatatt actaagactg atagtttttt   360
tgttgtcacc aattattttt gttaaattga cgaaaacaat tccaaaaact caaatgtaca   420
aaatcataca gtctcacaaa catctcatag agaaagatat aaatctccca tatgggaacg   480
```

```
ataacacgag gtcgaaatac tattcgtaaa actaaaacgc cttagttata aatcgttagt   540
tgtaaccgcg gtcgagaata catacagatc cacgaaacta ctactacaca tgctgctgaa   600
ttggaatttg gaaagacca tcttctttag gaagagctca cccaatgagt gacaaaggtg   660
tcggtggctt gttttctacc catatgtata catcaaatgg tagtttcatt aacgtttggt   720
tttgagaaaa gtaagacttt ggctagtagc taggttcgta taataaaac tcttttgaga    780
aagttcatca ctggtggaaa atgttaaacc ggttttttct cattttttcc gccatgttaa   840
ccaccggttt aaaagaccg taacacattg aaagattaat aagggtatat tgtaattac    900
ggtttgctgg caattttaa ttattatttt aattagagaa aatagagaag ccctatcaat    960
gtacatggta tatataaa aggcaaaacc ctagaaaacg atactattcg actcagccgt    1020
cctt                                                                1024

SEQ ID NO: 35           moltype = DNA  length = 1024
FEATURE                 Location/Qualifiers
misc_feature            1..1024
                        note = Ceres Promoter YP0050
source                  1..1024
                        mol_type = unassigned DNA
                        organism = Arabidopsis thaliana
SEQUENCE: 35
aatctgatct ctagtccagt cgattggtac ttgagggaaa catcatattt ttaaaccttg   60
tctcagtaag ctaacacaca cccttgtga ttacttatcc atgtttatcc acaagaatgc    120
agttggatta agatattttc ttctttgttg aaatcggtcc tcaaggtgtt catgtggtct   180
gcaaaaaat tcccaaaaat aaagatagtg acatctgaaa tcgataatgg attagacgaa    240
gagtttcgtg ttattccttg gtatgggcgg gtttggggac agatattttg gcacagacga   300
ggactaggcc actgtggtcc tgcagcatta ggtgtcccct tccatgtcctg cattacattt   360
tattgatgga ttcatcaccc tatctactac aacggctaca caaactatga agagttttgt   420
ttactaataa atgcccaagt gaggggtcga tcgaacccgg gacacgtttt tcagtttacc   480
atatagaatt atccttggaa cccttgatac tccatagaac atcaccacct ctgttgtcat   540
ctcaggaatc caggttcaaa cctagtctct ctctccctag tgggaggtat atggccactg   600
ggccaatgat gacaaaatgc aaaaaaaata aaatatttgg gggttcatta tctaaaatat   660
ctcttgtgtt tgtaagtttt ggttgcacac tcgtgtggtt gaagtgtgtg tgagaggtac   720
tatacaatac actctgcttt tgttttgtac ctatctcttt ctcttctcca catatccaag   780
actttgggga taaagctgag atcattggtt gccatttggt tgtgtagaag caatcaccca   840
tttgctttat ccgaggttga taaatttcct cgggttctcc ttctgacacg tatgacaaat   900
tctaatagta tattcctcgt agatattacc tatatattct caatagttgc aggtacttaa   960
ggctttgtct tggcatcctc gtcctcttca gcaaaactcg tctctcttgc actccaaaaa   1020
gcaa                                                                1024

SEQ ID NO: 36           moltype = DNA  length = 999
FEATURE                 Location/Qualifiers
misc_feature            1..999
                        note = Ceres Promoter YP0086
source                  1..999
                        mol_type = unassigned DNA
                        organism = Arabidopsis thaliana
SEQUENCE: 36
cttatccttt aacaatgaac aggttttttag aggtagcttg atgattcctg cacatgtgat   60
cttggcttca ggcttaattt tccaggtaaa gcattatgag atactcttat atctcttaca    120
tactttttgag ataatgcaca agaacttcat aactatatgc tttagtttct gcatttgaca    180
ctgccaaatt cattaatctc taatatcttt gttgttgatc tttggtagac atgggtacta   240
gaaaaagcaa actacaccaa ggtaaaatac ttttgtacaa acataaactc gttatccgta   300
aacatcaatg gagtgtatat ctaacggagt gtagaaacat ttgattattg caggaagcta   360
tctcaggata ttatcggttt atatggaatc tcttctacgc agagtatctg ttattcccct   420
tcctctagct ttcaatttca tggtgaggat atgcagtttt ctttgtatat cattcttctt   480
cttctttgta gcttggagtc aaaatcggtt ccttcatgta catcatcaa ggatatgtcc    540
ttctgaattt ttatatcttg caataaaaat gcttgtacca attgaaacac cagcttttttg   600
agttctatga tcactgactt ggttctaacc aaaaaaaaaa aaatgtttaa tttacatatc   660
taaaagtagg tttagggaaa cctaaacagt aaaaatttg tatattattc gaatttcact    720
catcataaaa acttaaattg caccataaaa ttttgtttta ctattaatga tgtaatttgt   780
gtaacttaag ataaaaataa tattccgtaa gttaaccggc taaaaccacg tataaaccag   840
ggaacctgtt aaaccggttc tttactggat aaagaaatga aagcccatgt agacagctcc   900
attagagccc aaaccctaaa tttctcatct atataaaagg agtgacatta gggttttgt    960
tcgtcctctt aaagcttctc gttttctctg ccgtctctc                          999

SEQ ID NO: 37           moltype = DNA  length = 1024
FEATURE                 Location/Qualifiers
misc_feature            1..1024
                        note = Ceres Promoter YP0088
source                  1..1024
                        mol_type = unassigned DNA
                        organism = Arabidopsis thaliana
SEQUENCE: 37
tcgattggga ttactacttc atctagtaag gttctgaaaa cgtttgttgt tgataaggaa   60
gattcgtctc aggttattac tgttgatctt caaggtttgt gattgtgacg cttatacatg    120
tgctgaaact gtggtgttta tttattgaaa acaaaaaaaa agtctctctt gtagtttcat    180
tgtactaaat agaaaacaag aaacgttttt tcctttaatc ttctacattg ataatattgg   240
atcaaaggat tgtttctgca agacacaaca caaacatact tatactagtt tacttctact   300
aagtactaac tacatacccta tacacacact tgcacctaga cttacttcct agacatcatt   360
accctaaggt agaaccaagc ttcaagcaa gttttaccga caactcttac attacaactc    420
```

```
tagtctgtag tctttaacgt agacttacta actagtcatt agtggtttaa tttttttaaat    480
tttcatccat atgttttgt tgtagatata aactaaagtc ggtcacattt aataattgtc     540
attatgtccg cgtaaaagtc aattcagcta ttggacattt atgaaatgta agattttctc    600
tctcatttcc ccgtgcgtga agacatgcat tggttttct gtaataatca acaaatccaa     660
accccttttc gatctttatt tggacattgt tagagacaaa atttctctat agtcttttc     720
ctaatttgat accatgtttt tgtttctgca caaatttact cactggttta actaactatc    780
cacttattta tgattttacc attaggcgtc agctagccct agtcaaattt gtaaacaagc    840
caagctatct acataaatcg agatgtcatt aacgttaatc gtcgttaatt cgaatttgaa    900
aacatagata gctttagcag tacaatgggc aatggtaaga agaatagcaa aaggcccaat    960
atttggtttg cagaaattaa agcctaaaaa aaagcccac agatatttgt caaagaaccc   1020
taat                                                                1024

SEQ ID NO: 38          moltype = DNA  length = 1024
FEATURE                Location/Qualifiers
misc_feature           1..1024
                       note = Ceres Promoter YP0092
source                 1..1024
                       mol_type = unassigned DNA
                       organism = Arabidopsis thaliana
SEQUENCE: 38
aaagattgag ttgagagaga tggtggagac gcagaacaga caaagggagt ttaccatata    60
gtgctctaaa gggcaatgag attgcagtga tgtggctatc cggggaatca tcgcaggtta   120
ttccttccca tgagcaacaa tcaatggatg ggttccaatt cagaggagaa acagaagaag   180
aaacgtttcc agagaaccac agtagggatt ctcgatcttg cgagttgcag agagcctctg   240
aaactgcaat agaaaggaca ctgatgaaaa gaacacactg aaggagtatg ccaatcatgt   300
gaaaactcag agcttgtatt ggtcttgtgt ttgatgaagt tctcacaaaa cctttggctt   360
tgaatctccc ctcattagtc atggtgagaa caagaacaga acgagaaaca gacaaagaag   420
atgaaaaaac ttgttggcca gtgttgacta aggggggaata gccccagaca taacaaaatt   480
agacttgtcg tacatcttta atattttttt atctgtttct ttgtcctgac gctttcatta   540
ttcctgtgat caatttttctc ataccattgg tccatcgtta atcctttctt aatttcattt   600
tctacgtaac atgagaggag accaagtcct atgagaacag ttgacgtaac agtggttgtt   660
aagttaagtt aaaaagagga agctagtgag agtgaccgtt aggtagaaga gtgagatctt   720
taaccactct tctttctctc tctctctgct ttttcgtcg tctttcacat ctactgttcg    780
caaactctct tatgcttcca ataatggtga taccaattga gacttgcagg agaatctcct   840
cttctccaca ctctatcaac tggtcagcca tggaatggtc gtttcagttt caatattcct   900
ggattctttt taaggattcc tgtttctctt ctgttcctgg tatattctta acgacgaaat   960
tagtatcgga tcctggtaat acatttttgaa gcttttaagt accattgcac tgggatccaa   1020
caat                                                                1024

SEQ ID NO: 39          moltype = DNA  length = 1020
FEATURE                Location/Qualifiers
misc_feature           1..1020
                       note = Ceres Promoter YP0096
source                 1..1020
                       mol_type = unassigned DNA
                       organism = Arabidopsis thaliana
SEQUENCE: 39
gaggtcagtg agtcgattgg tgcaaaattg aaaaattgaa gggtgaaaca aatttaaaga    60
taatatctat taaatcctct aattttaaaa atttagcaaa aattgtattt tcttatggat   120
ctgttagttc acacgtatct taattagtac caaatcatat ctaatgatta gtgataaaac   180
tagttagata tctatatgtg tctttaccat ttaacttgaa tccttcttct ttttttacg    240
taaacaactt gaatccttcg ttaatacata aatttaaagc atttttttctt taattctatt   300
gatcggtata tatttactat aagttttagc tcatatgcaa tttcaaatga tatgcttta    360
aattttgtct aggtgtgata gttgtatctt taacataaat cttatagcaa aattatactt   420
gatattctaa atttatctat ttgctcttgt gaacctcata ttagtctaga gaaactttga   480
aatccttca attagttgta tgtccaaatc attttttacta acatttatta gtcttttaa   540
ttaagattat tgttagaaaa aaaaagattt tttaaaaata aataatatgt tttagataca   600
atgtgagtta ggcttcttat attttaaaaa ataaatttat ttcatactta aaaatagttt   660
ggaatttcaa tttatttggc tgaataccat aaaaatatgc aatttgaacc ttataccat    720
tgactatttg gtgttagaaa ccctttaaca aaaaaaaact atttggtgtt agatatcaaa   780
ataaaaaag tttaaccatt ggtttcttat attgaattgg atattgttac atgtattaaa   840
gttttttgg tttaattttg aaacgttgat agaaactatt aagtttaagt ttggtagtat    900
atttatttgt ggaaaattta attgccatta aatataacgt caacttttt tggttttttt   960
tgagaagtta cgttgtgatt ttgattccct atataaagt tagattacgt catttttaa    1020

SEQ ID NO: 40          moltype = DNA  length = 1000
FEATURE                Location/Qualifiers
misc_feature           1..1000
                       note = Ceres Promoter YP0097
source                 1..1000
                       mol_type = unassigned DNA
                       organism = Arabidopsis thaliana
SEQUENCE: 40
ttcatcttta tatttaagag tttaaaaact gcaactttg ttttttcttc actaagtctt     60
atggccacag ttaattaaaa gcagatgaaa ggtggtccaa tggaaaagga gaatgtgatt   120
gggctagttg ggagagttct gatgtctagt gttgggtaca cgtgtccgtc agttacacat   180
agcattaaat cagacggcat gtcattattc aaatctagtt cacatagtac gactaatagc   240
tgataaaatta atgattatac agcatatgaa ttatgaattc aaaaaaaaa aaaaattgaa   300
aatgttaagg agatgctata tttacaaaa ttcatcgcaa tgctttctac taatttgcta    360
```

```
agtggtcttc tccagttagt cttgtcgatt ccaagcgata ttattaaatc ttgaagcatc    420
gctcaaagca ttatagctta agataaccaa attgttatta aaaacaccta gtgaattttt    480
taaattaaaa caattttgat atctttgtaa tatctaatac tactcttcct gtgtctaaaa    540
ggattaattt tcaaaaattt cacacatatt aaaaaaaaaa aaaattact agctaaacaa     600
ttttcaataa tcataaaaca atagtaactt aataattctt ttttattttc aaaatagtcc    660
ttcaagttta caattcattt tagtattata atcaacaaaa tttgtattaa aaagttggaa    720
aattaatctt tgtggaacaa aaaaatctag aaatcattt  ttagaattag agagaggttt    780
gataaaaaaa aataaaaaaa aatagagaga ggtagtacat actaaacgat gtgatactac    840
tattgacaaa atcttaattc tcagtttagt agaataaact agaaggaatg aatgaagtaa    900
atgcgaatcc aactactaac aaaccctact tagtcatcat attttcccat atgaaatccc    960
tatataaacc catcatcatc tcccactttt ttcatatcca                         1000

SEQ ID NO: 41               moltype = DNA    length = 1004
FEATURE                     Location/Qualifiers
misc_feature                1..1004
                            note = Ceres Promoter YP0101
source                      1..1004
                            mol_type = unassigned DNA
                            organism = Arabidopsis thaliana SEQUENCE: 41
ttctcgttct ctagaatatt gctggaccgg attaggtcaa tattattggg ccagattaga    60
tattgaattg tcgacgttgc ttacgttacg ttatatcttg tttaagaatt aaacctatcg    120
acttagtctt aattaagaaa acattgcctt aaattctctg gtctgcgacc gttttttttga   180
ccgttaaccc ctaattaaag aaacaaaata attatagaaa gagcactgaa atgtgattat    240
tttaacagta ctcttatgag aaaattcgta cttttttagtt ttttttttgt acaaatctct   300
aagaaaaaca ctactactaa ttaagaaacg tttcaaacaa tttttattttc gttggctcat   360
aatctttctt tctcggtccg ggactaaccg ttggcaaaaa aaaaaaaaaa gttgacaata    420
attattaaag cgtaaatcat acctctcaaa taaaaacttg aatttggaaa caaagacaac    480
taaaaaactc gaatttaaga gaattcctaa atcaagtga agtatcatca cttggtaaaa     540
tttcataacc gttggcttct atttctatgt gtgccttggt ttgcaggaga taatatttca    600
tttccaacca atgatattcg tacacatagt caaacaaatg tttgtctttg ttattatatt    660
gagaaagaaa caagaagag agagagagat agataagacg aaggaagtga agcttccaag     720
cgcccaccgt taaaaatctc gtgtgcaagt ttcaaataca agtggccggt ggtctccata    780
atttgatcgt catccaatta aaaaggaaga aaaagcgtgt tttatacaag aaaactcatt    840
aaaatagcaa gtctagaaat atctcaacac taatctacca cgtctattac acacacacac    900
acacacactt gatcttaatt tattttcaag attcaagaaa atacccattc cattaccaca    960
acttgaccac acgcctatat ataaaacata aagcccttt  cccc                   1004

SEQ ID NO: 42               moltype = DNA    length = 1000
FEATURE                     Location/Qualifiers
misc_feature                1..1000
                            note = Ceres Promoter YP0102
source                      1..1000
                            mol_type = unassigned DNA
                            organism = Arabidopsis thaliana SEQUENCE: 42
atttggttga taacgttttc actcgactaa ttatatactt cagaaggata gtaatagaat    60
accaaaataa ttaaatgatt ggttagtgcc ttagtggaga cttttttaacc gattctaata   120
gactaatgat gtagctaagc atttatttgg gatcatcact gtttgaaaac gtgaaatgtg    180
ataaaagtta tgaaacgatt aaaatataaa ataaccgtac aaaacattat gtaccgtttt    240
tttctctgtt cttttggcga tttggtttag ttcgttacta tctaaatgtt attgcagata    300
tatatataat gatgcatttg catctgagga acatataatt ccggttaaca cttccaaatc    360
ttatatccgt ctaggtaggg attttataaa tcatttgtgt catcatgcgt tatgcttgtc    420
ggctttgacc ataacgcaga gatatagaac tagcttttac ttaacttta gatttattat     480
ttgatctaga gttaagtgga gatatatagt gttttttgtta gattattggt ggatgtgaga    540
gtttgtcttt agtttcaagt tgagaatata aggcaagagg agactctgag gcaatcagag    600
gttttgattg gcaaaatatc caaaaggccc aaccaagtc gaagcccatc tcgtacaaaa     660
aaagaaagag atctgtaaga aaaaatattc tttgatattc ttacaaaaat aagtgtaaaa    720
cttttattag tcaaaatctt caatctttaa aaactctcat cactcctacg aaaagcgcgtg   780
agagttatga gacattcctt aatagcatta ctcacaagtc acaagttcaa aacgtctgac    840
tgaaacagaa acaagccttt gttgaagtct tgaagaagag acattagtac tcgtcgtata    900
gccataaaag gtaatatacg aaatttcttc gctaatctct tcaccttcct ctacgcgttt    960
cactttcact ttataaatcc aaatctccct tcgaaaacat                        1000

SEQ ID NO: 43               moltype = DNA    length = 1004
FEATURE                     Location/Qualifiers
misc_feature                1..1004
                            note = Ceres Promoter YP0103
source                      1..1004
                            mol_type = unassigned DNA
                            organism = Arabidopsis thaliana SEQUENCE: 43
gttttgaaga acaatctgga tcgaaatcta acataaggtc atcgtattca agttacgcag    60
tcaaggactt gacatcatcc tactctggtc tgaggttacc acttccaaag atgggatttt    120
tcgactcggt atgcttccta agaaattcgt tttattgaac ctagcaaata tcttgtaatg    180
taagattcct gagatgatga agaaaaaaca aactttgttt acagcaggag aacggagaga    240
aagaaaacag agaccaaaat gctcttgaag caaacagaag aagaagacac aaatccaaac    300
ttgagacttc ttctacacca gaaaccgca gcattctggg acaacgcaaa acacgaaagt    360
gaaacgggca atgatatata tgtcttgggt gcgttacaag gcatcgtttg caactgttga    420
```

```
gttggataag tcaactgtct tcttttcctt tggttgtagt agctgccttt tttttccttt    480
gttgctttaa gaaatagccc gaaaaaaaga atgttctaca tttcggagca gaaaactaac    540
cgaatgagtt tttggtcgga tcatcggatc gatcagatat attttgagtt acgaactgtt    600
ataaaaaaag ccataatttt gtgttgagtt tgcaaaatac cttataactt gttatttgag    660
attgcacctc catatatatt aattcgtaag agtatttatt aagtaagctt tagtataaat    720
cctttttttcc tttaaagtaa gttaatgttc tactaaataa tagtaaagtt gaagaaccgc    780
tccgttttta caccatgcac gtgttatcta acaaagaaaa tatggtacac ctaatggcta    840
atgcaaagga caacacaatg aaactaactt gactctgtgt tatagaaacc catagacatc    900
tgcatacatc ctagtatttg tataaattgg actcaaattc ctgaggacaa tcatagcaaa    960
caatcacatc atcgcaatat acataaacaa aagaggaaga aaaa                    1004

SEQ ID NO: 44           moltype = DNA   length = 1003
FEATURE                 Location/Qualifiers
misc_feature            1..1003
                        note = Ceres Promoter YP0107
source                  1..1003
                        mol_type = unassigned DNA
                        organism = Arabidopsis thaliana
SEQUENCE: 44
taacaatcct tgggaacatt gcatccatag atatccggtt aagatcgatc tttgaactca     60
taaaaactag tagattggtt ggttggtttc catgtaccag aaggcttacc ctattagttg    120
aaagttgaaa ctttgttccc tactcaattc ctagttgtat atatgtaatg                180
tgtataaaac gtagtactta aatgactagg agtggttctt gagaccgatg agagatggaa    240
gcagaactaa agatgatgac ataattaaga acgaatttga aaggctctta ggtttgaatc    300
ctattcgaga atgttttttgt caaagatagt ggcgattttg aaccaaagaa acatttaaa    360
aaatcagtat ccggttacgt tcatgcaaat agaaagtgct ctaggatcg attgtaattt    420
tagactaaaa gagtctctta agattcaatc ctggctgtgt acaaaactac aaataatcta    480
ttttagacta tttgggcctt aactaaactt ccactccatt atttactgag gttagagaat    540
agacttgcga ataaacacat tccccgagaa atactcatga tcccataatt agtcggaggg    600
tatgccaatc agatctaaga acacacattc cctcaaattt taatgcacat gtaatcatag    660
tttagcacaa ttcaaaaata atgtagtatt aaagacagaa atttgtagac ttttttttgg    720
cgttaaaaga agactaagtt tatacgtaca ttttatttta agtggaaaac cgaaatttc    780
catcgaaata tatgaatta gtatatatat ttctgcaatg tactattttg ctattttggc    840
aactttcagt ggactactac tttattacaa tgtgtatgga tgcatgagtt tgagtataca    900
catgtctaaa tgcatgcttt gtaaaacgta acggaccaca aaagaggatc catacaaata    960
catctcatag cttcctccat tattttccga cacaaacaga gca                     1003

SEQ ID NO: 45           moltype = DNA   length = 1024
FEATURE                 Location/Qualifiers
misc_feature            1..1024
                        note = Ceres Promoter YP0110
source                  1..1024
                        mol_type = unassigned DNA
                        organism = Arabidopsis thaliana
SEQUENCE: 45
gggatgcggt tccgcttcct cttgatcttg gacgagtcgg aggacattgt tggatcccag     60
tgcaatggta atataaaaca agaaaacaag agattttata ggacaatcac taaatgacat    120
ttaattgatt aaacatttat tcattaataa ttgtatgtta ctaacttcaa catttaataa    180
ttttgtttaa gatacgttta catcagagac tattaatatt tttacaggtt gtaacttaaa    240
actttgtctt gaatcgaaca tgactataga tttttgggcaa acttaaagat aacaacattt    300
ccgtttttttt tcaaattatt acaaatcaaa ctgatatatt agacacaaca cgattacacg    360
taatgaaaaa agaaaaagat aaaaagataa aagaagggag cgattctgtt tggtctggtt    420
tagtgagatt caaagttaag ctcttccttt caagacatgc cttcttaaac cgggaatgtg    480
aacgtttgta atgtagtccg tccagttaat gcttccaaca tcaaatccaa attctctctt    540
ctcgtcctct gacatattct ccattaatct ctggggtatt gctgttatca aatctgtaaa    600
agaaaccaaa aaaaaaagat gaaaactttg cgggtaccgg ttttgtctgc tctaagaatt    660
agaatgttaa tgagttctgt cttaccttcc accatagaaa gtgtatggct cataaatagt    720
agcaaggtgt ttggcttgtt caacagattt cttgcatata aacttagct tctgcatcat    780
cttactatcc actgaactca taccactcat caacccactc cgttcttgag catctctcca    840
caaatgatcc gagaaatcat caacggaatt gaaaagtttc atcaaacgca ccataatagg    900
atcaccttta gagtccatgc atggagatgt tttgtagtgg ttataaagaa gctccgctaa    960
gtcttcgaaa accagcgggt ttatcgccga agaagcgatc tgatacacgt ttatttcagg   1020
ttcc                                                                1024

SEQ ID NO: 46           moltype = DNA   length = 1024
FEATURE                 Location/Qualifiers
misc_feature            1..1024
                        note = Ceres Promoter YP0111
source                  1..1024
                        mol_type = unassigned DNA
                        organism = Arabidopsis thaliana
SEQUENCE: 46
cgattggatt tagtctatac attataggc gcaagtttgt ggatttaaga attatataaa     60
aacttgaaat atatagtttt tatgcattct cctcttgtgt aatacataaa ccaaatatga    120
gataggttaa tctgtatttc agataatatt aaattccaaa caatattttt acttgttata    180
agaaggcaat taatatctct ctgttaatgg caagtggtac caagtagtat taaactatta    240
atgcaatgga agagtactgt tggaaattat aatcctctat cacacattca aacagatctc    300
ctgaaatctt ctcttccaaa cttgtacttc tctgatccaa atgtaggctc caaaatatag    360
acatttacca tttactaagt ccacaactcc tttcttgtct ccttcaaaaa tgactcttgt    420
```

```
gtaaccacca tatgactccg acagttcggc attgccatga tgagagctta aaaattcacc    480
ttcctgagca tttcaagtct tcactcccct agcttgacct gaaccaagat aaaatgcctt    540
tgtcgtcccg taatatccat cctgctttgg acggcatcat agttacattc gatccatcct    600
atttacaatg ttattttagt attaaaaaca tgacaataaa tttgttgtta aacatattca    660
aatacaatat gattggattt ataagtaatt gtaaatgaa  atgtccttag taatatgtta    720
aaaaatacat agatacacac acgtactaaa agaggcaacg cgggagatgt cattagagga    780
agaactagga agcagagcgt tcatgcaaaa tgctaccaaa aacgttaatg caatatctca    840
actaatcagc acagtccatt tcatactgag aatgtaaaaa ccaatcagca tcgtccattt    900
tttcatctaa ttatttgtta actcttaatt ggccacaact tccaaccaca tgacgctctt    960
tctattccct ttatatattc ccatctcaaa tgttcttgga gacacaaaat atcataaaca   1020
tata                                                                1024

SEQ ID NO: 47          moltype = DNA length = 996
FEATURE                Location/Qualifiers
misc_feature           1..996
                       note = Ceres Promoter YP0115
source                 1..996
                       mol_type = unassigned DNA
                       organism = Arabidopsis thaliana
SEQUENCE: 47
gtcgattgga tgatgaacat tctacatata taattattat gtttaagcac ttagacagca     60
taaattcttt ctaattatat aaatctaacc ttgttacatt gtacatctat aaattacttg    120
aagaaataac gagttctatt tcttttttaaa aattaaaaat actataccat atctcagtga   180
ttaagttgaa ccaaaaggta cggaggagaa acaagcattt gattcttcct tattttattt    240
tattcatctc tcactaatga tggtggaaa  aaaagaaaa  tacctaacaa acaaatatat    300
attgtcatac aaaaatattt ctatattttt agttaattag tttatattcc tcacttttca    360
gggcttatat aagaaagtga gcaaacacaa atcaaaatgc agcagcaaat actatcatca    420
cccatctcct tagttctatt ttataattcc tcttctttttt gttcatagct ttgtaattat    480
agtcttattt ctctttaagg ctcaataaga ggaggtacta ttactacact tctctctact    540
tttacttgta tttttagcatt aaaatcctaa aatccgtttt aaattcaaaa ataaacttag    600
agatgtttaa tctcgattcg gtttttcggc tttaggagaa taattatatg aaattagtat    660
ggatatcttt actagtttcc attcaaatga ttctgatttc aatctaatac tctcactctt    720
taattaaact atatgtagtg taatttcaca ctgttaaatt tctaccatgt catgtatatt    780
agagttgcat agaaaattgt aaaacatcca tttgaattcg aatgaaacaa aatgttttaa    840
aataaaattt tggtttttaa aagaaaaatc taaaactgaa ttatatcgtt taaccaagtt    900
gtaaaagtca taaaacgtag tatcctgtaa atcgctcttc cacggtccaa atagacttct    960
agtaataaac aagtaaaact aattttggtt tcttac                              996

SEQ ID NO: 48          moltype = DNA length = 1024
FEATURE                Location/Qualifiers
misc_feature           1..1024
                       note = Ceres Promoter YP0117
source                 1..1024
                       mol_type = unassigned DNA
                       organism = Arabidopsis thaliana
SEQUENCE: 48
gtcagtgagt cgattggatc acagtccttt atgataaaac aaactcataa ttattccacc     60
gacaacatgc gtttaaatt  attttttctt aaattatatt atattatatt gatatcaacc    120
tagctaaaat aattcggatg gcgaaatcgg acaattttta atagaaaaaa tgggtatgaa    180
gatagtctat gattccgttc ttagcgacta gagggacctg ctcaaatctc ccgggtgata    240
cgcgatgtca agctcaatag aaccccacaa ccgacgaacg cgagaaatcc ttgatttggg    300
ctagaagatt tgaaataaa  tttaatatat tctaagtaac ttgcttaaat ttttttttcaa    360
actctaaaga cataactaac ataaagtaaa aaaaaaaaag ttaatacatg ggaagaaaaa    420
aattaaaacta atgattagct ctctaacgtg tttaatctcg tatcaagttt ttttttaaaa    480
attatattgc tattaaaaca ttgtactatt gtttctattt tgtttagcta ttattcttgt    540
gaaatgaaaa gttgtgttta ttcaattact aaatggcaat atttatcttg gaaaactata    600
cctctaattg gattaggccc tagacatcct ctttagctta ttgacgttaa aattattccc    660
aaaactatta aagtttagta gtttgaaaga tgcatcaaga cctactcaga taggtaaaag    720
tagaaaacta cagttagtgt gattatattt taaaatatat aaaacaatct tattaaacta    780
aatattcaag atatatactc aaatggaaga taaaaacatt tagtctgtta ccactaccag    840
cctagctagt cactaatagt cactttggaa ctgagtagat atttgcatct tgagttacca    900
tggactcaaa agtccaaaaa gagaccccga gtgaaaatgc taccaactta ataacaaaga    960
agcatttaca gcggtcaaaa agtatctata atgtttaca  caacagtagt cataagcacc   1020
attg                                                                1024

SEQ ID NO: 49          moltype = DNA length = 1000
FEATURE                Location/Qualifiers
misc_feature           1..1000
                       note = Ceres Promoter YP0119
source                 1..1000
                       mol_type = unassigned DNA
                       organism = Arabidopsis thaliana
SEQUENCE: 49
taccaaaaat aaggagtttc caaaagatgg ttctgatgag aaacagagcc catccctctc     60
cttttcccct tcccatgaaa gaaatcggat ggtcctcctt caatgtcctc cacctactct    120
tctcttcttt cttttttttct ttcttattat taaccattta attaatttcc ccttcaattt    180
cagtttctag ttctgtaaaa agaaaataca catctcactt atagatatcc atatctatttt    240
atatgcatgt atagagaata aaaagtgtg  agtttctagg tatgttgagt atgtgctgtt    300
tggacaattg ttagatgatc tgtccatttt tttcttttt  cttctgtgta taaatatatt    360
```

-continued

```
tgagcacaaa gaaaaactaa taaccttctg ttttcagcaa gtagggtctt ataaccttca    420
aagaaatatt ccttcaattg aaaacccata aaccaaaata gatattacaa aaggaaagag    480
agatattttc aagaacaaca taattagaaa agcagaagca gcagttaagt ggtactgaga    540
taaatgatat agtttctctt caagaacagt ttctcattac ccaccttctc cttttttgctg   600
atctatcgta atcttgagaa ctcaggtaag gttgtgaata ttatgcacca ttcattaacc    660
ctaaaaataa gagatttaaa ataaatgttt cttctttctc tgattcttgt gtaaccaatt    720
catgggtttg atatgtttct tggttattgc ttatcaacaa agagatttga tcattataaa    780
gtagattaat aactcttaaa cacacaaagt ttctttattt tttagttaca tccctaattc    840
tagaccagaa catggatttg atctatttct tggttatgta ttcttgatca ggaaaaggga    900
tttgatcatc aagattagcc ttctctctct ctctctagat atctttcttg aatttagaaa    960
tcttttattta attatttggt gatgtcatat ataggatcaa                        1000

SEQ ID NO: 50        moltype = DNA  length = 999
FEATURE              Location/Qualifiers
misc_feature         1..999
                     note = Ceres Promoter YP0120
source               1..999
                     mol_type = unassigned DNA
                     organism = Arabidopsis thaliana SEQUENCE: 50
tagtttttga tttaatctac gttttcttta atcataaatg ggtaattatt agttttgca     60
aaatcaaaat ccaaaaattg ttctaaacac tgcaacatt taaggcctat atcactcaga    120
aaatttctgg tgggagaact aatcgtttgt cctttctaaa tctcacatat tagaatttag    180
aattagtgtg ctacataaga atattagttc agctcggaac aactattttt tggtaaaaca    240
gagaacttaa acaaatgcat tatttatca acatgcattt tgaattgaat ataaaatttc     300
ataattgtaa agacataaat tacataaaat ttttacatgaa aaatagata tagaaagaaa    360
atgaaactaa ctgatgatat gctctctaaa ttttttaatc tcataacaag aattcaaatt    420
aattagttca tattttggt taatataaca tttacctgtc taagtggaa ctttcattt      480
tttctgtttt gttagtcag tattcttaat gtgaaacgga aagttgaatt tattcaaact    540
taaattcaat agcattaatt aaaggcgaaa gctattatct ctacatgtgg ttcaaactag   600
acatccaatt taattagctt attgacgttg aaatgttttc caaaactact atagtttggc   660
aatttgaaag atgcatcaga actactcaga caggtaaaag tagaacctct agctgtgtga   720
attgtatgtt agtccataaa gaacatcttg taaacttcat acttaagata tatattacaa   780
tatatacttg aatggtagat aaaaacgatt agtctgatct ctagcatact cacaactatt   840
tggaaatgag taagatattg gcattctaga gttactacta tggagacaaa agtcgaataa   900
aagagacctc acgtgaaaat gttacgagct agtaaaaaaa gcatttcacac taacggtaaa   960
aaaagtatct ataaatgttt acacaaggta gtagtcatt                           999

SEQ ID NO: 51        moltype = DNA  length = 999
FEATURE              Location/Qualifiers
misc_feature         1..999
                     note = Ceres Promoter YP0121
source               1..999
                     mol_type = unassigned DNA
                     organism = Arabidopsis thaliana SEQUENCE: 51
ttggattttt ttttttgttga gtcagcagac catctaatct ctcttttcc accacagcct     60
gctttctatg aagcatttgg gcttacggtt gtggaatcaa tgacttgtgc actcccaacg   120
tttgctacct gtcatggtgg acccgcagag attatcgaaa acggagtttc tgggttccac   180
attgacccat atcatccaga ccaggttgca gctaccttgg tcagcttctt tgagacctgt   240
aacaccaatc caaatcattg ggttaaaatc tctgaaggag ggctcaagcg aatctatgaa   300
aggttggccc attctccttg acaggcttaa caatacaact tgtatcgctt caacaagatg   360
atggcttaat aaggattttt gcatgtatag gtacacatgg aagaagtact cagagagact   420
gcttaccctg gctggagtct atgcattctg gaaacatgtg tctaagctcg aaggagaga    480
aacacgacgt tacctagaga tgttttactc attgaaattt cgtgatttgg ttagtgtaac   540
ccactgttat tcttttgatg tctacatcta ctttacttac attattcttt tcttcggttt   600
gcaggccaat tcaatcccgc tggcaacaga tgagaactga tcatgacagg gtaggatttt   660
atttcctgca ctttctttag atcttttgtt tgtgttatct tgaataaaaa ttgttgggtt   720
ttgttttcctt cagtggtttg atttttggact tatttgtgtt aatgttgttt tggctgtttct  780
cttaatatca ataacaaata aatttactgg ttggtatcta agatctaaca atagttacta   840
tttttagagg taaagacacc aaccttgtta tattggtcag agagctaaaa ccttgacttg   900
ttgggaaaac aaaactctaa tgacagaaaa tctgacatga tgccttataa ttcacagcct   960
catgttctac ataaatccta acaatagcac tttgtttct                           999

SEQ ID NO: 52        moltype = DNA  length = 1004
FEATURE              Location/Qualifiers
misc_feature         1..1004
                     note = Ceres Promoter YP0128
source               1..1004
                     mol_type = unassigned DNA
                     organism = Arabidopsis thaliana SEQUENCE: 52
gataaactga taatggaaaa gaacaaagaa accagttttt aactatttgc atatgtaatt     60
tatttgttgc aaattatatt tagttaaaat gtttcctcta tttatatata tatatatcag   120
tcaagcacta tgtataagaa atgtcaattt ataaattttt acatgtcctt taacagaaag   180
aaaatgaatt tttacatgtc attcatagag agtcactcgt ttattcctta tatagagaat   240
aacacactca catgcatatg catgcaatat gatacatttt atgacaaaga taatcaacgg   300
aaacggtcaa gacataattt gataaacaac ttgcacgatg cacagatctg atcaaatata   360
taactctttta acatatccaa aatattcaaa aagaaaaact cgatccaaac tagcaacatc   420
```

-continued

```
acgctcacgc ggtaggctaa aaatttatta atctccaaaa gtctttctta tgaacactgc    480
aaacacaaca acttgaaaag tcatataggt ttagatgatg acgcgtattg gctatcgctt    540
accggagtgg ctcataaata caataaacaa tacgtaaaag tcaaagtcaa atatatttag    600
tcaactataa ccattaatcg ggcaaaacct ttagctgtca aaacaacgtg aaaacgatat    660
ttgtatatat catcaagaat cagtagataa gagaatgatt taatccctg actattacaa     720
ttttggtgta ataaacagtc tctattggtt tttattcttt gttttaattt ctcatgacct    780
atagagagaa ttaggtagtt tcgaaaattg gctaatcaac ttttgaaaac tactgtctac    840
tttgcttaaa ttctctacac ttagtttcgg ataagataat tgtcggacta atagttaatc    900
ccttgacaat ctttgatatt ataaaaggtt tagtaatct cttctctata taaatattca     960
tacaccagct ttcaaaaata tataatccaa acaccaaaaa caaa                     1004
```

```
SEQ ID NO: 53           moltype = DNA   length = 1001
FEATURE                 Location/Qualifiers
misc_feature            1..1001
                        note = Ceres Promoter YP0137
source                  1..1001
                        mol_type = unassigned DNA
                        organism = Arabidopsis thaliana
SEQUENCE: 53
gtggcacatg ctgaaacccc gagcatctct ccggaagaca cgcgtcgttc gctccaaaga    60
aaacagtcac agctgccgga gaatctccgc cgtcttcttc tgccaccgga aaaactctct   120
ccaccacttt cagtgcccac ctcgtgttat atccactgta tcctcgtagc accatatcag   180
cctaataaaa ttttatgtat caaattttaa gacatagccg aaactacact atactagaca   240
ataataatat gatttgtttc ctgaaaaatt atggtttcat gagaaacatt aatcatctat   300
aaaacaaatt agctatggca tcgaagagtt atcaatcaaa actgatgaat ctttacttaa   360
tatatacaac atatctttac cttgcggcgg agaagatcga cgagagaagc accccagcca   420
ccgtcactaa aggattcttc agtgatggaa tcaccaaaga gaaaaaccct ccgtctcatc   480
atcttccaca caatcttctt gagaaaatct gagagataag aaaggtgtag tggttttgct   540
gaagtgatcg tgtttgattt agtaaagaaa tgctttattt attgttgggg gaaacataaa   600
taaataaagt aaaagtggat gcactaaatg ctttcaccca ctaatcaccg acctttcatg   660
gtttattgtg aaatacactc atagatagac atacaatacc ttatgtacgt aaataacatt   720
ttatttgtcg acacttatgt aagtaacgca tagattattc tctatgtgat tgccactctc   780
agactctcag tttcaaccaa taataacaat aactacaaca acattaatca taaacatatg   840
ctctggttta caattaaagc ttagattaag aaactgtaac aacgttacag aaaaaaaatg   900
ttatttacgt tttgtaagat tagtctctag aatcatcacg gttttttata tattaatgat   960
tctttcttat atataaaacc tttctcgaaa tacccatgaa a                       1001
```

```
SEQ ID NO: 54           moltype = DNA   length = 1001
FEATURE                 Location/Qualifiers
misc_feature            1..1001
                        note = Ceres Promoter YP0143
source                  1..1001
                        mol_type = unassigned DNA
                        organism = Arabidopsis thaliana
SEQUENCE: 54
atacaacaga tggcagatat cgagttaaat acgtgaatca gccgttacga tattttaaaa    60
ctagaaaatt attaaaaaat attgcaaaat accatttaa ttcattgttc ataaaaaaaa    120
gaaattcaaa aacttaaaaa ctgattcaaa aatttggatt aattctcatt aacagtcttc   180
aacactacaa caacatgttt ctaatttatt ttatatttta ataattaaac aatatatacg   240
tctgcacatt gttgctccga cataatctag tataaaaata gttgcagcat atgtgaaaag   300
caagcagcat ttatcactca atactttaa ttttatctgt tgtatgtatt aaggttttgt    360
agcttttaaga aaacgcttat aatataaaat aacttctaaa agatatttca tgcgtataca   420
ataaatattt gtgaaaaaac atttcgaaaa cgtgtacaat atataaacta ttgtgttatc   480
ttttgacatt caaacaaatg ttgacaatgt aatttttatcc atgatatgat tggccaatta   540
gctgcgaggt aaaaatccgt atacgagtaa aagtaagata aaatttcgca agaagatttt   600
tagcaggaaa tctaagacaa gtgtcatgaa cgtgtcaatc aacaaacgaa aaggagaatt   660
atagaatcca gattcgacgt accacattaa taaatatcaa aacatttat gttatttat    720
ttttgctctg gcagttacac tcttttcat tgctccaata aaaaaatcac tcgcatgcat    780
gcatatatat acaccatagt aaactccgcc tcttcttcat tttaaaagta tcagtttaca   840
ctgacacaat ccttaactat tttcctttgt tcttcttcat ctttattaca cattttttc    900
aaggtaacaa ataatcttt taagtcactt ttatactctt taaatcttag attgatatat    960
gaatgcatgt taatatttca agatttatag gtctaccaaa c                      1001
```

```
SEQ ID NO: 55           moltype = DNA   length = 1003
FEATURE                 Location/Qualifiers
misc_feature            1..1003
                        note = Ceres Promoter YP0144
source                  1..1003
                        mol_type = unassigned DNA
                        organism = Arabidopsis thaliana
SEQUENCE: 55
aaacgttgca agattattga ttgtgagaaa gagtgctcaa ggtagtactg atttctgtaa    60
agctcacggt ggtgggaaac gatgttcttg gggagatggg aaatgtgaga aaatttgcta   120
gaggaaagaa gcggtttatg cgctgcgcat aacactatta tgtctcggga gaacaaagat   180
ggaagcaaga gcggtttgat tggaccggga ctctttagtg gccttgtttt tggctctact   240
tctgatcatt ctcagtctgg agctagcgct gtctctgatt gtactgattc tgttgaacga   300
atacagtttg agaataggca gaagaacaag agatgatga taccgatgca ggttctagta    360
ccttcatcaa tgaaatctcc aagtaattca catgaaggag aaacaaacat ctatgacttc   420
atggttccgg aggagagagt tcacggcggt gggctagtaa tgtctttact tggtggctcc   480
```

```
attgatcgaa actgaaagcc atttatggta aaagtgtcac attctcagca aaaacctgtg    540
taaagctgta aaatgtgtgg gaatctccga atctgtttgt agccggttac gttatgctgg    600
atcaaaaact caagatttgt tggatattgt tatgctggat cggtggtgaa accacttccc    660
ggttgctaaa taaataaacg ttttgtttt ataatcttt tcactaaacg gcagtatggg      720
cctttagtgg gcttccttta agcgaccaat acaatcgttg caccggaatc tactaccatt    780
tataggttta ttcatgtaaa acctcggaaa atttgagagc cacaacggtc aagagacaaa    840
aacaacttga agataaaggg ataaggaagg cttcctacat gatggacaac atttctttcc    900
acacaaattc tcataataaa aatcttataa tacaaatact tacgtcataa tcattcaatc    960
tagtccccat gttttaaggt cctgtttctt gtctgataca aat                     1003

SEQ ID NO: 56              moltype = DNA   length = 1004
FEATURE                    Location/Qualifiers
misc_feature               1..1004
                           note = Ceres Promoter YP0156
source                     1..1004
                           mol_type = unassigned DNA
                           organism = Arabidopsis thaliana
SEQUENCE: 56
ttggtttgca ttgtgaagat ttgtattaac tatagaacat tgaattgatg gtgttaagtt     60
cttacacaag cgtgcttctc ggtttgaact gtttcttttg tatgttgaat cagagcttag    120
tttataggaa ccagagtatc tacttagtca ttctctgatg ctaagtgcta aggttctacc    180
tagttgccct ctaggccctt atgttattga taacttagta acacttgatt                240
cttaggagac ctaagttggt acagccagat agagtgtatg ttcttgttct ctatgtgaca    300
ggatcaagct gccacacata gttcaagggt atgctctgtg tgggtttgct cagattgagg    360
acaaatctat acaaggaagt agagtctttg acattttgat gttgtatgat aagaagaaga    420
aaggagagta ataaagaaag agaaaaggga aacagaaaca cgtgggagaa catcccaaag    480
aggaagcaca cgcggatctt catgcaaagc tccccgattc tcccatgtgg tcccttctc    540
cctttgtccc cctcctcttt cttcttttct cattttactc cttttttac cattatacaa    600
cgaatctttt ttatcataat ttttttggttt tggtttattt tccaataaca ctttcttggt    660
tacttcccat tctcacttttt tcatataaga aactcacttt gggaaactta tgtttgagaa    720
tgacaagtct ttttagagaa agtgatgtaa caaatctaaa gtgattatat aataaccttg    780
cacaatgttt ttgatttttt gtaagattcg aatattaggt ttattattcg tagggaataa    840
acttactttc aaaagcgttc ataagttaat actttcatat atgatcataa gtacggacac    900
tattgttttt tgtttgtttg tgtttattct aaaagaaagt agcttttaat tgaaatgtcc    960
tcggaggcac agtttaaagt tcgagtgtaa cagtttctaa ggca                    1004

SEQ ID NO: 57              moltype = DNA   length = 1000
FEATURE                    Location/Qualifiers
misc_feature               1..1000
                           note = Ceres Promoter YP0158
source                     1..1000
                           mol_type = unassigned DNA
                           organism = Arabidopsis thaliana
SEQUENCE: 57
ttattagatt aatagattgc attgcattgc ttgtgctttc aatttacaaa ttgtctccca     60
actccatcga cacatctctt tttgtgtata taagattcag acttgttata ttttttttat    120
aaatatgtta ttagcatctt aagttaaatt gatttttat atctgcatta aggattacac    180
gactatattt gcgattgtgt gttggttaaa atataattta ggattgtctt taactacatt    240
taggattata tgactatatt tggttaaata taaaatctag ctgtgattat tagtattcaa    300
aaataagtag cctaaccaat taaaacaacg gctattgggg caaattagaa catttagtg    360
tgtccaaaat ataatggtca ttaggtcata ttcctcctag cttcatcgca gcataattga    420
atgattgcct tatttagaag agcttttcca ctttcccaaa atctaggtgg gatctttttg    480
ttttgacctt cattttctt gttaccatt tttagctaaa ttatttacga ttacaaaga      540
tatcaaaagt tggatcataa tacaattat agacttactg tagaaaattc gtatgtacaa    600
gtacaacaaa ttcttcatta taaattttga aaattctatt acaaatgttg taagaaatag    660
aatttgaaat atatataaac taaggagaaa aaaagagaga acatgcattg ctctagtcag    720
agtggaccaa catcaacgag ataagataac ataaaaccaa actcaccata actaaaaaca    780
tcccaagaga tccaacgatt catatcaaac acaaaaacat cgaacgatca gatttaaacc    840
atctctggta tctccaaaac acaaacactt ttttttttct tttgtctgaa tggaacaaaa    900
gcatgcgaca tctctgtgtc tttatcttct ctctcctctt cttgaaaaac tgaaccttta    960
attctttctt cacatctcct ttagctttct gaagctgcta                         1000

SEQ ID NO: 58              moltype = DNA   length = 1005
FEATURE                    Location/Qualifiers
misc_feature               1..1005
                           note = Ceres Promoter YP0188
source                     1..1005
                           mol_type = unassigned DNA
                           organism = Arabidopsis thaliana
SEQUENCE: 58
gattggtatg aaatttcgga gaccaacaaa aaaaacttta ttgagcttgg agtgaagcta     60
tatatatggg gcaagatcat aatatgttta tatcggcctt ttcgttaact gaaaataata    120
gttttgagaa atatatcaaa tggtaaacag acatcatctt tgaaaaatac catcaatgaa    180
gttaatattg ttattggcat atggtttacc catcttaatt ttaatgcaac caaacaaaca    240
agaaacaaaa actgtataag atacaaggtg ttttacgatt ttcgtcttca aaaccgaaat    300
attttttgttc ctacgacttt aaacggactt tgctaagtt gtgtgcatgt aagctcgtcg    360
tccctcgatt gtcatcaaca ttcaccaata tcagcctcta tcacgcgagt gaaggtggtg    420
attcggctta atgaaaacag agaaatattt caatatgatt cctattaaat ttaaatcttt    480
ttttctcaat ctctagattt tcattaaaag catcatgatt ttttttccact atgttcatat    540
```

```
atctctatca cagttttagg tacattgtag aaattggata agatacgtca tacgtctaac   600
atgaatttgg tctagcaagg aaggtttgag ataataagtg aaaagaaaac acaagataat   660
aaattataat ttataaatgc tttatagtat tgaaaaataa gatgattttt tttttttta    720
ataccggatt ggctgatcca cttatgatga ctcaaatgtt attaagtttc aagacaattt   780
atgatgacac aaatcacaat gagtcaatag tagccacgaa gccagaaaaa aaaaatgtac   840
tacaaaaaga taatgatagt acaaaatgat acgtcgtact gccacatgta cgacacaact   900
cgattaccaa aaagcagagc catccaacca taaaactcaa aacacacaga ttccactggc   960
gtgtgctctc ctcacttcac tcgtccttga aacttgaggt actga                  1005
```

| | |
|---|---|
| SEQ ID NO: 59 | moltype = DNA   length = 1002 |
| FEATURE | Location/Qualifiers |
| misc_feature | 1..1002 |
| | note = Ceres Promoter YP0190 |
| source | 1..1002 |
| | mol_type = unassigned DNA |
| | organism = Arabidopsis thaliana |

```
SEQUENCE: 59
taaatagtga cattggtaag aagaaaaaaa acactattaa atagtgaaaa aatggtttat    60
aactctctta attaacatta cttattattg ctagcaccta aaatctccca caaaatattt   120
gttgtaaaac acaaatttac aaaatgattt tgtttttaaa ttagtaacac atgttcatat   180
atacgttaat aagaacatac cctatatgat tttatataaa aaaattctt tgagacgtct    240
tattctttt tctttaataa tatgcaattg tgagagtttg gatttgaatg gtagcattag    300
aagcaaactt gaaccaaaca tatttcatga agtcaaactt gaaccaatgt gatcactaat   360
cacagtgttc gcagtgtaag gcatcagaaa atagaagaag ggacatagct atgaatcata   420
taatcttgac acatgtttta taggttttag gtgtgtatgc taacaaaaaa tgagacagct   480
ttcttctaat agacttaata tttgggctaa atgtaccaca gttgtgaatt tcttacaaaa   540
atgggccgag ctacaaaaaa ctacaggccc actctcaact cttatcaaac gacagcgttt   600
tacttttta aaagcacaca cttttttgttt ggtgtcggtg acgtgagtt tcgtccgctc    660
ttcctttaaa ttgaagcaac ggttttgatc cgatcaaatc caacggtgct gattacacaa   720
agcccgagac gaaaacgttg actattaagt taggtttaa tctcagccgt taatctacaa    780
atcaacggtt ccctgtaaaa cgaatcttcc ttccttcttc acttccgcgt cttctctctc   840
aatcacctca aaaaatcga tttcatcaaa atattcaccc gcccgaattt gactctccga    900
tcatcgtctc cgaatctaga tcgacgagat caaaacccta gaaatctaaa tcggaatgag   960
aaattgattt tgatacgaat tagggatctg tgtgttgagg ac                     1002
```

| | |
|---|---|
| SEQ ID NO: 60 | moltype = DNA   length = 995 |
| FEATURE | Location/Qualifiers |
| misc_feature | 1..995 |
| | note = Ceres Promoter YP0212 |
| source | 1..995 |
| | mol_type = unassigned DNA |
| | organism = Arabidopsis thaliana |

```
SEQUENCE: 60
agtcgattgg tacactctta atttaattag agtaagagat caacaaaaat atagaatttt    60
ctttatatcg aagtgctacg acctatata tatagaaaaa aaagcatagg tgaatctcta    120
aattgagatt gtgctgtagt aaacatatta agttttagt tttttaaga aatgaatctt     180
tttgttgatt aattcaaact agtagtcatt aagattccaa ggatccaat ttagaaaagt    240
caaagattca aagaacaagt ccaggtccac atgttgaatc cgattcatca tccactcatc   300
cttcatatct tcctccaccg tctccgccca aaaaatcaat aacaataaaa aatcctaaaa   360
aaacatattt gattttgaaa aactttatc atatattata ttaattaaat agttatccga    420
tgactcatcc tatggtcagg gccttgctgt ctctgacgtc cttaattatc attatttta    480
aatttgtctc tctcagaaaa ttacgccaca atcttcctct ttccctttc cgaaaacagc    540
taatatttgt ggacctaaac taaataacgt agccctctaga ttttatataa ttactaaatac  600
tatatgctac tacttgttat tatttactcc aatcatatat gataccaatc aagaatcact    660
acataagtag aaaactttgc aatgagtcca ttaattaaaa ttaagaataa acttaaaatt    720
ttatggtatt ttaagattcc ctttggattg taatgacaag aaatcagcaa attagtcgta    780
actcgtaaga ataacaaga tcaatttta cttcttttac aaagattccg ttgtaatttt     840
agaaatttt ttttgtcact gtttttttat agattaattt atctgcatca atccgattaa    900
gaagtgtaca catgggcatc tatatatc taacaggtaa aacgtgtatg tacatgcata     960
aggttttacg tgcttctata aatatatgtg gcagt                             995
```

| | |
|---|---|
| SEQ ID NO: 61 | moltype = DNA   length = 1024 |
| FEATURE | Location/Qualifiers |
| misc_feature | 1..1024 |
| | note = Ceres Promoter YP0214 |
| source | 1..1024 |
| | mol_type = unassigned DNA |
| | organism = Arabidopsis thaliana |

```
SEQUENCE: 61
ccagtcgatt ggcgcctcgc atgcctatca tatttaaccg tcaataatgg atttggcggt    60
tttggtaggc cgggtcaacc ggattaaaag aaaacggttt ggagtccttc cttgcaattg   120
aattttcaca cattcgggtt ttgtgatttc tctgtcataa tgggcccggc acatatggtt   180
cataacccat gtgggcctat ggtataattt ttccaattaa aactattgtt aggtcgataa   240
aacaaaaac aataaaaacg agtggaatac acataccaaa aagaatgtga tgaactag      300
taattttatt ttgatggtta atgaaaaaca aaataaatgc atcttggcat cttccgttgg   360
aaagcgcaaa tagggcagat tttcagacag atatcactat gatgggggt gagagaaaga   420
aaacgaggcg tacctaatgt aacactactt aattagtcgt tagttatagg acttttttt    480
tgtttggcc tagttatagg atcataaggt aaaaatgaag aatgaatatt agattagtag    540
gagctaatga tggagttaag tatgcacgtg taagaactgg gaagtgaaac ctcctgtatg   600
```

```
gtgaagaaac tatacaacaa agcccttttgt tggtgtatac gtattaattt ttattcttt     660
atcacaagcg atacgtatct taagacataa taaatatata tcttactcat aataaatatc     720
ttaagatata tatacagtat acacctgtat atatataata aataggcata tagtagaaat     780
taatatgagt tgttgttgtt gcaaatatat aaatcaatca aaagatttaa aacccaccat     840
tcaatcttgg taagtaacga aaaaaaaggg aagcaagaag aaccacagaa aaggggggcta    900
acaactagac acgtagatct tcatctgccc gtccatctaa cctaccacac tctcatcttc     960
tttttcccgt gtcagtttgt tatataagct ctcactctcc ggtatatttc cccattgcac    1020
tgga                                                                 1024

SEQ ID NO: 62           moltype = DNA   length = 911
FEATURE                 Location/Qualifiers
misc_feature            1..911
                        note = Ceres Promoter YP0263
source                  1..911
                        mol_type = unassigned DNA
                        organism = Arabidopsis thaliana
SEQUENCE: 62
atctagctgt ggattccacc aaaattctgg cagggccatg atctaaaaac tgagactgcg      60
cgtgttgttt tgcagtgatt tgtatttcat atttgcacca tcctacacag tcccacttggt    120
atcgtaacca aacataagga gaacctaatt acattattgt tttaatttcg tcaaactggt     180
ttttaccttt tagttacata gttgattctt catttgtttt agtagttatg gagcacaata     240
atgtgcaaca aagaaagatc atagtggatt aaatatgttg gaggtcagaa attcttggtt     300
aacaaaaaaa agttacaagg actgagattt tgggtgggag aaagccatag cttttaaaac     360
atgattgaac ttaaaagtga tgttatggtt tgagggggaaa aaggttgatg tcaactaaga    420
tagttgaagt aatgtcttaa actaaagtaa accaccggtc caaccgtggt ccggaagcat     480
ctctggtatg atttatccta aaaatcaaaa tagtagaaac tatctttaat tatatacatt     540
gatcggacga aaattgtaaa ctagtatagt ttcaaaaact agttgaacag gttatgtacc     600
ttaaacattt atttcaaact taaacactaa agaacatata tgaatagaag tttatataaa     660
ttactatata tctaccataa atctcttata attatgatgt cacgatgagg aagtgttgaa     720
acgttaaaat gccaaaatat aagcatgcga cggaattttg tcagaagatt gtagagttgt    780
aatctgtcgc aatcattact cgtgctagca tttttcattt tcccttcatt tgtggataac    840
gcacgatata acattctaca caccaacaag attctataaa aacgcaaagg ttgtctccat     900
agaatatcgt c                                                         911

SEQ ID NO: 63           moltype = DNA   length = 999
FEATURE                 Location/Qualifiers
misc_feature            1..999
                        note = Ceres Promoter YP0275
source                  1..999
                        mol_type = unassigned DNA
                        organism = Arabidopsis thaliana
SEQUENCE: 63
aaacattaat atgtagtaac tatgggcgta tgctttactt tttaaaatgg gcctatgcta      60
taattgaatg acaaggatta aacaactaat aaaattgtag atgggttaag atgacttatt     120
ttttttactta ccaatttata aatgggcttc gatgtactga aatatatcgc gcctattaac    180
gaggccattc aacgaatgtt ttaagggccc tatttcgaca ttttaaagaa cacctaggtc     240
atcattccag aaaatggatat tataggattt agataatttc ccacgtttgg tttatttatc    300
tattttttga cgttgaccaa cataatcgtg cccaaccgtt tcacgcaacg aatttatata     360
cgaaatatat atatttttca aattaagata ccacaatcaa aacagctgtt gattaacaaa     420
gagatttttt tttttttggtt tgagttaca ataacgttag aggataaggt ttcttgcaac     480
gattaggaaa tcgtataaaa taaaatatgt tataattaag tgttttattt tataatgagt     540
attaatataa ataaaacctg caaaaggata gggatattga ataataaaga gaacgaaag     600
agcaattttta cttctttata attgaaatta tgtgaatgtt atgttacaa tgaatgattc     660
atcgttctat atattgaagt aaagaatgag tttattgtgc ttgcataatg acgttaactt     720
cacatataca cttattacat acatttttatc acatgtgcgt ctttttttttt tttttacttg    780
taaaatttcc tcacttttaaa gacttttata acaattacta gtaaaataaa gttgcttggg    840
gctacacccct ttctccctcc aacaactcta tttatagata acattatatc aaaatcaaaa    900
catagtcccct ttcttctata aaggttttt cacaaccaaa tttccattat aaatcaaaaa    960
ataaaaactt aattagttt tacagaagaa agaaaaca                             999

SEQ ID NO: 64           moltype = DNA   length = 981
FEATURE                 Location/Qualifiers
misc_feature            1..981
                        note = Ceres Promoter YP0285
source                  1..981
                        mol_type = unassigned DNA
                        organism = Arabidopsis thaliana
SEQUENCE: 64
gggattatat atgatagacg attgtatttg cgggacattg agatgtttcc gaaaatagtc      60
atcaaatatc aaaccagaat ttgatgtgaa aacactaatt aaaacatata attgacaact    120
agactatatc atttgttaag ttgagcgttg aagaaaatg aaagagtgta gactgtagta    180
cgtatgagtt tcccaaaaga tggtgcttga atattattgg gaagagactt tggttggttc     240
ggttgaatga agatttttac ctgccatgtt gatagagaaa ggcaaataaa tgtagggggtc    300
gatgtctaac gtaaagactg gatcaaccaa gagtcctcct cctcgtcttc accaaaaaaa     360
aagagtcctc ctcgtgggaaa cttatttctt ctccagccaa gatctcatct catctcttca    420
ctctatgaaa tataaaggaa tcttatggtt ttttaaaaaa ctatagtacg tctatatacc     480
aaaggaaaca atataaaatc agttaatctg ataaattttg agtaaataat aaagttaact     540
ttgtacttac ctatatcaaa ctaattcaca aaataaagta ataataacaa agaatttta     600
gtagatccac aatatacaca cacactatga gaaatcataa tagagaattt taatgatttt     660
```

```
gtctaactca tagcaacaag tcgctttggc cgagtggtta aggcgtgtgc ctgctaagta    720
catgggctct gcccgcgaga gttcgaatct ctcaggcgac gttcttttg ttttcggcca    780
taaaggaaaa agcccaatta acacgtctcg cttataagcc cataaagcaa acaatgggct    840
gtctctgtct cactcacaca cgcgttttcc tactttttga ctattttat aaccggcggg    900
tctgacttaa ttagggtttt ctttaataat cagacactct ctcactcgtt tcgtcaacat    960
tgaacacaga caaaaccgcg t                                              981

SEQ ID NO: 65           moltype = DNA  length = 996
FEATURE                 Location/Qualifiers
misc_feature            1..996
                        note = Ceres Promoter YP0286
source                  1..996
                        mol_type = unassigned DNA
                        organism = Arabidopsis thaliana
SEQUENCE: 65
gaaaacaatc ataggttacg ctattatcat cgaaaggtat gtgatgcata ttcccattga     60
accagatttc catatatttt atttgtaaag tgataatgaa tcacaagatg attcaatatt    120
aaaaatgggt aactcactt gacgtgtagt acgtggaaga atagttagct atcacgcata    180
catatatcta tgaataagtg tgtatgacat aagaaactaa aatatttacc taaagtccag    240
ttactcatac tgatttcatg catatatgta ttatttattt attttaata aagaagcgat    300
tggtgttttc atagaaatca tgatagattg ataggtattt cagttccaca aatctagatc    360
tgtgtgctat acatgcatgt attaattttt tccccttaca tcatttcagt tgataatatt    420
gctctttgtt ccaactttag aaaaggtatg aaccaacctg acgattaaca agtaaacatt    480
aattaatctt tatatgagat aaaaccgagg atatatatga ttgtgttgct gtctattgat    540
gatgtgtcga tattatgctt gttgtaccaa tgctcgagcc gagcgtgatc gatgccttga    600
caaactatat atgtttccg ttaattaattaa gttttgtata ttaattagaa taacattttt    660
atacaatgta atttctcaag cagacaagat atgtatccta tattaattac tatatatgaa    720
ttgccgggca cctaccagga tgtttcaaat acgagagccc attagtttcc acgtaaatca    780
caatgacgcg acaaaatcta gaatcgtgtc aaaactctat caatacaata atatatattt    840
caagggcaat ttcgacttct cctcaactca atgattcaac gccatgaatc tctatataaa    900
ggctacaaca ccaaaagga tcatcagtca tcacaaccac attaactctt caccactatc    960
tctcaatctc tcgtttcatt tcttgacgcg tgaaaa                              996

SEQ ID NO: 66           moltype = DNA  length = 1000
FEATURE                 Location/Qualifiers
misc_feature            1..1000
                        note = Ceres Promoter YP0337
source                  1..1000
                        mol_type = unassigned DNA
                        organism = Arabidopsis thaliana
SEQUENCE: 66
taattttttt attttttggaa ctaacactta ttagtttagg tttccatcac ctatttaatt     60
cgtaattctt atacatgcat ataatagaga tacatatata caaatttatg atcattttg    120
cacaacatgt gatctcattc attagtatgc attatgcgaa aacctcgacg cgcaaaagac    180
acgtaatagc taataatgtt actcattat aatgattgaa gcaagacgaa acaacaaca    240
tatatatcaa attgtaaact agatatttct taaagtgaa aaaaacaaa gaaatataaa    300
ggacaatttt gagtcagtct cttaatatta aaacatatat acataaataa gcacaaacgt    360
ggttacctgt cttcatgcaa tgtggacttt agtttatcta atcaaaatca aaataaaagg    420
tgtaatagtt ctcgtcattt ttcaaattttt aaaaatcaga accaagtgat ttttgtttga    480
gtattgatcc attgtttaaa caattaaaca cagtatatac gtctcttgag atgttgacat    540
gatgataaaa tacgagatcg tctcttggtt ttcgaattt gaactttaat agtttttta    600
tttagggaaa ctttaatagt tgtttatcat aagattagtc acctaatggt tacgttcag    660
taccgaacca attttttacc cttttttcta aatgtggtcg tggcataatt tccaaaagag    720
atccaaaacc cggtttgctc aactgataag ccggtcggtt ctggtttgaa aaacaagaaa    780
taatctgaaa gtgtgaaaca gcaacgtgtc tcggtgttca atgagccacc tgccacctca    840
ttcacgtcgg tcatttttgtc gtttcacggt tcacgctcta gacacgtgct ctgtccccac    900
catgactttc gctgccgact cgcttcgctt tgcaaactca acatgtgtg tatatgtaag    960
tttcatccta ataagcatct cttaccacat taattaaaaa                          1000

SEQ ID NO: 67           moltype = DNA  length = 1000
FEATURE                 Location/Qualifiers
misc_feature            1..1000
                        note = Ceres Promoter YP0356
source                  1..1000
                        mol_type = unassigned DNA
                        organism = Arabidopsis thaliana
SEQUENCE: 67
ttagttcatt gaaacgtcaa ctttttactt gcaaccactt tgtaggacca ttaactgcaa     60
aataagaatt ctctaagctt cacaagggt tcgtttggtg ctataaaaac attgttttaa    120
gaactggttt actggttcta taaatctata aatccaaata tgaagtatgg caataataat    180
aacatgttag cacaaaaaat actcattaaa ttcctaccca aaaaaaatct ttatatgaaa    240
ctaaaactta tatacacaat aatagtgata caaagtaggg cttgatattc aactattcgg    300
gattttctgg tttcgagtaa ttcgtataaa aggtttaaga tctattatgt tcactgaaat    360
cttaactttg tttttgttcc agttttaact agtagaaatt gaaattttta aaaattgtta    420
cttacaataa aatttgaatc aatatccttta atcaaaggat cttaagacta gcacaattaa    480
aacatataac gtagaatatc tgaaataact cgaaatatc tgaactaagt tagtagtttt    540
aaaatataat cccggtttgg accgggcagt atgtacttca atcttgtgg gttttgacga    600
ttttggatcg gattgggcgg gccagccaga tgatctatt acaaatttca cctgtcaacg    660
ctaactccga acttaatcaa agattttgag ctaaggaaaa ctaatcagtg atcacccaaa    720
```

```
gaaaacattc gtgaataatt gtttgctttc catggcagca aaacaaatag gacccaaata    780
ggaatgtcaa aaaaaagaaa gacacgaaac gaagtagtat aacgtaacac acaaaaataa    840
actagagata ttaaaaacac atgtccacac atggatacaa gagcatttaa ggagcagaag    900
gcacgtagtg gttagaaggt atgtgatata attaatcggc ccaaatagat tggtaagtag    960
tagccgtcta tatcatccat actcatcata acttcaacct                          1000

SEQ ID NO: 68           moltype = DNA   length = 1000
FEATURE                 Location/Qualifiers
misc_feature            1..1000
                        note = Ceres Promoter YP0374
source                  1..1000
                        mol_type = unassigned DNA
                        organism = Arabidopsis thaliana
SEQUENCE: 68
aagacacccg taaatgttgt catgtagaag aaactagaaa cgttaaacgc atcaaatcaa     60
gaaattaaat tgaaggtaat ttttaacgcc gcctttcaaa tattcttcct aggagaggct    120
acaagacgcg tatttctttc gaattctcca aaccattacc attttgatat ataataccga    180
catgccgttg ataaagtttg tatgcaaatc gttcattggg tatgagcaaa tgccatccat    240
tggttcttgt aattaaatgg tccaaaaata gtttgttccc actactagtt actaatttgt    300
atcactctgc aaaataatca tgatataaac gtatgtgcta tttctaatta aaactcaaaa    360
gtaatcaatg tacaatgcag agatgaccat aaaagaacta taaaacacta cttccactaa    420
atctatgggg tgccttggca aggcaattga ataaggaaga tgcatcaaga tgatatagaa    480
aatgctattc agtttataac attaatgttt tggcggaaaa ttttctatat attagaccttt   540
tctgtaaaaa aaaaaaaatg atgtagaaaa tgctattatg tttcaaaaat ttcgcactag    600
tataatacgg aacattgtag tttacactgc tcattaccat gaaaaccaag gcagtatata    660
ccaacattaa taaactaaat cgcgatttct agcaccccca ttaattaatt ttactattat    720
acattctctt tgcttctcga ataataaac ttctctatat cattctacat aataaataag     780
aaagaaatcg acaagatcta aatttagatc tattcagctt tttcgcctga gaagccaaaa    840
ttgtgaatag aagaaagcag tcgtcatctt cccacgtttg gacgaaataa aacataacaa    900
taataaaata ataaatcaaa tatataaatc cctaatttgt ctttattact ccacaatttt    960
ctatgtgtat atatatacccc acctctctct tgtgtatttg                         1000

SEQ ID NO: 69           moltype = DNA   length = 998
FEATURE                 Location/Qualifiers
misc_feature            1..998
                        note = Ceres Promoter YP0377
source                  1..998
                        mol_type = unassigned DNA
                        organism = Arabidopsis thaliana
SEQUENCE: 69
tataaaccat tcctataaca ccatatttaa acataacaat gaattgcttg gatttcaaac     60
tttattaaat ttggatttta aattttaatt tgattgaatt atacccccctt aattggataa    120
attcaaatat gtcaacttttt tttttgtaag atttttttat ggaaaaaaaa attgattatt    180
cactaaaaag atgacaggtt acttataatt taatatatgt aaaccctaaa aagaagaaaa    240
tagtttctgt tttcacttta ggtcttatta tctaaacttc tttaagaaaa tcgcaataaa    300
ttggtttgag ttctaacttt aaacacatta atatttgtgt gctatttaaa aaataattta    360
caaaaaaaaa aacaaattga cagaaaaatat caggtttttgt ataagatatt ttcctgataa    420
atatttaggg aatataacat atcaaaagat tcaaattctg aaaatcaaga atggtagaca    480
tgtgaaagtt gtcatcaata tggtccactt ttctttgctc tataacccaa aattgacccct   540
gacagtcaac ttgtacacgc ggccaaacct ttttataatc atgctattta tttccttcat    600
ttttattcta tttgctatct aactgatttt tcattaacat gataccagaa atgaattttag   660
atggattaat tcttttccat ccacgacatc tggaaacact tatctcctaa ttaaccttac    720
ttttttttta gtttgtgtgc tccttcataa aatctatatt gttaaaaaca aaggtcaata    780
aatataaata tggataagta taataaatct ttattggata tttcttttttt taaaaagaaa    840
ataaatcttt tttggatatt ttcgtggcag catcataatg agagactacg tcgaaaccgc    900
tggcaaccac ttttgccgcg tttaatttct ttctgaggct tatataaata gatcaaaggg    960
gaaagtgaga tataatacag acaaaacaag agaaaaga                            998

SEQ ID NO: 70           moltype = DNA   length = 999
FEATURE                 Location/Qualifiers
misc_feature            1..999
                        note = Ceres Promoter YP0380
source                  1..999
                        mol_type = unassigned DNA
                        organism = Arabidopsis thaliana
SEQUENCE: 70
acaagtacca ttcacttttt tacttttcaa tgtatacaat catcatgtga taaaaaaaaa     60
aatgtaacca atcaacacac tgagatacgg ccaaaaaatg gtaatacata aatgtttgta    120
ggttttgtaa tttaaatact ttagttaagt tatgatttta ttatttttgc ttatcactta    180
tacgaaatca tcaatctatt ggtatctctt aatcccgctt tttaatttcc accgcacacg    240
caaatcagca aatggttcca gccacgtgca tgtgaccaca tattgtggtc acagtactcg    300
tccttttttt tctttttgta atcaataaat ttcaatccta aaacttcaca cattgagcac    360
gtcggcaacg ttagctccta aatcataacg agcaaaaaag ttcaaattag ggtatatgat    420
caattgatca tcactacatg tctacataat taatatgtat tcaaccggtc ggtttgttga    480
tactcatagt taagtatata tgtgctaatt agaattagga tgaatcagtt cttgcaaaca    540
actacggttt catataatat gggagtgtta tgtacaaaat gaaagaggat ggatcattct    600
gagatgttaa gggctcccag tcaatcatgt tttgctcgca tatgctatct tttgagtctc    660
ttcctaaaact catagaataa gcacgttggt ttttcacc gtcctcctcg tgaacaaaag      720
tacaattaca ttttagcaaa ttgaaaaataa ccacgtggat ggaccatatt atatgtgatc    780
```

```
atattgcttg tcgtcttcgt tttcttttaa atgtttacac cactactcc tgacacgtgt    840
ccctattcac atcatccttg ttatatcgtt ttacttataa aggatcacga acaccaaaac   900
atcaatgtgt acgtcttttg cataagaaga aacagagagc attatcaatt attaacaatt   960
acacaagaca gcgagattgt aaaagagtaa gagagagag                          999
```

```
SEQ ID NO: 71           moltype = DNA   length = 1000
FEATURE                 Location/Qualifiers
misc_feature            1..1000
                        note = Ceres Promoter YP0381
source                  1..1000
                        mol_type = unassigned DNA
                        organism = Arabidopsis thaliana
SEQUENCE: 71
cacggtcaaa gtattgctaa catggtcatt acattgaaaa agaaaattaa ttgtctttac    60
tcatgtttat tctatacaaa taaaaatatt aaccaaccat cgcactaaca aaatagaaat   120
cttattctaa tcacttaatt gttgacaatt aaatcattga aaaatacact taaatgtcaa   180
atattcgttt tgcatacttt tcaatttaaa tacatttaaa gttcgacaag ttgcgtttac   240
tatcatagaa aactaaatct cctaccaaag cgaaatgaaa ctactaaagc gacaggcagg   300
ttacataacc taacaaatct ccacgtgtca attaccaaga gaaaaaaaga gaagataagc   360
ggaacacgtg gtagcacaaa aaagataatg tgatttaaat taaaaaacaa aaacaaagac   420
acgtgacgac ctgacgctgc aacatcccac cttcaacgt ataaccact gaacataaga    480
cacgtctacg atcttgtctt tgttttctcg atgaaaacc cgtgggtgct caaagtcctt   540
gggtcagagt cttccatgat tccacgtgtc gttaatgcac caaacaaggg tactttcggt   600
attttggctt ccgcaaatta gacaaaacag cttttttgttt gattgatttt tctcttctct   660
ttttccatct aaattctctt tgggctctta atttcttttt gagtgttcgt tcgagatttg   720
tcggagagtt tttcggtaaa tgttgaaatt ttgtgggatt tttttttatt tcttttattaa   780
acttttttt attgaattta taaaaaggga aggtcgtcat taatcgaaga aatgaatct    840
tccaaaattt gatattttgc tgttttcttg ggatttgaat tgctctttat catcaagaat   900
ctgttaaaat ttctaatcta aaatctaagt tgagaaaaag agagatctct aatttaaccg   960
gaattaatat tctccgaccg aagttattat gttgcaggct                        1000
```

```
SEQ ID NO: 72           moltype = DNA   length = 999
FEATURE                 Location/Qualifiers
misc_feature            1..999
                        note = Ceres Promoter YP0384
source                  1..999
                        mol_type = unassigned DNA
                        organism = Arabidopsis thaliana
SEQUENCE: 72
tttaaaaaat tggataaaac accgataaaa attcacattt gcaaatttta ttcagtcgga    60
atatatattt gaaacaagtt ttgaaatcca ttggacgatt aaaattcatt gttgagagga   120
taaatatgga tttgttcatc tgaaccatgt cgttgattag tgattgacta ccatgaaaaa   180
tatgttatga aaagtataac aacttttgat aaatcacatt tattaacaat aaatcaagac   240
aaaatatgtc aacaataata gtagtagaag atattaattc aaattcatcc gtaacaacaa   300
aaaatcatac cacaattaag tgtacagaaa aacctttttgg atatattat tgtcgctttt   360
caatgatttt cgtgaaaagg atatatttgt gtaaaataag aaggatcttg acgggtgtaa   420
aacatgcac aattcttaat ttagaccaat cagaagacaa cacgaacact tcttatattt   480
aagctattaa acaaaatctt gcctattttg cttagaataa tatgaagagt gactcatcag   540
ggagtggaaa atatctcagg atttgctttt agctctaaca tgtcaaacta tctagatgcc   600
aacaacacaa agtgcaaatt cttttaatat gaaaacaaca ataatatttc taatagaaaa   660
ttaaaagggg aaataaaata tttttttaaa atatacaaaa gaagaaggaa tccatcatca   720
aagtttttata aaattgtaat ataatacaaa cttgttgct tccttgtctc tccctctgtc    780
tctctcatct ctcctatctt ctccatatat acttcatctt cacacccaaa actccacaca   840
aaatatctct ccctctatct gcaaattttc caaagttgca tcctttcaat ttccactcct   900
ctctaatata attcacattt tcccactatt gctgattcat tttttttttgt gaattattc   960
aaacccacat aaaaaaatct ttgtttaaat ttaaaacca                          999
```

```
SEQ ID NO: 73           moltype = DNA   length = 998
FEATURE                 Location/Qualifiers
misc_feature            1..998
                        note = Ceres Promoter YP0385
source                  1..998
                        mol_type = unassigned DNA
                        organism = Arabidopsis thaliana
SEQUENCE: 73
actcaacaat aggacaagcc aaaaaaattc caattattgt gttactctat tcttctaaat    60
ttgaacacta atagactatg acatatgagt atataatgtg aagtcttaag atatttttcat   120
gtgggagatg aataggccaa gttggagtct gcaaacaaga agtcttgag ccacgacata   180
agccaagttg atgaccgtaa ttaatgaaac taaatgtgtg tggttatata ttagggaccc   240
atggccatat acacaatttt tgtttctgtc gatagcatgc gtttatatat atttctaaaa   300
aaactaacat atttactgga tttgagttcg aatattgaca ctaatataaa ctacgtacca   360
aactacatat gtttatctat atttgattga tcgaagaatt ctgaactgtt ttagaaaatt   420
tcaatacact taacttcatc ttacaacggt aaaagaaatc accactagac aaacaatgcc   480
tcataatgtc tcgaaccctc aaactcaaga gtatcatttt tactagatta gagaatttga   540
tatcctcaag ttgccaaaga attggaagct tttgttacca aacttagaaa cagaagagc   600
cacaaaaaaa gacaaaggga gttaaagatt gaagtgatgc atttgtctaa gtgtgaaagg   660
tctcaagtct caactttgaa ccataataac attactcaca ctcccttttt ttttctttt    720
tttcccaaa gtacccttt taattccctc tataacccac tcactccatt ccctcttct    780
gtcactgatt caacacgtgg ccacactgat gggatccacc tttcctctta cccacctccc   840
```

```
ggtttatata aacccttcac aacacttcat cgctctcaaa ccaactctct cttctctctt    900
ctctcctctc ttctacaaga agaaaaaaaa cagagccttt acacatctca aaatcgaact    960
tactttaacc accaaatact gattgaacac acttgaaa                            998

SEQ ID NO: 74           moltype = DNA   length = 1000
FEATURE                 Location/Qualifiers
misc_feature            1..1000
                        note = Ceres Promoter YP0396
source                  1..1000
                        mol_type = unassigned DNA
                        organism = Arabidopsis thaliana
SEQUENCE: 74
catagtaaaa gtgaatttaa tcatactaag taaaataaga taaaacatgt tatttgaatt     60
tgaatatcgt gggatgcgta tttcggtatt tgattaaagg tctggaaacc ggagctccta    120
taacccgaat aaaaatgcat aacatgttct tccccaacga ggcgagcggg tcagggcact    180
agggtcattg caggcagctc ataaagtcat gatcatctag gagatcaaat tgtatgtcgg    240
ccttctcaaa attacctcta agaatctcaa acccaatcat agaacctcta aaaagacaaa    300
gtcgtcgctt tagaatgggt tcggttttg gaaccatatt tcacgtcaat ttaatgttta    360
gtataatttc tgaacaacag aattttggat ttatttgcac gtatacaaat atctaattaa    420
taaggacgac tcgtgactat ccttacatta agtttcactg tcgaaataac atagtacaat    480
acttgtcgtt aatttccacg tctcaagtct ataccgtcat ttacggagaa agaacatctc    540
tgttttcat ccaaactact attctcactt tgtctatata tttaaaatta agtaaaaaag     600
actcaatagt ccaataaaat gatgaccaaa tgagaagatg gttttgtgcc agattttagg    660
aaaagtgagt caaggtttca catctcaaat ttgactgcat aatcttcgcc attaacaacg    720
gcattatata tgtcaagcca atttttccatg ttgcgtactt ttctattgag gtgaaaatat    780
gggttttgttg attaatcaaa gagtttgcct aactaatata actacgactt tttcagtgac    840
cattccatgt aaactctgct tagtgtttca tttgtcaaca atattgtcgt tactcattaa    900
atcaaggaaa aatatacaat tgtataattt tcttatattt taaaattaat tttgatgtat    960
tacccttta taaataggct atcgctacaa caccaataac                          1000

SEQ ID NO: 75           moltype = DNA   length = 1514
FEATURE                 Location/Qualifiers
misc_feature            1..1514
                        note = Ceres Promoter p13879
source                  1..1514
                        mol_type = unassigned DNA
                        organism = Arabidopsis thaliana
SEQUENCE: 75
tttcgatcct cttctttttt aggtttcttg atttgatgat cgccgccagt agagccgtcg     60
tcggaagttt cagagattaa aaccatcacc gtgtgagttg gtagcgaatt aacgaaaagt    120
ctaagtcaag attttttaaa aagaaattta tgtgtgaaaa gaagccgttg tgtatattta    180
tataatttag aaaaatgttc atcattttaa ttaaaaaatt aataatttgt agaagaaaga    240
agcatttttt atacataaat catttacctt ctttactgtg ttttctctca cttactttcat    300
tttttactttt ttacaaaaaa gtgaaaagta aattacgtaa ttggtaacat aaattcactt    360
taaatttgca tatgttttgt ttcttcgga aactatatcg aaaagcaaac ggaaagaact    420
tcacaaaaaa ccctagctaa ctaaagacgc atgtgttctt cttattcttc atatatcctc    480
tgttcttgt gttctgtttt gagtcttaca ttttcaatat ctgactctga ttactatatc    540
taaaagggaa catgaagaac ttgagaccat gttaaactgt acaatgcctt caaacatggc    600
taactaaaga tacattagat ggctttacag tgtgtaatgc ttattatctt taggtttttt    660
aaatccctttg tattaagtta tttaccaaat tatgttcttg tactgcttat tggcttggtt    720
gttgtgtgct ttgtaaacaa cacctttggc tttatttcat cctttgtaaa cctactggtc    780
tttgttcagc tcctcttgga agtgagtttg tatgcctgga acgggtttta atggagtgtt    840
tatcgacaaa aaaaaatgt agcttttgaa atcacagaga gtagttttat attcaaatta    900
catgcatgca actaagtagc aacaaagttg atatggccga gttggtctaa ggcgccagat    960
taaggttctg gtccgaaagg gcgtgggttc aaatcccact gtcaacattc tcttttttctc   1020
aaattaatat ttttctgcct caatggttca ggcccaatta tactagacta ctatcgcgac   1080
taaaataggg actagccgaa ttgatccggc ccagtatcag ttgtgtatca ccacgttatt   1140
tcaaatttca aactaaggga taaagatgtc atttgacata tgagatattt ttttgctcca   1200
ctgagatatt tttctttgtc ccaagataaa atatctttc tcgcatcgtc gtctttccat   1260
ttgcgcatta aaccaaaaag tgtcacgtga tatgtcccca accactacga atttaacta   1320
cagatttaac catggttaaa ccagaattca cgtaaaccga ctctaaacct agaaaatatc   1380
taaaccttgg ttaatatctc agccccctta taaataacga gacttcgtct acatcgttct   1440
acacatctca ctgctcacta ctctcactgt aatccccttag atcttctttt caaatttcac   1500
cattgcactg gatg                                                     1514

SEQ ID NO: 76           moltype = DNA   length = 1954
FEATURE                 Location/Qualifiers
misc_feature            1..1954
                        note = Ceres Promoter p326
source                  1..1954
                        mol_type = unassigned DNA
                        organism = Arabidopsis thaliana
SEQUENCE: 76
gtgggtaaaa gtatccttct ttgtgcattt ggtatttta agcatgtaat aagaaaaacc     60
aaaatagacg gctggtattt aataaaagga gactaatgta tgtatagtat atgatttgtg    120
tggaatataa taaagttgta aaatatagat gtgaagcgag tatctatctt ttgacttca    180
aaggtgatcg atcgtgttct ttgtgatagt tttggtcgtc ggtctacaag tcaacaacca    240
ccttgaagtt ttcgcgtctc ggtttcctct tcgcatctgg tatccaatag catacatata    300
ccagtgcgga aaatggcgaa gactagtggg cttgaaccat aaggtttggc cccaatacgg    360
```

```
attccaaaca acaagcctag cgcagtcttt tgggatgcat aagactaaac tgtcgcagtg  420
atagacgtaa gatatatcga cttgattgga atcgtctaag ctaataagtt taccttgacc  480
gtttatagtt gcgtcaacgt ccttatggag attgatgccc atcaaataaa cctgaaaatc  540
catcaccatg accaccataa actcccttgc tgccgctgct ttggcttgag caaggtgttt  600
ccttgtaaag ctccgatctt tggataaagt gttccacttt ttgcaagtag ctctgacccc  660
tctcagagat gtcaccggaa tcttagacag aacctcctct gccaaatcac ttggaagatc  720
ggacaatgtc atcattttg caggtaattt ctccttcgtt gctgctttgg cttgagcacg  780
gtgcttcttt gtaaagctcc gatctttgga taagagcgga tcggaatcct ctaggaggtg  840
ccagtccctt gacctattaa tttatagaag gttttagtgt attttgttcc aatttcttct  900
ctaacttaac aaataacaac tgcctcatag tcatgggctt caaattttat cgcttggtgt  960
atttcgttat ttgcaaggcc ttggcccatt ttgagcccaa taactaaatc tagccttttc 1020
agaccggaca tgaacttcgc atattggcgt aactgtgcag ttttaccttt tcggatcag  1080
acaagatcag atttagacca cccaacaata gtcagtcata tttgacaacc taagctagcc 1140
gacactacta aaaagcaaac aaaagaagaa ttctatgttg tcattttacc ggtggcaagt 1200
ggacccttct ataaaagagt aaagagacag cctgtgtgtg tataatctct aattatgttc 1260
accgacacaa tcacacaaac ccttctctaa tcacacaact tcttcatgat ttacgacatt 1320
aattatcatt aactctttaa attcacttta catgctcaaa aatatctaat ttgcagcatt 1380
aatttgagta ccgataacta ttattataat cgtcgtgatt cgcaatcttc ttcattagat 1440
gctgtcaagt tgtactcgca cgcggtggtc cagtgaagca aatccaacgg tttaaaacct 1500
tcttacattt ctagatctaa tctgaaccgt cagatatcta gatctcattg tctgaacaca 1560
gttagatgaa actgggaatg aatctggacg aaattacgat cttacaccaa cccctcgac  1620
gagctcgtat atataaagct tatacgctcc tccttcacct tctgtactact actaccacca 1680
catttcttta gctcaacctt cattactaat ctcccttttaa ggtatgttca cttttcttcg 1740
attcatactt tctcaagatt cctgcatttc tgtagaattt gaaccaagtg tcgatttttg 1800
tttgagagaa gtgttgattt atagatctgg ttattgaatc tagattccaa ttttttaattg 1860
attcgagttt gttatgtgtg tttatactac ttctcattga tcttgtttga tttctctgct 1920
ctgtattagg tttctttcgt gaatcagatc ggaa                              1954

SEQ ID NO: 77           moltype = DNA   length = 2016
FEATURE                 Location/Qualifiers
misc_feature            1..2016
                        note = Ceres Promoter p32449
source                  1..2016
                        mol_type = unassigned DNA
                        organism = Arabidopsis thaliana
SEQUENCE: 77
gatcggcctt cttcaggtct tctctgtagc tctgttactt ctatcacagt tatcgggtat   60
ttgagaaaaa agagttagct aaaatgaatt tctccatata atcatggttt actacaggtt  120
tacttgattc gcgttagctt tatctgcatc caaagttttt tccatgatgt tatgtcatat  180
gtgataccgt tactatgttt ataacttat acagtctggt tcactggagt ttctgtgatt  240
atgttgagta catactcatt catcctttgg taactctcaa gtttaggttg tttgaattgc  300
ctctgttgtg atacttattg tctattgcat caatcttcta atgcaccacc ctagactatt  360
tgaacaaaga gctgtttcat tcttaaacct ctgtgtctcc ttgctaaatg gtcatgcttt  420
aatgtcttca cctgtctttc tcttctatag atatgtagtc ttgctagata gttagttcta  480
cagctctctt ttgtagtctt gttagagagt tagttgagat attacctctt aaaagtatcc  540
ttgaacgctt tccggttatg accaatttgt tgtagctcct tgtaagtaga acttactggg  600
accagcgaga cagtttatgt gaatgttcat gcttaagtgt cgaacgtatc tatctctact  660
atagctctgt agtcttgtta gacagttagt tttatatctc catttttttg tagtcttgct  720
agttgagata ttacctcttc tcttcaaagt atccttgaac gctcaccggt tatgaaatct  780
ctacactata gctctgtagt cttgctagat agttagttct ttagctctct ttttgtagcc  840
tagttcttta gctctccttt tgtagccttg ctacagagta agatgggata ttacctccctt  900
gaacgctctc cggttatgac caatttgttg tagctccttg taagtagaac ttaggataga  960
gtgagtcaac tttaagaaag aacctagtat gtggcataac cagattgcag gctctgtctc 1020
ggctacagta acgtaactct atagctcttt gttttgttca gaaagaacca gtgattggat 1080
gattcgtcct tagaaactgg acctaacaac agtcattggc tttgaaatca agccacaaca 1140
atgcctatat gaaccgtcca tttcatttat ccgtttcaaa ccagcccatt acatttcgtc 1200
ccattgataa ccaaaagcgg ttcaatcaga ttatgtttta attttaccaa attctttatg 1260
aagtttaaat tatactcaca ttaaaaggat tattggataa tgtaaaaatt ctgaacaatt 1320
actgattttg gaaaattaac aaatattctt tgaaatagaa gaaaaagcct ttttcctttt 1380
gacaacaaca tataaaatca tactcccatt aaaaagattt taatgtaaaa ttctgaatat 1440
aagatatttt ttacaacaac aaccaaaaat atttattttt ttcctttttt acagcaacaa 1500
gaaggaaaaa cttttttttt tgtcaagaaa agggagatt atgtaaacag ataaaacagg 1560
gaaaataact aaccgaactc tcttaattaa catcttcaaa taaggaaaat tatgatccgc 1620
atatttagga agatcaatgc attaaaacaa cttgcacgtg gaaagagaga ctatacgctc 1680
cacacaagtt gcactaatgg tacctctcac aaaccaatca aaatactgaa taatgccaac 1740
gtgtacaaat tagggttta cctcacaacc atcgaacatt ctcgaaacat tttaaacagc 1800
ctggcgccat agatctaaac tctcatcgac caattttga ccgtccgatg gaaactctag 1860
cctcaaccca aaactctata taagaaatc ttttccttcg ttattgctta ccaaaatacaa 1920
accctagccg ccttattcgt cttcctcgtt ctctagtttt ttccctcagtc tctgttctta 1980
gatcccttgt agtttccaaa tcttccgata aggcct                           2016

SEQ ID NO: 78           moltype = DNA   length = 857
FEATURE                 Location/Qualifiers
misc_feature            1..857
                        note = Ceres Promoter PD1367
unsure                  116
                        note = n is a, c, t, g, unknown, or other
unsure                  136
                        note = n is a, c, t, g, unknown, or other
```

```
unsure              154
                    note = n is a, c, t, g, unknown, or other
unsure              159
                    note = n is a, c, t, g, unknown, or other
unsure              168
                    note = n is a, c, t, g, unknown, or other
unsure              172
                    note = n is a, c, t, g, unknown, or other
unsure              175
                    note = n is a, c, t, g, unknown, or other
unsure              679
                    note = n is a, c, t, g, unknown, or other
unsure              680
                    note = n is a, c, t, g, unknown, or other
unsure              686
                    note = n is a, c, t, g, unknown, or other
unsure              724
                    note = n is a, c, t, g, unknown, or other
unsure              737
                    note = n is a, c, t, g, unknown, or other
source              1..857
                    mol_type = unassigned DNA
                    organism = Arabidopsis thaliana
SEQUENCE: 78
ttggaattaa ttctgcggcc atggggctgc aggaattcga tggcccgatc ggccacagtt    60
ttcttttctc atcttacaac aagtttccag gaggatagaa acataaacga agctcnggat   120
tgtatcgttc tttttnagct tttattcaca tccngaaang tcctgtangt tntangattc   180
tgttatcttg cggttttgag ttaatcagaa acagagtaat caatgtaatg ttgcaggcta   240
gatctttcat ctttggaaat ttgttttttt ctcatgcaat ttctttagct tgaccatgag   300
tgactaaaag atcaatcagt agcaatgatt tgatttggct aagagacatt tgtccacttg   360
gcatcttgat ttggatggtt acaacttgca agacccaatt ggatacttgc tatgacaact   420
ccaactcaag agtgtcgtgt aactaagaac cttgactaat ttgtaatttc aatcccaagt   480
catgttacta tatgttttt  tgtttgtatt attttctctc ctacaattaa gctctttgac   540
gtacgtaatc tccggaacca actcctatat ccaccattta ctcccacgttg tctccaatta  600
ttggacgttg aaacttgaca caacgtaaac gtatctacgt ggttgattgt atgtacatat   660
gtacaaacgt acacctttnn ctcctncttt cacttcatca cttggcttgt gaattcatta   720
attncctgcg aaggccntgc agggccatca ccactgcagt ggaacaatga agactaatct   780
ttttctcttt ctcatctttt cacttctcct atcattatcc tcggccgaat tcagtaaagg   840
agaagaactt ttcactg                                                  857

SEQ ID NO: 79          moltype = DNA  length = 1032
FEATURE                Location/Qualifiers
misc_feature           1..1032
                       note = Ceres CLONE ID no. 8686
misc_feature           1..1032
                       note = Ceres Seed Line ID no. ME03807
misc_feature           1..1032
                       note = Encodes the peptide given in SEQ ID NO: 80
source                 1..1032
                       mol_type = unassigned DNA
                       organism = Arabidopsis thaliana
SEQUENCE: 79
aaaaaaacac tagtatcaaa aattgaaccc gttaaccggc gacccgaaac aatgacccgg    60
tccgtcagtt tccctctctt cctcttcgcc gttgtactct ccctctcttc ttctctcctc   120
gccgacgatc ccaaaccaat ccgccgtgag gtctacgaag gaggtaagat atacgacatc   180
agccatcgtt acacgccgga gattccagct tgggaatctt cggaaggatt gggaaagacg   240
ttcctgcgat tagccgcgag tatgaagaat ggatcattcg ctaacgtatc ggagatgaaa   300
ctatctgttc actctggaac tcacgtggat gctccaggtc acttttggga taattattac   360
gatgctggtt ttgatactga ttcgcttgat ctccaagtcc taaatggtcc tgctttgttg   420
gttgatgttc cgagagataa gaacattact gctgaggtaa tggaatcact tcatatacaa   480
agaggagttc gtcgtgtgct ctttagaaca tccaacaccg acaagcggct tatgtttaag   540
aaaagagtttg attcaagctt tgctgggttc atgaccgatg gggctaaatg gttggttgag   600
aatacagaca tcaaacttat tgggcttgat tatctttcat ttgctgcttt tgaggaatca   660
cctgcaacac acagggttat acttaaagga cgggatataa tcccagtgga agcgctgaag   720
ctggatggtg tggaggtagg aacatactgc cttcattgct taccgctgag attagttgga   780
gcggaaggag caccgacaag atgcattctc atcaagtgat tcagttcttc ttcttcttct   840
tcttcttctg tgtaagttgt tcagtatacc aaactgataa tgaataatat gcttcttact   900
ttacaagatc tcagaaccca tgaagcagat gtgatgattc agttgtaaaa ggaagcatac   960
ctttataaac gtgtgaatgt attatgtatg acagtatatt tgtaattctg aaggacatga  1020
taataaacct ag                                                      1032

SEQ ID NO: 80          moltype = AA  length = 255
FEATURE                Location/Qualifiers
REGION                 1..255
                       note = Ceres CLONE ID no. 8686
REGION                 1..255
                       note = Ceres Seed Line ID no. ME03807
REGION                 40..241
                       note = Pfam Name: Cyclase Pfam Description: Putative cyclase
```

```
source                  1..255
                        mol_type = protein
                        organism = Arabidopsis thaliana
SEQUENCE: 80
MTRSVSFPLF LFAVVLSLSS SLLADDPKPI RREVYEGGKI YDISHRYTPE IPAWESSEGL    60
GKTFLRLAAS MKNGSFANVS EMKLSVHSGT HVDAPGHFWD NYYDAGFDTD SLDLQVLNGP   120
ALLVDVPRDK NITAEVMESL HIQRGVRRVL FRTSNTDKRL MFKKEFDSSF AGFMTDGAKW   180
LVENTDIKLI GLDYLSFAAF EESPATHRVI LKGRDIIPVE ALKLDGVEVG TYSLHCLPLR   240
LVGAEGAPTR CILIK                                                   255

SEQ ID NO: 81           moltype = AA  length = 204
FEATURE                 Location/Qualifiers
REGION                  1..204
                        note = Ceres CLONE ID no. 1096546
REGION                  1..185
                        note = Pfam Name: Cyclase Pfam Description: Putative cyclase
REGION                  1..204
                        note = Functional Homolog of Ceres CLONE ID no. 8686 at SEQ
                         ID NO. 80 with e-value of 8.19E-91 and BLAST sequence
                         identity of 87.2
VARIANT                 88
                        note = Xaa is any aa, unknown or other
VARIANT                 99
                        note = Xaa is any aa, unknown or other
VARIANT                 134
                        note = Xaa is any aa, unknown or other
VARIANT                 152
                        note = Xaa is any aa, unknown or other
VARIANT                 171
                        note = Xaa is any aa, unknown or other
VARIANT                 194
                        note = Xaa is any aa, unknown or other
VARIANT                 196
                        note = Xaa is any aa, unknown or other
VARIANT                 200
                        note = Xaa is any aa, unknown or other
source                  1..204
                        mol_type = protein
                        organism = Brassica napus
SEQUENCE: 81
MPAWESKEGL SNHLRLIASM KNGSFANVSE MKLSVHSGTH VDAPGHFIDE YYDAGFDCDS    60
LDLQTLNGPA LLVDVPRDKN ITAEVMEXLH IPRGVRRVXF RTSNTDKRLM FKKEFDSSFS   120
GFMTDGAKWL VENXDIKLVG LDYLSFAAFD EXPATHKVIL RGRDIIPVEA XKLDGVEAGM   180
YSLHCLPLRL VGAXGXPTRX ILIK                                         204

SEQ ID NO: 82           moltype = AA  length = 157
FEATURE                 Location/Qualifiers
REGION                  1..157
                        note = Ceres CLONE ID no. 1311812
REGION                  1..157
                        note = Functional Homolog of Ceres CLONE ID no. 8686 at SEQ
                         ID NO. 80 with e-value of 2.60E-64 and BLAST sequence
                         identity of 86.7
REGION                  13..141
                        note = Pfam Name: Cyclase Pfam Description: Putative cyclase
VARIANT                 37
                        note = Xaa is any aa, unknown or other
VARIANT                 58
                        note = Xaa is any aa, unknown or other
source                  1..157
                        mol_type = protein
                        organism = Brassica napus
SEQUENCE: 82
MDKVLTNAGF DSDSLDLQVL HGPALLVDVP RDKNITXVMK SLHIPKGVRR VLFRTLNXDR    60
RLMFKKEFDS SFAGFMMDGA KWLVENTDIK LIGLDYLSFA AYEEAPETHK FILGERDIIP   120
VEALKLDGVE VGVYSLHCLP LRLPGAEGAP TRCILIK                            157

SEQ ID NO: 83           moltype = AA  length = 204
FEATURE                 Location/Qualifiers
REGION                  1..204
                        note = Ceres CLONE ID no. 952461
REGION                  1..204
                        note = Functional Homolog of Ceres CLONE ID no. 8686 at SEQ
                         ID NO. 80 with e-value of 1.79E-88 and BLAST sequence
                         identity of 85.7
REGION                  1..182
                        note = Pfam Name: Cyclase Pfam Description: Putative cyclase
VARIANT                 76
                        note = Xaa is any aa, unknown or other
```

```
VARIANT                 77
                        note = Xaa is any aa, unknown or other
VARIANT                 78
                        note = Xaa is any aa, unknown or other
VARIANT                 88
                        note = Xaa is any aa, unknown or other
VARIANT                 99
                        note = Xaa is any aa, unknown or other
VARIANT                 134
                        note = Xaa is any aa, unknown or other
VARIANT                 152
                        note = Xaa is any aa, unknown or other
VARIANT                 171
                        note = Xaa is any aa, unknown or other
VARIANT                 194
                        note = Xaa is any aa, unknown or other
VARIANT                 196
                        note = Xaa is any aa, unknown or other
VARIANT                 200
                        note = Xaa is any aa, unknown or other
source                  1..204
                        mol_type = protein
                        organism = Brassica napus
SEQUENCE: 83
MPAWESKEGL SNHLRLIASM KNGSFANVSE MKLSVHSGTH VDAPGHFIDE YYDAGFDCDS    60
LDLQTLNGPA LLVDVXXXKN ITAEVMEXLH IPRGVRRVXF RTSNTDKRLM PKKEFDSSFS   120
GFMTDGAKWL VENXDIKLVG LDYLSFAAFD EXPATHKVIL RGRDIIPVEA XKLDGVEAGM   180
YSLHCLPLRL VGAXGXPTRX ILIK                                          204

SEQ ID NO: 84           moltype = AA  length = 233
FEATURE                 Location/Qualifiers
REGION                  1..233
                        note = Ceres CLONE ID no. 954851
REGION                  1..233
                        note = Functional Homolog of Ceres CLONE ID no. 8686 at SEQ
                          ID NO. 80 with e-value of 4.70E-95 and BLAST sequence
                          identity of 80.4
REGION                  20..216
                        note = Pfam Name: Cyclase Pfam Description: Putative cyclase
VARIANT                 112
                        note = Xaa is any aa, unknown or other
VARIANT                 113
                        note = Xaa is any aa, unknown or other
VARIANT                 134
                        note = Xaa is any aa, unknown or other
source                  1..233
                        mol_type = protein
                        organism = Brassica napus
SEQUENCE: 84
MTSSDDLKPI RQEVYGERKI FDITHRYTQD MPVWESTEGV KPFLRLTTSM KNQSLSNTSE    60
MKLSVHTGTH LDAPGHFHDK YYDAGFDSDS LDLQVLHGPA LLVDVPRDKN IXXVMKSLHI   120
PKGVRRVLFR TLNXDRRLMF KKEFDSSFAG FMMDGAKWLV ENTDIKLIGL DYLSFAAYEE   180
APETHKFILG ERDIIPVEAL KLDGVEVGVY SLHCLPLRLP GAEGAPTRCI LIK          233

SEQ ID NO: 85           moltype = AA  length = 271
FEATURE                 Location/Qualifiers
REGION                  1..271
                        note = Ceres CLONE ID no. 1064137
REGION                  1..271
                        note = Functional Homolog of Ceres CLONE ID no. 8686 at SEQ
                          ID NO. 80 with e-value of 1.00E-90 and BLAST sequence
                          identity of 75.2
REGION                  57..257
                        note = Pfam Name: Cyclase Pfam Description: Putative cyclase
source                  1..271
                        mol_type = protein
                        organism = Zea mays
SEQUENCE: 85
MAVPPLLLLT LLSLPSLLIH AAISDAYPTI PGTAPIDGGF SDELKPIRRE VYGEGKIFDI    60
SHRYTPEMPA WESKEGIGRF LWLAASMKNG SLANNSEMKI PTHTGTHVDS PGHVYDEYYD   120
AGFDVDSLDL QVLNGPALLV DVPRNKNITA EVMKSLNIPR GVRRVLFRTL NTDRRLMFKK   180
EFDTSYVGFM KDGAQWLVDN TDIKLVGVDY LSVAAYDDLI PSHLVFLKGR ETILVEGLKL   240
DDVKAGVYSV HCLPLRLVGA EGSPIRCILI S                                  271

SEQ ID NO: 86           moltype = AA  length = 121
FEATURE                 Location/Qualifiers
REGION                  1..121
                        note = Ceres CLONE ID no. 368629
REGION                  1..121
```

|  |  |  |
|---|---|---|
|  | note = Functional Homolog of Ceres CLONE ID no. 8686 at SEQ ID NO. 80 with e-value of 9.09E-37 and BLAST sequence identity of 72.8 |  |
| REGION | 1..103 |  |
|  | note = Pfam Name: Cyclase Pfam Description: Putative cyclase |  |
| source | 1..121 |  |
|  | mol_type = protein |  |
|  | organism = Zea mays |  |
| SEQUENCE: 86 |  |  |

```
MPEWESSEGS GEFLQLARSM RNGSDIANFS ELRLTAHSGT HVDAPGHVFE HYYDTGFDVD    60
TLDLAVLNGP ALLVDVPRDK NITADVMASL NMPKGVRRVL FRTLNTDRMV HNGWLIIQTS   120
N                                                                  121
```

|  |  |  |
|---|---|---|
| SEQ ID NO: 87 | moltype = AA   length = 205 |  |
| FEATURE | Location/Qualifiers |  |
| REGION | 1..205 |  |
|  | note = Ceres CLONE ID no. 473732 |  |
| REGION | 1..205 |  |
|  | note = Functional Homolog of Ceres CLONE ID no. 8686 at SEQ ID NO. 80 with e-value of 3.60E-74 and BLAST sequence identity of 71.2 |  |
| REGION | 1..191 |  |
|  | note = Pfam Name: Cyclase Pfam Description: Putative cyclase |  |
| source | 1..205 |  |
|  | mol_type = protein |  |
|  | organism = Glycine max |  |
| SEQUENCE: 87 |  |  |

```
MPVWDSTEGL GQHFLWLEKS MKNGSRANNS NMKLGVHTGT HVDAPGHFYD NYYDAGFDVD    60
SLDLTLLNGL ALLVDVPRDK NITAEVMKSL NIPRGVSRVL FRTLNTDRQL MFKKEFDTSY   120
VGFKEDGAKW LAENTDIKLV GVDYLSVAAY DHSIPSHLVF LESKEIILVE GLKLDDVPAG   180
IYSLNCLPLR LVHSEASPIR CILIK                                        205
```

|  |  |  |
|---|---|---|
| SEQ ID NO: 88 | moltype = DNA   length = 831 |  |
| FEATURE | Location/Qualifiers |  |
| misc_feature | 1..831 |  |
|  | note = Ceres ANNOT ID no. 1441150 |  |
| misc_feature | 1..831 |  |
|  | note = Encodes the peptide given in SEQ ID NO. 89 |  |
| source | 1..831 |  |
|  | mol_type = unassigned DNA |  |
|  | note = Populus balsamifera subsp. trichocarpa |  |
|  | organism = Populus balsamifera |  |
| SEQUENCE: 88 |  |  |

```
atggcatccc tcctcttgtt actgctcctg tctccctct  ccaccaccgc agcctccagc    60
ggcgcttacc ccaccatccc tggcagcata gacacctctt tccccgcttc acaagacagc   120
aaacttatcc caatcaggcg tgaggtgtat ggtgatggga gaatatttga cataacccac   180
aggtacacaa gcgacaatgc gtccatggga tcagaaaatg ggctgggtca gttcctgagg   240
ctccctgaaa gcatgaagaa tgggtccttc gccaacatat cggagatgaa gttgatcact   300
catactggca cacgtcga   tgcacctgga cattactatg atcattactt cgatgctggg   360
tttgatgtgg acactcttga ccttgaagta cttaatggtc ctggactatt aattgatgtt   420
ccaaggggga cgaacataac tgctgaagtt atgaagtcct tacatattcc caaaggagct   480
cgacgtgttc ttttcaggac agaaaatacc gacaggcgac ttatgttcaa aaatcagatc   540
gatacaagct ttgtgggatt tacaacggat ggagcaaaat ggttggtaga caacactgac   600
attaagcttg ttggaattga ttacttagct gttgctgctt ggagtgattt ggttccagct   660
catcttgtcc ttttggaaag cagggtgaga ctaatgcagt gtaaagaaat catcattgtg   720
gaaggcctaa aactcgatga catccaacct ggtgtgtatt ctatccattg tttgcctata   780
agattgctcg gtgctgaagg atcaccaacg cgatgcattc tcatcaaatg a             831
```

|  |  |  |
|---|---|---|
| SEQ ID NO: 89 | moltype = AA   length = 211 |  |
| FEATURE | Location/Qualifiers |  |
| REGION | 1..211 |  |
|  | note = Ceres ANNOT ID no. 1441150 |  |
| REGION | 1..211 |  |
|  | note = Functional Homolog of Ceres CLONE ID no. 8686 at SEQ ID NO. 80 with e-value of 2.30E-72 and BLAST sequence identity of 68.6 |  |
| REGION | 13..197 |  |
|  | note = Pfam Name: Cyclase Pfam Description: Putative cyclase |  |
| source | 1..211 |  |
|  | mol_type = protein |  |
|  | note = Populus balsamifera subsp. trichocarpa |  |
|  | organism = Populus balsamifera |  |
| SEQUENCE: 89 |  |  |

```
MPSMGSENGL GQFLRLPESM KNGSFANISE MKLITHTGTH VDAPGHYYDH YFDAGFDVDT    60
LDLEVLNGPG LLIDVPRGTN ITAEVMKSLH IPKGARRVLF RTENTDRRLM FKNQIDTSFV   120
GFTTDGAKWL VDNTDIKLVG IDYLAVAAWS DLVPAHLVLL ESRVRLMQCK EIIIVEGLKL   180
DDIQPGVYSI HCLPIRLLGA EGSPTRCILI K                                 211
```

|  |  |  |
|---|---|---|
| SEQ ID NO: 90 | moltype = AA   length = 251 |  |

```
FEATURE                     Location/Qualifiers
REGION                      1..251
                            note = Ceres CLONE ID no. 554272
REGION                      1..251
                            note = Functional Homolog of Ceres CLONE ID no. 8686 at SEQ
                             ID NO. 80 with e-value of 1.90E-75 and BLAST sequence
                             identity of 68.0
REGION                      37..237
                            note = Pfam Name: Cyclase Pfam Description: Putative cyclase
source                      1..251
                            mol_type = protein
                            organism = Glycine max
SEQUENCE: 90
MNCYWWHALI MSGCVLGLCV GIGGCVCVVE NENGRIIIDI SHRYHPDMPA WESKDSLGQF      60
LWLTRSMANG SLANFSQFKL PAHSGTHVDA PGHVFDHYFH SGFDVDSLDL LLLNGPALLV     120
DVPRDTNISA GVMKSLNIPR GVRRVLFRTL NTYRRLMYQK EFDTSYVGFT EDGANWLVEN    180
TDIKLVGIDY LSVAAYDHLI PAHLVFLKGR EIILVEGLKL DDVAAGIYTV HCLPLRLAGA    240
EGSPIRCILI K                                                         251

SEQ ID NO: 91               moltype = AA  length = 255
FEATURE                     Location/Qualifiers
REGION                      1..255
                            note = Ceres CLONE ID no. 511015
REGION                      1..255
                            note = Functional Homolog of Ceres CLONE ID no. 8686 at SEQ
                             ID NO. 80 with e-value of 1.40E-81 and BLAST sequence
                             identity of 66.3
REGION                      40..240
                            note = Pfam Name: Cyclase Pfam Description: Putative cyclase
source                      1..255
                            mol_type = protein
                            organism = Glycine max
SEQUENCE: 91
MKRGALLSVL ACAFAAVIWA ANGDDNLVPP RREVYGNGRI FDISHRYQPE MPEWESNDGI      60
GQFLWLPKSM KNGSLANNSE MKFPTHTGTH VDAPGHVFDH YFHAGFDVDT LDLDILNGPA    120
MLVDVPRDSN ITAQVMKSLN IPRGVIRVLF RTLNTDRRLM FQKEWDSSYV GPTADGAKWL    180
VENTDIKLVG IDYLSVASYD YLIPSHLVFL KDREIILVEG LKLDDVPAGL YSVHCLPLRL    240
AGAEGSPIRC ILIKN                                                     255

SEQ ID NO: 92               moltype = AA  length = 265
FEATURE                     Location/Qualifiers
REGION                      1..265
                            note = Ceres CLONE ID no. 881632
REGION                      1..265
                            note = Functional Homolog of Ceres CLONE ID no. 8686 at SEQ
                             ID NO. 80 with e-value of 2.10E-78 and BLAST sequence
                             identity of 66.3
REGION                      51..251
                            note = Pfam Name: Cyclase Pfam Description: Putative cyclase
source                      1..265
                            mol_type = protein
                            organism = Triticum aestivum
SEQUENCE: 92
MAPPLLLLLL VPLVAATAPC AHPAHPSQPA SCAAEPVLAP ERREAHGGGR ILDITHYYRE      60
DMPSWESGAG VGQFLWLPAS MRNGSLANNS EMRMPTHTGT HIDASGHVFQ HYFDAGFDVD    120
TLDLDVLNGP ALLVDVPRDE NITAKTMESL HIPKGVQRVL FRTLNTDRNL MWKKEFDTSY    180
VGFMKDGAQW LVDNTDIKLV GIDYLSVAAF DDLIPSHLVL LENRDIILVE GLKLENVIPG    240
IYSLHCLPLR LRGAEGSPIR CILIK                                           265

SEQ ID NO: 93               moltype = AA  length = 269
FEATURE                     Location/Qualifiers
REGION                      1..269
                            note = Functional Homolog of Ceres CLONE ID no. 8686 at SEQ
                             ID NO. 80 with e-value of 1.40E-79 and BLAST sequence
                             identity of 66.2
REGION                      55..255
                            note = Pfam Name: Cyclase Pfam Description: Putative cyclase
source                      1..269
                            mol_type = protein
                            note = Oryza sativa subsp. japonica
                            organism = Oryza sativa
SEQUENCE: 93
MAHLAPLFLL LLLLLLPLHA AATPSAHPAY PNEPPSCAAA VPVPERREAH GGGRILDITH      60
YYREDMPSWE SDGGVGQFLW LPASMRNGSR ANNSEMRLPT HTGTHVDAPG HVFQHYFDAG    120
FDVDSLDLEV LNGLALLVDV PRDDNITAKM MESLHIPKGI QRVLFRTLNT DRQLMWKKEF    180
DTSYVGFMED GAQWLVDNTD IKLVGIDYLS VAAFDDLIPS HLVLLKNRDI ILVEGLKLEN    240
IMPGIYSLHC LPLRLRGAEG SPIRCILIK                                      269

SEQ ID NO: 94               moltype = DNA  length = 825
```

| FEATURE | Location/Qualifiers |
|---|---|
| misc_feature | 1..825 |
| | note = Ceres ANNOT ID no. 1494052 |
| misc_feature | 1..825 |
| | note = Encodes the peptide given in SEQ ID NO. 95 |
| source | 1..825 |
| | mol_type = unassigned DNA |
| | note = Populus balsamifera subsp. trichocarpa |
| | organism = Populus balsamifera |

SEQUENCE: 94

```
atgtccacca ccaaaaccat gatccctctc ctcctcctcc tcctcctctc tcccctctcc   60
accaccgctt ctaccgccgc ctaccccaca atcccgggca ccatagacac ctcagtctcc  120
tcctcccaac ccgacaacct gattccaatc cgcaacgaaa tctacggcaa tggtaaaatc  180
tttgacataa gtcacagata cataaacgat atgccggttt gggactctaa agacgggttg  240
ggaaagttcc tgtctcttta ccagcaagca tgaaaaatgg gtctctcgct aacaactcag  300
atgaagttac ctactcatac tggcacgcat gttgactcac ctggacatgt ttttgatcat  360
tactttgatt ctgggttcga tgttgatact cttgatcttg aagtccttaa tggtcctgct  420
ttgctagtgg atgttccaag gcattccaat ataactgctg aagttatgaa gtccttacac  480
attccaaagg gagtgcgtcg cgtgcttttc agaacactaa acactgacag gcggcttatg  540
ttcaaaaggg agtttgatag aagttatgtg gggttcacaa aggatggtgc aaaatggttg  600
gtagacaaca ctgacatcaa gcttgttgga attgattacc tatctgttgc tgcctggagt  660
gatttgattc catctcatct tgtctttcta gaaggcaggg aaatcatcct tgtggaggct  720
ttaaaactgg atgacatcca acctggagta tattctgtcc attgtttacc cctgaggttg  780
tttggcgccg agggatctcc aataagatgc gttctcatca aatga              825
```

| SEQ ID NO: 95 | moltype = AA length = 274 |
|---|---|
| FEATURE | Location/Qualifiers |
| REGION | 1..274 |
| | note = Ceres ANNOT ID no. 1494052 |
| REGION | 1..274 |
| | note = Functional Homolog of Ceres CLONE ID no. 8686 at SEQ ID NO. 80 with e-value of 4.30E-85 and BLAST sequence identity of 65.6 |
| REGION | 60..260 |
| | note = Pfam Name: Cyclase Pfam Description: Putative cyclase |
| source | 1..274 |
| | mol_type = protein |
| | note = Populus balsamifera subsp. trichocarpa |
| | organism = Populus balsamifera |

SEQUENCE: 95

```
MSTTKTMIPL LLLLLLSPLS TTASTAAYPT IPGTIDTSVS SSQPDNLIPI RNEIYGNGKI   60
FDISHRYIND MPVWDSKDGL GKFLSLPASM KNGSLANNSE MKLPTHTGTH VDSPGHVFDH  120
YFDSGFDVDT LDLEVLNGPA LLVDVPRHSN ITAEVMKSLH IPKGVRRVLF RTLNTDRRLM  180
FKREFDRSYV GFTKDGAKWL VDNTDIKLVG IDYLSVAAWS DLIPSHLVFL EGREIILVEA  240
LKLDDIQPGV YSVHCLPLRL FGAEGSPIRC VLIK                              274
```

| SEQ ID NO: 96 | moltype = DNA length = 1005 |
|---|---|
| FEATURE | Location/Qualifiers |
| misc_feature | 1..1005 |
| | note = Ceres ANNOT ID no. 1441151 |
| misc_feature | 1..1005 |
| | note = Encodes the peptide given in SEQ ID NO. 97 |
| source | 1..1005 |
| | mol_type = unassigned DNA |
| | note = Populus balsamifera subsp. trichocarpa |
| | organism = Populus balsamifera |

SEQUENCE: 96

```
atgtccacca ccaaaaccat gatccctctc ctcctcctcc tcctcctctc tcccctctcc   60
accaccgctt ctaccgccgc ctaccccaca atcccgggca ccatagacac ctcagtctcc  120
tcctcccaac ccgacaacct gattccaatc cgcaacgaaa tctacggcaa tggtaaaatc  180
tttgacataa gtcacagata cataaacgat atgccggttt gggactctaa agacgggttg  240
ggaaagttcc tgtctcttta ccagcaagca tgaaaaatgg gtctctcgct aacaactcag  300
atgaagttac ctactcatac tggcacgcat gttgactcac ctggacatgt ttttgatcat  360
tactttgatt ctgggttcga tgttgatact cttgatcttg aagtccttaa tggtcctgct  420
ttgctagtgg atgttccaag gcattccaat ataactgctg aagttatgaa gtccttacac  480
attccaaagg gagtgcgtcg cgtgcttttc agaacactaa acactgacag gcggcttatg  540
ttcaaaaggg agtttgatag aagttatgtg gggttcacaa aggatggtgc aaaatggttg  600
gtagacaaca ctgacatcaa gcttgttgga attgattacc tatctgttgc tgcctggagt  660
gatttgattc catctcatct tgtctttcta gaaggcaggg aaatcatcct tgtggaggct  720
ttaaaactgg atgacatcca acctggagta tattctgtcc attgtttacc cctgaggatc  780
ctttattcac acttgttcaa tgctgctacc agctcacatg ccacaccatg gcacaacagg  840
caagatacaa tctaccacaa caaaagccta ctgtttatcc cacgtgaatt gtctggtcag  900
aaaggatcac aaacagaggc cagtgactca aatttaggcg gcgcttcat tgactggcaa   960
gtggcaacag aaacctttcca cgacccagga tcagtgcttg tatag             1005
```

| SEQ ID NO: 97 | moltype = AA length = 334 |
|---|---|
| FEATURE | Location/Qualifiers |
| REGION | 1..334 |
| | note = Ceres ANNOT ID no. 1441151 |

| REGION | 1..334 |
| | note = Functional Homolog of Ceres CLONE ID no. 8686 at SEQ ID NO. 80 with e-value of 6.10E-79 and BLAST sequence identity of 64.5 |
| REGION | 60..260 |
| | note = Pfam Name: Cyclase Pfam Description: Putative cyclase |
| source | 1..334 |
| | mol_type = protein |
| | note = Populus balsamifera subsp. trichocarpa |
| | organism = Populus balsamifera |

SEQUENCE: 97

```
MSTTKTMIPL LLLLLLSPLS TTASTAAYPT IPGTIDTSVS SSQPDNLIPI RNEIYGNGKI   60
FDISHRYIND MPVWDSKDGL GKFLSLPASM KNGSLANNSE MKLPTHTGTH VDSPGHVFDH  120
YFDSGFDVDT LDLEVLNGPA LLVDVPRHSN ITAEVMKSLH IPKGVRRVLF RTLNTDRRLM  180
FKREFDRSYV GFTKDGAKWL VDNTDIKLVG IDYLSVAAWS DLIPSHLVFL EGREIILVEA  240
LKLDDIQPGV YSVHCLPLRI LYSHLFNAAT SSHATPWHNR QDTIYHNKSL LFIPRELSGQ  300
KGSQTEASDS NLGGRFIDWQ VATETFHDPG SVLV                             334
```

| SEQ ID NO: 98 | moltype = DNA length = 1888 |
| FEATURE | Location/Qualifiers |
| misc_feature | 1..1888 |
| | note = Synthesized Sequence |
| misc_feature | 1..1888 |
| | note = Ceres CDNA ID no. 23799376 |
| misc_feature | 1..1888 |
| | note = Ceres Clone ID no. 375578 |
| misc_feature | 1..1888 |
| | note = Ceres Seed Line ID no. ME02064 |
| misc_feature | 1..1888 |
| | note = Encodes the peptide given in SEQ ID NO. 99 |
| misc_feature | 1..1888 |
| | note = Encodes the peptide given in SEQ ID NO. 180 |
| source | 1..1888 |
| | mol_type = other DNA |
| | organism = synthetic construct |

SEQUENCE: 98

```
cccggtttat ttttcttcg tcctggatgc gtcggtcgcg tgtttgatct gactaagccg    60
cggaggaggg tgctagatgt ccgtgcggtg ggcggtggct cccgagggcg accggagtta   120
ggtccttgcc gccttcagtg cggtggggaa gcgagacatt gaaggcgcag aacccaaaga   180
atgggtaaga gaggaaagtg gtttagtgcg gtgaagaaag tcttcagctc ctccgatcca   240
gatgaaaggg aagccaaggc ccagaaggca gacaaatcga atccaagag gagatggcca    300
tttggaaagt ccaagcactc ggagccttcc atatcgacgg tgccaggcac tgctccagca   360
gtagctccgt tgccatcacc accagcaact cagcccccact ctctggagat caaagatgtc   420
aatccagttg aaacagacag tgagcagaac aagcatgcct actccgttgc gcttgcgtct   480
gctgtcgctg ctgaagctgc agcagttgct gcccaggctc tgcggaagt tgtccgcctc    540
acagcagtta ccacggctgc accaaagatg cctgttagtt cgagggaata acttgccgcc   600
accaagattc agactgcctt caggggttat ctggcaagga gagcattgcg tgcactaaga   660
gggctagtta gattgaagtc gcttgttgat ggaaatgctg tcaaacgcca aaccgctcac   720
accttgcaat gcacacaagc aatgacaaga gttcaaactc aaatctactc tagaagggtg   780
aagttggagg aggagaaaca ggctcttcaa agacaactcc aattgaaaca tcaaagggaa   840
cttgagaaaa tgaagattga tgaagattgg gatcacagcc atcaatccaa agagcaaatt   900
gaggccaacc taatgatgaa acaggaagct gcactgaggc gagagagagc acttgcatat   960
gcattttctc accagtggag gaattctggt cgaactataa cccctacttt tacgaaacct  1020
gggaacccca actggggctg gagctggatg gagcgctgga tgacagcaag accatggag   1080
agtcggttgg cggccgcatc ggacaaggac cctaaagaac gtgctgtgac aaagaatgcg  1140
agcaccagtg ctgttcgagt acctgtatcc cgtgccatct cgattcagag accagcaaca  1200
ccaaacaagt cgagccgccc accaagccgg cagtcacttt caaccccgcc atcgaagacc  1260
ccgtcagcct caggaaaggc caggccggca agtccaagga acagttggct gtacaaggag  1320
gatgacctga ggagcatcac gagcatccgc tccgagcgcc caaggaggca gagcacgggt  1380
ggaggctcgg tccgggacga taccagcctg accagcacac cacctctccc cagctacatg  1440
cagtcgaccg agtctgcacg ggccaagtct cggtaccgca gtctactact gactgagaag  1500
cttgaggttc ctgagagagc gcctctggcc cactccgttg tcaagaagcg cctgtcgttc  1560
cccgtcgtcg agaagccaag cgttgtgccg acagagaagc cagggaaag agtgaggcgc   1620
cattccgacc ctccgaaggt cgatcctgcg acgctcaagg atgccctgc tgcctgacca   1680
gtgaccaggc cttatgtgat tgttaggttt cgtgctcttt taacaccgtg atgtattatc   1740
tgagttaggt tgctttgttc gtgtcatcgt atgatctgtc cggtttgatt tgagacagt   1800
tctaactgtg tttacagaca atgcgtgatg ctaaatgtat gtgtggttgg ttggctttaa   1860
atgtactgat atgatagtat ttgatttc                                      1888
```

| SEQ ID NO: 99 | moltype = AA length = 311 |
| FEATURE | Location/Qualifiers |
| REGION | 1..311 |
| | note = Synthesized Sequence |
| REGION | 1..311 |
| | note = Ceres CDNA ID no. 23799376 |
| REGION | 1..311 |
| | note = Ceres Clone ID no. 375578 |
| REGION | 1..311 |
| | note = Ceres Seed Line ID no. ME02064 |

```
source                  1..311
                        mol_type = protein
                        organism = synthetic construct
SEQUENCE: 99
MTRVQTQIYS RRVKLEEEKQ ALQRQLQLKH QRELEKMKID EDWDHSHQSK EQIEANLMMK   60
QEAALRRERA LAYAFSHQWR NSGRTITPTF TEPGNPNWGW SWMERWMTAR PWESRLAAAS  120
DKDPKERAVT KNASTSAVRV PVSRAISIQR PATPNKSSRP PSRQSLSTPP SKTPSASGKA  180
RPASPRNSWL YKEDDLRSIT SIRSERPRRQ STGGGSVRDD TSLTSTPPLP SYMQSTESAR  240
AKSRYRSLLL TEKLEVPERA PLAHSVVKKR LSFPVVEKPS VVPTEKPRER VRRHSDPPKV  300
DPATLKDAPA A                                                      311

SEQ ID NO: 100          moltype = AA  length = 500
FEATURE                 Location/Qualifiers
REGION                  1..500
                        note = Functional Homolog of Ceres Clone ID no. 375578 at
                         SEQ ID NO. 252 with e-value of 2.59E-135 and BLAST
                         sequence identity of 83.4
REGION                  142..162
                        note = Pfam Name: IQ Pfam Description: IQ
                         calmodulin-binding motif
source                  1..500
                        mol_type = protein
                        note = Oryza sativa subsp. japonica
                        organism = Oryza sativa
SEQUENCE: 100
MGKKGNWFSA VKKVFSSSDP DGREAKIEKA DKSRSRRKWP FGKSKKSDPW TSTVAVPTST   60
APPPQPPPPP PTHPIQPQPE EIKDVKAVET DSEQNKHAYS VALASAVAAE AAAVAAQAAA  120
EVVRLTTATT AVPKSPVSSK DELAAIKIQT AFRGYLARRA LRALRGLVRL KSLVDGNAVK  180
RQTAHTLHCT QTMTRVQTQI YSRRVKMEEE KQALQRQLQL KHQRELEKMK IDEDWDHSHQ  240
SKEQVETSLM MKQEAALRRE RALAYAFSHQ WKNSGRTITP TFTDQGNPNW GWSWMERWMT  300
SRPWESRVIS DKDPKDHYST KNPSTSASRT YVPRAISIQR PATPNKSSRP PSRQSPSTPP  360
SRVPSVTGKI RPASPRDSWL YKEDDLRSIT SIRSERPRRQ STGGASVRDD ASLTSTPALP  420
SYMQSTESAR AKSRYRSLLT DRFEVPERVP LVHSSIKKRL SFPVADKPNG EHADKLMERG  480
RRHSDPPKVD PASLKDVPVS                                             500

SEQ ID NO: 101          moltype = DNA  length = 1470
FEATURE                 Location/Qualifiers
misc_feature            1..1470
                        note = Ceres ANNOT ID no. 1465047
misc_feature            1..1470
                        note = Encodes the peptide given in SEQ ID NO. 102
source                  1..1470
                        mol_type = unassigned DNA
                        note = Populus balsamifera subsp. trichocarpa
                        organism = Populus balsamifera
SEQUENCE: 101
atggggaaaa gagggagttg gttctctgct ttgaagaaag ccctcggttc tctctaagaaa   60
tccaaatcaa agaagaaatg gtcagaaaaa gagaagaacc gggatctagg tgtttcttca  120
catgaagaaa ccgttgcacc ctctctttct cctcctcgta caccacctcc tcctacagca  180
gaagatgtga aattaactga agctgagaac gagcagagca agcatgctta ttccgtggcg  240
cttgccactg ctgtggccag tgaggcagct gttgcagccg cccaggctgc cgctgaggtt  300
gttcggctta ctacagtggc acattactct ggaaaatcga aggaggaaat agctgcaatc  360
aggattcaaa cagcatttag aggataccgc gcgaggaggg cattacgtgc tttgagaggg  420
ctggtgagat tgaagtcatt gatacaaggg caatctgtca aacggcaagc aactgccaca  480
ttacgagcca tgcagactct tgctcgtgtg cagtctcaga ttcgtgcaag aaggatcaga  540
atgtccgagg aaaatgaggc cctccaacgg cagctccagc agaaacatga caaagaactt  600
gagaagttga gaacttctat tggagaacaa tgggatgata gcccacaatc aaaggaagaa  660
gttgaagcca gcctactaca aaagcaagaa gctgccatga agagaaaag ggcactggct  720
tatgcatact cgcatcagca aatgtggaag caatcttcaa aatcagcaaa tgctacattc  780
atggatccaa acaatcctcg ttggggatgg agttggttag agaggtggat ggcagcccga  840
ccttgggaga gccgaagcac aatagataac aatgatcggg cctctgttaa gagtacaaca  900
agccgtacca tgtctcttgg agaaatcagc agagcttatt ctcgtcgtga tcttaaccat  960
gacaataaag cttctcctgg tgcgcaaaaa tcaagtcggc ctcccagtcg gcaatcacct 1020
tctactcccc cctctaaggc accatctaca tcttcagtaa caggaaagc aaagccacta 1080
agccctagag ggagtgcttg ggaggagac gaggactcca ggagcacatt cagtgtccag 1140
tctgagcgct atcggagaca tagcatagca gggtcatcaa taagagatga tgagagtctt 1200
gcaagttcgc cttcagttcc aagttacatg gcacccacac ggtcacagtc agcaaaggca 1260
aaatcccgct tgtcaagccc gttaggcata gataataatg gacaccagat aaggcatca 1320
gtgggttatg taaagaagcg gctttccttc tctgcttcac cagctggagc aaggagacac 1380
tctggtcctc ctagggtgga tgccagtgct gttaaagaca ttcaaatgca cagagaagag 1440
aaaatgagca atggagcaag cagcaagtag                                  1470

SEQ ID NO: 102          moltype = AA  length = 489
FEATURE                 Location/Qualifiers
REGION                  1..489
                        note = Ceres ANNOT ID no. 1465047
REGION                  1..489
                        note = Functional Homolog of Ceres Clone ID no. 375578 at
                         SEQ ID NO. 252 with e-value of 3.29E-71 and BLAST sequence
```

```
                        identity of 56.8
REGION                  116..136
                        note = Pfam Name: IQ Pfam Description: IQ
                        calmodulin-binding motif
source                  1..489
                        mol_type = protein
                        note = Populus balsamifera subsp. trichocarpa
                        organism = Populus balsamifera
SEQUENCE: 102
MGKRGSWFSA LKKALGSSKK SKSKKKWSEK EKNRDLGVSS HEETVAPSLS PPRTPPPPTA    60
EDVKLTEAEN EQSKHAYSVA LATAVAAEAA VAAAQAAAEV VRLTTVAHYS GKSKEEIAAI   120
RIQTAFRGYL ARRALRALRG LVRLKSLIQG QSVKRQATAT LRAMQTLARV QSQIRARRIR   180
MSEENEALQR QLQQKHDKEL EKLRTSIGEQ WDDSPQSKEE VEASLLQKQE AAMRRERALA   240
YAYSHQQMWK QSSKSANATF MDPNNPRWGW SWLERWMAAR PWESRSTIDN NDRASVKSTT   300
SRTMSLGEIS RAYSRRDLNH DNKASPGAQK SSRPPSRQSP STPPSKAPST SSVTGKAKPP   360
SPRGSAWGGD EDSRSTFSVQ SERYRRHSIA GSSIRDDESL ASSPSVPSYM APTRSQSAKA   420
KSRLSSPLGI DNNGTPDKAS VGYVKKRLSF SASPAGARRH SGPPRVDASA VKDIQMHREE   480
KMSNGASSK                                                           489

SEQ ID NO: 103          moltype = AA  length = 367
FEATURE                 Location/Qualifiers
REGION                  1..367
                        note = Ceres CLONE ID no. 474985
REGION                  1..367
                        note = Functional Homolog of Ceres Clone ID no. 375578 at
                        SEQ ID NO. 252 with e-value of 1.39E-63 and BLAST sequence
                        identity of 52.4
REGION                  11..31
                        note = Pfam Name: IQ Pfam Description: IQ
                        calmodulin-binding motif
source                  1..367
                        mol_type = protein
                        organism = Glycine max
SEQUENCE: 103
MPHYTGRTKE EIAAIKVQTA FRGYMARRAL RALRGLVRLK TLVQGQSVKR QAASTLRSMQ    60
TLARLQSQIR ERRIRMSEEN QALQRQLHQK HEKELEKLRA AVGEEWDDSS QSKEQIEAKL   120
LHRQEAALRR ERALAYSFSH QQTWKGSSKS LNPTFMDPNN PQWGWSWLER WMATRPWDGH   180
STVVDHNDHA SVKSAASRAV SVGQITKLYS LQDKKPSPFG SKARRPAPQS SHSKAPSTNG   240
KARPSSSTKG SSVWGGDEDS RSMFSVQSER YRRHSIAGSS VRDDDSRAST PAIPSYMAAT   300
SSAKARSKII RHSPEKKGGG GSVSARKRLS FSPSSAANSR RHSDPPKVEM VYNKDAAAAT   360
VSNGRGR                                                             367

SEQ ID NO: 104          moltype = AA  length = 378
FEATURE                 Location/Qualifiers
REGION                  1..378
                        note = Ceres CLONE ID no. 826796
REGION                  1..378
                        note = Functional Homolog of Ceres Clone ID no. 375578 at
                        SEQ ID NO. 252 with e-value of 5.20E-57 and BLAST sequence
                        identity of 50.3
REGION                  4..24
                        note = Pfam Name: IQ Pfam Description: IQ
                        calmodulin-binding motif
source                  1..378
                        mol_type = protein
                        organism = Triticum aestivum
SEQUENCE: 104
MSRELAATKI QTAFRGHLAR RALRALKGLV RLKSLVQGHS VKRQATSTLR CMQTLSRVQS    60
KIRTRRIKMA EENQALQRQL LLNQELETLR MGDQWNTSLQ SKEQIEASLV SRQEAAARRE   120
RALAYAFSHQ WKSTSRSANP MFVDPSNPHW GWSWLERWMA SRPFDGRNGA SEKEGSSVDR   180
TSVHSTSLSM NLGEGETVTK ADNQVVDSLK PNDDKPPPLS TPKPSGPAPR QSPSTPSPAL   240
ARKKSATPKS GDCDGDDARS VVSTVRSERP RRHSIGASSV RDDAGSSPSV PSYMAATKSA   300
SARAKSRVQS PTLTEGAAQA ETLEKGWSSV GSAKKRLSFP AGTPPPVPAA AARRHSGPPK   360
VRQAGVEGGT EERDSSLA                                                 378

SEQ ID NO: 105          moltype = DNA  length = 1366
FEATURE                 Location/Qualifiers
misc_feature            1..1366
                        note = Ceres CDNA ID no. 23363195
misc_feature            1..1366
                        note = Ceres Clone ID no. 105319
misc_feature            1..1366
                        note = Ceres Seed Line ID no. ME04074
misc_feature            1..1366
                        note = Encodes the peptide given in SEQ ID NO. 106
source                  1..1366
                        mol_type = unassigned DNA
                        organism = Arabidopsis thaliana
SEQUENCE: 105
```

```
aaattgttgt cttttaggtt ttgacagtag caaagaaaag ctgaatctag ttagaaattg    60
cttttgcagg gttttttgaat agtttgtgta ttgaagattg tctgaaatgg aagcagctat   120
tactcagagg attcagtacc catcatgggt tgattgtaga aaagttgagt gtaagccgca    180
gcgtggttca ttgcggtatt ctcagcaggt taaggtagag agaaggttta gaggtctttc    240
tttggctcgc ttgcaacctg aaagaagaat tgatcaacga acagcagttt ctccagcggt    300
ttcctgttct gataacaatt cctcagcgtt gttggagact ggaagtgttt atccatttga    360
tgaagatatt ctcaagagaa aagcagaaga ggttaaaccg tatttgaatg gacgatctat    420
gtaccttgtc ggaatgatgg gttctgggaa acaactgtg ggaaagttaa tgtccaaagt     480
gctcggttat acgttctttg actgcgacac tttgattgaa caggcagtga atgaacttc     540
tgttgcagag atatttgttc atcacggaga gaattttttt agaggaaagg agaccgatgc    600
gcttaagaag ctctcttcga ggtatcaagt tgttgtttcc acaggtggag gtgcagttat    660
aagacccatt aactggaagt atatgcataa aggaatcagc attttggctag atgtgcctct    720
agaagcatta gcccatagaa tcgctgctgt tggaactgat tcacgaccac tgctaacga     780
tgaatcagga gatgcatact cagtggcttt caaacgtctc tcggctattt ggacgacgcg    840
cggtgaagca tacacaaacg caaatgccag agtctcctta gaaaatattg cagcaaagcg    900
tggctataaa aatgtctcag atctcacacc aactgaaatt tgtatcgagg ccttcgagca    960
agttctgagc tttctagaga aagaagaaac tatggagatc ccagacggcg acctctaatt  1020
tcccagcctt ctgttctccg tctcttcatt tatctgttta atcaactaaa cgaagcaatc  1080
actcatcacc aggccattga gcaagttcag agacaaagaa gacctctagt tactggttcc  1140
gggtcattgg agcttacacg agcctaattt tgactggaac tatggtttat tgaaagaaga  1200
ttcaatacat gtatatataa aatatatact tttttttttg tttcagtatc atccttcttc  1260
tcttttcctt acaataagaa ttaaggaaaa gtagccgtgt ttgttaacat gggccaagaa  1320
caagcaaagt gatcattcaa atataaaagt agctttctca tggaat                 1366

SEQ ID NO: 106           moltype = AA  length = 303
FEATURE                  Location/Qualifiers
REGION                   1..303
                         note = Ceres CDNA ID no. 23363195
REGION                   1..303
                         note = Ceres Clone ID no. 105319
REGION                   1..303
                         note = Ceres Seed Line ID no. ME04074
REGION                   111..287
                         note = Pfam Name: SKI Pfam Description: Shikimate kinase
source                   1..303
                         mol_type = protein
                         organism = Arabidopsis thaliana
SEQUENCE: 106
MEAAITQRIQ YPSWVDCRKV ECKPQRGSLR YSQQVKVDRR FRGLSLARLQ PERRIDQRRA    60
VSPAVSCSDN NSSALLETGS VYPFDEDILK RKAEEVKPYL NGRSMYLVGM MGSGKTTVGK   120
LMSKVLGYTF FDCDTLIEQA MNGTSVAEIF VHHGENFFRG KETDALKKLS SRYQVVVSTG   180
GGAVIRPINW KYMHKGISIW LDVPLEALAH RIAAVGTDSR PLLHDESGDA YSVAFKRLSA   240
IWDERGEAYT NANARVSLEN IAAKRGYKNV SDLTPTEICI EAFEQVLSFL EKEETMEIPD   300
GDL                                                                 303

SEQ ID NO: 107           moltype = AA  length = 249
FEATURE                  Location/Qualifiers
REGION                   1..249
                         note = Ceres CLONE ID no. 463638
REGION                   1..249
                         note = Functional Homolog of Ceres CLONE ID no. 105319 at
                         SEQ ID NO. 106 with e-value of 2.29E-79 and BLAST sequence
                         identity of 66.6
REGION                   60..236
                         note = Pfam Name: SKI Pfam Description: Shikimate kinase
source                   1..249
                         mol_type = protein
                         organism = Glycine max
SEQUENCE: 107
MMRRRTTALE VSCSYGNISA SILESGSVRA PLDEELILKN RSQEIQPYLN GRCIYLVGMM    60
GSGKTTVGKI MSQVLGYSFC DSDALVEEEV GGNSVADIFK QHGETFFRNK ETEVLHKLSL   120
MHQLVISTGG GAVTRPINWK YMHKGVSVWL DVPVEALAQR IAAVGTNSRP LLHYEAGDPY   180
TRAFMRLSAL FEERGEAYAN ANARVSLKNI AIKLGKRDVS ELSPTDIAIE ALEQIDNFLK   240
GEGGRYAEC                                                           249

SEQ ID NO: 108           moltype = DNA  length = 570
FEATURE                  Location/Qualifiers
misc_feature             1..570
                         note = Ceres ANNOT ID no. 1504048
misc_feature             1..570
                         note = Encodes the peptide given in SEQ ID NO. 109
source                   1..570
                         mol_type = unassigned DNA
                         note = Populus balsamifera subsp. trichocarpa
                         organism = Populus balsamifera
SEQUENCE: 108
atgatgggct tggaaaaaac aacagtggga aagattctct cgcaagcaat tcattattca    60
ttctgtgaca gtgacacatt ggtggagaag gatgttggtg tgacttctgt agctgaaata   120
tttcaaatat atggagagga tttcttcaga gataaagaga ctgaggcatt agaaaagcta   180
```

```
tcactagagc accgatatgt cgtttctact ggtggaggtg ctgtgataca ggatgaaaac   240
tggacgtaca tgaggaaggg gattagtgtc tggttagatg tgcctttgga agaattggca   300
cagaggattg cggctgtagg aaccaagact cgccccpttt tggatagaga accaggagat   360
gcatacacca aggcgttcag gcgtctgtct gctctgtttg aacagagata taagcttat    420
gaaaatgcta atgcaagggt ttctctggaa aatattgcag ccaaattagg atataaagat   480
gtatccaata tcacaccacc tatgattgcg attgagaaca tggcttgggt gatgcattac   540
gcagcaggtt tccgtctatt accagtgtaa                                    570
```

| | | |
|---|---|---|
| SEQ ID NO: 109 | moltype = AA   length = 188 | |
| FEATURE | Location/Qualifiers | |
| REGION | 1..188 | |
| | note = Ceres ANNOT ID no. 1504048 | |
| REGION | 1..188 | |
| | note = Functional Homolog of Ceres CLONE ID no. 105319 at SEQ ID NO. 106 with e-value of 5.40E-55 and BLAST sequence identity of 64.2 | |
| REGION | 1..177 | |
| | note = Pfam Name: SKI Pfam Description: Shikimate kinase | |
| source | 1..188 | |
| | mol_type = protein | |
| | note = Populus balsamifera subsp. trichocarpa | |
| | organism = Populus balsamifera | |

SEQUENCE: 109
```
MGSGKTTVGK ILSQAIHYSF CDSDTLVEKD VGVTSVAEIF QIYGEDFFRD KETEALEKLS    60
LEHRYVVSTG GGAVIQDENW TYMRKGISVW LDVPLEELAQ RIAAVGTKTR PLLDREPGDA   120
YTKAFRRLSA LFEQRYKAYE NANARVSLEN IAAKLGYKDV SNITPPMIAI ENMAWVMHYA   180
AGFRLLPV                                                            188
```

| | | |
|---|---|---|
| SEQ ID NO: 110 | moltype = AA   length = 189 | |
| FEATURE | Location/Qualifiers | |
| REGION | 1..189 | |
| | note = Ceres CLONE ID no. 1565097 | |
| REGION | 1..189 | |
| | note = Functional Homolog of Ceres CLONE ID no. 105319 at SEQ ID NO. 106 with e-value of 3.00E-29 and BLAST sequence identity of 64.0 | |
| REGION | 100..173 | |
| | note = Pfam Name: SKI Pfam Description: Shikimate kinase | |
| source | 1..189 | |
| | mol_type = protein | |
| | organism = Zea mays | |

SEQUENCE: 110
```
MEAGGVGLAL QTRAAAFGSG QRRGGLQSPI GRLRVAEPAG AAVAVRARGS KPVVPLRAKK    60
SSGGHENLHN SVDEALLLKR KSEEVLFYLN GRCIYLVGMM GSGKSTVGKI MSEVLGYSFF   120
DSDKLVEQAV GMPSVAQIFK VHSEAFFRDN ESSVLRDLSS MRRLVVATGG GAVIPTVNWY   180
LEFTPFLSF                                                           189
```

| | | |
|---|---|---|
| SEQ ID NO: 111 | moltype = AA   length = 307 | |
| FEATURE | Location/Qualifiers | |
| REGION | 1..307 | |
| | note = Ceres CLONE ID no. 486613 | |
| REGION | 1..307 | |
| | note = Functional Homolog of Ceres CLONE ID no. 105319 at SEQ ID NO. 106 with e-value of 1.09E-63 and BLAST sequence identity of 63.0 | |
| REGION | 104..280 | |
| | note = Pfam Name: SKI Pfam Description: Shikimate kinase | |
| source | 1..307 | |
| | mol_type = protein | |
| | organism = Zea mays | |

SEQUENCE: 111
```
MEAGGIGLAL QARAAGFGSG SGRRRGGLQA PTGSLRVADP AGPAVAVRAR GSKPVAPLRL    60
RAKKSSGGHE NSHNSVDEAL LLKRKSEEVL FYLNGRCIYL VGMMGSGKST VGKIMSEVLG   120
YSFFDSDKLV EQAVGMPSVA QIFKVHSEAF FRDNESSVLR DLSSMRRLVV ATGGGAVIRP   180
INWRYMKKGL SVWLDVPLDA LARRIAKVGT ASRPLLDQPS GDPYAMAFSK LSMLAQQRGD   240
AYANADVRVS LEEIACKQGH DDVSKLTPTD IAIESLHKIE SFVIEHTADS SASDAQTESQ   300
IQRIQTL                                                             307
```

| | | |
|---|---|---|
| SEQ ID NO: 112 | moltype = AA   length = 295 | |
| FEATURE | Location/Qualifiers | |
| REGION | 1..295 | |
| | note = Ceres CLONE ID no. 749796 | |
| REGION | 1..295 | |
| | note = Functional Homolog of Ceres CLONE ID no. 105319 at SEQ ID NO. 106 with e-value of 7.79E-67 and BLAST sequence identity of 62.5 | |
| REGION | 108..284 | |
| | note = Pfam Name: SKI Pfam Description: Shikimate kinase | |
| source | 1..295 | |

```
                        mol_type = protein
                        organism = Triticum aestivum
SEQUENCE: 112
MDAGVGLRPR PRAAWAGRRK PQGFPPATVP AVRLDQNPAR RPLVLRSDAG SRSTDPIRGA    60
SLKGLCCHKS AGTEKVHYSA DEALVLKQKA EDVLPYLNDR CVYLVGMMGS GKTTVGKIIA   120
EVLGYSFFDS DKLVEQSVGI PSVAEIFQVH SEAFFRDNES EVLRDLSSMH RLIVATGGGA   180
VIRPINWSYM KKGLTIWLDV PLDALARRIA AVGTASRPLL HQESGDPYAK AYAKLTALFE   240
QRMDSYANAD ARVSLENIAL KQGHNDVNVL TPSTIAIEAL LKMESFLTEK AMVRN         295

SEQ ID NO: 113          moltype = AA  length = 308
FEATURE                 Location/Qualifiers
REGION                  1..308
                        note = Functional Homolog of Ceres CLONE ID no. 105319 at
                         SEQ ID NO. 106 with e-value of 5.09E-66 and BLAST sequence
                         identity of 62.1
REGION                  105..281
                        note = Pfam Name: SKI Pfam Description: Shikimate kinase
source                  1..308
                        mol_type = protein
                        note = Oryza sativa subsp. japonica
                        organism = Oryza sativa
SEQUENCE: 113
MEAGVGLALQ SRAAGFGGSD RRRSALYGGE GRARIGSLRV AEPAVAKAAV WARGSKPVAP    60
LRAKKSSGGH ETLHNSVDEA LLLKRKSEEV LFYLNGRCIY LVGMMGSGKS TVGKIMSEVL   120
GYSFFDSDKL VEQAVGMPSV AQIFKVHSEA FFRDNESSVL RDLSSMKRLV VATGGGAVIR   180
PVNWKYMKKG LSVWLDVPLD ALARRIAKVG TASRPLLDQP SGDPYTMAFS KLSMLAEQRG   240
DAYANADVRV SLEEIASKQG HDDVSKLTPT DIAIESFHKI ENFVIEHTVD NPVGDSQADS   300
RAQRIQTL                                                           308

SEQ ID NO: 114          moltype = AA  length = 189
FEATURE                 Location/Qualifiers
REGION                  1..189
                        note = Ceres CLONE ID no. 294723
REGION                  1..189
                        note = Functional Homolog of Ceres CLONE ID no. 105319 at
                         SEQ ID NO. 106 with e-value of 4.69E-56 and BLAST sequence
                         identity of 61.2
REGION                  2..178
                        note = Pfam Name: SKI Pfam Description: Shikimate kinase
source                  1..189
                        mol_type = protein
                        organism = Zea mays
SEQUENCE: 114
MMGSGKTTVG KILSEVLGYS FFDSDKLVEK AVGISSVAEI FQLHSETFFR DNESEVLTDL    60
SSMHRLVVAT GGGAVIRPIN WSYMKKGLTV WLDVPLDALA RRIAAVGTAS RPLLHQESGD   120
PYAKAYAKLT SLFEQRMDSY ANADARVSLE HIALKQGHND VTILTPSTIA IEALLKMESF   180
LTEKTMVRN                                                          189

SEQ ID NO: 115          moltype = AA  length = 302
FEATURE                 Location/Qualifiers
REGION                  1..302
                        note = Functional Homolog of Ceres CLONE ID no. 105319 at
                         SEQ ID NO. 106 with e-value of 3.70E-79 and BLAST sequence
                         identity of 61.0
REGION                  114..290
                        note = Pfam Name: SKI Pfam Description: Shikimate kinase
source                  1..302
                        mol_type = protein
                        organism = Fagus sylvatica
SEQUENCE: 115
MDGKVANGLV VSPRIGSERF ARRTCGSVRV SRRFREQDRL PVLVSAQLQD KTRNSNWHKT    60
ASLEVSCSYK NFPASVLESG GIHAPFDDAL ILKNKSQEIE PYLSGRCIYL VGMMGSGKTT   120
VGKVLSQVLS YAFFDSDTLV EQDVDANSVA EIFNLYGEGF FRDKETEVLR KLSLMHRLVV   180
STGGGAVVRP INWKYMQKGI SVWLDVPLEA LARRIAAVGT GSRPLLHHDS GDAYTKTFMR   240
LTSLMEERSE AYANANARVS LEDVAAKLGH RDVSNLTPTA IAIEALEQIE GFLKEENGDF   300
AL                                                                 302

SEQ ID NO: 116          moltype = AA  length = 189
FEATURE                 Location/Qualifiers
REGION                  1..189
                        note = Ceres CLONE ID no. 1374869
REGION                  1..189
                        note = Functional Homolog of Ceres CLONE ID no. 105319 at
                         SEQ ID NO. 106 with e-value of 4.69E-56 and BLAST sequence
                         identity of 60.7
REGION                  2..178
                        note = Pfam Name: SKI Pfam Description: Shikimate kinase
source                  1..189
                        mol_type = protein
```

```
                        organism = Zea mays
SEQUENCE: 116
MMGSGRTTVG KILSEVLGYS FFDSDKLVEK AVGISSVAEI FQLHSETFFR DNESEVLRDL      60
SSMHRLVVAT GGGAVIRPIN WSYMKKGLTV WLDVPLDALA RRIAAVGTAS RPLLHQESGD     120
PYAKAYAKLT SLFEQRMDSY ANADARVSLE HIALKQGHND VTILTPSTIA IEALLKMESF     180
LTEKTMVRN                                                             189

SEQ ID NO: 117          moltype = AA  length = 307
FEATURE                 Location/Qualifiers
REGION                  1..307
                        note = Functional Homolog of Ceres CLONE ID no. 105319 at
                          SEQ ID NO. 106 with e-value of 4.59E-65 and BLAST sequence
                          identity of 60.6
REGION                  103..279
                        note = Pfam Name: SKI Pfam Description: Shikimate kinase
source                  1..307
                        mol_type = protein
                        note = Oryza sativa subsp. japonica
                        organism = Oryza sativa
SEQUENCE: 117
MEARAGLAMQ SRAAVGVGAG PGVGRRGRAV IRVGKRPTAA SLRVGGPAGP AAAKPLAPLY      60
CLKASRGHDS LHNSVDEALL LKRKSEEVLF YLNGRCIYLV GMMGSGKSTV AKILAEVLGY     120
SFFDSDKLVE QAVGMPSVAQ IFKEHSEAFF RDNESSVLRD LSSMRRLVVA TGGGAVIRPV     180
NWKYMKKGLS VWLDVPLDAL ARRIAQVGTA SRPLLDQPSS DPYTAAFSKL SMLAEQRGDA     240
YANADARVSL EEIAAKQGHD DVSKLTPTDI AIEALLKIEN FVTEHSTSSG PVGDLIVDSQ     300
NRRTKAL                                                               307

SEQ ID NO: 118          moltype = AA  length = 205
FEATURE                 Location/Qualifiers
REGION                  1..205
                        note = Ceres CLONE ID no. 276706
REGION                  1..205
                        note = Functional Homolog of Ceres CLONE ID no. 105319 at
                          SEQ ID NO. 106 with e-value of 2.60E-55 and BLAST sequence
                          identity of 59.3
REGION                  2..178
                        note = Pfam Name: SKI Pfam Description: Shikimate kinase
source                  1..205
                        mol_type = protein
                        organism = Zea mays
SEQUENCE: 118
MMGSGKSTVG KIMSEVLGYS FFDSDKLVEQ AVGMPSVAQI FKVHSEAFFR DNESSVLRDL      60
SSMRRLVVAT GGGAVIRPVN WKYMKKGLSV WLDVPLDALA RRIAKVGTAS RPLLDQPSGD     120
PYTMAFSKLS MLAEQRGDAY ANADVRVSLE EIASKQGHGD VSKLMPTDIA IESLHKIESF     180
VIEHAADNPA SDSQAESQIQ RIQTL                                           205

SEQ ID NO: 119          moltype = AA  length = 305
FEATURE                 Location/Qualifiers
REGION                  1..305
                        note = Ceres CLONE ID no. 840744
REGION                  1..305
                        note = Functional Homolog of Ceres CLONE ID no. 105319 at
                          SEQ ID NO. 106 with e-value of 2.99E-61 and BLAST sequence
                          identity of 59.3
REGION                  105..281
                        note = Pfam Name: SKI Pfam Description: Shikimate kinase
source                  1..305
                        mol_type = protein
                        organism = Triticum aestivum
SEQUENCE: 119
MEAGVGLALQ SRAAGFGSGR RRSSMYGGES GARVVSLRVS DLVGSPAAVR ARGAKPVVPL      60
RAKKSSGGGH ENLHNSVDDA LLLKRKSEEV LFQLNGRCIY LVGMMGSGKS TVGKILAEVL     120
GYSFFDSDKL VEQAVGMPSV AQIFKVHSEA FFRDNESSVL RDLSSMRRLV VATGGGAVIR     180
PVNWKNMKKG LSVWLDVPLE ALARRIAKVG TASRPLLDQP SGDPYTMAFS KLSTLAEQRG     240
DAYANADVRV SLEEIASKLG HDDVSKLTPI DIALESLHKI ESFVVEDTAV ADSQTESQAQ     300
RIHTL                                                                 305

SEQ ID NO: 120          moltype = DNA  length = 936
FEATURE                 Location/Qualifiers
misc_feature            1..936
                        note = Ceres ANNOT ID no. 1456544
misc_feature            1..936
                        note = Encodes the peptide given in SEQ ID NO. 121
source                  1..936
                        mol_type = unassigned DNA
                        note = Populus balsamifera subsp. trichocarpa
                        organism = Populus balsamifera
SEQUENCE: 120
atggaggcaa atcttgcaca aagaatgcaa atttcgacaa catggattga ttcatacaag      60
```

```
tttccaagaa aaccaactag ttccctgcgg ttttcggga gatttaagga acagaagaga 120
ctccaagtgt ttgtttctgc tcagtttcgg cctgtaagag atgaaaatcg acatagacag 180
gcttcttttg aggtttcttg ttcttgtaac aattctcaag tttcaacgtt ggaatctgaa 240
agtctccagg atttgtttgg cgaggaagct ttgattttga agaataagtc acaagagatt 300
gagccatatt taaatggacg ctgtatatat ctttgttggg tgatgggctc tggaaaaact 360
acagtgggaa agattctctc acgatcaatt cgttattcat tctgtgactg tgacaaactg 420
gtggagcagg atgttggtgt gccttctgta gctgaaatat ttgaaatata tggagaggat 480
ttcttcagag ataaagagac tgaggcatta gaaaagctat caatagaaca ccggtttgtt 540
gtttccactg gtggcggtgc tgtgatacgg gatgaaaact ggatatacat gaggaagggg 600
attagtgtct ggttagatgt gcctttggaa gaattggcac agaggatcgc ggctgtagga 660
accaagtctc gccccctttt ggataatgaa tcaggagatg catacaacac tgcattcaga 720
cgcctttcta ctctgtttga agagacat aaagcttatg aaaatgccaa ggcgagggtt 780
tctctggaaa atattgcagc caaactagga tataaagatg tatccagtat cacacctgct 840
atgattgcga ttgagcagaa catggcttgt gtgatgcatg atgtggaagg tttccattta 900
ttaccagcag gatttgggat gcgaaagatg tgttag       936

SEQ ID NO: 121         moltype = AA  length = 303
FEATURE                Location/Qualifiers
REGION                 1..303
                       note = Ceres ANNOT ID no. 1456544
REGION                 1..303
                       note = Functional Homolog of Ceres CLONE ID no. 105319 at
                           SEQ ID NO. 106 with e-value of 4.50E-74 and BLAST sequence
                           identity of 59.3
REGION                 107..283
                       note = Pfam Name: SKI Pfam Description: Shikimate kinase
source                 1..303
                       mol_type = protein
                       note = Populus balsamifera subsp. trichocarpa
                       organism = Populus balsamifera
SEQUENCE: 121
MQISTTWIDS YKFPRKPTSS LRFSGRFKEQ KRLQVFVSAQ FRPVRDENRH RQASFEVSCS  60
CNNSQVSTLE SESLQDLFGE EALILKNKSQ EIEPYLNGRC IYLVGMMGSG KTTVGKILSR 120
SIRYSFCDCD KLVEQDVGVP SVAEIFEIYG EDFFRDKETE ALEKLSIEHR FVVSTGGGAV 180
IRDENWIYMR KGISVWLDVP LEELAQRIAA VGTKSRPLLD NESGDAYNTA FRRLSTLFEK 240
RHKAYENAKA RVSLENIAAK LGYKDVSSIT PAMIAIEQNM ACVMHDVEGF HLLPAGFGMR 300
KMC                                                                303

SEQ ID NO: 122         moltype = DNA  length = 655
FEATURE                Location/Qualifiers
misc_feature           1..655
                       note = Ceres CLONE ID no. 29658
misc_feature           1..655
                       note = Predicted sequence
misc_feature           1..655
                       note = Encodes the peptide given in SEQ ID NO. 123
source                 1..655
                       mol_type = unassigned DNA
                       organism = Arabidopsis thaliana
SEQUENCE: 122
attcatctcc aaactttcaa aaaaaaacct aaaacaaaaa aaatctcttt ccttcttctt  60
tctccatcaa tggcgtcaac aaaacccacc gatcaaatca aacaactcaa agatatcttc 120
gctcgcttcg acatggacaa ggacggaagc ttaacgcagc tagaactcgc cgctcttctg 180
cgttctctcg gaatcaaacc tcgcggcgat caaatctctc ttctgtaaaa ccaaatcgac 240
cgtaacggta acggatccgt agagttcgac gagctcgtcg tggcgatatt gccggatata 300
aacgaagagg tgttgataaa tcaagaacag ttgatggagg ttttccgttc gtttgatcgt 360
gacggtaacg gttcaataac ggcggcgaaa cttgctgggt caatggctaa aatgggacat 420
ccgttgactt accgtgaatt aacggaaatg atgacggaag ctgattcaaa cggtgacggt 480
gttattagtt ttaatgagtt ttctcatatt atggctaaat cggctgctga tttcttgga 540
ttaaccgctt cttgatctgt tttgttttaa ttactctctt tttttcttct cctgtcaatg 600
caacttgtgc aattaacaat gtcgtttggt gtgctaatct tcgtttggt gtgacgtaaa aattt 655

SEQ ID NO: 123         moltype = AA  length = 161
FEATURE                Location/Qualifiers
REGION                 1..161
                       note = Ceres CLONE ID no. 29658
REGION                 1..161
                       note = Ceres ANNOT ID no. 842118
REGION                 1..161
                       note = Phenotype: ROSETTE LEAVES Useful for making
                           ornamental plants with modified leaves
REGION                 48..76
                       note = Pfam Name: efhand Pfam Description: EF hand
REGION                 1..161
                       note = Full Length Peptide Sequence for Ceres CLONE ID no.
                           29658
source                 1..161
                       mol_type = protein
                       organism = Arabidopsis thaliana
```

```
SEQUENCE: 123
MASTKPTDQI KQLKDIFARF DMDKDGSLTQ LELAALLRSL GIKPRSDQIS LLLNQIDRNG     60
NGSVEFDELV VAILPDINEE VLINQEQLME VFRSFDRDGN GSITAAELAG SMAKMGHPLT    120
YRELTEMMTE ADSNGDGVIS FNEFSHIMAK SAADFLGLTA S                        161

SEQ ID NO: 124            moltype = DNA   length = 483
FEATURE                   Location/Qualifiers
misc_feature              1..483
                          note = Ceres ANNOT ID no. 1464081
misc_feature              1..483
                          note = Encodes the peptide sequence given in SEQ ID NO. 125
source                    1..483
                          mol_type = unassigned DNA
                          note = Populus balsamifera subsp. trichocarpa
                          organism = Populus balsamifera
SEQUENCE: 124
atggcaaccc ttcagaccga tcagctcaag cagctcaagg acatcttcat tcgcttcgac     60
atggattccg atggcagcct cacgcagctg gagctcgctg cgcttctacg ttctcttggc    120
ctcaaaccta caggtgatca acttcatgtt ctgttatcaa acatggatgc taatggaaat    180
ggttatgttg agtttgatga gctggtcagt gctatattgc ctgatatgaa tgaagaagta    240
ttgatcaacc aggagcagtt gttggaggtt tttcgatcat ttgacaggga tggcaatgga    300
ttcattactg ctgctgaaag ctgcaggatca atggctaaaa tgggacaccc tttgacgtat    360
cgtgagctat cagatatgat gagagaggct gacaccaatg gagatggtgt tttgagtttt    420
aatgagtttg caaacgtcat ggcaaaatct gctgctgatt tcttggcat caaagttcca    480
tag                                                                  483

SEQ ID NO: 125            moltype = AA    length = 140
FEATURE                   Location/Qualifiers
REGION                    1..140
                          note = Ceres ANNOT ID no. 1464081
REGION                    1..140
                          note = Functional Homolog of Ceres CLONE ID no. 29658 at
                            SEQ ID NO. 123 with e-value of 4.20E-55 and BLAST sequence
                            identity of 81.7
REGION                    27..55
                          note = Pfam Name: efhand Pfam Description: EF hand
source                    1..140
                          mol_type = protein
                          note = Populus balsamifera subsp. trichocarpa
                          organism = Populus balsamifera
SEQUENCE: 125
MDSDGSLTQL ELAALLRSLG LKPTGDQLHV LLSNMDANGN GYVEFDELVS AILPDMNEEV     60
LINQEQLLEV FRSFDRDGNG FITAAELAGS MAKMGHPLTY RELSDMMREA DTNGDGVLSF    120
NEFANVMAKS AADFLGIKVP                                                140

SEQ ID NO: 126            moltype = AA    length = 158
FEATURE                   Location/Qualifiers
REGION                    1..158
                          note = Ceres CLONE ID no. 651548
REGION                    1..158
                          note = Functional Homolog of Ceres CLONE ID no. 29658 at
                            SEQ ID NO. 123 with e-value of 2.80E-58 and BLAST sequence
                            identity of 78.9
REGION                    120..148
                          note = Pfam Name: efhand Pfam Description: EF hand
source                    1..158
                          mol_type = protein
                          organism = Glycine max
SEQUENCE: 126
MLETDQIKQL NDIFKRFDMD QDGSLTHLEL AALLRSLGIK PTGDEIYALL SNMDENGNGY     60
IEFDELVHAI MPDLTESVLI NQEQLLEVFR SFDRDGNGYI TASELAGSMA KMGQPLTYRE    120
LASMMAEADS NGDGVISFNE FAALMAKSAA EFLGVKVA                            158

SEQ ID NO: 127            moltype = AA    length = 173
FEATURE                   Location/Qualifiers
REGION                    1..173
                          note = Functional Homolog of Ceres CLONE ID no. 29658 at
                            SEQ ID NO. 123 with e-value of 4.80E-47 and BLAST sequence
                            identity of 65.3
REGION                    61..89
                          note = Pfam Name: efhand Pfam Description: EF hand
source                    1..173
                          mol_type = protein
                          note = Oryza sativa subsp. japonica
                          organism = Oryza sativa
SEQUENCE: 127
MTTMAARRSE AAPAPQQLRG SQLKQLRELF RRFDMNGDGS LTQLELAALL RSLGLRPTGD     60
EVHALLAGMD ANGNGSVEFD ELAAAIAPVL TTQTHLVDQA QLLEVFRAFD RDGNGFISAA    120
ELARSMARLG QPLTFEELTR MMRDADTDGD GVISFKEFAA VMAKSALDFL GVA           173
```

```
SEQ ID NO: 128          moltype = AA  length = 172
FEATURE                 Location/Qualifiers
REGION                  1..172
                        note = Ceres CLONE ID no. 287120
REGION                  1..172
                        note = Functional Homolog of Ceres CLONE ID no. 29658 at
                          SEQ ID NO. 123 with e-value of 1.49E-45 and BLAST sequence
                          identity of 64.0
REGION                  60..88
                        note = Pfam Name: efhand Pfam Description: EF hand
source                  1..172
                        mol_type = protein
                        organism = Zea mays
SEQUENCE: 128
MTRSAPPASP PAPKPVLRGS QLEQLREIFR RFDMDGDGSL TQLELGALLR SLGLRPTGEE    60
ARALLAAMDS NGNGAVEFGE LAAAIAPLLT TQTHLVDQAQ LLEVFRAFDR DGNYISAAE    120
LARSMARIGQ PLTFEELTRM MRDADADGDG VISFNEFAAV MAKSALDFLG VA           172

SEQ ID NO: 129          moltype = AA  length = 177
FEATURE                 Location/Qualifiers
REGION                  1..177
                        note = Ceres CLONE ID no. 759217
REGION                  1..177
                        note = Functional Homolog of Ceres CLONE ID no. 29658 at
                          SEQ ID NO. 123 with e-value of 1.29E-44 and BLAST sequence
                          identity of 63.3
REGION                  62..90
                        note = Pfam Name: efhand Pfam Description: EF hand
source                  1..177
                        mol_type = protein
                        organism = Triticum aestivum
SEQUENCE: 129
MTKPSPSPSP APAKGAGSLR GSQLKQLRSL FDRFDMDGDG SLTQLELAAL LRSLGLRPTG    60
DESRALLLAI DADGSGTVEF DELARAIAPV LTAHAPRLVD QAQLLEVFRA FDRDGNYIS   120
AAELARSMAK LGQPLTFEEL RTMMRDADAD GDGVISFGEF AAVMARSALD FLGVPAA     177

SEQ ID NO: 130          moltype = AA  length = 149
FEATURE                 Location/Qualifiers
REGION                  1..149
                        note = Functional Homolog of Ceres CLONE ID no. 29658 at
                          SEQ ID NO. 123 with e-value of 2.29E-24 and BLAST sequence
                          identity of 43.3
REGION                  12..40
                        note = Pfam Name: efhand Pfam Description: EF hand
source                  1..149
                        mol_type = protein
                        note = Malus x domestica
                        organism = unidentified
SEQUENCE: 130
MADQLTDDQI SEFKEAFSLF DKDGDGCITT KELGTVMRSL GQNPTEAELQ DMINEVDADG    60
NGTIDFPEPL NLMARKMKDT DSEEELKEAF RVFDKDQNGF ISAAELRHVM TNLGEKLTDE   120
EVDEMIREAD VDGDGQINYE EFVKVMMAK                                     149

SEQ ID NO: 131          moltype = DNA  length = 679
FEATURE                 Location/Qualifiers
misc_feature            1..679
                        note = Ceres CLONE ID no. 2767
misc_feature            1..679
                        note = Ceres Seed Line ID no. ME00774
misc_feature            1..679
                        note = Encodes the peptide given in SEQ ID NO. 132
source                  1..679
                        mol_type = unassigned DNA
                        organism = Arabidopsis thaliana
SEQUENCE: 131
agaagctaga agaagaaagg agaagaagaa acaaagagag aagatgaaga atgttatgct    60
gattattgac gagagcaacg caagttatga tttactcatt tgggcacttg aaaaccaaaa   120
agataccatt gagagctcca aagtttatat ctttgcaaaa cgccacaaa attcctttac   180
tcctcctacc gtactttctt catcagtcgg ctttgctcaa attttctatc cattttcacc   240
taattcagaa ctcataagat tggctcaaga aaagaatatg aaaattgctt tgggtatatt   300
agagaaagcc aagaagatat gtttaaatca tgggatcaag gcagagacat ttactaatgt   360
tggagaccct aaagatctaa tccgcaagat aattcaagaa cgaaatatca atttaatagt   420
tacgacgcat caacaaaatgc tcaaaaagtg tacacaaaat acagattgtt ctcttccttg   480
cgtgaagaaa agacttcgca agattaaag attaaggaag ttacaaaatt caccaatata   540
tataattttc tatgtggtta attgagattg tgtaatgatt tggggttgta gtttcaggtg   600
ttgatttggg gttgtagttt gaacttataa ttgtgttatg tgtataaata tttgtgttta   660
tatatatcaa gttagtatg                                                679
```

```
SEQ ID NO: 132          moltype = AA   length = 154
FEATURE                 Location/Qualifiers
REGION                  1..154
                        note = Ceres CLONE ID no. 2767
REGION                  1..154
                        note = Ceres Seed Line ID no. ME00774
REGION                  1..148
                        note = Pfam Name: Usp Pfam Description: Universal stress
                         protein family
source                  1..154
                        mol_type = protein
                        organism = Arabidopsis thaliana
SEQUENCE: 132
MKNVMLIIDE SNASYDLLIW ALENQKDTIE SSKVYIFAKQ PQNSFTPPTV LSSSVGFAQI    60
FYPFSPNSEL IRLAQEKNMK IALGILEKAK KICLNHGIKA ETFTNVGDPK DLIRKIIQER   120
NINLIVTSDQ QSLKKCTQNT DCSLLVVKKR LRKD                               154

SEQ ID NO: 133          moltype = DNA   length = 597
FEATURE                 Location/Qualifiers
misc_feature            1..597
                        note = Ceres ANNOT ID no. 1486744
misc_feature            1..597
                        note = Encodes the peptide given in SEQ ID NO. 134
source                  1..597
                        mol_type = unassigned DNA
                        note = Populus balsamifera subsp. trichocarpa
                        organism = Populus balsamifera
SEQUENCE: 133
atggagaaac aaatagaagg gtctaagaag agggtgatgg tgatcataga tgagagcgag    60
tacagttatc attccttcat gtgggtagtt gacaatctca aagaatttat cactgagtcg   120
ccgcttgtca tccttgctgc acttcctgct cctaactgta aatttttta tggggcacag   180
tttggcaccg ctgccctctg ttgtccagtc tctcccaccc tagatttgat ctgtgccatt   240
caagaaaaaa acaagaagat cttattaggt atcttggaga aagctgtgaa tatctgtgct   300
agtcgagggg tgaaagcaga aacaatttta gaagccgggg agccttatga actcacatgc   360
aatgctgttc agaagaacaa tattaatctc ctcgtgattg gtaacacatc cattaatgaa   420
actctcaaaa ggttaggaaa tttctttgta acttcaaaaa tcatttcgac agctctcgaa   480
agtcgcataa attgtatgaa cctgattcaa aatgagttat ttcaagaact tgaacatgct   540
ggcatggttg tcaaccctat taactcttgc aacaagctcc actaccagaa gcactga     597

SEQ ID NO: 134          moltype = AA   length = 186
FEATURE                 Location/Qualifiers
REGION                  1..186
                        note = Ceres ANNOT ID no. 1486744
REGION                  1..186
                        note = Functional Homolog of Ceres CLONE ID no. 2767 at SEQ
                         ID NO. 132 with e-value of 1.90E-18 and BLAST sequence
                         identity of 43.4
source                  1..186
                        mol_type = protein
                        note = Populus balsamifera subsp. trichocarpa
                        organism = Populus balsamifera
SEQUENCE: 134
MVIIDESEYS YHSFMWVVDN LKEFITESPL VILAALPAPN CKFFYGAQFG TAALCCPVSP    60
TLDLICAIQE KNKKILLGIL EKAVNICASR GVKAETILEA GEPYELTCNA VQKNNINLLV   120
IGNTSINGTL KRLGNFFVTS KIISTALESR INCMNLIQNE LFQELEHAGM VVNPINSCNK   180
LHYQKH                                                              186

SEQ ID NO: 135          moltype = DNA   length = 540
FEATURE                 Location/Qualifiers
misc_feature            1..540
                        note = Ceres ANNOT ID no. 1463968
misc_feature            1..540
                        note = Encodes the peptide given in SEQ ID NO. 136
source                  1..540
                        mol_type = unassigned DNA
                        note = Populus balsamifera subsp. trichocarpa
                        organism = Populus balsamifera
SEQUENCE: 135
atggagaaac aaatagaagg gtctaatcag aaggtgatgg tgatcataga tgagagtgag    60
tgcagttatc atgcactcat gtgggtgctt gaaaatctca aaggattcat tactgactca   120
ccgcttgtca tgtttgctgc actacctact cctaactgta actttgcata tggggcacaa   180
cttggcacca ctgcgttgta ttgtacagtc tcacccaccc taggtttgat tgttccatg    240
caagaaaaaa gcaagaaaat cttattgggt gtcttggaga aagctgtgga tatctgtgat   300
agtcgagggg tgaaagcaga gacaatcaca gaagctgggg agccttatga gctcataagc   360
agtgctgttc aaaagaacaa gattaatcta ctagtgatcg gtgacacact cgttaatgga   420
acccttaaaa gtcacatgtc tcttgatact ggaatggtta cagtgacgtt aacctgttac   480
ccaaaacctc atcctactca aaatatagat tatcattcag atgggtacca atacaaatga   540

SEQ ID NO: 136          moltype = AA   length = 167
```

```
FEATURE                 Location/Qualifiers
REGION                  1..167
                        note = Ceres ANNOT ID no. 1463968
REGION                  1..167
                        note = Functional Homolog of Ceres CLONE ID no. 2767 at SEQ
                         ID NO. 132 with e-value of 7.09E-19 and BLAST sequence
                         identity of 43.0
source                  1..167
                        mol_type = protein
                        note = Populus balsamifera subsp. trichocarpa
                        organism = Populus balsamifera
SEQUENCE: 136
MVIIDESECS YHALMWVLEN LKGFITDSPL VMFAALPTPN CNFAYGAQLG TTALYCTVSP    60
TLGLICSMQE KSKKILLGVL EKAVDICDSR GVKAETITEA GEPYELISSA VQKNKINLLV   120
IGDTLVNGTL KSHMSLDTGM VTVTLTCYPK PHPTQNIDYH SDGYQYK                167

SEQ ID NO: 137          moltype = DNA  length = 447
FEATURE                 Location/Qualifiers
misc_feature            1..447
                        note = Ceres ANNOT ID no. 1517263
misc_feature            1..447
                        note = Encodes the peptide given in SEQ ID NO. 138
source                  1..447
                        mol_type = unassigned DNA
                        note = Populus balsamifera subsp. trichocarpa
                        organism = Populus balsamifera
SEQUENCE: 137
atggagaaac aaatagaagg gtctaatcag aaggtgatgg tgatcataga tgagagtgag    60
tgcagttatc atgcactcat gtgggtgctt gaaaatctca aaggattcat tactgactca   120
ccgcttgtca tgtttgctgc actaccta cctaactgta actttgcata tggggcacaa    180
cttggcacca ctgcgttgta ttgtacagtc tcacccaccc taggtttgat ttgttccatg   240
caagaaaaaa gcaagaaaat cttattgggt gtcttggaga aagctgtgga tatctgtgat   300
agtcgagggg tgaaagcaga gacaatcaca gaagctgggg agccttatga gctcataagc   360
agtgctgttc aaaagaacaa gattaatcta ctagtgatcg gtgacacact cgttaatgga   420
acccttaaaa gttcccgacc ccactag                                      447

SEQ ID NO: 138          moltype = AA  length = 136
FEATURE                 Location/Qualifiers
REGION                  1..136
                        note = Ceres ANNOT ID no. 1517263
REGION                  1..136
                        note = Functional Homolog of Ceres CLONE ID no. 2767 at SEQ
                         ID NO. 132 with e-value of 7.09E-19 and BLAST sequence
                         identity of 43.0
source                  1..136
                        mol_type = protein
                        note = Populus balsamifera subsp. trichocarpa
                        organism = Populus balsamifera
SEQUENCE: 138
MVIIDESECS YHALMWVLEN LKGFITDSPL VMFAALPTPN CNFAYGAQLG TTALYCTVSP    60
TLGLICSMQE KSKKILLGVL EKAVDICDSR GVKAETITEA GEPYELISSA VQKNKINLLV   120
IGDTLVNGTL KSSRPH                                                  136

SEQ ID NO: 139          moltype = AA  length = 162
FEATURE                 Location/Qualifiers
REGION                  1..162
                        note = Ceres CLONE ID no. 684584
REGION                  1..162
                        note = Functional Homolog of Ceres CLONE ID no. 2767 at SEQ
                         ID NO. 132 with e-value of 2.29E-13 and BLAST sequence
                         identity of 37.6
REGION                  11..159
                        note = Pfam Name: Usp Pfam Description: Universal stress
                         protein family
source                  1..162
                        mol_type = protein
                        organism = Triticum aestivum
SEQUENCE: 139
MAAQAPPPPP PEQKMMVAID ESECSHYALE WALRNLAPRR LILFTVQPFS PLSYLPVGSP    60
LGPSVASPEL IRSVTEHQRQ LAQALVDKAK AICAEHGVDA ETVIEVGDPK ETICEAAEKL   120
NVDLLILGSH SRGPVQRFFL GSVSNYCSHH AKCPVLVVKK KE                      162

SEQ ID NO: 140          moltype = DNA  length = 468
FEATURE                 Location/Qualifiers
misc_feature            1..468
                        note = Ceres ANNOT ID no. 1463969
misc_feature            1..468
                        note = Encodes the peptide given in SEQ ID NO. 141
source                  1..468
```

```
                        mol_type = unassigned DNA
                        note = Populus balsamifera subsp. trichocarpa
                        organism = Populus balsamifera
SEQUENCE: 140
atggcggagc acgtgacgga aaatggaggg gtaccacttg agaggaaagt gatggttgcc    60
gttgatgatg gtgagtatag ccactatgct ctcatgtggg tacttgacaa tcttgaggaa   120
tctatcacta aatcacctct agttatcttc accgcacagc ctcctcccag caataaccat   180
tcttttactg ccgctgctct cagttctgct cgcatgtact gctcggtttc agccaatccg   240
gagtatactt acactatcca agaccagaat aagaagatcg cgtttgcttt gctggagaaa   300
gctaaagaaa tttgtgctgg tcgaggagtt gatgctgaga cattaacaga ggtgggtgat   360
cctcaaacag ccatatgcga tgcagttcaa aggctcaata ttagcctgct tgttttaggg   420
gagcgcggca ttggcaaaat caaaaggtgg gatgatggcg caagttaa                468

SEQ ID NO: 141          moltype = AA   length = 138
FEATURE                 Location/Qualifiers
REGION                  1..138
                        note = Ceres ANNOT ID no. 1463969
REGION                  1..138
                        note = Functional Homolog of Ceres CLONE ID no. 2767 at SEQ
                         ID NO. 132 with e-value of 1.19E-16 and BLAST sequence
                         identity of 36.0
REGION                  1..136
                        note = Pfam Name: Usp Pfam Description: Universal stress
                         protein family
source                  1..138
                        mol_type = protein
                        note = Populus balsamifera subsp. trichocarpa
                        organism = Populus balsamifera
SEQUENCE: 141
MVAVDDGEYS HYALMWVLDN LEESITKSPL VIFTAQPPPS NNHSFTAAAL SSARMYCSVS    60
ANPEYTYTIQ DQNKKIAFAL LEKAKEICAG RGVDAETLTE VGDPQTAICD AVQRLNISLL   120
VLGERGIGKI KRWDDGAS                                                 138

SEQ ID NO: 142          moltype = AA   length = 148
FEATURE                 Location/Qualifiers
REGION                  1..148
                        note = Ceres CLONE ID no. 1059727
REGION                  1..148
                        note = Functional Homolog of Ceres CLONE ID no. 2767 at SEQ
                         ID NO. 132 with e-value of 1.90E-9 and BLAST sequence
                         identity of 31.6
REGION                  1..145
                        note = Pfam Name: Usp Pfam Description: Universal stress
                         protein family
source                  1..148
                        mol_type = protein
                        organism = Glycine max
SEQUENCE: 142
MVAIDDSDCS KHALRWTLSY LKDSLADSDI ILFTAQPQLD LSSVYASSYG AAPIELINSM    60
QQNYKNAALN RIEEGTKICA ESGVTPKKVM EFGNPKEAIC DAVEKLGVDL LIVGSHGKGA   120
LERTFLGSVS NYCVNKAKCP VLVVRTKA                                      148

SEQ ID NO: 143          moltype = AA   length = 165
FEATURE                 Location/Qualifiers
REGION                  1..165
                        note = Ceres CLONE ID no. 1272732
REGION                  1..165
                        note = Functional Homolog of Ceres CLONE ID no. 2767 at SEQ
                         ID NO. 132 with e-value of 2.29E-6 and BLAST sequence
                         identity of 27.7
REGION                  12..161
                        note = Pfam Name: Usp Pfam Description: Universal stress
                         protein family
source                  1..165
                        mol_type = protein
                        organism = Zea mays
SEQUENCE: 143
METAAVAASS AGRRIMVAVD EGEESLHALN WCLANVVSPA GGDTLVLVHA RRPRPVYAAM    60
DSAGYMMTSD VLASVERHAN AVSAAAVDKA KRVCADHPHV KVETTVESGD PRDVICDAAN   120
KMAADLLVMG SHGYGFIQRA FLGSVSNHCA QNCKCPVLIV KRPKE                   165

SEQ ID NO: 144          moltype = AA   length = 145
FEATURE                 Location/Qualifiers
REGION                  1..145
                        note = Ceres CLONE ID no. 283925
REGION                  1..145
                        note = Functional Homolog of Ceres CLONE ID no. 2767 at SEQ
                         ID NO. 132 with e-value of 2.29E-6 and BLAST sequence
                         identity of 27.6
```

```
REGION                  1..141
                        note = Pfam Name: Usp Pfam Description: Universal stress
                         protein family
source                  1..145
                        mol_type = protein
                        organism = Zea mays
SEQUENCE: 144
MVAVDEGEES LHALNWCLAN VVSPAGGDTL VLVHARRPRP VYAAMDSAGY MMTSDVLASV  60
ERHANAVSAA AVDKAKRVCA DHPHVKVETM VESGDPRDVI CDAANKMAVG SHGYGFIQRA 120
FLGSVSNHCA QNCKCPVLIV KRPKE                                      145

SEQ ID NO: 145          moltype = DNA   length = 901
FEATURE                 Location/Qualifiers
misc_feature            1..901
                        note = Ceres CLONE ID no. 16403
misc_feature            1..901
                        note = Ceres Seed Line ID no. ME01468
misc_feature            1..901
                        note = Encodes the peptide given in SEQ ID NO. 146
source                  1..901
                        mol_type = unassigned DNA
                        organism = Arabidopsis thaliana
SEQUENCE: 145
gtcttgtgaa ttgtagccac tatggcagtc tcctcactct caatccgctg tggtggtttc  60
tcaccaacaa tctcccacaa gacagaaatt ctctgtccaa atccatcact caaagcttgt 120
tgtttacttt catccggtgg taaggccgac tcctcggaga tgacttacca aaaaggcagc 180
ggaaacaatt ggaagagaag gcaagctctt gtgggagtag aactttagt ggcaacttca  240
attccagcaa ctttgcttct tgctgaagag ataccaaaaa gctactgcc ttttgtggat  300
cgagaagacg gtattctta ctattaccca tcagactgga gggaatttga cttcaggca  360
catgattcag cctccaaaga tagatacttg caactgcaa atgtgcgggt caggttcata  420
ccaacggaga aaaacgacat ccatgaagta ggtcctatgg aagaggtggt ttatgatcta  480
gtgaagcata agtttgcagc accaaaccaa gtagctacca tctacgatat gaaagagagg  540
gtggaagatg gaaagaacta ttacacgttt gagtatggac taagaactcc tatctatgca  600
accacttcct ttgcaacagt ggcagttgga aacaacagt actacactct catagttgga  660
gcaaatgaga aaggtgggag gaaagtgaaa aagcagcttc aagttgtggc cgactctttg  720
aagatccttc agatttgaca aacacaagaa acatcttact cctatatatc tttctctctc  780
tgtggttaca aaactgtctg tagataacaa tttgatattt tcatattctc tataactcca  840
acgatggttt tggcattgtg agttagattc tgagttggtt cagtaattca atcaaacttg  900
c                                                                901

SEQ ID NO: 146          moltype = AA  length = 238
FEATURE                 Location/Qualifiers
REGION                  1..238
                        note = Ceres CLONE ID no. 16403
REGION                  1..238
                        note = Ceres Seed Line ID no. ME01468
REGION                  1..238
                        note = Phenotype: Cold Germination Useful for making plants
                         with increased tolerance to cold stress
REGION                  1..238
                        note = Phenotype: Cold Growth Useful for making plants with
                         increased tolerance to cold stress
REGION                  54..236
                        note = Pfam Name: PsbP Pfam Description: PsbP
source                  1..238
                        mol_type = protein
                        organism = Arabidopsis thaliana
SEQUENCE: 146
MAVSSLSIRC GGFSPTISHK TEILCPNPSL KACCLLSSGG KADSSESTYQ KGSGNNWKRR  60
QALVGVGTLV ATSIPATLLL AEEIPKSYSP FVDREDGYSY YYPSDWREFD FRAHDSAFKD 120
RYLQLQNVRV RFIPTEKNDI HEVGPMEEVV YDLVKHKFAA PNQVATIYDM KERVEDGKNY 180
YTFEYGLRTP IYATTSFATV AVGNNRYYTL IVGANERRWR KVKKQLQVVA DSLKILQI   238

SEQ ID NO: 147          moltype = AA  length = 234
FEATURE                 Location/Qualifiers
REGION                  1..234
                        note = Ceres CLONE ID no. 611156
REGION                  1..234
                        note = Functional Homolog of Ceres CLONE ID no. 16403 at
                         SEQ ID NO. 146 with e-value of 7.29E-67 and BLAST sequence
                         identity of 58.9
REGION                  63..232
                        note = Pfam Name: PsbP Pfam Description: PsbP
source                  1..234
                        mol_type = protein
                        organism = Glycine max
SEQUENCE: 147
MVVSSCSLSW ISPCLSHKLN LPHTNCLPRN IATSSSNTVF CELDTTPSGE SHCRRRPLLL  60
GIGALTANLQ PTNLVFAQEK PDRYRAFVDY EDGYSYVYPI DWKEFDFRAH DSAFKDRYLQ 120
```

```
LQNVRVRFIP TEKKDIRDLG PMEEVIYDLV KHRYAAPNQR PTINDMQEKT IDGKHYYTFE    180
YILTSPNYSS ASFATIAIGN GRYYTLIVGA NERRWKRFRD QLKVVADSFR LLDI          234

SEQ ID NO: 148           moltype = DNA   length = 699
FEATURE                  Location/Qualifiers
misc_feature             1..699
                         note = Ceres ANNOT ID no. 1464944
misc_feature             1..699
                         note = Encodes the peptide given in SEQ ID NO. 149
source                   1..699
                         mol_type = unassigned DNA
                         note = Populus balsamifera subsp. trichocarpa
                         organism = Populus balsamifera
SEQUENCE: 148
atggcaatat cttcactctc attgagttgg gcttccacta ccttatccca aaagttaagt    60
gtccctggtt caaatgaaat attgcctaga gtagcagcat tttctggcaa taactctgta   120
acatgcacgg cagaggcaac cttcaatgaa gaaagcaatt gcaagagacg tctgctactg   180
ctaggagttg gagcactaac gacaagttta gtcccagcaa atttcctttt tgctgaagag   240
ataccaaaga actacacatc ttttgtggac tttgaagatg gtattcata ttattacccc    300
tcagactgga ttgattttga cttcaggggca catgattctg catttaagga cagaacgaag   360
caattgcaga atgttagggt gagatttata ccaaccgaga aaaagacat tcatgaattg    420
ggtccaatgg aagagtatga cagtcacatg cagcaagaaa ttatgaacgt gaaactttca   480
aattttcttg aaaaccagaa aaccgtagag ggaaaaaact actacacctt cgagtacgaa   540
cttacatctc caaactactc aagtgtttca tttgcaacca tagttattgc caatgggaga   600
ttttacactc tgatagttgg cgcaaatgaa agacggtgga agatatcg cagtcagcta     660
aaagtggtag cagactcttt caaggtgctt gacatctaa                          699

SEQ ID NO: 149           moltype = AA   length = 232
FEATURE                  Location/Qualifiers
REGION                   1..232
                         note = Ceres ANNOT ID no. 1464944
REGION                   1..232
                         note = Functional Homolog of Ceres CLONE ID no. 16403 at
                           SEQ ID NO. 146 with e-value of 4.39E-60 and BLAST sequence
                           identity of 56.2
REGION                   53..230
                         note = Pfam Name: PsbP Pfam Description: PsbP
source                   1..232
                         mol_type = protein
                         note = Populus balsamifera subsp. trichocarpa
                         organism = Populus balsamifera
SEQUENCE: 149
MAISSLSLSW ASTTLSQKLS VPGSNEILPR VAAFSGNNSV TCTAEATFNE ESNCKRRLLL    60
LGVGALTTSL VPANFLFAEE IPKNYTSFVD FEDGYSYYYP SDWIDFDFRG HDSAFKDRTK   120
QLQNVRVRFI PTEKKDIHEL GPMEEYDSHM QQEIMNVKLS NFLENQKTVE GKNYYTFEYE   180
LTSPNYSSVS FATIVIANGR FYTLIVGANE RRWRRYRSQL KVVADSFKVL DI           232

SEQ ID NO: 150           moltype = AA   length = 178
FEATURE                  Location/Qualifiers
REGION                   1..178
                         note = Functional Homolog of Ceres CLONE ID no. 16403 at
                           SEQ ID NO. 146 with e-value of 4.20E-32 and BLAST sequence
                           identity of 39.8
REGION                   20..175
                         note = Pfam Name: PsbP Pfam Description: PsbP
source                   1..178
                         mol_type = protein
                         note = Oryza sativa subsp. japonica
                         organism = Oryza sativa
SEQUENCE: 150
MLLAAGAAVF LSWPNLAANA AEAKKGFLPV TDKKDGYSFL YPFGWQEVVV QGQDKVYKDV    60
IEPLESVSVN TIPTSKQDIR ELGPPDQVAE ALIRKVLAAP TQKTKLIEAK ENDVDGRTYY   120
TFEFTAQAPN FTRHALGAIA IANGKFYTLT TGANERRWEK IKDRLHTVVD SFKIEARV     178

SEQ ID NO: 151           moltype = AA   length = 257
FEATURE                  Location/Qualifiers
REGION                   1..257
                         note = Functional Homolog of Ceres CLONE ID no. 16403 at
                           SEQ ID NO. 146 with e-value of 4.69E-33 and BLAST sequence
                           identity of 39.5
REGION                   86..241
                         note = Pfam Name: PsbP Pfam Description: PsbP
source                   1..257
                         mol_type = protein
                         note = Oryza sativa subsp. japonica
                         organism = Oryza sativa
SEQUENCE: 151
MATHSTSAPA APAFSAFPLA AAVRFPCASA TSNTCAFSLA EHLTREGMFF DLQSIKREAE    60
ERSRRRMLLA AGAAMFLSWP NPAAYAAEAK KGFLPVTDKK DGYSFLYPFG WQEVVVQGQD   120
```

```
KVYKDVIEPL ESVSVNTIPT SKQDIRELGP PDQVAEALIR KVLAAPTQKT KLIEAKENDV    180
DGRTYYTFEF TAQAPNFTRH ALGAIAIANG KFYTLTTGAN ERRWEKIKDR LHTVVDSFKI    240
EAREVRFNGK CREHGSY                                                   257

SEQ ID NO: 152          moltype = AA   length = 242
FEATURE                 Location/Qualifiers
REGION                  1..242
                        note = Ceres CLONE ID no. 1551032
REGION                  1..242
                        note = Functional Homolog of Ceres CLONE ID no. 16403 at
                          SEQ ID NO. 146 with e-value of 2.39E-32 and BLAST sequence
                          identity of 39.2
REGION                  59..239
                        note = Pfam Name: PsbP Pfam Description: PsbP
source                  1..242
                        mol_type = protein
                        organism = Zea mays
SEQUENCE: 152
MATAVPAACL RAPCSSPAAV ARRLGAGGPS LRKRHCAVAP VAAACGPAPP RLLDNEEAVC    60
SVRRRVLVAG AAAFLSRPNP AAFAAEAKKG FLPVVDKKAG YSFLYPFGWE EVAVQGQDKV   120
YKDVIEPLES VSVNSIPTSK EDIRDLGPPD KVAEALIKKV LAPSTQKTKL IEAKENDVDG   180
RAYYTFEFTA QAPNYTRHAL GAIVIANGKF YTLTTGANER RWEKMKDRLH TVVDSFKIEN   240
RI                                                                  242

SEQ ID NO: 153          moltype = DNA   length = 1172
FEATURE                 Location/Qualifiers
misc_feature            1..1172
                        note = Ceres CLONE ID no. 3964
misc_feature            1..1172
                        note = Ceres Seed Line ID no. ME00199
misc_feature            1..1172
                        note = Encodes the peptide given in SEQ ID NO. 154
source                  1..1172
                        mol_type = unassigned DNA
                        organism = Arabidopsis thaliana
SEQUENCE: 153
aaagcatcaa ataagtaaat aaaaactctt ttatgttcac cttttcact  atcctctctt    60
tgtgtttcaa atcgtgggaa caaattatca caatggaggc ttctaaagaa gctcatcacc   120
ttccaaacta catgaaagac gacaacgtta gtcaagaaac caagaacttg atcacttctc   180
taccttcaga caaagatttc atgggttatg gtctctacaa ctacaaaggt tgttggtact   240
atccaaacac actccaagcc gttcttgacg tccaaaaaca cttcaagcca cgagatactg   300
atataatcct cgcttctttg cccaaaggtg gaacccacttg gctcaaatcc ctaattttcg   360
ctgttgtaca tagagaaaag taccgcggaa cccctcaaaa acatcctttg ctcttacaaa   420
accctcatga ccttgtccca tttcttgagg ttgagttata cgctaatagc caaattccgg   480
atctcgcaaa gtattcttct cctatgatct tttctacaca catgcactta caagcattgc   540
gtgaagccac cacaaaagct tgcaaaaccg tatatgtgtg tagaggtatc aaagatacgt   600
ttgtctccgg ctggcattat agaaacatgt tgcatcgcac caagatggat caagccactt   660
ttgagctcat gtttgatgct tattgtagag gagttctctt atatggacct tattgggaac   720
atgtattgag ctattggaaa gggagcttgg aagcaaagga gaatgttctt ttcatgaagt   780
acgaagagat aattgaggag cctcgtgttc aagtcaagag actcgccgag ttcttggaat   840
gtccattcac caaggaagaa gaagaaagtg gatcggtgga ggagatcttg aagttgtgta   900
gtttacgaaa tttaagcaat ttggaggtta ataagaatgg gacaacgaga attggtgtag   960
attctcaggt gttctttagg aaaggtgaag ttggtgattg gaagaatcat cttacgccac  1020
aaaatggcgaa aaccctttga tgagattattg actatagact aggagactcc ggtttgatat  1080
ttcaataagg ttgtgttgtg ttttttttct tttgtcatcc gaaaataaat taggactcaa  1140
acgagtcatt cttgaaaaaa aaaaaaaaaa aa                                 1172

SEQ ID NO: 154          moltype = AA   length = 351
FEATURE                 Location/Qualifiers
REGION                  1..351
                        note = Ceres CLONE ID no. 3964
REGION                  1..351
                        note = Ceres Seed Line ID no. ME00199
REGION                  1..351
                        note = Phenotype: Dark Green Useful for increasing
                          chlorophyll and photosynthetic capacity
REGION                  1..351
                        note = Phenotype: WHOLE PLANT Useful for making bigger
                          plants
REGION                  1..351
                        note = Phenotype: Curled 3 Useful for making plants with
                          altered leaf shape eg curled leaves
REGION                  1..351
                        note = Phenotype: Standing Rosette Shaped Useful for making
                          plants with increased biomass and foliage
REGION                  88..347
                        note = Pfam Name: Sulfotransfer_1 Pfam Description:
                          Sulfotransferase domain
source                  1..351
```

```
                         mol_type = protein
                         organism = Arabidopsis thaliana
SEQUENCE: 154
MFTFFTILSL CFKSWEQIIT MEASKEAHHL PNYMKDDNVS QETKNLITSL PSDKDFMGYG    60
LYNYKGCWYY PNTLQAVLDV QKHFKPRDTD IILASLPKGG TTWLKSLIFA VVHREKYRGT   120
PQTHPLLLQN PHDLVPFLEV ELYANSQIPD LAKYSSPMIF STHMHLQALR EATTKACKTV   180
YVCRGIKDTF VSGWHYRNML HRTKMDQATF ELMFDAYCRG VLLYGPYWEH VLSYWKGSLE   240
AKENVLFMKY EEIIEEPRVQ VKRLAEFLEC PFTKEEEESG SVEEILKLCS LRNLSNLEVN   300
KNGTTRIGVD SQVFFRKGEV GDWKNHLTPQ MAKTFDEIID YRLGDSGLIF Q            351

SEQ ID NO: 155           moltype = AA  length = 337
FEATURE                  Location/Qualifiers
REGION                   1..337
                         note = Functional Homolog of Ceres CLONE ID no. 3964 at SEQ
                           ID NO. 154 with e-value of 1.49E-61 and BLAST sequence
                           identity of 48.6
REGION                   73..324
                         note = Pfam Name: Sulfotransfer_1 Pfam Description:
                           Sulfotransferase domain
source                   1..337
                         mol_type = protein
                         note = Oryza sativa subsp. japonica
                         organism = Oryza sativa
SEQUENCE: 155
MAPSFRLSSA PESADEATAH KEIYDQLRRV AETFPSAPSL IGLPCSRHPD GWYTFTNGVV    60
SSMVIKEHLT ARATDIFLTT FPKSGTTWLK VLLYSTLRPG TDELVAHSPH QLVPFLESQV   120
FVNDRIPDLS SLSSPRLFMT HIPSQSLPNS VATSGCKVVY LCRDPKDCFV SLWHFWNRFM   180
PWDIDEAHRQ FCDGVSQFGP FWEHILGYWR WHVEKPNQVL FLTYEELAAD TLGQLRRLAE   240
FVGCPFTTEE QKHGVDRNIV EACALENMSG LEVNRSGTIT IVDSTVPNNT FFRRGVVGDW   300
RNHLTPEMAR RIDEITKSKF KGSGLLLHPQ FLQVKRE                            337

SEQ ID NO: 156           moltype = DNA  length = 1119
FEATURE                  Location/Qualifiers
misc_feature             1..1119
                         note = Ceres ANNOT ID no. 1448303
misc_feature             1..1119
                         note = Encodes the peptide given in SEQ ID NO. 157
source                   1..1119
                         mol_type = unassigned DNA
                         note = Populus balsamifera subsp. trichocarpa
                         organism = Populus balsamifera
SEQUENCE: 156
atgcctgcct ctactacaac ttccatggtt ctcaaccatt tcacaaagaa tcaagcaaat    60
gacaatggag aggatttaga gagattaacc aatgagtgca aggaattgct gctttcactc   120
ccaagagaga agggttggag aactgcatgc ctctataaat acaaaggggtt ttggtgccaa   180
ccaaaagaaa tccaagcgat aatctctttt caaaaacact ttgaaccaag agacactgat   240
gttatcctag catcaatacc taaatcagga actacctggc tcaaagccct atcttttgcc   300
atcttgaatc gcaagaaatt tgcaatctct agtaatgacc ccctttgct cgtctctaat    360
cctcacgatc ttgcacctttt ctttgagtac aagctttatg cagacaagca agttcctgac   420
ctctcgaaac tccctgatcc tagactttt gccacccaca ttccatttgc ttcacttcaa   480
gactccatca agaagtctaa ttgccggatt atttatatct gtagaaaccc ttttgacact   540
tttatttcct catggacttt cagcaacaag ctgagatcag aaactgttcc tccactgtta   600
ctagaggaaa ccttcaaaat gtattgcgaa ggggttgtag ggtcggtcc cttctgggac   660
catatgttgg gatactggaa ggaaagcttg gagagacaag acaaggtgtt gttcttgaag   720
tatggagaca tgaaagcaga tgttacgttt tacttgaaga agattgccaa atttcttggc   780
tgcccctttt caatggaaga agaaaaggaa ggtgtagtgg aaaagatagc cagcctttgt   840
agcttttgaga agatgaagaa tttagaagtt aacaaatctg gaaggtctat tacgaacttc   900
gaaaataagc acttgtttag gaaagctgaa gtcggagatt gggtgaatta tctgtctcct   960
tcaatggtga agcaattatc tcaattaata gaggaaaagt tgggtggatc tggaggtgtc  1020
caagctgctg ctgctgctgc ttcttcttct tcttctgtta taaagaagaa attcgagcta  1080
cagagatatg gagagaataa gaatacaaat gtcaattga                         1119

SEQ ID NO: 157           moltype = AA  length = 364
FEATURE                  Location/Qualifiers
REGION                   1..364
                         note = Ceres ANNOT ID no. 1448303
REGION                   1..364
                         note = Functional Homolog of Ceres CLONE ID no. 3964 at SEQ
                           ID NO. 154 with e-value of 2.89E-72 and BLAST sequence
                           identity of 47.4
REGION                   70..330
                         note = Pfam Name: Sulfotransfer_1 Pfam Description:
                           Sulfotransferase domain
source                   1..364
                         mol_type = protein
                         note = Populus balsamifera subsp. trichocarpa
                         organism = Populus balsamifera
SEQUENCE: 157
MVLNHFTKNQ ANDNGEDLER LTNECKELLL SLPREKGWRT ACLYKYKGFW CQPKEIQAII    60
```

```
SFQKHFEPRD TDVILASIPK SGTTWLKALS FAILNRKKFA ISSNDHPLLV SNPHDLAPFF    120
EYKLYADKQV PDLSKLPDPR LFATHIPFAS LQDSIKKSNC RIIYICRNPF DTFISSWTFS    180
NKLRSETVPP LLLEETFKMY CEGVVGFGPF WDHMLGYWKE SLERQDKVLF LKYEDMKADV    240
TFYLKKIAKF LGCPFSMEEE KEGVVEKIAS LCSFEKMKNL EVNKSGRSIT NFENKHLFRK    300
AEVGDWVNYL SPSMVKQLSQ LIEEKLGGSG GVQAAAAAAS SSSSVIKKKF ELQRYGENKN    360
TNVN                                                                364

SEQ ID NO: 158           moltype = DNA  length = 1233
FEATURE                  Location/Qualifiers
misc_feature             1..1233
                         note = Ceres ANNOT ID no. 1501305
misc_feature             1..1233
                         note = Encodes the peptide given in SEQ ID NO. 159
source                   1..1233
                         mol_type = unassigned DNA
                         note = Populus balsamifera subsp. trichocarpa
                         organism = Populus balsamifera
SEQUENCE: 158
atgcctgcct ctactacaac ttccatggtt ctcaaccatt tcacaaagaa tcaagcaaat     60
gacaatggag aggatttaga gagattaacc aatgagtgca aggaattgct gctttcactc    120
ccaagagaga agggttggag aactgcatgc ctctataaat acaagggtt ttggtgccaa     180
ccaaaagaaa tccaagcgat aatctctttt caaaaacact ttgaaccaga agacactgat    240
gttatcctag catcaatacc taatcagga actacctggc tcaaagccct atcttttgcc     300
atcttgaatc gcaagaaatt tgcaatctct agtaatgacc cctttgct cgtctctaat      360
cctcacgatc ttgcacctt ctttgagtac aagctttatg cagacaagca agttcctgac    420
ctctcgaaac tccctgatcc tagacttttt gccacccaca ttccatttgc ttcacttcaa    480
gactccatca agaagtctaa ttgccggatt atttatatct gtagaaaccc tttttgacact    540
tttatttcct catggacttt cagcaacaag ctgagatcag aaactgttcc tccactgtta    600
ctagaggaaa ccttcaaaat gtattgcgaa ggggttgtag ggtcggtcc ttctgggac      660
catatgttgg gatactggaa ggaaagcttg gagagacaag acaaggtgtt gttcttgaag    720
tatgaggaca tgaaagcaga tgttacgttt tacttgaaga agattgccaa atttcttggc    780
tgcccttttt caatggaaga agaaaaggaa ggtgtagtgg aaaagatagc cagccttgt    840
agctttgaga agatgaagaa tttagaagtt aacaaatctg gaaggtctat tacgaacttc    900
gaaaataagc acttgtttag gaaagctgaa gtcggagatt gggtggatc tggtattgaa    960
tcaatggtta agcaattatc tcaattaata gaggaaaagt tgggtggatc tggtattgaa   1020
ttcaaagtgt ttcctatac tagcactact ccgtctacat ctccaaggct tttcgctgct    1080
cacattccct attcatcatt gcccgaatcc atcaagaagt ctaattgtcg tgaagttac    1140
atttatcgta acccttttaa cgtggtggca tcctggtttc atttttccaa tgttgaaggt   1200
gaaccagaga agctggatga ggagtatttt tga                                1233

SEQ ID NO: 159           moltype = AA  length = 410
FEATURE                  Location/Qualifiers
REGION                   1..410
                         note = Ceres ANNOT ID no. 1501305
REGION                   1..410
                         note = Functional Homolog of Ceres CLONE ID no. 3964 at SEQ
                          ID NO. 154 with e-value of 6.70E-73 and BLAST sequence
                          identity of 47.0
REGION                   353..397
                         note = Pfam Name: Sulfotransfer_1 Pfam Description:
                          Sulfotransferase domain
source                   1..410
                         mol_type = protein
                         note = Populus balsamifera subsp. trichocarpa
                         organism = Populus balsamifera
SEQUENCE: 159
MPASTTTSMV LNHFTKNQAN DNGEDLERLT NECKELLLSL PREKGWRTAC LYKYKGFWCQ     60
PKEIQAIISF QKHFEPRDTD VILASIPKSG TTWLKALSFA ILNRKKFAIS SNDHPLLVSN    120
PHDLAPFFEY KLYADKQVPD LSKLPDPRLF ATHIPFASLQ DSIKKSNCRI IYICRNPFDT    180
FISSWTFSNK LRSETVPPLL LEETFKMYCE GVVGFGPFWD HMLGYWKESL ERQDKVLFLK    240
YEDMKADVTF YLKKIAKFLG CPFSMEEEKE GVVEKIASLC SFEKMKNLEV NKSGRSITNF    300
ENKHLFRKAE VGDWVNYLSP SMVKQLSQLI EEKLGGSGIE FKVFPYTSTT PSTSPRLFAA    360
HIPYSSLPES IKKSNCREVY IYRNPFNVVA SWFHFSNVEG EPEKLDEEYF               410

SEQ ID NO: 160           moltype = AA  length = 312
FEATURE                  Location/Qualifiers
REGION                   1..312
                         note = Functional Homolog of Ceres CLONE ID no. 3964 at SEQ
                          ID NO. 154 with e-value of 6.40E-61 and BLAST sequence
                          identity of 46.6
REGION                   49..308
                         note = Pfam Name: Sulfotransfer_1 Pfam Description:
                          Sulfotransferase domain
source                   1..312
                         mol_type = protein
                         organism = Flaveria chloraefolia
SEQUENCE: 160
MEDIIKTLPQ HTCSFLKHRF TLYKYKDAWN HQEFLEGRIL SEQKFKAHPN DVFLASYPKS     60
GTTWLKALAF AIITREKFDD STSPLLTTMP HDCIPLLEKD LEKIQENQRN SLYTPISTHF    120
```

```
HYKSLPESAR TSNCKIVYIY RNMKDVIVSY YHFLRQIVKL SVEEAPFEEA FDEFCQGISS    180
CGPYWEHIKG YWKASLEKPE IFLFLKYEDM KKDPVPSVKK LADFIGHPFT PKEEEAGVIE    240
DIVKLCSFEK LSSLEVNKSG MHRPEEAHSI ENRLYFRKGK DGDWKNYFTD EMTQKIDKLI    300
DEKLGATGLV LK                                                       312

SEQ ID NO: 161          moltype = AA  length = 343
FEATURE                 Location/Qualifiers
REGION                  1..343
                        note = Ceres CLONE ID no. 703785
REGION                  1..343
                        note = Functional Homolog of Ceres CLONE ID no. 3964 at SEQ
                          ID NO. 154 with e-value of 1.30E-60 and BLAST sequence
                          identity of 46.2
REGION                  74..332
                        note = Pfam Name: Sulfotransfer_1 Pfam Description:
                          Sulfotransferase domain
source                  1..343
                        mol_type = protein
                        organism = Triticum aestivum
SEQUENCE: 161
MASSPQSSSS APKADDKAAS HKEIYDQLLE VVSTYPTAPS GIGRPYTHHP DGWYAFTPAV     60
VNAMVIKRHL KACDTDVFLS TFPKSGTTWL KALLFATLRR TADGPAIAAL AAHSPHQLIP    120
FLEVQVFSNG RIPDLSSLPA PRLLMTHIPS RSLPESVAAS GCKVVYLCRD PKDCFVSLWH    180
FWNRFAPSPW DLGEALQQFC DGVSLFGPFW EHVLGYWRWH VERPEQVLFL TYEELAADTL    240
GQLKRLAAFL GRPFTSEERE ARVDREIVEA CAMESLAGLE VNRSGKTDMT ESSVANNIFF    300
RRGVVGDWKN HLTPEMARRI DEITDSKFRG SGLALTPATA DQN                     343

SEQ ID NO: 162          moltype = AA  length = 325
FEATURE                 Location/Qualifiers
REGION                  1..325
                        note = Functional Homolog of Ceres CLONE ID no. 3964 at SEQ
                          ID NO. 154 with e-value of 4.99E-61 and BLAST sequence
                          identity of 45.8
REGION                  65..320
                        note = Pfam Name: Sulfotransfer_1 Pfam Description:
                          Sulfotransferase domain
source                  1..325
                        mol_type = protein
                        organism = Brassica napus
SEQUENCE: 162
MSSSSSVPDY LRDEKLTQET RDLISSLPSE KGWLVSQIYQ FQGRWHTEAL LQGILTCQKH     60
FKAKDSDIIL VTNPKSGTTW LKSLVFALIN RHKFPVSSGD HPLLVTNPHL LVPFMEGVYY    120
ESPDFDFSLL PFPRLMNTHI SHLSLPESVK SSSCQIVYCC RNPKDMFVSL WHFGKKLAPQ    180
ETADYPLEKA VEAFCQGKFI AGPFWDHVLE YWYASLENPN KVLFVTYEEL KKQTEVEVKR    240
IAEFIGCGFT AEEEVSEIVK LCSFESLSRL EVNRQGKLPN GIETNAFFRK GEIGGWRDTL    300
SESLADAIDR TTEEKFGGSG LKFSC                                         325

SEQ ID NO: 163          moltype = AA  length = 312
FEATURE                 Location/Qualifiers
REGION                  1..312
                        note = Functional Homolog of Ceres CLONE ID no. 3964 at SEQ
                          ID NO. 154 with e-value of 2.70E-60 and BLAST sequence
                          identity of 45.8
REGION                  49..308
                        note = Pfam Name: Sulfotransfer_1 Pfam Description:
                          Sulfotransferase domain
source                  1..312
                        mol_type = protein
                        organism = Flaveria bidentis
SEQUENCE: 163
MEDIIKTLPQ HTCSFLKQRF TLYKYQDVWN HQEFLEGRML SEQTFKAHPN DVFLASYPKS     60
GTTWLKALAF AIITREKFDD STSPLLTTMP HDCIPLLEKD LEKIQENQRN SLYTPISTHF    120
HYKSLPESAR TSNCKIVYIY RNMKDVIVSY YHFLRQIVKL SVEEAPFEEA VDEFCQGISS    180
CGPYWEHILG YWKASLEKPE IFLFLKYEDM KKDPVPSVKK LADFIGHPFT PKEEEAGVIE    240
NIIKLCSFEK LSSLEVNKSG MHRPEEAHSI ENRLYFRKGK DGDWKNYFTD EMIEKIDKLI    300
DEKLGATGLV LK                                                       312

SEQ ID NO: 164          moltype = AA  length = 323
FEATURE                 Location/Qualifiers
REGION                  1..323
                        note = Functional Homolog of Ceres CLONE ID no. 3964 at SEQ
                          ID NO. 154 with e-value of 1.30E-60 and BLAST sequence
                          identity of 44.4
REGION                  64..318
                        note = Pfam Name: Sulfotransfer_1 Pfam Description:
                          Sulfotransferase domain
source                  1..323
                        mol_type = protein
                        organism = Brassica napus
```

```
                                          -continued

SEQUENCE: 164
MESSSVPVYL KDENLTQETR DLLSSLPSEK GWLVSQMYQF EGIWQTQALV QGIVNCQKHF    60
EANDSDVILA TLAKSGTTWL KALLFALIHR HKFPVSGKHP LLVTNPHSLV PYLEGDYCSS   120
PEVNFAELPS PRLMQTHLTH HSLPVSIKSS SCKIIYCCRN PKDMFVSIWH FGRKLAPEKT   180
AEYPIETAVA AFCKGKFIGG PFWDHVLEYW YESLKNPNKV LFVTYEELKK QTEVEVKRIA   240
EFIGCGFTAE EEVSEIVKLC SFESLSSLEV NRQGKLPNGI ESNAFFRKGE TGGWRDTLSE   300
SLADVIDRTT EQKFGGSGLK FSS                                          323

SEQ ID NO: 165          moltype = AA  length = 323
FEATURE                 Location/Qualifiers
REGION                  1..323
                        note = Functional Homolog of Ceres CLONE ID no. 3964 at SEQ
                         ID NO. 154 with e-value of 2.20E-58 and BLAST sequence
                         identity of 44.4
REGION                  63..318
                        note = Pfam Name: Sulfotransfer_1 Pfam Description:
                         Sulfotransferase domain
source                  1..323
                        mol_type = protein
                        organism = Brassica napus
SEQUENCE: 165
MSSSSSSYLR DEDLTQETRD LISSLPSEKG WLVSQMYQFQ GRWHTQALLQ GLLQYQKHFE    60
AKDSDIILVT NPKSGTTWLK ALVFSLINRH KFPVSSGDHP LLVTNPHLLI PFLEGVYYES   120
PNFDFTELPS PRLMNTHISL LSLPESVKSS SCKIVYCCRN PKDMFVSLWH FGKKLASQET   180
ADYPIEKAVE AFCQGKFIGG PFWDHVLEYW YASLENPNKV LFVTYEELKK QTGDTIKRIA   240
EFLGCGFIEE EEVGGIVKLC SFESLSSLEA NREGKLPNGV ETKAFFRKGE VGGWRDTLSE   300
SLAEEIDRTM EEKFQGSGLK FSC                                          323

SEQ ID NO: 166          moltype = AA  length = 324
FEATURE                 Location/Qualifiers
REGION                  1..324
                        note = Functional Homolog of Ceres CLONE ID no. 3964 at SEQ
                         ID NO. 154 with e-value of 9.20E-53 and BLAST sequence
                         identity of 44.1
REGION                  65..319
                        note = Pfam Name: Sulfotransfer_1 Pfam Description:
                         Sulfotransferase domain
source                  1..324
                        mol_type = protein
                        organism = Brassica napus
SEQUENCE: 166
MSSSSSSVPDY LRDENLTQKT KDLISSLPSE KGWLVCQMYQ FQGRWHTQAL LQGILTCQKH    60
FEAKDSDIIL VTNPKSGTTW LKALVFALIN RHKFPVYSVI ILSCYQSALL VPFLGRSLLR   120
SPDFDFSQLS SPRLMNTHIS HLSLPESVKS SSCKIVYCCR NPKDMFVSLW HFGKKLAPEE   180
TADYPIEKAV EAFCQGKFIG GPFWDHVLEY WYASLENPNK VLFVSYEEPK KKTGETIKRI   240
AEFLGCGLVG EEEVRAIVKL CSFESLSSLE VNREGKLPSG METRAFFRKG EVGGWRDTLT   300
ESLAEVIDRT IEEKFQGSGL KFSC                                         324

SEQ ID NO: 167          moltype = AA  length = 290
FEATURE                 Location/Qualifiers
REGION                  1..290
                        note = Functional Homolog of Ceres CLONE ID no. 3964 at SEQ
                         ID NO. 154 with e-value of 3.59E-42 and BLAST sequence
                         identity of 44.1
REGION                  182..290
                        note = Pfam Name: Sulfotransfer_1 Pfam Description:
                         Sulfotransferase domain
source                  1..290
                        mol_type = protein
                        note = Oryza sativa subsp. japonica
                        organism = Oryza sativa
SEQUENCE: 167
MAPSFPLSFA PQSADEAAAH KEIYDQLRQT VETFPTAPNS SNSFTYSRHP DGWYTFPEGV    60
VSAMVIKSHL TARTTDIFMV TFPKSGTTWL KTLLHSALHR GANDLAAHSP HQLVPFLETQ   120
VFIKDRIPDL SSLPAPRLLM THIPSQSLPD SVADSGCKVV YLCRDPNRKF RPWDINEAHR   180
HFCDGVSLFG PYWEHVLGYW RWHTKRPSQV LFLTYEELTT DTLGQLRHLA EFVGCPFMVE   240
EQELGVDRKI VEACAMESLS RLEVNQSGTT DMVDKTYVNN IFFRRGVVGD              290

SEQ ID NO: 168          moltype = AA  length = 345
FEATURE                 Location/Qualifiers
REGION                  1..345
                        note = Ceres CLONE ID no. 1064128
REGION                  1..345
                        note = Functional Homolog of Ceres CLONE ID no. 3964 at SEQ
                         ID NO. 154 with e-value of 1.19E-59 and BLAST sequence
                         identity of 43.8
REGION                  74..332
                        note = Pfam Name: Sulfotransfer_1 Pfam Description:
                         Sulfotransferase domain
```

```
source                  1..345
                        mol_type = protein
                        organism = Zea mays
SEQUENCE: 168
MATVFPRDAG VSTPEADEAK KIYDEARRVV STYETVPSPS GTLQDYCRHP SGWCITLPIM    60
VSSMVAEQHF EARGTDVLLV TMPKSGTTWI KALLYAAAHR TDDTSSSILR QLASHNSHQL   120
VPFLEAQVYT KDQIPDLSSL PAPRLFATHI PAESLPPSVV ASGCKVVYLC RDPKDCFVSL   180
WHFMNKFTPW DIDEAHGRFC EGVSLYGPFW EHVLSYWRWH VDRPGQVLFL TYEELSADPL   240
GQLRRLAEFI GRPFTPGEQE AGVDREIAEA CAMKSMVNQE VNQSRTTEIV EMPIPNGIFF   300
RRGVVGDWTN YLTPEMAGRI DEITKSKFEG SGLMLPKTIS EISKI                   345

SEQ ID NO: 169          moltype = AA  length = 279
FEATURE                 Location/Qualifiers
REGION                  1..279
                        note = Functional Homolog of Ceres CLONE ID no. 3964 at SEQ
                         ID NO. 154 with e-value of 1.90E-54 and BLAST sequence
                         identity of 43.0
REGION                  11..262
                        note = Pfam Name: Sulfotransfer_1 Pfam Description:
                         Sulfotransferase domain
source                  1..279
                        mol_type = protein
                        note = Oryza sativa subsp. japonica
                        organism = Oryza sativa
SEQUENCE: 169
MVVKSHLTAR ATDIFLVTFP KSGTTWIKAL PYSALHRRAD ELLAHSPHQL ISFLESQVFV    60
KDRIPDLSSL PEPWLLMTHI PSQSLPDSVA ASGCKVVYLC RDPKDCFVSL WHFWNRFMPW   120
NIDDAHRQFC NGVSLFGLYW EHVLSYWNWH VERPSEVLFL TYEELAADTL GHLRRLAEFV   180
GRPFTTEEQD ARVDRKIVEI CAMESLSGLE VNRSGMTNFT KKDVPNNISF RRGVVGDWRN   240
HLTPEMARRI DEITEVKFKG SGLLLHPPFL QVKRELNEL                          279

SEQ ID NO: 170          moltype = AA  length = 250
FEATURE                 Location/Qualifiers
REGION                  1..250
                        note = Functional Homolog of Ceres CLONE ID no. 3964 at SEQ
                         ID NO. 154 with e-value of 6.29E-38 and BLAST sequence
                         identity of 39.0
REGION                  55..248
                        note = Pfam Name: Sulfotransfer_1 Pfam Description:
                         Sulfotransferase domain
source                  1..250
                        mol_type = protein
                        organism = Triticum monococcum
SEQUENCE: 170
MNKRLLDSRH CLANANCGLA LPLVLFNVCC YEGLWVHYFH VAGAVALQLR LAPLQDDVIV    60
ASFPKSGTTW LNALTFATMA RRTNPAAGAG HPLLRLNPHQ CIPFLDKLFQ SCTEAKLEAL   120
PSPRLMNTHM PIDMIMPGGG GCKVVYICRE PKDMVISQWH FLRRLQPDLP LADLLESVCS   180
GAMPYGPVWD HILGYWRAST ARPDGVLFLR YEELLRNPAE KVRELARFVG LPFSDAEEEA   240
GVVHDIVKLE                                                          250

SEQ ID NO: 171          moltype = DNA  length = 865
FEATURE                 Location/Qualifiers
misc_feature            1..865
                        note = Ceres CLONE ID no. 965405
misc_feature            1..865
                        note = Ceres Seed Line ID no. ME09814
misc_feature            1..865
                        note = Encodes the peptide given in SEQ ID NO. 172
source                  1..865
                        mol_type = unassigned DNA
                        organism = Brassica napus
SEQUENCE: 171
agtcgtcgtc ttctgtgtaa gaaatatctt atcttaggtg tgcagaccga agtctagagt    60
atcttcaagc ttcaacttct tagctatgtc ggccgatgat tcttcaaatg ctacagatgt   120
tgacgggaag ctcggctccg atttaaacgt taactctgac ggtgaagatg cggcggataa   180
tgattcctca aagacattga ctattcctgc tcccgccgtt tgtcttgtcc ggttcgccgg   240
agatgcagct ggtggtgccg tcatgggctc tatctttgga tatggttcag gattgttcaa   300
gaagaaaggc tttaaaggat catttgcaga tgcaggacag tctgcaaaga cttttgctgt   360
tttgtccgga gtacacagtt tggttgtttg ccttctgaaa caactcagag ggaaagatga   420
tgccattaat gttggagttg ctgggtgctg caccggtctt gctcttagtt tccctggtgc   480
tccacaggct cttctacaga gttgcctcac ttttggggct ttctctttta tccttggaggg   540
actaaacaaa agacaaacag ccttggctca ctctgtctcc ttaagacacc aaaccggaaa   600
cttttggagat catcaacaac gtcctttaca actctccctg gctctcccaa tccatgaaga   660
aatcaaagga ttctctcttt tctgcaagtc cttaactaaa cccaagaaga tctaatttcg   720
ccatggattat ccttttcttg ttccttatgt tctctctgta gattcttaat gattccctgc   780
ttttgctgta cttgtgaga gaatatttta tgaaagatct tttgatataa attttgcacc   840
gtttgctcta aaaaaaaaaa aaaaa                                         865

SEQ ID NO: 172          moltype = AA  length = 209
```

```
FEATURE                 Location/Qualifiers
REGION                  1..209
                        note = Ceres CLONE ID no. 965405
REGION                  1..209
                        note = Ceres Seed Line ID no. ME09814
REGION                  39..157
                        note = Pfam Name: Tim17 Pfam Description: Tim17/Tim22/Tim23
                          family
source                  1..209
                        mol_type = protein
                        organism = Brassica napus
SEQUENCE: 172
MSADDSSNAT DVDGKLGSDL NVNSDGEDAA DNDSSKTLTI PAPAVCLVRF AGDAAGGAVM    60
GSIFGYGSGL FKKKGFKGSF ADAGQSAKTF AVLSGVHSLV VCLLKQLRGK DDAINVGVAG   120
CCTGLALSFP GAPQALLQSC LTFGAFSFIL EGLNKRQTAL AHSVSLRHQT GNFGDHQQRP   180
LQLSLALPIH EEIKGFSSFC KSLTKPKKI                                    209

SEQ ID NO: 173          moltype = AA   length = 210
FEATURE                 Location/Qualifiers
REGION                  1..210
                        note = Ceres CLONE ID no. 5367
REGION                  1..210
                        note = Functional Homolog of Ceres CLONE ID no. 965405 at
                          SEQ ID NO. 172 with e-value of 6.89E-87 and BLAST sequence
                          identity of 85.5
REGION                  40..158
                        note = Pfam Name: Tim17 Pfam Description: Tim17/Tim22/Tim23
                          family
source                  1..210
                        mol_type = protein
                        organism = Arabidopsis thaliana
SEQUENCE: 173
MAANDSSNAI DIDGNLDSDS NLNTDGDEAT DNDSSKALVT IPAPAVCLFR FAGDAAGGAV    60
MGSIFGYGSG LFKKKGFKGS FADAGQSAKT FAVLSGVHSL VVCLLKQIRG KDDAINVGVA   120
GCCTGLALSF PGAPQALLQS CLTFGAFSFI LEGLNKRQTA LAHSVSLRHQ TGLFQDHHRA   180
LPLSLALPIP EEIKGAFSSF CKSLAKPRKF                                   210

SEQ ID NO: 174          moltype = AA   length = 214
FEATURE                 Location/Qualifiers
REGION                  1..214
                        note = Functional Homolog of Ceres CLONE ID no. 965405 at
                          SEQ ID NO. 172 with e-value of 4.30E-78 and BLAST sequence
                          identity of 79.6
REGION                  40..158
                        note = Pfam Name: Tim17 Pfam Description: Tim17/Tim22/Tim23
                          family
source                  1..214
                        mol_type = protein
                        organism = Arabidopsis thaliana
SEQUENCE: 174
MAAENSSNAI NVDTSLDSDS KPNRDANDMT DHDSSSKALV IPAPAVCLVR FAGDAASGAF    60
MGSVFGYGSG LFKKKGFKGS FVDAGQSAKT FAVLSGVHSL VVCLLKQIRG KDDAINVGVA   120
GCCTGLALSF PGAPQAMLQS CLTFGAFSFI LEGLNKRQTA LAHSVSFRQQ TRSPQHDLPL   180
LSLAIPIHDE IKGAFSSFCN SLTKPKKLKF PHAR                              214

SEQ ID NO: 175          moltype = AA   length = 212
FEATURE                 Location/Qualifiers
REGION                  1..212
                        note = Functional Homolog of Ceres CLONE ID no. 965405 at
                          SEQ ID NO. 172 with e-value of 7.30E-76 and BLAST sequence
                          identity of 79.4
REGION                  40..156
                        note = Pfam Name: Tim17 Pfam Description: Tim17/Tim22/Tim23
                          family
source                  1..212
                        mol_type = protein
                        organism = Arabidopsis thaliana
SEQUENCE: 175
MAAENSSNAI NVDTSLDSDS KPNRDANDMT DHDSSSKALV IPAPAVCLVR FAGDAASGAF    60
MGSVFGYGLF KKKGFKGSFV DAGQSAKTFA VLSGVHSLVV CLLKQIRGKD DAINVGVAGC   120
CTGLALSFPG APQAMLQSCL TFGAFSFILE GLNKRQTALA HSVSFRQQTR SPQHDLPLLS   180
LAIPIHDEIK GAFSSFCNSL TKPKKLKFPH AR                                212

SEQ ID NO: 176          moltype = AA   length = 213
FEATURE                 Location/Qualifiers
REGION                  1..213
                        note = Ceres CLONE ID no. 1060894
REGION                  1..213
                        note = Functional Homolog of Ceres CLONE ID no. 965405 at
```

```
                              SEQ ID NO. 172 with e-value of 3.50E-76 and BLAST sequence
                              identity of 77.5
REGION                        39..157
                              note = Pfam Name: Tim17 Pfam Description: Tim17/Tim22/Tim23
                              family
source                        1..213
                              mol_type = protein
                              organism = Zea mays
SEQUENCE: 176
MAAENPSNGV DVDTSLASDS NDNRKASDLT NHDSSMALTV PSTAVCLGRF AGDAAGGAVM       60
GSIFGYGSGL FKKKGFKGSF ADAGQSAKNF AILSGVHSLV VCLLKKLRGK DDAINVGIAG      120
CCTGLALSYP GAPQAMLQSC VTFGAFSFIL EGLNKRQTAL AHSVSSRHDQ TRSLKDDLPL      180
SLALPIHEEI KGAFSSFCKS LTKPKKLAFP SSR                                   213

SEQ ID NO: 177                moltype = AA  length = 203
FEATURE                       Location/Qualifiers
REGION                        1..203
                              note = Ceres CLONE ID no. 639280
REGION                        1..203
                              note = Functional Homolog of Ceres CLONE ID no. 965405 at
                              SEQ ID NO. 172 with e-value of 6.40E-45 and BLAST sequence
                              identity of 68.0
REGION                        29..147
                              note = Pfam Name: Tim17 Pfam Description: Tim17/Tim22/Tim23
                              family
source                        1..203
                              mol_type = protein
                              organism = Triticum aestivum
SEQUENCE: 177
MAARSENESD GDVGTNPAEG GSSLSLPPLA AGPAVCVLRS AGDFAGGAFV GSIFGYGQGL        60
LSKKGLKGSL GNAGSSAKSF AVLSGVQSLV LCLLRKLRGK DDIINSGIAG CCTGLALSFP      120
GTPQALLQNC ATFAAFSCIM EGLNKQQTAM AHTLTGNALT FAHDNGAGVL PPSLSPQSSM      180
LPMLSPHAAR PWSPSLRSTR QQH                                              203

SEQ ID NO: 178                moltype = DNA  length = 645
FEATURE                       Location/Qualifiers
misc_feature                  1..645
                              note = Ceres ANNOT ID no. 1494390
misc_feature                  1..645
                              note = Encodes the peptide given in SEQ ID NO. 179
source                        1..645
                              mol_type = unassigned DNA
                              note = Populus balsamifera subsp. trichocarpa
                              organism = Populus balsamifera
SEQUENCE: 178
atggcgacgg cgaattctcc aaacaccagc aacaactctg attccgatgt cgaagaccct       60
aaccctaatc cttcaagtaa taataacaat gcatcaatta ttccttctgc tgagtccagt      120
accccttccg tctgcctcat ccgcttcgct ggtgactccg ctgcaggcgc ctttatgggc      180
tccatcttcg gctacggttc gggattgatt aagaagaaag gcttcaaagg atcctttggg      240
gaagcaggat cttgtgccaa gactttgca gttctatctg gagtacacag tttggttgtc       300
tgcttctgaa gaggctgcg agggaaggat gatgtcatca atgctggagt agctgcaggt      360
tgtactggtc ttgctctgag ttttccaggt gcacctcagg cacttctgca gagttgcctt      420
actttttggag cattctcatt catcatcgaa gggctgaaca agaagcaagc agcactggct      480
cactctattt cttcaaggaa taatgtgac tatcacagca aaccttgtcc gctagcactc       540
cctctttcag tccctcttcc agatgaacta aaaggggcct tctccttttt ctgcaagtcc      600
ttaaggaaac ccagagtgc caattttccc gccgccgccc cctga                       645

SEQ ID NO: 179                moltype = AA  length = 214
FEATURE                       Location/Qualifiers
REGION                        1..214
                              note = Ceres ANNOT ID no. 1494390
REGION                        1..214
                              note = Functional Homolog of Ceres CLONE ID no. 965405 at
                              SEQ ID NO. 172 with e-value of 8.10E-61 and BLAST sequence
                              identity of 67.1
REGION                        38..156
                              note = Pfam Name: Tim17 Pfam Description: Tim17/Tim22/Tim23
                              family
source                        1..214
                              mol_type = protein
                              note = Populus balsamifera subsp. trichocarpa
                              organism = Populus balsamifera
SEQUENCE: 179
MATANSPNTS NNSDSDVEDP NPNPSSNNNN ASIIPSAESS TPSVCLIRFA GDSAAGAFMG        60
SIFGYGSGLI KKKGFKGSFG EAGSCAKTFA VLSGVHSLVV CFLKRLRGKD DVINAGVAGC      120
CTGLALSFPG APQALLQSCL TFGAFSFIIE GLNKKQAALA HSISSRNKCD YHSKPCPLAL      180
PLSVPLPDEL KGAFSFFCKS LRKPKSANFP AAAP                                  214

SEQ ID NO: 180                moltype = AA  length = 136
```

| FEATURE | Location/Qualifiers |
|---|---|
| REGION | 1..136 |
| | note = Synthesized Sequence |
| REGION | 1..136 |
| | note = Ceres CDNA ID no. 23799376 |
| REGION | 1..136 |
| | note = Ceres Clone ID no. 375578 |
| REGION | 1..136 |
| | note = Ceres Seed Line ID no. ME02064 |
| source | 1..136 |
| | mol_type = protein |
| | organism = synthetic construct |

SEQUENCE: 180

```
MGKRGKWFSA VKKVFSSSDP DGKEAKAQKA DKSKSKRRWP FGKSKHSEPS ISTVPGTAPA   60
VAPLPSPPAT QPHSLEIKDV NPVETDSEQN KHAYSVALAS AVAAEAAAVA AQAAAEVVRL  120
TAVTTAAPKM PVSSRE                                                 136
```

| SEQ ID NO: 181 | moltype = DNA length = 1020 |
|---|---|
| FEATURE | Location/Qualifiers |
| misc_feature | 1..1020 |
| | note = Ceres CLONE ID no.19199 |
| misc_feature | 1..1020 |
| | note = Encodes the peptide given in SEQ ID NO. 182 |
| source | 1..1020 |
| | mol_type = unassigned DNA |
| | organism = Arabidopsis thaliana |

SEQUENCE: 181

```
acccactaga accgttgtaa cctacgaccc ataataatgt accatctcct tatcattatc   60
actacactct ccttctcttc aattaacata accttcgccg tcgatgaagc tttcccttca  120
attcccacta ccttcagcgt cgcaacgaaa caacactacg cgtaaaacc aatccaccat   180
gaagtttatg acgagaaag gaagatatac gacatcagcc accagtacac gccggagttg   240
ccggtttggg agtcttcaga aggactaggg aactttctta gacttgccgt gagtatgaag   300
aatggatccg atgctaatat ctcgaagatg gaactatctg ttcactctgg aactcatgtt   360
gatgcaccag gccatttcca tgaccattat tatgagtcgt gttttgatac tgattcactt   420
gatcttcaaa tccttaatgg tcctgcttta ttggttgatg ttccaagaga taagaacatt   480
tcagctgagg ttatgaaatc actacatatt ccaagaggga tccgtcgtgt tctctttaaa   540
acattgaaca ctgataggag gcttatgttt aagaaagaat tgattcaag ctttgtcggg    600
tttatggtcg atggggcgaa atggttggtt gaaaatacag acatcaaact tgttgggctt   660
gattatcttt catttgctgc ttatgatgaa gcacctgacg cgcataggtt tatacttgaa   720
cgacgggata taatccctgt cgaagcgctg aagctggatg acgtggaggt aggaatgtac   780
acgcttcatt gcttaccgtt aagattggtt ggagcggaag gagcaccaac gagatgcatt   840
ctcatcaagt gattcagttc atctttttct atctaagttg tatatgaatt actgataata   900
aacaataggc ttttttggctt cttgcttcca agatctcata accatatcga gatgttaac   960
atatggatg attttgttgt aaaagaagcg tctaatctta ttatataaag tatggttttc  1020
```

| SEQ ID NO: 182 | moltype = AA length = 271 |
|---|---|
| FEATURE | Location/Qualifiers |
| REGION | 1..271 |
| | note = Ceres CLONE ID no. 19199 |
| REGION | 57..257 |
| | note = Pfam Name: Cyclase Pfam Description: Putative cyclase |
| REGION | 1..271 |
| | note = Functional Homolog of Ceres CLONE ID no. 8686 at SEQ |
| | ID NO. 80 with e-value of 2.60E-100 and BLAST sequence |
| | identity of 83.4 |
| source | 1..271 |
| | mol_type = protein |
| | organism = Arabidopsis thaliana |

SEQUENCE: 182

```
MYHLLIIITT LSFSSINITF AVDEAFPSIP TTFSVATKQH YDVKPIHHEV YDGERKIYDI   60
SHQYTPELPV WESSEGLGNF LRLAVSMKNG SDANISKMEL SVHSGTHVDA PGHFHDHYYE  120
SGFDTDSLDL QILNGPALLV DVPRDKNISA EVMKSLHIPR GIRRVLFKTL NTDRRLMFKK  180
EFDSSFVGFM VDGAKWLVEN TDIKLVGLDY LSFAAYDEAP ATHRFILERR DIIPVEALKL  240
DDVEVGMYTL HCLPLRLVGA EGAPTRCILI K                                271
```

| SEQ ID NO: 183 | moltype = DNA length = 1291 |
|---|---|
| FEATURE | Location/Qualifiers |
| misc_feature | 1..1291 |
| | note = Ceres CLONE ID no.1940431 |
| misc_feature | 1..1291 |
| | note = Encodes the peptide given in SEQ ID NO. 184 |
| source | 1..1291 |
| | mol_type = unassigned DNA |
| | organism = Gossypium hirsutum |

SEQUENCE: 183

```
agggtatcac gatcccttaa aagcggcaca gcaagccaat gagtggagcg cagatttaa    60
acgcaaaaaa ccaacttcac ttcccatttc ctagtcttcc acgatgactc ccctccactt  120
cttcctcctc ctcctccttt cgtcagctgc tttaatctcc gcggccgcg ccaccgccac    180
caccgcatat ccttccatcc cgggcaccga ttccacaact gattgtggcc tatccggagg  240
```

```
ggacgagaat ccagttccca tccgtcgcga agtctacggt aacggcaaga tattcgacat    300
cagccatagg tacaccgtcg acatgccgtc ttgggaatcc aaggacggcg tgggacagtt    360
cctatggttg cctaaaagca tgaagaacgg ttccctcgct aataattcgg agatgaaact    420
cccaactcac accggcaccc accttgacgc tcccggacac gtcatcgatc ggtacttcga    480
tgccggcttc gatgtcgata ccctagattt ggaagtactt aatggtcctg ccctgttgat    540
agatgttcca agggataaaa acattactgc cgaggttatg gagtctttga aaataccaaa    600
gggagtacgt agagttcttt tcagaacatt aaatactgac aggcggctaa tgtttaagaa    660
agagtttgat acaagctacg ttggatttat gaaggatgga gcagagtggt tggttaaaca    720
cactgacata aaacttattg gaattgatta cttatctgtt gctgcctttg atgatttgat    780
tccatctcat atagtttcc tagaagaccg ggatatcatt cttgtggaag gtttaaaact    840
cgataacgtt caacctggaa tatattcagt ccattgctta ccattaagat tgcttggtgc    900
tgaaggatca ccaacaagat gcattctcat caaatgatgt tgttgtcctt gttactataa    960
aagacttgag ataagtgggt acgttttcaa ggcaatgatg atgctaatgg cacaccgtca   1020
tcttacaccg tcgtccttat aggcatgttg tttggaaaga ggaaatggct gggtgacatt   1080
aagggtggtg tttgattgga acaaggcaaa taacgggttt atgagttaga acttgacgct   1140
gttaggaatc ctagaaggga gcttcagtat agaaatttgg ttgcagtgaa ctacacttt    1200
cgtgtaatat atcattatga tatttcttt aagttccctt ttattcata aataataata    1260
cacttacgcc atatttttgg ttggttggag t                                   1291

SEQ ID NO: 184          moltype = AA   length = 277
FEATURE                 Location/Qualifiers
REGION                  1..277
                        note = Ceres CLONE ID no. 1940431
REGION                  63..263
                        note = Pfam Name: Cyclase Pfam Description: Putative cyclase
REGION                  1..277
                        note = Functional Homolog of Ceres CLONE ID no. 8686 at SEQ
                         ID NO. 80 with e-value of 1.49E-86 and BLAST sequence
                         identity of 72.1
source                  1..277
                        mol_type = protein
                        organism = Gossypium hirsutum
SEQUENCE: 184
MTPLHFFLLL LLSSAALISA AAATATTAYP SIPGTDSTTD CGLSGGDENP VPIRREVYGN     60
GKIFDISHRY TVDMPSWESK DGVGQFLWLP KSMKNGSLAN NSEMKLPTHT GTHLDAPGHV    120
IDRYFDAGFD VDTLDLEVLN GPALLIDVPR DKNITAEVME SLKIPKGVRR VLFRTLNTDR    180
RLMFKKEFDT SYVGFMKDGA EWLVKHTDIK LIGIDYLSVA AFDDLIPSHI VFLEDRDIIL    240
VEGLKLDNVQ PGIYSVHCLP LRLLGAEGSP TRCILIK                             277

SEQ ID NO: 185          moltype = DNA   length = 1349
FEATURE                 Location/Qualifiers
misc_feature            1..1349
                        note = Ceres CLONE ID no.1646125
misc_feature            1..1349
                        note = Encodes the peptide given in SEQ ID NO. 186
source                  1..1349
                        mol_type = unassigned DNA
                        organism = Glycine max
SEQUENCE: 185
aatatgtcgc cgcctcaatt tttcagacca aaatgatttt ttaaaatttt tttgtcattg     60
ttgtaaaaat aacaaataat aaataaaaaa attaaaaaat aacattctgt caagagatgg    120
atgtgtttca ttcatctttg tgtttcattc atctttctca gtcaaccatg aactctcgat    180
cactctttgc cttcctcttc gcaatttgcg cgcactccgt cgccgttgcc gacacctcct    240
ccgcgtatcc ttccatcccc ggcacggaaa ccggtgagtg ctccctccgc ggcgtgggcg    300
tgggcgacgg tgttctggtt cctccacggc gagaagtata cgaggagggg cgaatccttc    360
acatcactca cagatatgtc cccgagatgc cggtgtggga ctcgacggag gggctcgggc    420
aacacttcct gtggctcgat aagagcatga agaatggctc gctcgctaac agctctaaca    480
tgaagctcgg tgttcacacc ggcacccatg tcgacgcgcc cggtcacttt tacgacaatt    540
actacgacgc tggcttcgac gttgactcac tcgacctaac gctcctcaat ggccttgcac    600
ttctggttga tgttccgcgg gataaaaaca ttactgctga ggttatgagg tccctgaata    660
tccctagagg tgtaagccgt gtgcttttca gaactttaaa cactgacagg cgactcatgt    720
ttaagaaaga atttgacaca agctatgtgg gattcaagga ggatggtgca aaatggctgg    780
cagagaacac tgacatcaaa cttgtaggag ttgattactt atctgttgct gcttatgatc    840
actccattcc atctcatctt gttttttctgg aaagcaagga aatcattctt gtggaaggcc    900
taaagcttga tgatgtccca gcaggaatat attcattgaa ttgcttgcct cttaggttgg    960
ttcactctga ggcatcacca attcgatgta ttctgatcag atgatccatg atgggggtcaa   1020
acctggtttt caattgcacg gatgaacctg ccattagaag caacgtagcc ccgaatacaa   1080
ttagtggtgt ccataagaag cagtttgatg caaattgcaa gctaagctga tagtagtacg   1140
ttgaaattac tcgtatttta cgtccttggg ttgtaaacta ccagttatt gtgattaaac    1200
ttcagttgcg gactagggggt ccacctgtat taacttatgt ttttaatatt tacctaggca   1260
agtacttgcg caattctgaa tacgcatgct tgtacgcctc aataattata tctatttctc   1320
tatgaaaaat aaaaaaaaaa aaaaaaaa                                       1349

SEQ ID NO: 186          moltype = AA   length = 278
FEATURE                 Location/Qualifiers
REGION                  1..278
                        note = Ceres CLONE ID no. 1646125
REGION                  63..264
                        note = Pfam Name: Cyclase Pfam Description: Putative cyclase
```

|  |  |
|---|---|
| REGION | 1..278<br>note = Functional Homolog of Ceres CLONE ID no. 8686 at SEQ ID NO. 80 with e-value of 5.39E-84 and BLAST sequence identity of 71.3 |
| source | 1..278<br>mol_type = protein<br>organism = Glycine max |

SEQUENCE: 186

```
MNSRSLFAFL FAICAHSVAV ADTSSAYPSI PGTETGECSL RGVGVGDGVL VPPRREVYEE    60
GRIFDITHRY VPEMPVWDST EGLGQHFLWL DKSMKNGSLA NSSNMKLGVH TGTHVDAPGH   120
FYDNYYDAGF DVDSLDLTLL NGLALLVDVP RDKNITAEVM RSLNIPRGVS RVLFRTLNTD   180
RRLMFKKEFD TSYVGFKEDG AKWLAENTDI KLVGVDYLSV AAYDHSIPSH LVFLESKEII   240
LVEGLKLDDV PAGIYSLNCL PLRLVHSEAS PIRCILIR                          278
```

|  |  |
|---|---|
| SEQ ID NO: 187 | moltype = DNA  length = 953 |
| FEATURE | Location/Qualifiers |
| misc_feature | 1..953<br>note = Ceres CLONE ID no.1759790 |
| misc_feature | 1..953<br>note = Encodes the peptide given in SEQ ID NO. 188 |
| source | 1..953<br>mol_type = unassigned DNA<br>organism = Panicum virgatum |

SEQUENCE: 187

```
acgtgtcaac tgcacttcca gaaaggcaaa tccattccat ggagctcgcg ccgctgctcc    60
tgctccccc gctgctgctg ctcccggcgg cggccgtcgc ctccggcggt gagccgccgc   120
tggcgcaccc ggcctatgcg cgcggcgcc aggaggcatg cggcgtggcg gcgctgccag   180
cgccggagcg gcgcgaggag ttcgacggcg ggcggatcgt ggacatcagc cactactacc   240
gcgcggacat gccggcgtgg gagtcggcgg agggctccgg cgagttcctg cggctggcgc   300
ggtccatgcg caacggctcc gacatcgcca acttctcgga gctccgcctc accgcgcact   360
ccggcaccca cgtcgacgcg ccggggcacg tcttcgagca ctactacgac accggcttcg   420
acgtcgacac gctcgacctc gccgtcctca acgggccagc gctgttggtt gacgttcccc   480
gagataagaa cataacaggt gttcgacgtg tactcttccg aaccttaaat actgacagaa   540
agcttatgtg gaagaaagag tttgatacta gttatgttgg cttcatgaag gatggtcgac   600
aatggctggt cgacaatact gacatcaaac tagttgaagt tgattacttg tctgtgggtg   660
catttgacga atgcattcca gctcatctag tatttcttga aaaagggag gtaatccttg   720
tggaagcctt aaatctggag catgctaccc tggaatata tgccttgcat tgcttgccac   780
taagattgcg tggtgctgaa ggttctcctg caaaatgcat ccttatcaag tgacacatgg   840
ttacaaccat ctagaaaacc tttgtactat cttatgcac gtatgataat gaaataagaa   900
aaggtcaacg catatgactt cttctcttgc atcaaaaaaa aaaaaaaaaa aaa           953
```

|  |  |
|---|---|
| SEQ ID NO: 188 | moltype = AA  length = 264 |
| FEATURE | Location/Qualifiers |
| REGION | 1..264<br>note = Ceres CLONE ID no. 1759790 |
| REGION | 60..250<br>note = Pfam Name: Cyclase Pfam Description: Putative cyclase |
| REGION | 1..264<br>note = Functional Homolog of Ceres CLONE ID no. 8686 at SEQ ID NO. 80 with e-value of 8.09E-74 and BLAST sequence identity of 68.2 |
| source | 1..264<br>mol_type = protein<br>organism = Panicum virgatum |

SEQUENCE: 188

```
MELAPLLLLP PLLLLPAAAV ASGGEPPLAH PAYARGAEEA CGVAALPAPE RREEFDGGRI    60
VDISHYYRAD MPAWESAEGS GEFLRLARSM RNGSDIANFS ELRLTAHSGT HVDAPGHVFE   120
HYYDTGFDVD TLDLAVLNGP ALLVDVPRDK NITGVRRVLF RTLNTDRKLM WKKEFDTSYV   180
GFMKDGAQWL VDNTDIKLVG VDYLSVGAFD ECIPAHLVFL EKREVILVEA LNLEHATPGI   240
YALHCLPLRL RGAEGSPAKC ILIK                                         264
```

|  |  |
|---|---|
| SEQ ID NO: 189 | moltype = DNA  length = 1029 |
| FEATURE | Location/Qualifiers |
| misc_feature | 1..1029<br>note = Ceres CLONE ID no.741003 |
| misc_feature | 1..1029<br>note = Encodes the peptide given in SEQ ID NO. 190 |
| source | 1..1029<br>mol_type = unassigned DNA<br>organism = Triticum aestivum |

SEQUENCE: 189

```
agcaccacct actagcccac acatatccgc gacgccgatg ccccaaatgg cgtctcctct    60
cctcctcctc cctctcgccg ccgccaccgc accgtgcgcc catccggcct acccgagcca   120
gccggctcg tgccgccggg agcccgcgct ggcgccgggg cgccgggaga cgcacggccg   180
gggccgcatc ctggacatca cccactacta ccgggaggac atgccctcgt gggagtccga   240
cgccggggtg ggccagttcc tgtggctgcc cgctcccatg cgcaacggct ccctcgccaa   300
caactccgag atgcggatgc ccacccacac cggcacccac gtcgacgccc ccggccacgt   360
cttccagcac tacttcgacg ctggcttcga cgtcgacacc ctcgacctcg acgtcctcaa   420
cggtcctgca ctgctggttg atgttccaag ggatcaaaat attactgcta aaacgatgga   480
```

```
atctttgcat attcctaaag gagttcaacg ggtactttc agaacattaa acactgacag    540
gaacctaatg tggaagaaag agtttgacac aagctatgta ggttttatga aagatggtgc   600
ccaatggttg gtagacaaca cggatattaa gcttgtcgga atagactatt tgtccgttgc   660
agctttcgat gacctgatcc cttcacattt agttttctc gaaaaccggg atgtcattct    720
tgtggagggc ctcaaactgg agaatgtcaa acctgggata tactcgttgc attgcctgcc   780
acttcggttg cgtggagcgg aaggttcgcc gatcagatgc atccttataa agtgaagaca   840
cttgtatccc gctgcgattt agttttatac cgcaagcact cttataaact agactagaga   900
tgtgtacaaa accccatctt tgatagcgga cgagtattgt aaatgtctcc acaaacatgg   960
tggcactttg acgcttagta aggagcgaca aacgactagg ggtgcaaatg tgtaaaaaaa   1020
aaaaaaaaa                                                           1029

SEQ ID NO: 190         moltype = AA   length = 265
FEATURE                Location/Qualifiers
REGION                 1..265
                       note = Ceres CLONE ID no. 741003
REGION                 51..251
                       note = Pfam Name: Cyclase Pfam Description: Putative cyclase
REGION                 1..265
                       note = Functional Homolog of Ceres CLONE ID no. 8686 at SEQ
                         ID NO. 80 with e-value of 9.39E-80 and BLAST sequence
                         identity of 67.2
source                 1..265
                       mol_type = protein
                       organism = Triticum aestivum
SEQUENCE: 190
MPQMASPLLL LPLAAATAPC AHPAYPSQPA SCAAEPALAP ERRETHGGGR ILDITHYYRE    60
DMPSWESSAG VGQFLWLPAS MRNGSLANNS EMRMPTHTGT HVDAPGHVFQ HYFDAGFDVD   120
TLDLDVLNGP ALLVDVPRDQ NITAKTMESL HIPKGVQRVL FRTLNTDRNL MWKKEFDTSY   180
VGFMKDGAQW LVDNTDIKLV GIDYLSVAAF DDLIPSHLVF LENRDVILVE GLKLENVKPG   240
IYSLHCLPLR LRGAEGSPIR CILIK                                        265

SEQ ID NO: 191         moltype = AA   length = 269
FEATURE                Location/Qualifiers
REGION                 1..269
                       note = Public GI ID no. 35215089
REGION                 55..255
                       note = Pfam Name: Cyclase Pfam Description: Putative cyclase
REGION                 1..269
                       note = Functional Homolog of Ceres CLONE ID no. 8686 at SEQ
                         ID NO. 80 with e-value of 1.90E-79 and BLAST sequence
                         identity of 66.2
source                 1..269
                       mol_type = protein
                       note = Oryza sativa subsp. japonica
                       organism = Oryza sativa
SEQUENCE: 191
MAHLAPLFLL LLLLLLPLHA AATPSAHPAY PNEPPSCAAA VPVPERREAH GGGRILDITH    60
YYREDMPSWE SDGGVGQFLW LPASMRNGSR ANNSEMRLPT HTGTHVDAPG HVFQHYFDAG   120
FDVDSLDLEV LNGLALLVDV PRDDNITAKM MESLHIPKGI QRVLFRTLNT DRQLMWKKEF   180
DTSYVGFMED GAQWLVDNTD IKLVGIDYLS VAAFDDLIPS HLVLLKNRDI ILVEGLKLEN   240
IMPGIYSLHC LPLRLRGAEG SPIRCILIK                                    269

SEQ ID NO: 192         moltype = AA   length = 270
FEATURE                Location/Qualifiers
REGION                 1..270
                       note = Public GI ID no. 115475854
REGION                 56..256
                       note = Pfam Name: Cyclase Pfam Description: Putative cyclase
REGION                 1..270
                       note = Functional Homolog of Ceres CLONE ID no. 8686 at SEQ
                         ID NO. 80 with e-value of 1.90E-79 and BLAST sequence
                         identity of 66.2
source                 1..270
                       mol_type = protein
                       note = Oryza sativa subsp. japonica
                       organism = Oryza sativa
SEQUENCE: 192
MMAHLAPLFL LLLLLLLPLH AAATPSAHPA YPNEPPSCAA AVPVPERREA HGGGRILDIT    60
HYYREDMPSW ESDGGVGQFL WLPASMRNGS RANNSEMRLP THTGTHVDAP GHVFQHYFDA   120
GFDVDSLDLE VLNGLALLVD VPRDDNITAK MMESLHIPKG IQRVLFRTLN TDRQLMWKKE   180
FDTSYVGFME DGAQWLVDNT DIKLVGIDYL SVAAFDDLIP SHLVLLKNRD IILVEGLKLE   240
NIMPGIYSLH CLPLRLRGAE GSPIRCILIK                                   270

SEQ ID NO: 193         moltype = DNA   length = 909
FEATURE                Location/Qualifiers
misc_feature           1..909
                       note = Ceres ANNOT ID no.1450986
misc_feature           1..909
                       note = Encodes the peptide given in SEQ ID NO. 194
```

| source | 1..909 |
| --- | --- |
| | mol_type = unassigned DNA |
| | note = Populus balsamifera subsp. trichocarpa |
| | organism = Populus balsamifera |

SEQUENCE: 193

```
atggagggaa attttgcaca aagaatgcaa atttcgacaa catgattga tacaggcaat     60
cttgcaagaa aaccaactgg ttttctacgg ttttcgggga gattaaagga acagaagaga   120
ctccaagtgt ttgtttctgc tcagtttcga cctgtaagag atgaaaatcg acatagattg   180
gcttcttttg aggtttctcg ctcttataac aattctcgag tttcgacgtt ggaatctgag   240
agtctccagg atttgcttga cgatgaagct ttgattttga agaataagtc gcaggagatt   300
gagcccatt taaacggacg ctgtatatat cttgttggaa tgatgggctc tggaaaaaca   360
acagtgggaa agattctctc gcaagcaatt cattattcat tctgtgacag tgacacattg   420
gtggagaagg atgttggtgt gacttctgta gctgaaatat ttcaaatata tggagaggat   480
ttcttcagag ataaagagac tgaggcatta gaaaagctat cactagagca ccgatatgtc   540
gtttctactg gtggaggtgc tgtgatacag gatgaaaact ggacgtacat gaggaagggg   600
attagtgtct ggttagatgt gcctttggaa gaattggcac agaggattgc ggctgtagga   660
accaagactc gccccctttt ggatagagaa ccaggagatg catacaccaa ggcgttcagg   720
cgtctgtctg ctctgtttga acagagatat aaagcttatg aaaatgctaa tgcaaggatt   780
tctctggaaa atattgcagc caaattagga tataaagatg tatccaatat cacaccacct   840
atgattgcga ttgagaacat ggcttgggtg atgcattacg cagcaggttt ccgtctatta   900
ccagtgtaa                                                          909
```

| SEQ ID NO: 194 | moltype = AA length = 302 |
| --- | --- |
| FEATURE | Location/Qualifiers |
| REGION | 1..302 |
| | note = Ceres ANNOT ID no. 1450986 |
| REGION | 115..291 |
| | note = Pfam Name: SKI Pfam Description: Shikimate kinase |
| REGION | 1..302 |
| | note = Functional Homolog of Ceres cDNA ID no. 23363195 at SEQ ID NO. 106 with e-value of 2.09E-73 and BLAST sequence identity of 55.9 |
| source | 1..302 |
| | mol_type = protein |
| | note = Populus balsamifera subsp. trichocarpa |
| | organism = Populus balsamifera |

SEQUENCE: 194

```
MEGNFAQRMQ ISTTWIDTGN LARKPTGFLR FSGRLKEQKR LQVFVSAQFR PVRDENRHRL    60
ASFEVSRSYN NSRVSTLESE SLQDLLDDEA LILKNKSQEI EPYLNGRCIY LVGMMGSGKT   120
TVGKILSQAI HYSFCDSDTL VEKDVGVTSV AEIFQIYGED FFRDKETEAL EKLSLEHRYV   180
VSTGGGAVIQ DENWTYMRKG ISVWLDVPLE ELAQRIAAVG TKTRPLLDRE PGDAYTKAFR   240
RLSALFEQRY KAYENANARV SLENIAAKLG YKDVSNITPP MIAIENMAWV MHYAAGFRLL   300
PV                                                                302
```

| SEQ ID NO: 195 | moltype = DNA length = 1392 |
| --- | --- |
| FEATURE | Location/Qualifiers |
| misc_feature | 1..1392 |
| | note = Ceres CLONE ID no.1973421 |
| misc_feature | 1..1392 |
| | note = Encodes the peptide given in SEQ ID NO. 196 |
| source | 1..1392 |
| | mol_type = unassigned DNA |
| | organism = Gossypium hirsutum |

SEQUENCE: 195

```
ctctccgtta tttggatctg atgttgattt tatgttttaa agtgcttgt tttcagtttt     60
ttttttttggt gaagtagagc acataatttc agcattgcat gcaacttcaa tctgaattta    120
gggttttat tatgaaccga acccgttttg caaagattta aaactatggg atctgcaagt    180
tatctgaaat agtcttcatt tctcttggag tcagagagca aagcccttca caaaattcat    240
tttctcttta ttaattatcc aaggggctga gaatggaggc tggagttgca tgcaagttga    300
attatccgac atggattgag tcagaaaggt ttgggaggaa ctcgactggt acttttgcggt   360
tcagtcggat agcaaagcaa gaacacaagg cccggctggt tgtttcggcg cacttttccgg   420
ttctgacatc ttctaatcgg tttagatcgg tctcttttcga ggtttcctgc tcttcctcta   480
agaacttttc agcttcaaca attgaaactg gtagcgttca tgcacccttat gatgaagctt   540
tagtgttaaa gaataagtca ctagaggttg agccatatt aaatgggcac agtatatatc    600
ttgttggatt gatgggttct ggaaaaacta cagtgggaaa aattctgtct aacgtactca    660
gttattcatt ttgtgacagt gacgtgttaa tagagcagga ggtgaatgga atgtctgtag    720
ccgaagtatt taagcttcat ggtgagagat tcttcagaaa gaaggagact gaggtattgc    780
agaggctctc ttcaaagaaa cagcttgttg tttctactgg cggaggtgca gttgtatggg   840
atgtgaactg ggattatatg caaaagaagg gggttgttgt ctggttagat gtacctttgg    900
aagccttggc acagaggatt gctgcagtag gtactcattc tcgtccccct ttgcattatg    960
aacatggcga tccctataca aaggcttaa aacggctgtc ttacctttg gaactgaggg    1020
gtaaaaatta tgctaaagca aatgcccggg tttcattgaa agaaattgca ggcaaactag    1080
gttatagaga tgtatcagat cttactccaa cagagattgc aatcgaggca ttgcaacaaa    1140
ttgaaggggta tctaaaggag gaaggtggca tgggattatag ttttgaaaaa               1200
gctatagata tggtgattga atttcgtttt atttgtggca tagcatgtca aaattgacca    1260
gtttttttttt ccatctctgc accggtgtag tttgtttcca caactaagtt gtgtaactca    1320
caatgtattg tcactaaaata tcatgaacat gatgcacttg tatatgtttg cctaattcat    1380
ttttgtttta gt                                                      1392
```

```
SEQ ID NO: 196            moltype = AA  length = 305
FEATURE                   Location/Qualifiers
REGION                    1..305
                          note = Ceres CLONE ID no. 1973421
REGION                    114..291
                          note = Pfam Name: SKI Pfam Description: Shikimate kinase
REGION                    1..305
                          note = Functional Homolog of Ceres CDNA ID no. 23363195 at
                          SEQ ID NO. 106 with e-value of 2.90E-78 and BLAST sequence
                          identity of 55.8
source                    1..305
                          mol_type = protein
                          organism = Gossypium hirsutum
SEQUENCE: 196
MEAGVACKLN YPTWIESERF GRNSTGTLRF SRIAKQEHKA RLVVSAHFPV LTSSNRFRSV    60
SFEVSCSSSK NFSASTIETG SVHAPYDEAL VLKNKSLEVE PYLNGHSIYL VGLMGSGKTT   120
VGKILSNVLS YSFCDSDVLI EQEVNGMSVA EVFKLHGERF FRKKETEVLQ RLSSKKQLVV   180
STGGGAVVWD VNWDYMQKKG VVVWLDVPLE ALAQRIAAVG THSRPLLHYE HGDPYTKALK   240
RLSYLLELRG KNYAKANARV SLKEIAGKLG YRDVSDLTPT EIAIEALQQI EGYLKEEGGM   300
VIAGL                                                              305

SEQ ID NO: 197            moltype = AA  length = 287
FEATURE                   Location/Qualifiers
REGION                    1..287
                          note = Public GI ID no. 38344899
REGION                    100..276
                          note = Pfam Name: SKI Pfam Description: Shikimate kinase
REGION                    1..287
                          note = Functional Homolog of Ceres CDNA ID no. 23363195 at
                          SEQ ID NO. 106 with e-value of 3.39E-66 and BLAST sequence
                          identity of 55.5
source                    1..287
                          mol_type = protein
                          note = Oryza sativa subsp. japonica
                          organism = Oryza sativa
SEQUENCE: 197
MDAGVGLRAK PGAWAGLGNP RRSSTARVPV RFAVEKFAQP LVLGSDRRSC GAKLKVSCSR    60
KPAGIDKTYY SADEALVLKQ KAEDVVPYLN DRCIYLVGMM GSGKTTVGKI LAEVLGYSFF   120
DSDKLVEKAV GISSVAEIFQ LHSEAFFRDN ESEVLRDLSS MHRLVVATGG GAVIRPINWS   180
YMKKGSTIWL DVPLDALARR IAAVGTASRP LLHQESGDPY AKAYAKLTAL FEQRMDSYAN   240
ADARVSLEHI AVKQGHSNVT TLTPSAIAIE ALLKMESFLT EKAMIRN                 287

SEQ ID NO: 198            moltype = AA  length = 300
FEATURE                   Location/Qualifiers
REGION                    1..300
                          note = Public GI ID no. 114200
REGION                    113..288
                          note = Pfam Name: SKI Pfam Description: Shikimate kinase
REGION                    1..300
                          note = Functional Homolog of Ceres CDNA ID no. 23363195 at
                          SEQ ID NO. 106 with e-value of 6.80E-77 and BLAST sequence
                          identity of 54.7
source                    1..300
                          mol_type = protein
                          organism = Lycopersicon esculentum
SEQUENCE: 198
MEARVSQSLQ LSSWINSDKV VRKPSGLLRF SEKWNEKPRH RVVVSCHLQP RKAAHSDRRV    60
QLKVSCSPQN VQASVLESGC FSASIDEIET LKNKAEEVEE YLDGRCVYLV GMMGCGKTTV   120
GRILAETLGY SFFDCDRLIE QAVGGITVAE IFELRGESFF RDNETEVLHK LSLMHRLVVS   180
TGGGAVVRPI NWRHMHKGIS VWLDVPLEAL AKRITTEGTK SRPLLHEESG DVYDTTLKRL   240
TTLMETRGEN YANASARVSL ENIALKREKD VCHITPAEIT LEVLLIQIENF LKTQKSVVVL   300

SEQ ID NO: 199            moltype = DNA  length = 1248
FEATURE                   Location/Qualifiers
misc_feature              1..1248
                          note = Ceres CLONE ID no.1769327
misc_feature              1..1248
                          note = Encodes the peptide given in SEQ ID NO. 200
source                    1..1248
                          mol_type = unassigned DNA
                          organism = Panicum virgatum
SEQUENCE: 199
ctccttcaat tccctctcat ctcgcgtctc cgcacggaga gccgccctcc tcgtccgccg    60
ccgcctgccg ccggcgagct cttcattacc ccggcgatgg ccgccgcatc caaaaccacc   120
atcaccaatc acgtctagca catctcgccc gagcggctga gccacacgtc acagcaacac   180
atcaagccgc gcggatcgac aggaagatgg aggcagcgt gggcatccgg gcgcggcccg   240
gtgcgtgggc cgggctcgag aagcgcgcg gcgcttgctc tgcaagagtc ccggcggcgg   300
ggctcacggg ggagaagctg ccggcgaggc tggctctggg aaccgatccg cggaggagca   360
cggatccgt gctccgtgcc gcaaagatga aagcttcgtg ttgcaagaaa tcgacaggta   420
```

```
ctgaaaaggt ccactactct gccgatgaag ctctcatact acagcaaaaa gcccaggatg    480
ttctccctta cttggatggc cgatgcattt atctagtcgg aatgatgggt tcaggcaaaa    540
ctacagttga gaagatatta gctgaagtac taggttattc tttcttcgac agtgataagt    600
tggtagagaa ggctgtcggt atatcatctg ttgctgagat ttttcagctc cacagtgaag    660
cattcttcag agataatgag agtgaggtcc taagggattt gtcatcaatg catcggttag    720
ttgttgcaac tggaggtggt gccgtgatcc gaccaatcaa ttggagttac atgaagaaag    780
ggctgactgt gtggttagat gttccactgg atgcacttgc aagaaggatt gctgccgtgg    840
gaactgcatc tcggcccctc ttgcatcagg aatctggtga cccatatgca aaggcttatg    900
caaaacttac atcacttttt gagaaaagaa tggactcgta tgctaatgcg gatgccagag    960
tttcacttga acatattgca ttaaaacaag ggcatatata tgtcactata cttacaccta   1020
gtaccattgc cattgaggca ttattaaaga tggaaagttt tcttactgag aaggccatgg   1080
tcagaaactg accgcttgtt gctggggaaa agggcaccaa cagcatatgg cccctgtttg   1140
tttaattgtg cttgtacata tgcctttgca tgagctcttt acagtactgt tagattgttg   1200
ttcatgcaac atgaaagatg attattcgaa aaaaaaaaaa aaaaaaaa                1248

SEQ ID NO: 200            moltype = AA  length = 294
FEATURE                   Location/Qualifiers
REGION                    1..294
                          note = Ceres CLONE ID no. 1769327
REGION                    107..282
                          note = Pfam Name: SKI Pfam Description: Shikimate kinase
REGION                    1..294
                          note = Functional Homolog of Ceres CDNA ID no. 23363195 at
                            SEQ ID NO. 106 with e-value of 2.79E-64 and BLAST sequence
                            identity of 53.0
source                    1..294
                          mol_type = protein
                          organism = Panicum virgatum
SEQUENCE: 200
MEASVGIRAR PGAWAGLEKP RGACSARVPA AGLTAEKLPA RLALGTDPRR STDPVLRAAK    60
MKASCCKKST GTEKVHYSAD EALILQQKAQ DVLPYLDGRC IYLVGMMGSG KTTVEKILAE   120
VLGYSFFDSD KLVEKAVGIS SVAEIFQLHS EAPFRDNESE VLRDLSSMHR LVVATGGGAV   180
IRPINWSYMK KGLTVWLDVP LDALARRIAA VGTASRPLLH QESGDPYAKA YAKLTSLFEK   240
RMDSYANADA RVSLEHIALK QGHNDVTILT PSTIAIEALL KMESFLTEKA MVRN         294

SEQ ID NO: 201            moltype = DNA  length = 745
FEATURE                   Location/Qualifiers
misc_feature              1..745
                          note = Ceres CLONE ID no.1728680
misc_feature              1..745
                          note = Encodes the peptide given in SEQ ID NO. 202
source                    1..745
                          mol_type = unassigned DNA
                          organism = Musa acuminata
SEQUENCE: 201
gctctcgtcg ctaccgcaat ggcagcatca catggttggc tcacttctct gcccaaccaa    60
ttggctgtcg caagctctgt cgtcaaccat cgatccgctc cggctgcttc gttcgtcgtc   120
agggcgagct cgacggatgc atcacttacg gagaaggatt gtttaaggag aaggcaggtt   180
ttagttggac tcagttcctt gaccgctgct tgtcccggg caaatttgc aagtgctgaa    240
gatataccg agaattttcg agctttcgtg gatttacag atggatatgc atactattat    300
ccttcgatt ggagagattt tgattacatg ggccatgatt cagcatttaa agatcgattt    360
gcagcattgc aacatgtcag agtcagtttc attcctaccg aaaagaaaga tattcgtgat    420
ttgggatcca tggaggaggt catttttcaac ttggtaaaaa atatttatgc tgcaccaaat    480
cagattccga gcatatatga gatgcaggag cgaactgtcg atggaagaa ctattggaca    540
ttcgaatacg aacttgaatc cccaagcttt tcccgtacgg cctttgcgac aatagctatt    600
ggcaatgggc ggtactacac attagttgtt ggtgcaaatg agaggcggtg gactagactt    660
cggaacaagc tcaaggtggt agcagactct ttcaagattc ttgacatatg aaactagaag    720
tgcttgcctg ccgaaccatg agtcc                                          745

SEQ ID NO: 202            moltype = AA  length = 230
FEATURE                   Location/Qualifiers
REGION                    1..230
                          note = Ceres CLONE ID no. 1728680
REGION                    48..228
                          note = Pfam Name: PsbP Pfam Description: PsbP
REGION                    1..230
                          note = Functional Homolog of Ceres CLONE ID no. 16403 at
                            SEQ ID NO. 146 with e-value of 1.10E-58 and BLAST sequence
                            identity of 60.2
source                    1..230
                          mol_type = protein
                          organism = Musa acuminata
SEQUENCE: 202
MAASHGWLTS LPNQLAVASS VVNHRSAAAA SFVVRASSTD ASLTEKDCLR RRQVLVGLSS    60
LTAALSRANF ASAEDIPENF RAFVDFTDGY AYYYPSDWRD FDYMGHDSAF KDRFAALQHV   120
RVSFIPTEKK DIRDLGSMEE VIFNLVKNIY AAPNQIPSIY EMQERTVDGK NYWTFEYELE   180
SPSFSRTAFA TIAIGNGRYY TLVVGANERR WTRLRNKLKV VADSFKILDI              230

SEQ ID NO: 203            moltype = DNA  length = 842
```

```
FEATURE                 Location/Qualifiers
misc_feature            1..842
                        note = Ceres CLONE ID no.1807796
misc_feature            1..842
                        note = Encodes the peptide given in SEQ ID NO. 204
source                  1..842
                        mol_type = unassigned DNA
                        organism = Gossypium hirsutum
SEQUENCE: 203
atggcagtgg caatggcgat gaattcagtt tcattgaact gggttccacc ttcctttaca   60
aagaaggcaa attatgtgac aaactccact gagctagccc caccttctgc tttttcttcg  120
caaaactcac tcacgtacac caaagaaacc atttccaatg aagaaaacaa ttgcaagaga  180
agactgttgc tcttgggtgt tggagttatt acagctaatt tactccctgc aaattccctt  240
ctagcagaag agataccaca aaactatcga gcttttgttg acattccaga tgggtattct  300
tattactacc catcagattg gagggaattt gattttaggg acatgattc agcattcaaa  360
gacaggtttc ttcaactgca aaatgtaagg gtgagattca taccaactga taagcaagac  420
atccatgagt tggggccaat agaagaggtt gtttacaatt tggtgaatca tgtttatgct  480
gcaccaaatc aaatggtcaa tatacttgat atgcaagaga caaaagtga tgggaaaaac  540
tattatacct tgaatatga actcacctct ccaaactatg ctagtgcttc ctttgcaaca  600
atagctattg gaaatgggag atattacaca ctggttgttg gagcacttga agacggtgg   660
agaaggcttc gaaacaaget gaaagtggtg gccgactcct tcaaggtgct tgacatctga  720
tgacccccca acttatcttt tcattgtata taaaccccga aacataccat tggttttgtt  780
tagttgagcg tcatcgtcaa cttaactat ttctcctict tcaaaaaaa aaaaaaaaa    840
aa                                                                842

SEQ ID NO: 204          moltype = AA   length = 235
FEATURE                 Location/Qualifiers
REGION                  1..235
                        note = Ceres CLONE ID no. 1807796
REGION                  51..233
                        note = Pfam Name: PsbP Pfam Description: PsbP
REGION                  1..235
                        note = Functional Homolog of Ceres CLONE ID no. 16403 at
                        SEQ ID NO. 146 with e-value of 5.30E-70 and BLAST sequence
                        identity of 59.1
source                  1..235
                        mol_type = protein
                        organism = Gossypium hirsutum
SEQUENCE: 204
MAMNSVSLNW VPPSFTKKAN YVTNSTELAP PSAFSSQNSL TYTKETISNE ENNCKRRLLL   60
LGVGVITANL LPANSLLAEE IPQNYRAFVD IPDGYSYYYP SDWREFDFRG HDSAFKDRFL  120
QLQNVRVRFI PTDKQDIHEL GPIEEVVYNL VNHVYAAPNQ MVNILDMQER TSDGKNYYTF  180
EYELTSPNYA SASFATIAIG NGRYYTLVVG ALERRWRRLR NKLKVVADSF KVLDI       235

SEQ ID NO: 205          moltype = DNA  length = 883
FEATURE                 Location/Qualifiers
misc_feature            1..883
                        note = Ceres CLONE ID no.1771837
misc_feature            1..883
                        note = Encodes the peptide given in SEQ ID NO. 206
source                  1..883
                        mol_type = unassigned DNA
                        organism = Panicum virgatum
SEQUENCE: 205
ataactgatg ctgggataca agcgtcagag aacacttcct cgagctcagt gctatcctaa   60
actactgaag aaatggcaag cctgcagaat ctgatttgct ccgtatctaa caaactggtt  120
gcgccaaatt ttgcggtgac tgccaaactg aatggggctt ctcactctgt tgtcccagca  180
agctcaagcg gagcatcttc gcatgaaaag aatgtcacga aaaggcagtt agcttgtcctt 240
ggtgctggag cattagccac cggcctactg aagacaagct ccgcatttgc tgaagaagta  300
cctaagaatt acaagtctta cgtggatgca aagatggatt attcgtatct ttatccagcc  360
gagtggaggg atttcgactt cttgggtcat gattcagcat tcaaagatcg taatctggct  420
cttcagtgtg tccgtgtggg gtttattcct actgataaaa cagatattcg cgacctagga  480
ccaatggatg aggccatctt caatttggta acaacgtttt acgctgcccc aaatcaaaaa  540
ccgtcgatct atgacatgca agagcgcacg gtggacggca agaactactg gacgttcgag  600
tacgatctgg aggctccggg ctacggcgta tccgcgttcg cgacagtcgc cattggaaac  660
ggtcggtact acacgctgat cgtgaccgcg aacgaacgcc ggtggagcag gctccggaac  720
aggctcaaag tcgtcgcgga ctcttttcaag atctccgacc tgaccgcgtg accgccagcg  780
ttctcgttaa ctgtaatgga cggtctcatt cagtcatggt atatatactt acgcgcgcca  840
taatcgtgcg tgtttcattt gctaaaaaaa aaaaaaaaa aaa                     883

SEQ ID NO: 206          moltype = AA   length = 232
FEATURE                 Location/Qualifiers
REGION                  1..232
                        note = Ceres CLONE ID no. 1771837
REGION                  73..228
                        note = Pfam Name: PsbP Pfam Description: PsbP
REGION                  1..232
                        note = Functional Homolog of Ceres CLONE ID no. 16403 at
                        SEQ ID NO. 146 with e-value of 6.49E-56 and BLAST sequence
```

```
                                  identity of 52.3
source                            1..232
                                  mol_type = protein
                                  organism = Panicum virgatum
SEQUENCE: 206
MASLQNLICS VSKQLVAPNF AVTAKLNGAS HSVVPASSSG ASSHEKNVTK RQLALLGAGA    60
LATGLLKTSS AFAEEVPKNY KSYVDAKDGY SYLYPAEWRD FDFLGHDSAF KDRNLALQCV   120
RVGFIPTDKT DIRDLGPMDE AIFNLVNNVY AAPNQKPSIY DMQERTVDGK NYWTFEYDLE   180
APGYGVSAFA TVAIGNGRYY TLIVTANERR WSRLRNRLKV VADSFKISDL TA           232

SEQ ID NO: 207                    moltype = DNA   length = 841
FEATURE                           Location/Qualifiers
misc_feature                      1..841
                                  note = Ceres CLONE ID no.1853106
misc_feature                      1..841
                                  note = Encodes the peptide given in SEQ ID NO. 208
source                            1..841
                                  mol_type = unassigned DNA
                                  organism = Gossypium hirsutum
SEQUENCE: 207
aagcacggat tcaaagtgat aaaaaaaaaa tccttcattt tgcaggaaaa aaaatggctg    60
atttggattc ttcaagctct tcctctgaag atattgaaaa aaactctgat cctaattcgt   120
caaaagctat aatccccaat cctctcaatt ccaattctaa ttcacctgcc gtatgcctcc   180
tccaattcgc aggagactcc accgctggtg ccttcatggg ctccatcttc ggctacggtt   240
cgggattgat taaaagaag ggttttaaag gatcctttgt ggaggctgga tcttatgcca    300
agacatttgc agttttgtcg ggtgtacaca gtttggtcgt ttgcttcttg aagaggttgc   360
ggggaaaaga tgatgttatt aatgctgggg tagctggatg ttgcactggg cttgctctaa   420
gtttcccagg tgcaccccag gcacttatac agagctgtct cacatttggg gcattctcat   480
ttatcgttga agggcttaac aagcagcagc cagcattggc acattcattt tctgtgagaa   540
acaagagcgg gcactatgag gggcctcatc ctatagcgct ccctctttca ctccctattc   600
cagatgagct gaaaggagct ttttcttctt tctgcaggtc cttaagtaaa ccaaatgaag   660
gcaagttttc tactggtaac tgatgggaag gggccattca tcagtgttaa tcgtctgtta   720
tatgtagatt gttgattgtt gcgagtgttg ggagttacaa tgtaagaatg tagaatcaaa   780
attatctgag agctaggaaa tgggaaattg ttttttgtcc taaaaaaaaa aaaaaaaaaa   840
a                                                                   841

SEQ ID NO: 208                    moltype = AA   length = 209
FEATURE                           Location/Qualifiers
REGION                            1..209
                                  note = Ceres CLONE ID no. 1853106
REGION                            34..152
                                  note = Pfam Name: Tim17 Pfam Description: Tim17/Tim22/Tim23
                                   family
REGION                            1..209
                                  note = Functional Homolog of Ceres CLONE ID no. 965405 at
                                   SEQ ID NO. 172 with e-value of 5.20E-63 and BLAST sequence
                                   identity of 71.4
source                            1..209
                                  mol_type = protein
                                  organism = Gossypium hirsutum
SEQUENCE: 208
MADLDSSSSS SEDIETNSDP NSSKAIIPNP LNSNSNSPAV CLLQFAGDST AGAFMGSIFG    60
YGSGLIKKKG FKGSFVEAGS YAKTFAVLSG VHSLVVCFLK RLRGKDDVIN AGVAGCCTGL   120
ALSFPGAPQA LIQSCLTFGA FSFIVEGLNK QQPALAHSFS VRNKSGHYEG PHPIALPLSL   180
PIPDELKGAF SSFCRSLSKP NEGKFSTGN                                     209

SEQ ID NO: 209                    moltype = DNA   length = 867
FEATURE                           Location/Qualifiers
misc_feature                      1..867
                                  note = Ceres CLONE ID no.1899181
misc_feature                      1..867
                                  note = Encodes the peptide given in SEQ ID NO. 210
source                            1..867
                                  mol_type = unassigned DNA
                                  organism = Gossypium hirsutum
SEQUENCE: 209
aggcacgtcg agaaaggggg aaaaggaact catagtagtt tttggacaaa aatggctact    60
tcggattctc caaacacttc agctggatct gatattgaaa caaaccctaa tcctaattct   120
tcaaaagcca taatcctaac accatccaat tccaattccc ctgccgtatg cctcttccaa   180
ttcgcaggag actccgccgc cggtgccttc atgggctcca tctttggcta cgggtcagga   240
ttgattaaaa agaaaggctt taagggatcc tttgtggagg caggatctta cgccaagaca   300
tttgcagttt tgtccggcgt tcacagtttg gttgtttgct tttgaagag gcttcgggga    360
aaagatgatg ttattaatgc cggtgtagcc ggatgctgca ctggacttgc tctaagtttc   420
ccaggtgcac ctcaggcact tctacagagc tgtctcacct tgggcatt ctcattttc      480
atcgaagggc ttaacaagca gcagccagca ttggcacatt catttctgc gagaaacaag   540
agtgcacacc acaagggacc tcgtccttta gcactacccc tttctatccc tattccggat   600
gagctgaaag gagcttttc ttcgttctgc aagtccttgg taaaccaaa taaggtagg     660
tttcctacag gtaactaagt agtaggtgga ccatttttca ttttttcctgt tgtttgtaga   720
attttgcaag tgttgagaat gtagactgaa agttttgtct gagatttgaa gcttttttaca  780
```

```
agcagaaaga tgaaattgct tcttttcttg tgttgattca attatattat ctgtctggtt   840
cagtagtaaa aaaaaaaaaa aaaaaaa                                        867
```

| SEQ ID NO: 210 | moltype = AA  length = 208 |
|---|---|
| FEATURE | Location/Qualifiers |
| REGION | 1..208 |
| | note = Ceres CLONE ID no. 1899181 |
| REGION | 33..151 |
| | note = Pfam Name: Tim17 Pfam Description: Tim17/Tim22/Tim23 family |
| REGION | 1..208 |
| | note = Functional Homolog of Ceres CLONE ID no. 965405 at SEQ ID NO. 172 with e-value of 4.09E-63 and BLAST sequence identity of 71.2 |
| source | 1..208 |
| | mol_type = protein |
| | organism = Gossypium hirsutum |

SEQUENCE: 210
```
MATSDSPNTS AGSDIETNPN PNSSKAIILT PSNSNSPAVC LFQFAGDSAA GAFMGSIFGY    60
GSGLIKKKGF KGSFVEAGSY AKTFAVLSGV HSLVVCFLKR LRGKDDVINA GVAGCCTGLA   120
LSFPGAPQAL LQSCLTFGAF SFIIEGLNKQ QPALAHSFSA RNKSAHHKGP RPLALPLSIP   180
IPDELKGAFS SFCKSLVKPN KGRFPTGN                                      208
```

| SEQ ID NO: 211 | moltype = DNA  length = 919 |
|---|---|
| FEATURE | Location/Qualifiers |
| misc_feature | 1..919 |
| | note = Ceres CLONE ID no.1758700 |
| misc_feature | 1..919 |
| | note = Encodes the peptide given in SEQ ID NO. 212 |
| source | 1..919 |
| | mol_type = unassigned DNA |
| | organism = Panicum virgatum |

SEQUENCE: 211
```
ggaacacgat aacgagacgg caggtgggg aggagccgag gagggcttca ggggtttcag    60
ggcggagagg agaagatggc ggcgaagcgc ggcgaaccga gtcggacggcga agagctcggc   120
ggcgaggcct ccaaccctgc gagcggtggc gcgactccgc cgcccctagc cgcagctccc   180
gtcgtctgcc tcctccgctc cgctggggac ttcgccggcg gcgccttcgt cggatccatc   240
gtcggatatg gacaaggcct gatcactaag aaaggtttca agggtttcatt cagcaatgct   300
gggtcctctg ctaagacttt tgcagttcta tctggggtcc agagtttggt tgtgtgcttg   360
ctgagaaggc tgcgtgggaa agatgacatt gtcaatgctg gtatagcggg ttgttgcact   420
ggcattgctt tgagcttccc aggagcacca aagcgttgc ttcagagctg tgccaccttt   480
gcagcgtttt cttgcatcat ggaggggctc aacaagcagc aggctgcaat ggctcacact   540
cttggcacaa ctgcattgac ggttgcgcat gataaaggag gtgtactgcc cccattcacg   600
cttccaccaa ttctggatgc atcagatgct ttagcttcat gctgccaagc cttagtaaag   660
cctaagcact agactacagg ataggggaga gagacatgct gaagaaagat agcttcagtt   720
ttcatttctt tattatgttg acctagcata tctgcatatg taaattttgc ttctggacaa   780
gctgtggaac gtgcctaaaa cctagttttg ctttgagcaa ctggacaggt tttcttgatg   840
tgttcgtgtt gcgaattccg ctggttctgg cattattaaa atcataaata cttgcctcga   900
aaaaaaaaaa aaaaaaaa                                                  919
```

| SEQ ID NO: 212 | moltype = AA  length = 198 |
|---|---|
| FEATURE | Location/Qualifiers |
| REGION | 1..198 |
| | note = Ceres CLONE ID no. 1758700 |
| REGION | 31..149 |
| | note = Pfam Name: Tim17 Pfam Description: Tim17/Tim22/Tim23 family |
| REGION | 1..198 |
| | note = Functional Homolog of Ceres CLONE ID no. 965405 at SEQ ID NO. 172 with e-value of 3.10E-49 and BLAST sequence identity of 62.4 |
| source | 1..198 |
| | mol_type = protein |
| | organism = Panicum virgatum |

SEQUENCE: 212
```
MAAKRETESD GEELGGEASN PASGGATPPP LAAAPVVCLL RSAGDFAGGA FVGSIVGYGQ    60
GLITKKGFKG SFSNAGSSAK TFAVLSGVQS LVVCLLRRLR GKDDIVNAGI AGCCTGIALS   120
FPGAPQALLQ SCATFAAFSC IMEGLNKQQA AMAHTLGTTA LTVAHDKGGV LPPFTLPPIL   180
DASDALASCC QALVKPKH                                                 198
```

| SEQ ID NO: 213 | moltype = AA  length = 203 |
|---|---|
| FEATURE | Location/Qualifiers |
| REGION | 1..203 |
| | note = Public GI ID no. 108706643 |
| REGION | 35..153 |
| | note = Pfam Name: Tim17 Pfam Description: Tim17/Tim22/Tim23 family |
| REGION | 1..203 |
| | note = Functional Homolog of Ceres CLONE ID no. 965405 at |

|  |  |
|---|---|
|  | SEQ ID NO. 172 with e-value of 7.40E-48 and BLAST sequence identity of 59.0 |
| source | 1..203 |
|  | mol_type = protein |
|  | note = Oryza sativa subsp. japonica |
|  | organism = Oryza sativa |

SEQUENCE: 213
```
MAAKRGSESD GDELGGGGAA EGTSPNDGGA SPPPLAAAPA VCFIRSAGDF AGGAFIGSIV   60
GYGQGLFTKK GFKGSFSTAG SSAKTFAVLS GVQSLVVCLL RRLRGKDDIV NAGIAGCCTG  120
LALSFPGTPQ ALLQSCATFA AFSCIMEGLN KQQAAMAQTL GGSALTVSHQ NGGVLPPFTL  180
PPLLDASDAL SSCCQPLVLK PKH                                         203
```

|  |  |
|---|---|
| SEQ ID NO: 214 | moltype = DNA  length = 1066 |
| FEATURE | Location/Qualifiers |
| misc_feature | 1..1066 |
|  | note = Ceres CLONE ID no. 1096546 |
| misc_feature | 1..1066 |
|  | note = Encodes the peptide given in SEQ ID NO. 81 |
| source | 1..1066 |
|  | mol_type = unassigned DNA |
|  | organism = Brassica napus |

SEQUENCE: 214
```
atactctaaa tagctcgatg ccaaaaaatc agamtgattg aatagtttag ttcgatacca    60
tcaataaacc cgttgacccg atccaatgac ccgctccgtg aacttccctc tcctcggcct   120
cgccgccgca ctcctcctct cacctctcct cgccgtctct ggtaaactcg ccgacgacct   180
caagccaaac cgccaggagg tttayggcgg aggkaagata ttcgacatca gccaccgtta   240
cacgccggag atgccggcgt gggagtctaa ggagggactt tcgaaccacc tgagactgat   300
cgcgagtatg aagaacggat cgttcgctaa cgtgtcggag atgaaactgt ctgttcactc   360
cggaacacac gtggatgctc caggccactt cattgatgag tattacgacg ctggtttcga   420
ttgcgattcg cttgacctcc aaactctaaa cggtcctgct ttgttggttg atgttccgag   480
agacaagaac ataactgctg aggtaatgga atcmcttcat attccaaggg gagttcgtcg   540
tgtgctyttc agaacatcca acactgacaa gcggcttatg tttaagaaag agttcgattc   600
aagcttttct ggattcatga ctgatggggc caagtggttg gttgagaacm cggacatcaa   660
acttgttggg cttgattatc tttccttttgc tgcttttgac gagtcmccgg caactcacaa   720
ggttatactt agaggaaggg atataatccc tgtcgaagct ytgaagctgg atggtgttga   780
ggcaggaatg tactcgcttc attgcttacc gctgagattg gttggagcar aagggcmcc    840
aaccaggkgc attctcatca agtgattcag ttcttccgty ttcttttaa gttggtcagc    900
caactgatca taaataatat gtttattact tccaagatcc cmcaatcata aagcaggtat   960
catagatgag atgattccag ttgtaaaagt aaacaattac ttttatagacg tatgtgtatg  1020
tttgtatgtg taattytgaa agatattgat aataagtta agactg                   1066
```

|  |  |
|---|---|
| SEQ ID NO: 215 | moltype = DNA  length = 490 |
| FEATURE | Location/Qualifiers |
| misc_feature | 1..490 |
|  | note = Ceres CLONE ID no. 1311812 |
| misc_feature | 1..490 |
|  | note = Encodes the peptide given in SEQ ID NO. 82 |
| unsure | 263 |
|  | note = n is a, c, t, g, unknown, or other |
| unsure | 332 |
|  | note = n is a, c, t, g, unknown, or other |
| unsure | 362 |
|  | note = n is a, c, t, g, unknown, or other |
| unsure | 405 |
|  | note = n is a, c, t, g, unknown, or other |
| unsure | 429 |
|  | note = n is a, c, t, g, unknown, or other |
| unsure | 448 |
|  | note = n is a, c, t, g, unknown, or other |
| unsure | 454 |
|  | note = n is a, c, t, g, unknown, or other |
| source | 1..490 |
|  | mol_type = unassigned DNA |
|  | organism = Brassica napus |

SEQUENCE: 215
```
aatatcagtt tgattgatca tcataaaatt gacagaccaa taaacatta cgaacagaat    60
actatatgaa taccaaccaa ggttcatgaa tccacgttga cctacgaacc gagataatga   120
ttcctttcct caccatcgcc aggacactct tcctctcctc tgtcatcgcc gctcatgaag   180
cttttccgtc gattcccact accttccacg tagccatgac ctcctctgac gatctgaaac   240
cgatccgtca ggagggttat ggngaaagga agatattcga cataaaccca ccggtacacg   300
caggatatgc cggtctgggg aatcgacaga angaggtaaa ccggttcctg cgtctaacca   360
cngagtatga agaaaccaat cccctctcta ataccctcgg gagangaaaa ctatcttgtt   420
cacaccggnt acacacccct ggatggcncc aggncactt tcatggaca aggtattaac    480
gaacgctggg                                                          490
```

|  |  |
|---|---|
| SEQ ID NO: 216 | moltype = DNA  length = 1066 |
| FEATURE | Location/Qualifiers |
| misc_feature | 1..1066 |
|  | note = Ceres CLONE ID no. 952461 |

```
misc_feature          1..1066
                      note = Encodes the peptide given in SEQ ID NO. 83
source                1..1066
                      mol_type = unassigned DNA
                      organism = Brassica napus
SEQUENCE: 216
atactctaaa tagctcgatg ccaaaaaatc agactgattg aatagtttag ttcgatacca    60
tcaataaacc cgttgacccg atccaatgac ccgctccgtg aacttccctc tcctcggcct   120
cgccgccgca ctcctcctct cacctctcct cgccgtctct ggtaaactcg ccgacgacct   180
caagccaaac cgccaggagg tttacggcgg agggaagata ttcgacatca gccaccgtta   240
cacgccggag atgccggcgt gggagtctaa gagggacttc tcgaaccacc tgagactgat   300
cgcgagtatg aagaacggat cgttcgctaa cgtgtcggag atgaaactgt ctgttcactc   360
cggaacacac gtggatgctc caggccactt cattgatgag tattacgacg ctggtttcga   420
ttgcgattcg cttgacctcc aaactctaaa cggtcctgct ttgttggttg atgttccgag   480
agacaagaac ataactgctg aggtaatgga atcmcttcat attccaaggg gagttcgtcg   540
tgtgctyttc agaacatcca acactgacaa gcggcttatg tttaagaaag agttcgattc   600
aagcttttct ggattcatga ctgatgggc caagtggttg gttgagaacm cggacatcaa   660
acttgttggg cttgattatc tttcctttgc tgcttttgac gagtcmccgg caactcacaa   720
ggttatactt agaggaaggg atataatccc tgtcgaagct ytgaagctgg atggtgttga   780
ggcaggaatg tactcgcttc attgcttacc gctgagattg gttggagcar aaggggcmcc   840
aaccaggkgc attctcatca agtgattcag ttcttccgty ttctttttaa gttggtcagc   900
caactgatca taaataatat gtttattact tccaagatcc cmcaatccaa aagcaggtat   960
catagatgag atgattccag ttgtaaaagt aaacaatacc tttatagacg tatgtgtatg  1020
tttgtatgtg taattytgaa agatattgat aataaagtta agactg                 1066

SEQ ID NO: 217        moltype = DNA  length = 1071
FEATURE               Location/Qualifiers
misc_feature          1..1071
                      note = Ceres CLONE ID no. 954851
misc_feature          1..1071
                      note = Encodes the peptide given in SEQ ID NO. 84
source                1..1071
                      mol_type = unassigned DNA
                      organism = Brassica napus
SEQUENCE: 217
atcagtttga ttgatcatca taaaattgac agaccaataa aacattacga acagaatact    60
atatgaatac caaccaaggt tcatgaatcc acgttgacct acgaaccgag ataatgattc   120
ctttcctcac catcgccagt acactcttcc tctcctctgt catcgccgct gatgaagctt   180
ttccgtcgat tcccactacc ttccacgtag ccatgcctct ctctgacgat ctgaaaccga   240
tccgtcagga ggtttatggc gaaaggaaga tattcgacat aacccaccgg tacacgcagg   300
atatgccggt ctgggaatcg acagaaggag ttaaaccgtt cctgcgtcta accacgagta   360
tgaagaacca atccctctct aatacctcgg agatgaaact atctgttcac accggtacac   420
accttgatgc accaggccac tttcatgaca gtattacga cggtgtttc gattcggatt   480
cgcttgacct ccaagtccta catggccctg cctgttggt tgatgttcca agggataaga   540
atatcactgr ggttatgaaa tcacttcata ttccaaggg agttcgtcgt gtgctcttca   600
gaacattgaa cmctgatagg cggcttatgt ttaagaaaga gttcgattcg agctttgctg   660
gattcatgat ggatggggcg aaatggttgg ttgagaatac agatatcaaa cttattgggc   720
ttgattatct ttcttttgct gcttatgagg aagcgcctga aacgcacaag tttatactag   780
gagaacggga tataatccct gtggaagcgc tgaagctgga tggtgtggag gtaggagtgt   840
actcgcttca ttgcttaccg ttgagattgc ctggagcgga aggtgcacca acgagatgta   900
ttctcatcaa gtgattcagt tcatctcctt ctctataagc tagttgttca gtatacgaaa   960
gtgattataa gaacaaaata aaggcttytt acttccaaga tytgaacaa tagagcatat  1020
gttacatatg tcaagaattt taaagttcaa gattcacttg gatacctta t            1071

SEQ ID NO: 218        moltype = DNA  length = 933
FEATURE               Location/Qualifiers
misc_feature          1..933
                      note = Ceres CLONE ID no. 1064137
misc_feature          1..933
                      note = Encodes the peptide given in SEQ ID NO. 85
source                1..933
                      mol_type = unassigned DNA
                      organism = Zea mays
SEQUENCE: 218
aacaatggca gttcctccac ttctcctcct cacactcctc tccctccctt ctcttctcat    60
ccacgccgcc atctccgatg cttaccccac cattccggga accgctccga tcgacggagg   120
tttctccgat gaactcaaac ccatccgccg tgaggtctac ggcgaaggca aaatcttcga   180
catcagccac cgctacacgc cggagatgcc ggcgtgggga tcaaaagaag aatcggacg   240
gtttctatgg ctagccgcga gcatgaagaa cgggtcgctc gctaacaact ccgagatgaa   300
gatcccgact cacactggga cccacgtcga ttcgcctgga cacgtgtacg atgagtatta   360
cgacgctggg ttcgatgtag actcgcttga tctccaagtc ttaaacgtc ctgcgttgtt   420
ggttgatgtt ccaaggaaca agaacataac tgccgaagtg atgaagtctc ttaacatacc   480
aagaggagtc cgtcgtgtgc ttttcagaac attgaatact gacaggcgtc tgatgttcaa   540
gaaggagttt gatacaagct atgtcggatt catgaaggac ggcgcacaat ggttggtaga   600
caacactgac atcaaacttg tggggttga ttatcatca gtagctgcat atgatgatct   660
gattccgtcc cacctagtat tcctaaaagg ccgagagact atactggtgg agggattgaa   720
gctggatgat gtgaaggcag gagtctactc tgttcattgc ttacctctaa gacttgttgg   780
agcagaaggg tctccaattc gctgcatcct catcagttga tttcttcctc caaaactggg   840
agttgtctgt atgcaagtta acctttcgta tctttacttc aagatcttat gcttgacaaa   900
```

```
aaaaaaaagt aaaataaata aggaaacttg gcg                          933
```

| SEQ ID NO: 219 | moltype = DNA   length = 1179 |
|---|---|
| FEATURE | Location/Qualifiers |
| misc_feature | 1..1179 |
| | note = Ceres CLONE ID no. 368629 |
| misc_feature | 1..1179 |
| | note = Encodes the peptide given in SEQ ID NO. 86 |
| source | 1..1179 |
| | mol_type = unassigned DNA |
| | organism = Zea mays |

```
SEQUENCE: 219
aaaaactccc cagtcaaggc gcatatccat tccatggatc tcgcgccct  gctccttctc    60
tcccagctgc tgctgcttcc ggtggtggcg gttgtctccg gcgagaccgc cgcgcacccg  120
ggctacacac acgctgagga ggcatgcagc ggtgtgctag aggcagaggc ggagaaagca  180
acggtgctgg tgcctgcgcc agagcggcgc gaagagttcg acggggggcg gatcgtggac  240
atcagccact actaccgcga ggacatgccg gagtgggagt catcagaggg ctccggcgag  300
ttcctgcagc tggcgcgttc catgcgcaac ggctccgaca tcgctaactt ctcggagctc  360
cggctcactg cgcactccgg cacccacgtc gacgcgccgg gacacgtctt cgagcactac  420
tacgacaccg gcttcgacgt cgacccctc gacctgctg tcctcaacgg accagcgctg    480
ttggttgacg ttcccagaga taagaacatc acagctgatg ttatggcatc cctaaacatg  540
cctaaaggtg ttcgacgtgt actctttcgg acctaaata cagacaggat ggtgcacaat   600
ggttggttga taatacagac atcaaactag ttggagttga ctacttgtca gtgggcgcat  660
ttgatgaatg cattccagct catctagtat ttcttgaaaa aagggaggtc atacttgtcg  720
aagccttgaa tctggagcat gttagccctg aatatacat  cttgcattgc ttgccactaa   780
gattgcgggg tgctgaaggt tctcctgcaa gatgcatcct catcaagtga catggttata   840
accatcccaa aaagcattgt acaatcaatc ttgaaaccta cctattcagt cttttcgaag   900
tgcttatag  agtatggttt tcatgcgtgt gtttataggg atggtgtgag acccaataa    960
tatggagctg ggctagtact gatccaatcg acactaatat gagctgaaga tactacataa 1020
aacatgaaca atatggagtt ttatatactg gaccccagtc caggttttaa atccacccct 1080
gcaaggggtg aatttatgtt tgtgtttggg agtgtatatt tctatattgc agtttgaaaa 1140
aaactatgta tgtaataaaa taagaataca tcaattcat                        1179
```

| SEQ ID NO: 220 | moltype = DNA   length = 1195 |
|---|---|
| FEATURE | Location/Qualifiers |
| misc_feature | 1..1195 |
| | note = Ceres CLONE ID no. 473732 |
| misc_feature | 1..1195 |
| | note = Encodes the peptide given in SEQ ID NO. 87 |
| source | 1..1195 |
| | mol_type = unassigned DNA |
| | organism = Glycine max |

```
SEQUENCE: 220
aaagtaaacc atgaattctc tatcactctt caccttcctc tgcgcaattt gtgcgcactc   60
cgtcgccgtc acctccgcgg catatccttc catcccggc  acggaaaccg gagagtgctc  120
cctccgcggc gtcggcgtcg gcgacggtgt tctggtccct ccgcggcgag aagtgtacga  180
ggagggcga  atcttcgaca tcacccacag gtatgtccgc gagatgccgg tgtgggactc  240
gacggagggg ctcgggcagc acttcctgtg gctcgaaaag agcatgaaga atggctcgcg  300
cgctaacaac tccaacatga agctcggtgt tcacaccggc acccatgtcg acgcgcccgg  360
tcactttac  gacaattact acgacgccgg cttcgatgtt gactcactcg acctaacact  420
cctcaatgcc cttgcactt  tggttgatgt tccacggcat aaaaacatta ctgctgaggt  480
tatgaagtcc ttgaatatcc ctagaggtgt aagccgcgtg cttttcagaa ctttaaacac  540
tgacaggcaa ctcatgttta agaaagaatt tgacacaagc tatgtgggat tcaaggagga  600
tggtgcaaaa tggctggcag agaacaccga catcaaactt gtaggagtcg attacttatc  660
tgttgctgct tatgatcact ccattccatc tcatcttgtt ttcctggaaa gcaaggaaat  720
cattcttgtg gaaggcctaa agcttgatga tgtcccagca ggaatatatt cactgaattg  780
cttgcctctt aggttggttc actctgaggc atcaccaatt cgatgcattc tgatcaaatg  840
atcaaatgat ggggtcaaac ctggttttca attgcacgga tgaacctgcc acaagaagca  900
acgtagccac gaatacaatt agtggtgtcc ataagaagca gtttgatgca aattgcaagc  960
taagctgata gtagtatgtt gaattactct tagtttacgt ccttgggttg gaaagtactg 1020
aattattgtg attaaacttc agttgcggac taggggtcc  acctgtatta acttatgctt 1080
ttaatatttt cctaggcaag tacttgtgca attctgaaga cgcatgcttg tacgtctcaa 1140
taattatatc tatttctctt tgaaaaataa tgaaatacta ctaataatct cgggc       1195
```

| SEQ ID NO: 221 | moltype = DNA   length = 1200 |
|---|---|
| FEATURE | Location/Qualifiers |
| misc_feature | 1..1200 |
| | note = Ceres CLONE ID no.554272 |
| misc_feature | 1..1200 |
| | note = Encodes the peptide given in SEQ ID NO. 90 |
| source | 1..1200 |
| | mol_type = unassigned DNA |
| | organism = Glycine max |

```
SEQUENCE: 221
atgaatgagc taagtggaaa gtgaaaacgt gcctctttac taacgaaacc aaagcatgaa   60
gatgaattgc tactggtggc atgccctgat aatgagtggt tgtgtgttgg gcttgtgcgt  120
gggcatagga ggttgtgtat gtggtggtga aacgagaaat ggaagaatca tcattgatat  180
tagtcacagg taccatcctg atatgcctgc ctgggaatcc aaggatagcc ttgggcagtt  240
tttgtggctt acaagaagca tggccaatgg ttctctggct aacttctccc aattcaagct  300
```

```
cccgctcac agcggcaccc atgtcgatgc tcccggacat gttttcgatc actatttcca    360
ttctggcttt gatgtcgact ctctcgattt actactcctt aatggccctg cactattagt    420
tgatgttcca agagatacaa acatcagtgc tggtgttatg aagtcattga atattccgag    480
gggcgtacgt cgtgtgctct tccgaacatt aaatacttac aggcggctta tgtatcagaa    540
ggaatttgac acaagctatg tgggattcac agaagatgga gcaaattggc tagtggagaa    600
cactgacatt aagcttgtgg aatagatta tctatctgtt gctgcttacg accacttgat    660
tccagctcac cttgttttc tgaaaggcag ggaaatcatt ctcgtggaag gcctgaagct    720
tgatgatgtg gcagcaggaa tatatacggt ccattgctta cctcttaggt tggctggtgc    780
tgagggatca cccataagat gcattctcat caaataataa gtcaacagct agcagtccaa    840
atgccgacac gacatgcagc agtggtttat gcttggaaat gggtcttaat tacgagcata    900
aggttgagtt tcaatgtagt tttcttaaat acgaataagt tggaaaaata aatataaagt    960
ggtgtcccgt gtccatttgg agcaaggtat cataaatgct tagcaaagtg cataaacgct    1020
cctacaaatc atttcagaaa taaagcagta tggatattgg atgatatata aagtactatg    1080
taatatgcag tgaaggtata acaaatgtca aatagcaatt attcttgcgt acttttaaat    1140
acactatatg gatggatgtt tggaattatt attttttaag aaggatgttt ggaattgttt    1200
```

| | | |
|---|---|---|
| SEQ ID NO: 222 | moltype = DNA  length = 1251 | |
| FEATURE | Location/Qualifiers | |
| misc_feature | 1..1251 | |
| | note = Ceres CLONE ID no.511015 | |
| misc_feature | 1..1251 | |
| | note = Encodes the peptide given in SEQ ID NO. 91 | |
| source | 1..1251 | |
| | mol_type = unassigned DNA | |
| | organism = Glycine max | |

```
SEQUENCE: 222
gatgcgaaaa tatctcgttc atgttaatgt tatgataacg aggaatggac tatgatgctg    60
ttctgttggt gacggtgtga ttgattgtga cgaaatctga caatgaagcg tggagcattg    120
ttgtcagtgc ttgcctgcgc cttcgcggcg gtgatctggg cagcgaacgg cgacgacaac    180
ctcgtcccgc ctcgccggga agtgtacggc aatgggacga tattcgacat cagtcatcgg    240
taccaacccg agatgccgga atgggaatcg aatgacggca tagggcagtt cctgtggctt    300
cccaagagca tgaagaacgg ttccctcgcc aacaactccg aaatgaagtt tcccacccac    360
accggcacgc acgtcgatgc cccggtcac gtgttcgacc actacttcca cgccggcttc    420
gatgtcgaca cgctcgactt ggacatcctc aacggacctc ctatgttggt tgatgttcca    480
agagatagta atattaccgc tcaagttatg aagtcgttga atattccaag gggtgtaata    540
cgtgttctct tccgaacttt aaataccgac cggcggctga tgtttcagaa ggaatgggac    600
tcaagctatg tgggattcac agccgatgga gccaaatggc tagtggagaa cacagatatc    660
aaacttgtag gaattgatta cctatctgtt gcttcttatg attacttgat tccatctcac    720
cttgttttc taaaagacag ggagatcatt ctcgtggaag gcctgaagct tgatgatgtt    780
ccagcagggt tatattcagt ccattgctta cctcttaggt tggctggtgc tgagggatca    840
ccaatacggt gcattctgat taaaaattag ggtgtccaca tgtctgtgtt cggtgtccgc    900
gtcggtgtcg gtgcttcata ggctggaact gataaattgg catgggggtg tggtgtcctt    960
atggagcaag atagtttcaa tgttgtgcaa caactttgt agcttatgtt tacacttact    1020
aaaaacatgc ataagcactt caaaaaatca ttttgaaaag gaaaataatg tatatataga    1080
taatttgcac atttcattag cacttcaaga gagatgcaac gatattggca ttgcgctgaa    1140
tttggttttc ttttgtctgc taggttggaa aggaataagt tggcacaatg gtgtctttat    1200
ggagcaagat agtatcaata atgtttgtta aagaaaaaaa aaaaaaaaaa a          1251
```

| | | |
|---|---|---|
| SEQ ID NO: 223 | moltype = DNA  length = 1173 | |
| FEATURE | Location/Qualifiers | |
| misc_feature | 1..1173 | |
| | note = Ceres CLONE ID no.881632 | |
| misc_feature | 1..1173 | |
| | note = Encodes the peptide given in SEQ ID NO. 92 | |
| source | 1..1173 | |
| | mol_type = unassigned DNA | |
| | organism = Triticum aestivum | |

```
SEQUENCE: 223
gaataacccg cacctatcca cgacaccgag ggagaggagc aactgatccc cgacgcccca    60
aatggcgcct cccctcctcc tcctcctcct cgtccctctc gtcgccgcca ccgcaccgtg    120
cgcccacccg gcccacccga gccagccggc gtcgtgcgcc gcggagcccg tgctggcgcc    180
ggagcgccgg gaggcgcacg gcgggggccg catcctggac atcacccact actaccggga    240
ggacatgccc tcgtgggagt ccggcgccgg ggtgggccag ttcctctggc tgcccgcctc    300
catgcgcaac ggctccctcg ccaacaactc cgagatgcgg atgcccaccc acaccggcac    360
ccacatcgac gcctccggcc acgtcttcca gcactacttc gacgctggct tcgacgtcga    420
caccctcgac ctcgacgtcc tcaacggtcc tgcactgctg gttgatgttc aagggatga    480
aaatattact gctaaaacga tggaatcttt gcatattcct aaaggagttc aacgggtact    540
ttttagaaca ttaaacactg acaggaacct aatgtggaag aaagagtttg acacaagcta    600
tgtgggtttt atgaaagatg gtgccaatg gttggtagac aacacggata ttaagcttgt    660
cggaatagac tatttgtccg ttgcagcttt cgatgacttg atcccttcac atttagtttt    720
acttgaaaac cggdatatca ttcttgtgga gggcctcaaa ctgagaatg tcatacctgg    780
gatatactcg ttgcattgcc tgccacttcg gttgcgtgga gctgaaggtt cgccgatcag    840
atgcatcctt ataaagtgaa agacatttgc atcccgctgc ggcggtttag tttgataccg    900
caagcactta tatataaaaa tagaatgtgt atagcagcaa atctcgtgtc tttgatacca    960
gaggagtact gtcatgtgtc cagaaacatg gtgcacttc gatgcttagt aaggagcgac    1020
aaacggctag ggatgcaaat gtgtagcctc tagggtaccc tccgaacctt tagttgggct    1080
atagaaggga tggattacaa tacaaaccgc aatgttcggt ggtaccaaaa tcccaaaaaa    1140
aaaaaaaaaa aaaaagaaa aaaaaaaaaa aaa                                 1173
```

```
SEQ ID NO: 224           moltype = DNA    length = 1347
FEATURE                  Location/Qualifiers
misc_feature             1..1347
                         note = Ceres CLONE ID no.474985
misc_feature             1..1347
                         note = Encodes the peptide given in SEQ ID NO. 103
source                   1..1347
                         mol_type = unassigned DNA
                         organism = Glycine max
SEQUENCE: 224
aggaacagag caaacatgct gcttctttgg cttttgccac tgctgttgct gcagaggctg    60
ctgttgccgc tgctcaggct gctgccgagg ttgttcgtct cacaagtatg ccacattaca   120
ctggaaggac taaggaagaa attgcagcca tcaaggttca gactgcattc cgtggatata   180
tggcaagaag ggcattgcgt gcgttgagag gattggtgag gttgaaaaca ttagtacaag   240
ggcaatctgt taaacggcaa gctgctagca ccctacaag catgcaaact ctagcaagat    300
tacagtctca gattcgtgaa aggagaatta gaatgtccga agagaaccaa gctcttcagc   360
gccaactaca tcagaaacat gaaaagaac ttgagaagtt gcgtgctgct gttggagaag    420
aatgggatga tagctcgcag tcaaaggagc aaattgaagc aaaattgttg cacaggcaaa   480
aagctgcttt gagaagagag agagctttgg cctattcatt ctcacatcag caaacatgga   540
agggctcttc aaagtcatta aatccaacat ttatggatcc aaacaatccc caatgggggt   600
ggagttggct agagagatgg atggctacta ggccatggga tggccatagc actgtggtgg   660
atcacaatga ccatgcatct gtgaagagtg cagcgagccg tgccgtgtct gtagggcaaa   720
tcaccaaatt gtactctctc caagataaaa aaccttcccc ttttggctca aaagcaagaa   780
gacctgcccc tcaaagttcc cattcaaagg caccatctac taatgaaaaa gcaaggccat   840
caagctcaac aaagggtagt agtgtttggg gtggagatga ggactcaaga agcatgttta   900
gtgttcagtc ggagcgctac cgccgacaca gcattgcagg atcctcagtg agagatgatg   960
atagccgtgc aagcacacct gccattccaa gttacatggc agccacaagc tcagcaaagg  1020
ccaggtccaa aatcataagg cattcacctg aaaaaaaagg tggtggtggt tctgtttctg  1080
caaggaagcg actttctttc tcaccctctt ctgctgctaa ttcaagaagg cattctgatc  1140
ctcctaaggt ggaaatggtt tacaataagg atgctgctgc ggctacagta agcaatggaa  1200
ggggaaggta gtgtgctggg gatgtcattg ccacttcagc aattcttgta ggagcacaat  1260
atctatggat ctatttggat aaacttctcc ataatcactt ataaatgaag aaaaacaaaa  1320
gtaatataga aaaaaaaaa aaaaaaa                                       1347

SEQ ID NO: 225           moltype = DNA    length = 1716
FEATURE                  Location/Qualifiers
misc_feature             1..1716
                         note = Ceres CLONE ID no.826796
misc_feature             1..1716
                         note = Encodes the peptide given in SEQ ID NO. 104
source                   1..1716
                         mol_type = unassigned DNA
                         organism = Triticum aestivum
SEQUENCE: 225
ataggacttc acagacagac tgactcaatc ctaacccaat ccctcccatg cttccatcta    60
ctctagcaga aattgcagag gaggttggcc gccgccggct ccagcgcagg cgcagcctac   120
ccgcgggatc tgacgccctc cgcctcctac ctcgaggcac gcgcctcagg ctcagctccc   180
ccgcccgccc tccccgcta ccccgacgac ttccaagagg aggagcatga aattgagcat    240
gtcgccgccg cgccagcgcc agcgccagcc acggatgcgc cgctacctgc ccctcctgcc   300
gccgcaccac cacaggttca ggctgccatt gcgccggctt cttcctcttg tgtcatgtcc   360
agggagctcg ccgccaccaa gatccagacc gccttccgag gtcacctggc aagaagggcg   420
ctgcgggcat tgaaaggcct ggtcagactc aagtcgctgg tccaaggcca ctccgtcaag   480
cgccaggcca ccagcacgct tcgctgcatg cagactctgt cccgggtcca gtccaagata   540
cggacgagga ggatcaagat ggccgaggag aaccaggccc ttcagcgcca gctcttgttg   600
aaccaggaac tagagactct caggatggga gatcagtcga ataccagcct gcagtccaag   660
gagcaaatcg aggcgagcct cgtgagcagg caagaggccg cggctagaag agaacgggct   720
ctcgcatacg cattctccca ccagtggaag agcacctcaa ggtctgccaa cccgatgttc   780
gtggacccga gtaacccgca ctgggctgg agctggctgg agcggtggat ggcgtcgagg    840
ccgttcgacg gccgcaacgg ggcgtccgag aaggaggcga gcagcgtcga ccgcacgtcg   900
gtgcacagca ccagcctgag catgaacctc ggagaaggtg agacggtcac aaaggcggac   960
aaccaggtgg tggactcttt gaagccgaat gatgataagc cgccgccgct ttcgactccg  1020
aagccgtccg gccctgcccc caggcagtcc cgtcgacgc cctcgccggc gctggcgagg   1080
aagaagagcg cgacgcccaa gagtggagac tgcgacggcg acgacgcgag gagcgtggtc  1140
agcactgtcc ggtccgagcg gccccgaggc acagcatcg gcgcgtccag cgtgcgtgac    1200
gacgcgggct cttccccgtc ggtgccgagc tacatgcgg ccaccaagtc gcgtcggcc     1260
agggccaagt cgcgtgtgca gagcccgacg ctgaccgagg tgctgctca agctgagacg   1320
ctggagaaaa gatggtcttc tgtgggttca gcgaagaagc ggctgtcctt tccggctggg  1380
acgccaccgc cggtgccggc ggcggcggcg aggcggcact ccgggcctcc caaggtgcgg  1440
caggcggcg tggaaggtgg tacggaggaa ccggactcgt cccttgcgtg acatcatggg   1500
aagcagatta tggtgtggag cagagcagag cggaatttgt tgcatttgtt gagtgaaagg  1560
aacgcagaat gtgtgttgtg tggatccatt ggatttgatt tgatttgtat gatggcagta  1620
ttcctatttg attattcatt gaataatata agtatctgta atgaagataa aaggagggaa  1680
cacgaacatt atttcaaaag aaaaaaaaaa aaaaaa                            1716

SEQ ID NO: 226           moltype = DNA    length = 1381
FEATURE                  Location/Qualifiers
misc_feature             1..1381
                         note = Ceres CLONE ID no.463638
misc_feature             1..1381
```

```
                        note = Encodes the peptide given in SEQ ID NO. 107
source                  1..1381
                        mol_type = unassigned DNA
                        organism = Glycine max
SEQUENCE: 226
attagattct gcttccattt ttttttttct ctctacacct cttcttcttc acttcctctt   60
tactgtttgt tacttcaatt ttgtgattcg ttctttctgg attcaattga gtaaaaatct  120
gcgtggtttg agcaatggat gttaaagctg cgccgaggtt acaactttca gcggtggttc  180
aacccgaaag tattggaaga agaccaccca gcacatgtcg tttgggtgtg tctcgggaac  240
cgcagagcct tcgggttttt gtttcgtcaa cgatgatgcg ccgcagaaca accgctttgg  300
aggtttcctg ttcttacggc aacatttcag cttcaatatt ggaatctgga agtgttcgtg  360
ctcctcttga tgaagagctg attctaaaga atagatcgca agagatccag ccatatttaa  420
atggacgctg tatttatctt gttggaatga tgggctctgg gaaaacaacg gtggggaaga  480
taatgtcaca agtgcttggt tattcatttt gtgatagtga tgcattggtg gaggaggagg  540
ttggtggaaa ctctgtagct gatatattca agcaacatgg tgaaactttc tttcgtaata  600
aggagactga ggtgttgcat aagctatccc tgatgcatca acttgttatt tctactggtg  660
gaggtgctgt tacaaggccc atcaattgga aatatatgca caagggagtt agtgtttggt  720
tggatgtacc agtggaagcc tcggcacaga gaattgcagc tgtaggaact aattctcgcc  780
cccttctaca ctatgaagca ggagatcctt acacacgggc ttttatgcgt ttgtctgctc  840
tttttgaaga gagaggtgaa gcatacgcca acgccaatgc cagggtctca ttaaaaaata  900
tagcaataaa actgggcaaa agagatgtgt ccgaattgtc tccaacagat attgcaattg  960
aggcgctaga acaaattgac aacttttga aggggaaggg gggccgctat gcagaatgct  1020
agtacaagct ttggttacaa gcttcttttt gattgttcat atttttttt atgcaattgc  1080
gattaaggtc atgctgtcga cctcgctttt ggtaaaaaaa aaaaaaaggt ggtaatgcaa  1140
catggcactt gtttatgcat aatttgtgtt ggcaaatggg caaatccaa cagccaattg  1200
caacaacatt taatttatgt tctgtttatt gttgaatgtt gatgtgtgtg tgtatatata  1260
ctggagaacg aagtgttgta atcggagttg ggttgatcaa tttatgtatg ccctcctcta  1320
aagaggtttg tatgttgtaa agtgacacgc atattttaaa ttcttcttta tctatatttt  1380
g                                                                1381

SEQ ID NO: 227          moltype = DNA  length = 1542
FEATURE                 Location/Qualifiers
misc_feature            1..1542
                        note = Ceres CLONE ID no.1565097
misc_feature            1..1542
                        note = Encodes the peptide given in SEQ ID NO. 110
source                  1..1542
                        mol_type = unassigned DNA
                        organism = Zea mays
SEQUENCE: 227
aagtcgtagc cgactggtcg ccgcgtcccc ctttccccgc gcagcagcag agcaccatcc   60
ggtgaccgag caatggaggc gggggcgtg ggcctggcgc tgcagacgcg ggcggcggcc  120
ttcggctccg gccagccgcg gggcggccta cagtcgccca tcgggaggct gagagtcgtt  180
gaaccggcgg gagctgcggt tgccgtgcgg gctcgcgggt ccaagcccgt cgtaccgctc  240
cgtgcgaaga aatcatccgg aggtcatgaa aacttgcata actccgttga cgaagctctc  300
ctgttgaaga gaaaatcaga agaagttctg ttctacttaa acgggaggtg tatttactta  360
gtgggaatga tgggttctgg aaaaagtact gtggggaaga tcatgtctga agtcttgggt  420
tattcgttct tgatagtgaa caaattagtg gagcaagctg ttggaatgcc ttcagttgct  480
caaatattca aagttcacag tgaagccttc tttcgggata tgagagtag cgtcttgagg  540
gatctgtcct ccatgcgacg attagttgtt gccaccggag gtggtgctgt catccgacca  600
gttaactggt atctagagtt cactccattt cttttctttta aatgggtgc tttgttttct  660
ttgaatcaac agtattgtga cctgtcgttc cattatcagg aaatatatga gaaagggcct  720
atccgtttgg ttagatgtgc ccttggatgc tcttgctagg cgtattgcta aagtgggaac  780
cgcttctcgt cctcttctgg accaaccgtc cggtgatcca tacacaatgg tagctactta  840
ttcttcaat attctttcat gctcgtgaaa cggaattgtt tcttcattct atttggacaa  900
agaactgctc atagatccac ttgagccttg aagcccatc ctggattcca gtcctttact  960
tgtggacttg tggtagcaaa tgctcagact tcttatgcta gttctaatat ggatcactca  1020
ctgggttcct tatttgttat aggccttttc taagctcagc atgcttgcag agcaaagggg  1080
tgatgcttat gcaaatgcgg atgtaagggt ttctctggaa gagattgcat ctaaacaagg  1140
tcatggcgat gtctctaagc tgatgccgac tgatatcgca attgaggtaa gcttaccgcg  1200
aatatcatgt ctcttccag ataccatcag acagctttc aaaagataac acgcttaccg  1260
tcttcgcagt cacttcataa gatcgagagt ttcgtcatcg agcacgctgc tgataatcca  1320
gctagcgact cgcaagctga gtcacagatc caaaggatac agaccttgta atatcttaat  1380
ccttctgttt tgtaccgaag cgtaccccct agagcatcgt tggttattt gttcgttgaa  1440
gtgtcacgag ggagagaaaa aaaaaacccc gaagtatttc ttgttgtaag ttgtaaagga  1500
atggaataaa ggagctaata atccgaaaaa aaaaaaaaa aa                     1542

SEQ ID NO: 228          moltype = DNA  length = 1283
FEATURE                 Location/Qualifiers
misc_feature            1..1283
                        note = Ceres CLONE ID no.486613
misc_feature            1..1283
                        note = Encodes the peptide given in SEQ ID NO. 111
source                  1..1283
                        mol_type = unassigned DNA
                        organism = Zea mays
SEQUENCE: 228
gtcactgctt tacgtcccaa caggcggcac atttccgcca ccagctacca ccgcctgcgc   60
gcagcgcggt cctctctctc ctcttcttta cacctcacct ccggatcgct cagagattga  120
```

```
gccgtagccc gactggtcgc cgcgtcccct ccccccgcgc agcagcagag caccacccgg    180
cgagcgagca atggaggcgg ggggcatcgg cctggcgctg caggcgcggg cggcgggctt    240
cggctccggc tccggccggc gccggggcgg cctacaggcg cccaccggga gcttgagagt    300
cgctgatccg gcgggacctg cggtcgctgt gcgggctcgc gggtccaagc ccgttgcacc    360
gctccgactc cgtgcgaaga aatcgtccgg aggtcatgaa aactcgcaca actccgttga    420
cgaagctctc ctgttgaaga gaaaatcaga agaagttctg ttctacttga acgggaggtg    480
tatttaccta gtaggaatga tgggttctgg aaaaagtact gtggggaaga ttatgtctga    540
agtcttgggt tattcgttct ttgatagtga caagttagtg gagcaagctg ttggaatgcc    600
atcagttgcc caaatattca aggtccatag tgaagccttc tttcgggata atgagagtag    660
tgtcttgaga gatttgtcct ccatgcgacg attagttgtt gccaccggag gtggtgctgt    720
tatccgacca attaactgga gatatatgaa gaagggccta tctgtttggt tagatgtgcc    780
cttggatgct cttgctaggc gtattgctaa agtgggaact gcctctcgtc ctcttctgga    840
ccaaccatct ggtgatccgt acgcaatggc ctttctaag ctcagcatgc ttgcacagca    900
aagggtgat gcttatgcaa atgcagatgt aagggttctc ctggaagaga ttgcatgtaa    960
acaaggtcat gatgatgtct ctaagctgac acctactgat attgcaattg agtcacttca   1020
taagatcgag agcttcgtca tcgagcacac tgctatagt tcagctagcg acgcgcaaac   1080
tgagtcgcag atccagagga tacagacctt gtagaacctt aatccctttg tttgccacat   1140
agagcatcgt tgagttattt gttcgttgca cgtcacgacg ggagagaaaa aagagtgaaa   1200
cgtttcttga tgtgagttgt aaaggaatgg aagaagggag ctaataatcc aaagtgtgcc   1260
gttggctaaa aaaaaaaaaa aaa                                           1283

SEQ ID NO: 229          moltype = DNA  length = 1403
FEATURE                 Location/Qualifiers
misc_feature            1..1403
                        note = Ceres CLONE ID no.749796
misc_feature            1..1403
                        note = Encodes the peptide given in SEQ ID NO. 112
source                  1..1403
                        mol_type = unassigned DNA
                        organism = Triticum aestivum
SEQUENCE: 229
gcgatctccc aacccccct ttacctcttc tgtctcttct tccctccgcc gcggcgccgc     60
tcgccacgcc acccgcgtat ccatccacca ccgttcccgc gatggccgcc ggcgtactca   120
acacccagcc ccgcctcaac taaccacgga tgatacacat agctcctgtt aacttcctgc   180
cactcgtccc gtcccccctg agggagagga gatggacgcc ggcgtgggtc tccggccaag   240
gccccgtgca gcatgggccg gacgacgaaa gccgcaggga ttcccccgg cgacggtgcc    300
ggcggtgagg ctcgaccaga atccggcgcg cggccgctg gttctgcgct ccgacgcggg    360
gagccggagc accgatccca tccgtggcgc cagcctcaag gcctgtgct gccacaaatc     420
ggcaggtacc gagaaagtcc actattctgc tgatgagcgc ctcgtactga agcaaaaagc    480
agaggatgtg ctccccttacc tgaatgaccg ctgtgtttat ctagttggaa tgatgggttc    540
tggcaaaact acagttggga agataatagc tgaagtacta ggctattcat tctttgacag    600
tgataagctg gttgagcagt ctgttggcat accgtcggtg gctgagattt ttcaggtcca    660
cagtgaagca ttcttcagag ataacgagag tgaggtacta aggggatttgt cgtcaatgca    720
ccgattaatt gttgcaacgg gaggtggtgc ggtgatacga ccaatcaatt ggagttatat     780
gaagaaaagga ctcactattt ggttagatgt tccattggat gccctcgcaa gaaggattgc    840
tgcggtgggt actgcgtcac gacccctcct gcatcaggaa tctggtgatc cttatgcaaa    900
ggcctatgcc aaacttacag cacttttgta acaaagaatg gattcatatg ctaatgctga    960
tgcccgagtt tcccttgaaa atattgcact caaacaagga cataatgatg tgaatgtact   1020
tacaccaagt accatcgcta ttgaggcatt gctaaagatg gagagctttc ttactgagaa   1080
ggccatggtc agaaactgac cagatctcgg tggttaaaaa gaaagatgac aaccaatggt   1140
tcttggttgc cgtgatgtac atacctttgc ataagacatt cttcttgata tagccagagc   1200
tatgacagag gataacttgg gttttttactt gagtgaacta tatgtgaata gctctaaatt   1260
aagacaatgt ttgtcttgtc tttatcttgc tgcaatttga tatatgggat ttgggagtaa   1320
atattaagtg atatcccttg tacattttga agcaaccaga atttacatca atatattatt   1380
ttgagacaaa aaaaaaaaaa aaa                                           1403

SEQ ID NO: 230          moltype = DNA  length = 1347
FEATURE                 Location/Qualifiers
misc_feature            1..1347
                        note = Ceres CLONE ID no.294723
misc_feature            1..1347
                        note = Encodes the peptide given in SEQ ID NO. 114
source                  1..1347
                        mol_type = unassigned DNA
                        organism = Zea mays
SEQUENCE: 230
ctgattcctg aacacaccct cgtctccgca cggaggccgt cctctcctct cctctcctct     60
gcgtccgcca ctgccgccca ccgctcgccc acgcgcgctc cattacctcg gcgggcgatg    120
gccgacctat ccaacaccgg ctccacctaa cacgagcggc gcccccgcct aggccggctg    180
ctggtcggtc gtcgagcagc tagcggcggc agcgcccgga ggccgtctca ctctcctcgt    240
cggggcggca ggagatggag gccatcgtgg gcgtccgcgc gccgccgcgt ggccgtgcct    300
gggcggcct cgagaagccg ccgcgcgccg cttgctgcgc cagagtcccg acggcgaggc    360
tcgcggtcgc ggcggacagg ccgcggaggc tggtgctgct gggcgccgat acgcggaggg    420
ccgcggatta tcctgccctc cgttgcgccg cgcaatctga aggaacagga aagttccact    480
actctgctga tgacgctctc atactacagc aaaaagccca ggatgttctg ccttacttgg    540
atggccgttg cgtttatctt gttggaatga tgggttcagg caaaactaca gttgggaaga    600
tactatccga agtgttaggt tattcgttct tcgacagtga taagtggta gagaaggctg     660
ttggtatttc atctgttgct gagatctttc agctccatag cgaacattc ttcagagata    720
atgagagtga ggtcctgacg gatctgtcat caatgcatcg gttggttgtt gcaaccgag    780
```

```
gtggtgcagt gatccgacca atcaattgga gttacatgaa gaaagggctg accgtatggt    840
tagatgtccc actggatgca cttgcaagaa gaatcgctgc tgtaggaacc gcgtctcgac    900
cactcttgca tcaggaatcc ggtgatcctt atgcaaaggc ttatgcaaaa cttacgtcac    960
tttttgagca aagaatggac tcgtatgcta atgctgatgc cagagtttca cttgaacata   1020
ttgcattaaa acaaggccat aatgatgtca ctatacttac acctagtacc atcgccattg   1080
aggcattgct aaagatggaa agttttctta ccgagaagac catggtcaga aactgacctc   1140
ttgaatgaga gggaaaggat gctgacaaca tgtggcccct gtttgtttaa ttgtacatat   1200
acctttgcat tattgcctaa actctttcta cagtgttgtt ggattattgt ttgtgcagca   1260
tgaaagagga ccgtttgagt ttgtatttat gcaaatgaat aagtaaataa ctttcagtta   1320
aaacaatgac aattcgttat ttatcgc                                       1347

SEQ ID NO: 231            moltype = DNA   length = 1318
FEATURE                   Location/Qualifiers
misc_feature              1..1318
                          note = Ceres CLONE ID no.1374869
misc_feature              1..1318
                          note = Encodes the peptide given in SEQ ID NO. 116
source                    1..1318
                          mol_type = unassigned DNA
                          organism = Zea mays
SEQUENCE: 231
ctcctgaaca caccaccct cgtcgcacga cgatggaggc cgtcctctcc tctcctctgc     60
gtccgccact gcccaccgct cgcccgcgcg cgctccatta cctcggcggg cgatggccga   120
cctatccaac accggctcca cctaacacga gcagcgcccc cgcctaggcg gcagctggct   180
ggtcggtcgt cgagcagcta gcggcggcag cgcccggagg gaggccgtct cactctcctc   240
gtcggggcgg caggagatgg aggccatcgt gggcgtccgc gcgccgccgc cgtggccgtc   300
ctggggccggc ctcgagaagc gccgcgcgc cgcttgccgc gccagagtcc cgacggcgag   360
gctcgcggtc gcggcggaca ggccgcggag gctggtgctg ctgggcgccg atacgcggag   420
ggccgcggat cctgccctcc gttgcgccgc gcaatctgca ggaacaggaa aggtccacta   480
ctctgctgat gacgctctca tactacagca aaaagcccag gatgttctgc cttacttgga   540
tggccgttgc gtttatcttg ttggaatgat gggttcaggc agaactacag ttgggaagat   600
actatccgaa gtgttaggtt attccttctt cgacagtgat aagttggtag agaaggctgt   660
tggtatttca tctgttgctg agatctttca gctccatagc gaaacattct tcagagataa   720
tgagagtgag gtcctgaggg atctgtcatc aatgcatcgg ttggttgttg caaccggagg   780
tggtgcagtg atccgaccaa tcaattggag ttacatgaag aaagggctga ccgtatggtt   840
agatgtccca ctggatgcac ttgcaagaag aatcgctgct gtaggaaccg cgtctcgacc   900
actcttgcat caggaatctg gtgatcctta tgcaaaggct tatgcaaaac ttacatcact   960
ttttgagcaa agaatggact cgtatgctaa tgctgatgcc agagtttcac ttgaacatat  1020
tgcattaaaa caaggccata atgatgtcac tatacttaca cctagtacca tcgccattga  1080
ggcattgcta aagatggaaa gttttcttac cgagaagacc atggtcagaa actgacctct  1140
tgaatgagag ggaaaggatg ctgacaacat gtggcccttg tttgtttaat tgtacatata  1200
cctttgcatt attgcctaaa ctctttctac agtgttgttg gattattgtt tgtgcagcat  1260
gaaagaggac cgtttgagtt tgtatttatg caaatgaata agtaaataat tttcagtt    1318

SEQ ID NO: 232            moltype = DNA   length = 1234
FEATURE                   Location/Qualifiers
misc_feature              1..1234
                          note = Ceres CLONE ID no.276706
misc_feature              1..1234
                          note = Encodes the peptide given in SEQ ID NO. 118
source                    1..1234
                          mol_type = unassigned DNA
                          organism = Zea mays
SEQUENCE: 232
caccggctac cacctgccgc ctgcgccctg ccctcctct gttttctag acccccggat      60
cgctcagaga ttgagtcgta gtcgcacccg actagtcgcc gcgtcctcct ttccccgcgc   120
agcagcagag caccacccgg tgaccgagca atggaggcgg ggggcgtggg cctggcgctg   180
cagacgcggg cggcggcctt cggctccggc cagcgccggg gcggcctaca gtcgcccatc   240
gggaggctga gagtcgctga accgggcgga gctgcggttg ccgtgcgggt tcgcgggtcc   300
aagcccgtcg taccgctccg tgcgaagaaa tcatccgaag gtcatgaaaa cttgcataac   360
tccgttgacg aagctctcct gttgaagaga aaatcagaag aagttctgtt ctacttaaac   420
gggaggtgta tttacttagt gggaatgatg ggttctggaa aaagtactgt ggggaagatc   480
atgtctgaag tcttgggtta ttcgttcttt gatagtgaca aattagtgga gcaagctgtt   540
ggaatgcctt cagttgctca aatattcaaa gttcacagtg aagcctttctt tcgggataat   600
gagagtagcg tcttgaggga tctgtcctcc atgcgacgat tagttgttgc caccggaggt   660
ggtgctgtca tccgaccagt taactggaaa tatatgaaga agggcctatc cgtttggtta   720
gatgtgccct tggatgctct tgctaggcgc attgctaaag tgggaaccgc ttctcgtcct   780
cttctggacc aaaccgtccgg tgatccatac acaatggcct tttctaagct cagcatgctt   840
gcagagcaaa ggggtgtagc ttatgcaaat gcggatgtaa gggtttctct ggaagagatt   900
gcatctaaac aaggtcatgg cgatgtctct aagctgatgc cgactgatat cgcaattgag   960
tcacttcata agatcgagag tttcgtcatc gagcacgctg ctgataatcc agctagcgac  1020
tcgcaagctg agtcacagat ccaaaggata cagaccttgt aatatcttaa tccttctgtt  1080
ttgtaccgaa gcgtaccccc tagagcatcg ttggtttatt tgttcgttga agtgtcacga  1140
gggagagaaa aaaaaaaacc ctgaagtatt tcttcttgta agttgtaaag gaatggaata  1200
aaggagctaa taatccgaag tgtaccgttg gccg                              1234

SEQ ID NO: 233            moltype = DNA   length = 1254
FEATURE                   Location/Qualifiers
misc_feature              1..1254
```

```
                    note = Ceres CLONE ID no.840744
misc_feature        1..1254
                    note = Encodes the peptide given in SEQ ID NO. 119
source              1..1254
                    mol_type = unassigned DNA
                    organism = Triticum aestivum
SEQUENCE: 233
accactcgcc gcccccagc agccaccgga cacctgccga aagcgcgaga gagccgtagc    60
cgatcgcatc gccgcgtagt ggccgccgca gagcaaccgg cgagcaatgg aggcgggcgt   120
ggggctggcg ctgcagtcga gggccgccgg gttcggctcc ggccgccgcc ggagctcgat   180
gtacggcggc gagagcgggg ctcgggtcgt gagcttgcgg gtcagtgatc tggtggggtc   240
gccgccgcc gtgcgggcgc gcggggccaa gcccgtcgtc ccgctccgcg ccaagaaatc    300
gtccggagga ggtcatgaga acttgcataa ctccgttgac gatgccctct tgttgaagag   360
aaaatcagaa gaggttcttt tccagttgaa tggtcggtgc atttacctag ttggtatgat   420
gggttcgggc aaaagtacgg tggggaagat cttggctgaa gttttgggtt attcattctt   480
cgacagtgat aaattggtcg aacaagctgt tggcatgcct tcagttgctc aaattttcaa   540
ggttcacagt gaagccttct tcaggataa tgagagtagc gtcttgaggg atttgtcctc    600
aatgcggcga ttagttgttg caactggagg tggtgctgtt atccgaccag ttaactggaa   660
aaatatgaag aagggcctat ctgtttggtt ggatgtgccg ttggaagctc ttgcaaggcg   720
tattgctaaa gtggggactg cctcgcgtcc tcttctagat caaccatccg gcgatccata   780
cacaatggcc ttttcgaaac tcagcaccct cgcggagcaa aggggcgatg cttatgcaaa   840
tgctgatgtc agagtttccc tcgaagagat cgcatctcaa gtggccatg acgacgtctc    900
taagctgaca ccgattgata ttgctctcga gtcgctccac aagatcgaga ctttgtcgt    960
agaagacacc gccgtcgccg actcacaaac ggaatcgcaa gctcaaagga tacataccctt  1020
gtaggatatg aatcctttt gcaccatgta gggcgcggcg cggcccagcg cagctgagtt   1080
attcgttcgt tgtgtcgaca aggaggaagc tggagtatct cttttcttttg taagctgtaa  1140
aatggcggaa taatggagct agctaataca aagatccttg ttggttgaaa gaaccctggc   1200
ttccccctg gcttgatgaa aacaatatgt caccttccaa aaaaaaaaaa aaaa           1254

SEQ ID NO: 234      moltype = DNA  length = 746
FEATURE             Location/Qualifiers
misc_feature        1..746
                    note = Ceres CLONE ID no.651548
misc_feature        1..746
                    note = Encodes the peptide given in SEQ ID NO. 126
source              1..746
                    mol_type = unassigned DNA
                    organism = Glycine max
SEQUENCE: 234
ataaccgaac aaaattaaag aaaaaaaaaa cccactattc aaaaccaaat ccaaaaacca    60
agacaccccc attaggtagc taggccttaa ttgatctcct tttctttcac caccaccaac   120
aacgatgtcc atgctcgaaa ccgaccaaat caagcaactg aacgacatat tcaagcgctt   180
cgacatggac caggacggca gcctgaccca cctggagctg gcggcgctcc tccggtcctc   240
gggcatcaaa cccaccggcg acgaaatcta cgcctcctc tctaacatgg acgaaaacgg    300
caacggctac atcgagttcg acgagctcgt gcatgccatc atgcctgacc tcaccgagag   360
cgtcctcatc aaccaggagc agctcctcga ggtcttccgg tctttcgacc gtgatggcaa   420
cggctacatc acagccagcg agctcgcggg ttccatgggc aagatgggcc agccactcac   480
ctaccgcgag ctcgcctcca tgatggctga ggccgatagc aacggcgacg gcgtcattag   540
cttcaacgag ttcgccgccc tcatggccaa atccgccgct gaatttctcg gcgtcaaggt   600
cgcctagatg gctagatcaa tacggggcta ataatttcgt atgtttgtgt aacccttttt   660
atttttttgt gttttctta gggtacgtgt acgttggtgt aaaggcaagg agatcgaaca    720
aagataaaata attaagggat atttg                                         746

SEQ ID NO: 235      moltype = DNA  length = 851
FEATURE             Location/Qualifiers
misc_feature        1..851
                    note = Ceres CLONE ID no.287120
misc_feature        1..851
                    note = Encodes the peptide given in SEQ ID NO. 126
source              1..851
                    mol_type = unassigned DNA
                    organism = Zea mays
SEQUENCE: 235
atcatccctg cagttgtgga tcagttcgtc ctccgtctct ctccacaagt ctcctctagg    60
cgccaagcaa tgacaaggtc agcaccgccg gcctctcctc cggcgccgaa gcccgtgctg   120
cgcgggagcc agctggagca gctccgcgag atcttccggc gcttcgacat ggacggcgac   180
ggcagcctga cgcagctgga gctgggggcg ctgctgcggt cgctgggcct gcgccccacg   240
ggggaggagg cccgcgcgct gctggcggcc atggactcca acggcaacgg cgcggtggag   300
ttcggcgaac tggcggccgc catccgaccg ctgctcacca gcagacgca cctcgtcgac    360
caggcccagc tcctggaggt gttccgcgcc ttcgaccgcg acggcaacgg ctacatctcc   420
gccgccagc tggcgcgatc catgcgcgcg atcggccagc cgctcacctt cgaggagctc   480
acgcgcatga tgcgcgacgc cgacgccgac ggcgacggcg tcatcagctt caacgagttc   540
gccgccgtca tggccaagtc cgcgctcgac ttcctcggcg tcgcctgatg ccctctgatg   600
gaccgatcga tcgatcggtc tgctcaccg ccgcgcgtg taacccgtg tccctgtgac     660
cctgtccctc gcccgccatt gattaccgtg tctctctctc tctctctctc tcttttgtta   720
ggaagatgct catccggtta atgtaggata actgacacaa gataatgtaa ctcaaaaact   780
catcgctggt ttgtaacatg gatgaactcg gaaaatgtgt acatatttg gatggattg     840
ttcaatcttc c                                                        851
```

| SEQ ID NO: 236 | moltype = DNA   length = 848 |
| --- | --- |
| FEATURE | Location/Qualifiers |
| misc_feature | 1..848 |
| | note = Ceres CLONE ID no.759217 |
| misc_feature | 1..848 |
| | note = Encodes the peptide given in SEQ ID NO. 129 |
| source | 1..848 |
| | mol_type = unassigned DNA |
| | organism = Triticum aestivum |

SEQUENCE: 236

```
cggtctcacc ccaaacccat tgtgcatctc catcccacc tcctccgatc ccatccaccc   60
ccaccctcac cgccaccaag tcaaagatcc aaccttcact ccaccaccat gacgaagcca  120
tcgccatccc catcgccggc gccggccaag ggcgcgggt cgctgcgggg cagccagctg  180
aagcagctgc gctccctctt cgaccgcttc gacatgcagg gcgacggcag cctcacccag  240
ctcgagctgg cggccctgct ccgctccctc ggcctgcgcc cacgggcga cgagtcgcgg  300
gccctcctcc tcgccatcga cgccgacggc agcggcaccg tggagttcga cgagctggcg  360
cgggccatcg cgccggtgct caccgccac gcgccgcggc tcgtcgacca ggcgcagctg  420
ctcgaggtct tccgcgcctt cgaccgcgac ggcaacgcc acatctccgc cgagctc     480
gcgcgttcca tggccaagct gggccagccg ctcacgttcg aggagctgcg gaccatgatg  540
cgggacgcgg acgcggatgg ggacggcgtg attagctttg gggagttcgc cgccgtcatg  600
gccaggtccg cgctcgactt cctcggcgtc ccgccgcct gagatgtgag atgatgaccg  660
gccgggctcc ggctggctct gatcggatgg actggtagta tgattcttct tctttggtag  720
aactagtcgt agtagggtgg ttcaaggcc ggactggatc aactgtgacg aactcacacg  780
gagttgcaac gttgacctgg aatgtgtata aatttggta atttggtcaa tcgatgcgtc  840
cgctgctg                                                           848
```

| SEQ ID NO: 237 | moltype = DNA   length = 766 |
| --- | --- |
| FEATURE | Location/Qualifiers |
| misc_feature | 1..766 |
| | note = Ceres CLONE ID no.684584 |
| misc_feature | 1..766 |
| | note = Encodes the peptide given in SEQ ID NO. 139 |
| source | 1..766 |
| | mol_type = unassigned DNA |
| | organism = Triticum aestivum |

SEQUENCE: 237

```
cgaaaagtgg acctttgta ctagtacttc agacagacag aagcagaagc aaccagccga   60
agctcgttcc tcgtagacag ttggacagtc gtctcgatcc atcgtccatc ccgtctcgcc  120
agcagccgac catggccgcg caggcgccgc cgccgccgcc gccggagcag aagatgatgg  180
tggccatcga cgagagcgag tgcagccact acgcgctcga gtgggccctg cgcaacctcg  240
cgccccgccg cctcatcctc ttcaccgtcc agcccttctc ccctctcagc tacctccccg  300
tcggctcccc gcttggcccg tcggtggcgt cgccggagct catcaggtcg gtgaccgagc  360
accagcggca gctcgcccag gcgctcgtcg acaaggccaa ggccatctgc gccgagcacg  420
gggttgatgc agagaccgtc atcgaggtgg gtgatcccaa ggaaaccata tgcgaagctg  480
cggagaagtt gaatgttgat ctgctcatcc tgggaagcca cagccgtggg cctgtacaaa  540
ggtttttcct tggcagtgtg agcaactact gtagccacca cgcgaagtgc ccggttcttg  600
ttgtgaagaa gaaagaatga aactccgcta tctactgaca tcatggacat cgtgtgaaga  660
acccttgaga tgtgtatcta catgttgttt gtcacagcat ctagttgcat acttgcatat  720
gaataaacat actttgccaa tttgaaaaca actatatatt cagtct               766
```

| SEQ ID NO: 238 | moltype = DNA   length = 693 |
| --- | --- |
| FEATURE | Location/Qualifiers |
| misc_feature | 1..693 |
| | note = Ceres CLONE ID no.1059727 |
| misc_feature | 1..693 |
| | note = Encodes the peptide given in SEQ ID NO. 142 |
| source | 1..693 |
| | mol_type = unassigned DNA |
| | organism = Glycine max |

SEQUENCE: 238

```
gatcaaactg tagtcaaact catctgacga tcgatcgatc gatcatttgg aagaaaccat   60
ggtggaagag aaaagtggga agaagcaagt gatggtggcg atcgacgaca gcgattgcag  120
caaacacgct ctccgatgga cgctctcgta tctcaaagac agcctcgccg attccgtat   180
catcctcttc accgcgcagc ctcagctcga tctcagctcg gtctacgctt cctcttatgg  240
cgccgctccg atagagctga taaactcaat gcagcagaac tacaaaaacg cagcgttgaa  300
tcggattgag gaagggacca agatttgcgc tgagagcggg gttaccccaa agaaggtgat  360
ggagtttgga aaccctaaag aagcgatatg tgatgctgtt gagaagcttg gtgttgattt  420
gctaatcgtt ggtagccatg gcaaaggggc tctagagagg actttccttg gaagtgttag  480
caattactgt gttaacaagg ctaagtgccc agttcttgtg gtcaggacaa aggcttgaag  540
agtttgagaa ccgcctcgct tgctgtatgt gtgttgtgta aacatattga taataatgct  600
ttgtttgtat actactactg tttggaaaaa aactttgtga atggaaataa atatattatt  660
ggtttgataa ataacgagct ttgctgtgct ctt                              693
```

| SEQ ID NO: 239 | moltype = DNA   length = 853 |
| --- | --- |
| FEATURE | Location/Qualifiers |
| misc_feature | 1..853 |
| | note = Ceres CLONE ID no.1272732 |
| misc_feature | 1..853 |
| | note = Encodes the peptide given in SEQ ID NO. 143 |

```
source                     1..853
                           mol_type = unassigned DNA
                           organism = Zea mays
SEQUENCE: 239
aaagcggact gctctcctca attgtcaggc agtagcatcc atttgattgt tctatcctct   60
tctctgttct cacccccttg caagcaacaa tcgttcaccg atcgatccag tgcgtcctgc  120
atggaaactg ccgccgtcgc cgcctccagt gccgggcgcc gcatcatggt ggccgtggac  180
gagggcgagg agagcctgca cgcgctcaac tggtgcctcg ccaacgtcgt ctccccggca  240
ggaggcgaca cgctggtgct cgtccacgcc cgccgcccgc gcccggtcta cgccgccatg  300
gacagcgcag ggtacatgat gacctccggc gtgctggcga gcgttggaga gcacgccaac  360
gcggtctcgg cggcggcggt cgacaaggcc aagcgcgtct cgccgaccca cccgcacgtc  420
aaggtggaga cgacggtgga gagcggggac ccgcgggacg tcatctgcga cgcagccaac  480
aagatggccg cggacctgct cgtcatgggc agccatggtt acggcttcat ccagagggcg  540
ttcttgggca gcgtcagcaa ccactgcgcg cagaactgca aatgcccggt cctcattgtc  600
aagaggccca aggagtagaa ggttcctcgc atgtaacgct gcagcttagc caataatgtt  660
tcatggcgac catataggca tatatgtaca cacttcacat cccattgcat ggcagtgtct  720
tccctagttc aacaactagc tttctgctgg aataaggtgt tcagagttca gacagagtat  780
gtactgtaca tactatcttc ttgcatttgg tactcttgtt tagtgaaaag cgttccgtaa  840
aaaaaaaaaa aaa                                                     853

SEQ ID NO: 240            moltype = DNA   length = 812
FEATURE                   Location/Qualifiers
misc_feature              1..812
                          note = Ceres CLONE ID no.283925
misc_feature              1..812
                          note = Encodes the peptide given in SEQ ID NO. 144
source                    1..812
                          mol_type = unassigned DNA
                          organism = Zea mays
SEQUENCE: 240
agtagcatcc aattgattgt tctatcctct tctctgttct cacccccttg caagcgccaa   60
gcaacaatcg ttcaccgatc gatccagtgc gtcctgcatg gaaactgccg ccgtcgccgc  120
ctccggtgcc gggcgccgca tcatggtggc cgtggacgag ggcgaggaga gcctgcacgc  180
gctcaactgg tgcctcgcca acgtcgtctc cccggcagga ggcgacacgc tggtgctcgt  240
ccacgcccgc cgcccgcgcc cggtctacgc cgccatggac agcgcagggt acatgatgac  300
ttcggacgtg ctggcgagcg tcgagaggca cgccaacgcg gtctcggcgg cggcggtcga  360
caaggccaag cgcgtctgcg ccgaccatcc gcacgtcaag gtggagacga cggtggagag  420
cggggacccg cgggacgtca tctgcgacgc agccaacaag atggccgtgg cagccatggt  480
tacggcttc atccaaaggg cgttcttggg cagcgtcagc aaccactgcg cgcagaactg  540
caaatgcccg gtcctcattg tcaagaggcc caaggagtag aaggttcctc gcatgtaacg  600
ctgcagctta gccaataatg tttcatgggc gaccatatag gcatatatgt acacacctca  660
catcccattg catggcagtc ttcccttccc tagttcaaca actagctttc tgctggaata  720
aggtgttcag acagagtatg tactgtacat actatcttct tgcatttggt actcttgttt  780
ggagagaagc gttccgtaac cttcggttgc ct                                812

SEQ ID NO: 241            moltype = DNA   length = 1002
FEATURE                   Location/Qualifiers
misc_feature              1..1002
                          note = Ceres CLONE ID no. 611156
misc_feature              1..1002
                          note = Encodes the peptide given in SEQ ID NO. 147
source                    1..1002
                          mol_type = unassigned DNA
                          organism = Glycine max
SEQUENCE: 241
attatccagc aaacactatc tcaatagtga agctctaaac cactgccaag tatggtagtt   60
tcttcgtgct ctttgagctg gatttcacct tgcttatccc ataagctaaa cttgccacat  120
acaaattgtt tgcctcgcaa cattgcaact tcatcttcca acactgtctt ttgtgaattg  180
gacacaaccc ccagcggaga aagtcattgc cggagaagac cgctactgtt aggcattgga  240
gcattaactg caaattaca accaacaaat ttggtctttg ctcaagaaaa accagacaga  300
taccgagctt ttgtggacta tgaagatggg tattcttacg tatatcccat tgattggaag  360
gaatttgact tcagggctca tgattctgca ttcaaagaca gatatctaca gttacagaat  420
gtacgggtga gatttatacc aaccgagaag aaagacatcc gagatttggg tcctatggaa  480
gaggttatat acgatttggt gaaacataga tacgcagcac caaaccaaag accaacaata  540
aatgacatgc aggagaaaac catagatgga aaacattact ataccttttga atatatactt  600
acatcaccaa attattctag tgcctccttt gcaacaattg ctataggaaa tggaaggtac  660
tacacgttaa ttgttggagc caatgaaagg cgatggaaaa gatttcgaga tcagcttaaa  720
gtggtagcag actcctttag gcttcttgac atctgaaatg tcacgggaca atgcaaaaca  780
tgttttaatt tgcctacaga tcaagtttga taattcgta tatcagagca aaataagtta  840
ttacaagtga atgatatctt ctactatacc aatagaactc tcttttgtac atcgcatgca  900
aagtgacttt gtctgtcatt tgtggtgcaa actcaattcg ttgttcctcg tctactctta  960
cattgttcca ctgctactcc tttatggagt atttcggttg gg                    1002

SEQ ID NO: 242            moltype = DNA   length = 944
FEATURE                   Location/Qualifiers
misc_feature              1..944
                          note = Ceres CLONE ID no.1551032
misc_feature              1..944
                          note = Encodes the peptide given in SEQ ID NO. 152
```

```
source                  1..944
                        mol_type = unassigned DNA
                        organism = Zea mays
SEQUENCE: 242
agtcgcctcg attcgcttcc gccccatcct ccttcccgac gcctcacatg gcaacggccg   60
tgcccgccgc ctgcctccgc gcgccgtgct cctctccagc ggccgtcgca cgccgacttg  120
gggccggtgg cccgtcgctg cgcaagcggc attgcgccgt cgcgcccgtc gctgccgcct  180
gcggccccgc gccgccgcgg ctgcttgaca acgaggaggc ggtctgctcc gtacggcggc  240
gtgtgctggt tgccggtgcc gccgcgttcc tctcccggcc taatccggcg gcattcgcag  300
cagaggctaa gaaagggttc ctgcccgtcg tcgacaagaa ggctggctac tcttcctct   360
acccgttcgg atgggaggaa gtggctgtgc aagggcaaga caaggtgtac aaagatgtga  420
tagagcctct cgagagtgtg agcgtcaact ctattccaac tagcaaggag gatatccgtg  480
atcttggtcc tccggataag gttgccgagg ctctgattaa aaaggttttg gcaccatcaa  540
cacagaagac aaagttaatt gaggcgaaag agaatgatgt tgatgggagg gcttactaca  600
cttttgagtt cacagctcag gctccaaact acaccagaca tgcacttggt gctattgtaa  660
ttgcaaatgg caaattttac acattgacca ctggagcaaa cgagaggagg tgggaaagaa  720
tgaaggatag gctgcatact gttgtggatt ccttcaaaat cgaaatagaa atgagtgc   780
ctgaattgct gtgttgtttt tccttcgttg attcgctttt tcttacataa ctgcagtgct  840
gagatttttc agtagtaaat accgggattg tggattatgc tgatcagttt catttcgaaa  900
tgtttgttac cagacttgag caaaaataaa aaaaaaaaaa aaaa                   944

SEQ ID NO: 243         moltype = DNA  length = 1395
FEATURE                Location/Qualifiers
misc_feature           1..1395
                       note = Ceres CLONE ID no.703785
misc_feature           1..1395
                       note = Encodes the peptide given in SEQ ID NO. 161
source                 1..1395
                       mol_type = unassigned DNA
                       organism = Triticum aestivum
SEQUENCE: 243
atctgaatgc tagaaggagg tggttggacg atgaggcatc ccaacacggt agaaggagtt   60
ccgcctatcg aagttgagag ggccaatttg aaaaaaagaa aaagttgaga gggacagaga  120
gggaaacatc tgggcattct cgttgcagaa agtagagcgc tgtacaaacg ggccttcacg  180
aaccaagaga catccatcaa atttcatggc gtcctctcca caatcctcct cctctgcacc  240
caaagccgac gacaaggcag cgtcccacaa agaaatctac gaccagctac tagaggtcgt  300
gtccacctac ccgacggcgc ctagcggcat cggccgcccg tacacccacc cccagacggg  360
ctggtacgcg ttcacgccgg ccgtcgtgaa cgccatggtc atcaagcggc acctcaaggc  420
gtgcgacacc gacgtcttcc tctccacctt tcccaagtcc ggccaccact ggctcaaggc  480
gctcctgttt gcgaccctcc gccgcaccgc ggacgggcca gcgatcgcgg cgctcgcagc  540
ccacagcccc caccagctca tcccttcct cgaggtccag gttttcagca acggccggat  600
cccagacctg agctccctcc ctgcgccgcg gctcctgatg acgcacatcc cgtcccggtc  660
gctgccggag tccgtggccg cctccggctg caaggtggtg tacctgtgcc gggacccaa   720
ggactgcttc gtgtcgctct ggcacttctg gaaccgcttc gcgccgtcgc cgtgggacct  780
cggtgaggcg ctccagcagt tctgcgacgg cgtctccctg ttcgggcctt tctgggagca  840
cgtgctgggc tactggcgct ggcatgtgga gaggccggag caggttctat tcctgaccta  900
cgaggagctc gccgccgaca ccctcggcca gctgaagcgg ctcgctggct ttctcggggcg  960
cccgttcacg tcagaggagc gggaagccag ggtagacagg gagatcgtgg aggcatgcgc 1020
catggagagc ctggcgggac tggaggtgaa ccgctccggg aagacggaca tgaccgagtc 1080
ttcagtggcg aacaacatat tcttccggcg cggcgtcgtt ggcgactgga gaaccacct  1140
gacgccggaa atgctagaa ggatcgatga gatcaccgat agcaagttca gaggatcggg 1200
gttggcgttg acgccggcaa ccgcagatca gaactagtgg gttcatgatg gcagatgcta 1260
tataaataag gacgacttgc gcaacatttt tataaaatat tgtactatta atgtcaggca 1320
tgataacttg atcagcaaac atgcgaaggg aaataacaga agtgttacca tacagtaata 1380
tacatgaata tcgtt                                                  1395

SEQ ID NO: 244         moltype = DNA  length = 1320
FEATURE                Location/Qualifiers
misc_feature           1..1320
                       note = Ceres CLONE ID no. 1064128
misc_feature           1..1320
                       note = Encodes the peptide given in SEQ ID NO. 168
source                 1..1320
                       mol_type = unassigned DNA
                       organism = Zea mays
SEQUENCE: 244
atttacgatt agcctagcga ctcggcatgg ctactgtctt ccccgtgac gccggcgtct    60
ccacgccgga agccgacgag gctaagaaaa tctacgatga agcacggcga gtggtgtcca  120
cctacgagac tgttcccagt cccagccgaa ccctgcagga ttactgccgc caccccagcg  180
gctggtgcat aaccctgccg atcatggtga gctccatggt cgcagagcag cactttgagg  240
cgcgtggcac cgacgtgctc cttgttacga tgcccaagtc cgggactacc tggatcaagg  300
ccctcctcta tgctgcggcc caccgcactg acgacacatc atcgtccata ctccggcagc  360
tcgcctccca caactcccac cagctcgttc ctttcctcga ggcccaggtc tacaccaagg  420
accagattcc agacctgagc tcgttcccgc cgcacggtc cacacccgg                480
ctgagtcgct gccaccctcc gttgtggcgt ccggctgcaa ggtggtgtac ttgtgccggg  540
accccaagga ctgcttcgtg tctctctggc actttatgaa caagttcacc ccatgggaca  600
tcgacgaggc acacgccgg ttctgcgagg gtgtctcgtt gtatgggcca tttttgggagc  660
acgtgctgag ctactggcgt tggcacgtcg accgaccggg tcaggtgctc ttcctgactt  720
acgaggagct cagcgccgac ccgctcggcc aactgaggcg cctagccgag ttcattgggc  780
```

```
gcccnttcac gccggggagg caggaggcgg gagtggacag ggagattgcg gaggcatgtg    840
ccatgaaaag catggtcaac caggaggtga accagtccag gacgaccgaa atcgttgaga    900
tgccgattcc caacgggatc ttcttccggc gaggcgtggt cggagactgg accaactacc    960
tcacgccgga gatggcagga aggatcgatg agattaccaa gagcaagttt gaaggatccg   1020
gcctcatgct gccgaaaaca atctcggaaa tctcaaagat ctagcatccg tccgtcgtgt   1080
ttgatgtttg aaatcgttca cctttttttt ctcttgttgt aaactgcacc ctgctggcac   1140
tggcttggct gaataaaaaa agcttgcatt gttcttgttg atcaaacgaa ataccagctg   1200
gcgagttgtt gatgttacgg aaaaggcctg cttagtctta ggtattttc ttatcggttt    1260
aattgtgatc aaatgtgttt gtactctgct taattattaa taaaaatgat tgtatgcacc   1320

SEQ ID NO: 245            moltype = DNA   length = 864
FEATURE                   Location/Qualifiers
misc_feature              1..864
                          note = Ceres CLONE ID no. 5367
misc_feature              1..864
                          note = Encodes the peptide given in SEQ ID NO. 173
source                    1..864
                          mol_type = unassigned DNA
                          organism = Arabidopsis thaliana
SEQUENCE: 245
actatcaatt cgactggaaa aaggatattt ccagattagg tagagagaga gcaaaagtac     60
tttcattcag acttcagttt aagctatggc ggcgaacgtt tcttcaaatg tcattgacat    120
cgacgggaat ctcgactccg attcgaatct taacactgac ggtgacgaag cgaccgataa    180
tgattcctcg aaggcattgg ttactatccc tgctccagcc gtttgtcttt tccggttcgc    240
cggagatgct gctggtggcg ccgttatggg ctctatcttc ggatatggtt caggattgtt    300
caagaagaaa ggcttcaaag gatcatttgc agatgcaggc cagtctgctg agactttgc    360
tgttttatct ggagtccaca gtttggttgt ttgcctttctg aagcaaatcc gaggcaaaga   420
tgacgccatt aatgttggag tagcagggta ttgcactggt cttgctctta gtttccctgg   480
tgctccacag gctcttctac agagttgtct cacgtttggg gcattctctt ttattcttga   540
gggactcaac aaaagacaaa cagctttggc cacactcggtc tcgttgagac accaaaccgg   600
actgttccaa gatcatcatc gtgctttacc actctctctt gctctcccga tccctgaaga   660
aatcaaagga gccttttctt ctttctgcaa gtccttagct aaaccaagga agttctaatc   720
tcgtcttatt attctccctt tcttgtgtct taggctctct ctatgtagat gtaaaatttt   780
cccgcttttg ttgtactttg tgagacatgt tttgtgaaag gcttttgca agagccaatt    840
tgaagagaaa aagagttgtg tacg                                          864

SEQ ID NO: 246            moltype = DNA   length = 766
FEATURE                   Location/Qualifiers
misc_feature              1..766
                          note = Ceres CLONE ID no. 1060894
misc_feature              1..766
                          note = Encodes the peptide given in SEQ ID NO. 176
source                    1..766
                          mol_type = unassigned DNA
                          organism = Zea mays
SEQUENCE: 246
aggtagaaag cgaaactctc tctccagctt cagaggcttc agctatggcg gccgagaatc     60
cttcaaacgg tgtagacgtc gacacgagtc tcgcttccga ttcaaacgat aaccgcaaag    120
ccagtgattt gaccaatcat gactcttcca tggcattgac agtcccttcc accgccgttt    180
gtctcggccg tttcgccgga gatgcagcag gcggcgccgt catgggtct atattcggct     240
atggttctgg attgttttag aaaaaagggt ttaagggatc atttgcggat gcgggtcagt    300
ctgcaaagaa ttttgcgatt ttatctggag tgcacagttt ggttgtttgc cttctgaaga    360
aactgcgagg gaaagatgat gccattaacg ttggaattgc tggatgctgc actgccttg    420
ctcttagtta cccaggtgca ccacaagcaa tgctacaaag ctgtgtcact tttggtgcct    480
tttctttcat cctcgaagga ctcaacaaga ggcaaacagc tttggctcac tctgtctcct    540
cgagacatga tcaaaccaga agtctgaaag atgatttacc actctccttg gctctcccaa   600
tccatgaaga gatcaaagga gctttctcat ccttctgcaa atctttaaca aaacccaaga   660
agctcgcgtt ccctagctca cgttgatcga agttttttt gtatcctact acttcctttt    720
gtagatgtta aagaacagaa tgaaaacaag aatcatgttt caaaac                  766

SEQ ID NO: 247            moltype = DNA   length = 864
FEATURE                   Location/Qualifiers
misc_feature              1..864
                          note = Ceres CLONE ID no. 639280
misc_feature              1..864
                          note = Encodes the peptide given in SEQ ID NO. 177
source                    1..864
                          mol_type = unassigned DNA
                          organism = Triticum aestivum
SEQUENCE: 247
gaaacaggaa acgataacga aactcgcaga gagggcggac atggcggcga ggagcgagaa     60
cgagtcggac ggcgacgtgg gcaccaaccc cgccgagggg ggctcgtccc tgtccctgcc    120
gcctctagct gccggtccag ccgtgtgcgt cctccggtcc gccggggact cgccggcgg    180
cgccttcgtc ggatctatct ttggatatgg acaaggtttg ctatctaaga agggtttgaa   240
gggctcactc ggcaatgcag ggtcttctgc caaaagtttt gcagttcttt ctggcgtcca    300
gagtttggtt ttgtgcttgt tgaggaagct gcgtgggaaa gatgatatca tcaattccgg   360
cattgctggt tgttgcacag gtcttgcttt gagttttcca ggtacaccac aagcgctgct   420
tcagaactgc gccaccttcg cagcattctc atgcatcatg gaggggctca acaagcagca   480
gaccgcgatg gcgcacaccc tcactgggaa cgccttgacc tttgcacacg acaatggcgc   540
```

```
gggcgtcctc ccccctctcac tctccccca atcctcgatg cttccgatgc tttcgcctca    600
tgctgccagg ccttggtcgc caagcctaag aagcactaga cagcagcatt aggagggaga    660
gagtgagata tgctcaggaa acctagctag ctcctagcgt tatgtaaatt ttgcttttgg    720
ataatgtcga aaatctagat tgtttgcttt ttcagccggg tgttttttgt cgccgcgttt    780
cgtggcgtgg gcttgctttg ttgatgatat gtcaaggata gattttgttt accgggaaga    840
taagatgtcg tggaaaattt tgcc                                           864

SEQ ID NO: 248           moltype = DNA   length = 827
FEATURE                  Location/Qualifiers
misc_feature             1..827
                         note = Synthesized Sequence
misc_feature             1..827
                         note = Ceres CLONE ID no. 29658
misc_feature             1..827
                         note = Ceres Seed Line ID no. ME02907
misc_feature             1..827
                         note = Encodes the peptide given in SEQ ID NO. 249
misc_feature             1..827
                         note = Encodes the peptide given in SEQ ID NO. 250
misc_feature             1..827
                         note = Encodes the peptide given in SEQ ID NO. 251
source                   1..827
                         mol_type = other DNA
                         organism = synthetic construct
SEQUENCE: 248
gtaagggatg acgcacaatc ccactatcct tcgcaagacc cttcctctat ataaggaagt     60
tcatttcatt tggagagaac acggggggact ctggcctgca gggccatcac cactgcagtg   120
gtacctagaa catcctaatc gaaaaattca tctccaaact ttcaaaaaaa aacctaaaac   180
aaaaaaaatc tctttccttc ttctttctcc atcaatggcg tcaacaaaac ccaccgatca   240
aatcaaacaa ctcaaagata tcttcgctcg cttcgacatg gacaaggacg gaagcttaac   300
gcagctagaa ctcgccgctc ttctgcgttc tctcggaatc aaacctcgcg gcgatcaaat   360
ctctcttctg taaaaccaaa tcgaccgtaa cggtaacgga tccgtagagt tcgacgagct   420
cgtcgtggcg atattgccgg atataaacga agaggtgttg ataatcaag aacagttgat   480
ggaggttttc cgttcgtttg atcgtgacgg taacggttca ataacggcgg cggaacttgc   540
tgggtcaatg gctaaaatgg gacatccgtt gacttaccgt gaattaacgg aaatgatgac   600
ggaagctgat tcaaacggtg acggtgttat tagtttttaat gagttttctc atattatggc   660
taaatcggct gctgattttc ttggattaac cgcttcttga tctgttttgt tttaattact   720
ctcttttttt cttctcctgt caatgcaact tgtgcaatta acaatgtgct aatctttcgt   780
ttggtgtgac gtaaaatttt ataaaaaaaa aaaaaaaaa aaaaaa                   827

SEQ ID NO: 249           moltype = AA    length = 73
FEATURE                  Location/Qualifiers
REGION                   1..73
                         note = Synthesized Sequence
REGION                   1..73
                         note = Ceres CLONE ID no. 29658
REGION                   1..73
                         note = Ceres Seed Line ID no. ME02907
REGION                   1..73
                         note = Peptide encoded by SEQ ID NO. 248
REGION                   1..73
                         note = Phenotype: ROSETTE LEAVES Useful for making
                          ornamental plants with modified leaves
source                   1..73
                         mol_type = protein
                         organism = synthetic construct
SEQUENCE: 249
MEVFRSFDRD GNGSITAAEL AGSMAKMGHP LTYRELTEMM TEADSNGDGV ISFNEFSHIM     60
AKSAADFLGL TAS                                                       73

SEQ ID NO: 250           moltype = AA    length = 121
FEATURE                  Location/Qualifiers
REGION                   1..121
                         note = Synthesized Sequence
REGION                   1..121
                         note = Ceres CLONE ID no. 29658
REGION                   1..121
                         note = Ceres Seed Line ID no. ME02907
REGION                   1..121
                         note = Peptide encoded by SEQ ID NO. 248
REGION                   1..121
                         note = Phenotype: ROSETTE LEAVES Useful for making
                          ornamental plants with modified leaves
source                   1..121
                         mol_type = protein
                         organism = synthetic construct
SEQUENCE: 250
MTHNPTILRK TLPLYKEVHF IWREHGGLWP AGPSPLQWYL EHPNRKIHLQ TFKKKPKTKK     60
ISFLLLSPSM ASTKPTDQIK QLKDIFARFD MDKDGSLTQL ELAALLRSLG IKPRGDQISL   120
```

L                                                                121

```
SEQ ID NO: 251          moltype = AA  length = 52
FEATURE                 Location/Qualifiers
REGION                  1..52
                        note = Synthesized Sequence
REGION                  1..52
                        note = Ceres CLONE ID no. 29658
REGION                  1..52
                        note = Ceres Seed Line ID no. ME02907
REGION                  1..52
                        note = Peptide encoded by SEQ ID NO. 248
REGION                  1..52
                        note = Phenotype: ROSETTE LEAVES Useful for making
                         ornamental plants with modified leaves
source                  1..52
                        mol_type = protein
                        organism = synthetic construct
SEQUENCE: 251
MASTKPTDQI KQLKDIFARF DMDKDGSLTQ LELAALLRSL GIKPRGDQIS LL            52

SEQ ID NO: 252          moltype = AA  length = 498
FEATURE                 Location/Qualifiers
REGION                  1..498
                        note = Ceres Clone ID no. 375578
REGION                  1..498
                        note = Full Length Peptide Sequence for Ceres CLONE ID no.
                         375578
source                  1..498
                        mol_type = protein
                        organism = Zea mays
SEQUENCE: 252
MGKRGKWFSA VKKVFSSSDP DGKEAKAQKA DKSKSKRRWP FGKSKHSEPS ISTVPGTAPA    60
VAPLPSPPAT QPHSLEIKDV NPVETDSEQN KHAYSVALAS AVAAEAAAVA AQAAAEVVRL   120
TAVTTAAPKM PVSSREELAA TKIQTAFRGY LARRALRALR GLVRLKSLVD GNAVKRQTAH   180
TLQCTQAMTR VQTQIYSRRV KLEEEKQALQ RQLQLKHQRE LEKMKIDEDW DHSHQSKEQI   240
EANLMMKQEA ALRRERALAY AFSHQWRNSG RTITPTFTEP GNPNWGWSWM ERWMTARPWE   300
SRLAAASDKD PKERAVTKNA STSAVRVPVS RAISIQRPAT PNKSSRPPSR QSLSTPPSKT   360
PSASGKARPA SPRNSWLYKE DDLRSITSIR SERPRRQSTG GGSVRDDTSL TSTPPLPSYM   420
QSTESARAKS RYRSLLLTEK LEVPERAPLA HSVVKKRLSF PVVEKPSVVP TEKPRERVRR   480
HSDPPKVDPA TLKDAPAA                                                498

SEQ ID NO: 253          moltype = DNA  length = 1836
FEATURE                 Location/Qualifiers
misc_feature            1..1836
                        note = Ceres Promoter p530c10
source                  1..1836
                        mol_type = unassigned DNA
                        organism = Oryza sativa
SEQUENCE: 253
gcctctcgac cacgagttta gcacttgtgc aacatatatg cgtgcgatga acatctactg    60
atgcgccatg cgaattttag cgttcgttca tgacgcttcc aacggcacag aggctgagca   120
gcagcatgca tgcatggctc ttgtgaaaac aaaaaaggtt actggtaaat gacatgctgc   180
tgtagctagc tagcagaatg caaggcccat gcatatgcaa tgctatgcga caagtacagt   240
accagcatgt atggtagcca gctaactaat ctatcagcag aggcagcaag ctcgtgcatg   300
gtgtgatgca cttctctcca gtaatctagt ggtaattttc acccaaagcg ttgctcatat   360
ggacagtaat tagtaaatat taccaaggtt caacatcccgt tacctgacca aatactactc   420
acgaatggta tctctggttt tcgttaaaac cgttggtaaa ccagcaaaaa tagacaaaat   480
ttgtcaaaat tttaaatttt agttttttt ttttaactta gccgggaaac cttgaagttt    540
gtgctgtcga gctgtcctgg gaaggacggt tttggttggg attgtgaacc ctggttactg   600
cacttcattt ttgaacagat attagtgcaa cagacaaatg ccaacgcatt tttttctgtt   660
taccggcaag ctgaagcttt tacgatcccc atacagccgt tgctgcaaac ctgccaagaa   720
agagcagcag aaacaggtgt cattttgtgg tggaaagcca agtaaagtaa acagaagatg   780
gaagatagtg aggaccaggg agtgaggcag gggacacatg gcccacgcct ccctgcacat   840
tttcgtgtat aaatacaggt ggatgcatcg ctctcccagc atccatcggt tctctgctct   900
gttcatccat agagtttcct cctcttctcc tttagtgcaa ggtagagaag agcatgtgtg   960
tgtgtgtgtg tgtgtgaact gtgaagtgca gagtgcttct gtagttctgt gttatgtcca  1020
tagtgatctt gttaggattg ttgctatgga tgcatgatgt tatggttgat ctctgaatta  1080
cagtagggac tttttctgaga tctctggatt agtgggggt gctaaatttt tttctggttg  1140
catcagcttg ggtttctggt attggtgtgg gttcttgctc tgaattttgg ttcagaatgt  1200
cgatttgttt gtgtttgttc tctgaagttg agagtagcta tgatccatcc agcacagaac  1260
tgcaggtcct gcctgccggc tgcatataca ggacatgcca ttttgcaagc tctgggctta  1320
tggtttctct tttggagttc ttcttcttgc atgatctgtg ttctctaaca aaggaagcaa  1380
gattagcaa ctttattcag agacaagaaa aggatctggc aaccttttgt ttctgttttt   1440
tcctactcgt aaagattgtt atttaagcaa aaatttccca aaagtttaa atataatttc   1500
catgatgtgc cactctcatg tccttgaacc tggcactcat tatgggctcc tcagaagtgc  1560
tgtagctaat gtcactaatc ttttgtatct ttgttcatag tcttgtattt tatgatgctt  1620
atcccttttgt gctttccatg tttgatgtcc aaatgtcatg gcaatgtttt tgacttctag  1680
tagggggttt agtaccttttt tgttagataa gtacatccaa attctgttta tttattcaaa  1740
```

```
aatcattctg tttattcact gaaaacattt gtccattcaa tggactcata aactgtctgt    1800
gtttttcagg cttgaggatc catctagaag atagca                              1836

SEQ ID NO: 254          moltype = DNA   length = 3000
FEATURE                 Location/Qualifiers
misc_feature            1..3000
                        note = Ceres Promoter pOsFIE2-2
source                  1..3000
                        mol_type = unassigned DNA
                        organism = Oryza sativa
SEQUENCE: 254
gcttaacaca tgaactacca aaatatactg atcactttgt tctagtcata cataccttaa      60
gtcattttat tctgcagtgt ttggattgga gggagcattc tagcatccct tgggtcgttc     120
cagcaaatgt ggttctccaa agcagagtaa gcacaacaca gtattttagg ttatgtttcc     180
cctatctcgt cacggacagc tcacaagtta atgtgattta tctcactata gatacgaaga     240
acatggagta tcctacatcc aaaggaagtg cccatgaagt tgtggagcat cgctacgatt     300
tgtgaccaaa tttgggtgca tgtgggcaat cgtattacag ccaccctgtt gttgatctat     360
atcgactatt atccgacgat atttatcatt atattatgac tgattagttt gtagatttta     420
agagggcaac ataagaagca atccagctta acctgttatg ttcttgatgg tagattctag     480
ttcatgtgtt gaatctgttc tccctgctgt agaatgtatc gagttgctgc tctctactct     540
gtactttag aataccttt caatcatttg gagtcagctg attgttgtac tacttatacg       600
ccacctgatt agtcatgtca acaattaaac ttgagcactg gttaagttaa gagtggcctg     660
attgtagttg ataatcacat tttattcgta gacattgtat gctggatctt tatcagccac     720
cgtcagatca tcctctgtaa taatcttca tcagacgtgt gtgccaatcg caaggaaacac    780
gaaatgcatc cgaaatgtta ctctgagtta atcaatacta taattcttgg tcaaattaat    840
tatttatatc tataaagttt aaattaaatt taggaaaatg aattcatgca aatcttgtgg    900
taagttgtca atttcataaa aatccagct tactactccc tttttaggag tgtgttgtgg     960
ctgcacactt ctgcctttg atatatacgg ttctattctc ggtgtactcc tttattatta    1020
ttaaaacaat cccagttact tggtaagtgc taatcacgaa tcaaagtcaa cataacaaat   1080
catgtgcgta cagctataac tcgattacac aaacaacaaa attcatattt gaacataaat   1140
ccagttgtag catatctggt agtataaagt tttttttttg tatagaagag ttttaatttc   1200
tgtaagtttt ggaaagcatt taatcctaga aattgtagtg tagctcaact aaaaaataaa   1260
tgaacttgaa tcgaaattgg gttgtatcat aaatctttac cactcaaacg aatatttatc   1320
ctaaaccaca aatgactctt ttcatcaagg aatgtttgt tttcagcatt tcaaaaaaaa     1380
acttttctaa tatggttttc atgtttcgtt cttttgaaat ttaacatcta tttaatttgc   1440
acggctccat aaaattcaacg gatacatatt ctgaataatt actaaggagg catatatcgg  1500
ctctcttaat acaaccgctt gtttctcaaa atttattttg agttttgtct acacattctc    1560
aaggacggta caaacacact atagatgttc acaattttt ttttctaaag ttgattgatg    1620
gacaaatgtt tgaacatata aacataaag cactgaatat ttgcttatgc aggagggtatt  1680
tatatcaagt tcgatacttt actaccatag tccctaggac actaaaatgc ttcaatgat    1740
ctgatgaagc ctaagagaga atattgatca gtggagcgac ttgcaactac acatggcaca  1800
agtagactag acacggtata tattcatatt aacttgttaa aattttacta cttaacagtt  1860
cacttgtggt gcatccatat caattcttac ttacacaata caacacctaa caacctaaca  1920
ctataggatg acctagacaa cctttatgtc aatcacactt agaagatgat cgtcttttta  1980
ataaataatg tgtactacac accatgctct ccatatagat caagatctac aaaccccttcc  2040
acttataaac cttaccacca aaaactcatt aagttgcttc atttatctat gctattaaga    2100
aaaaaactta tttcgtttat gccatttcta gaaatggcca gtcacactat tcacaatatt   2160
atataataaa taaaagtttc aaatattcat ccaccaaaaa tcatcaagtc gtgggactta  2220
tatgttaatt agagaagtcc ctttgggtgc aatcgatttt ggaaccccta aattttttct  2280
atacatagaa gagagagatg tctagttgca attgcttttg cgatgtgcca accacccttc   2340
tagctttcat ccacgtctac ttaattgcca ttcttcttct tctttttctt cactattact  2400
acctcctatc ttagcgaatc ttcttcttct tcactattac tacctcccac cttagtgaat   2460
tcatcctcat tgttcacaat gacattgcta agttaactag gtatgctaag tacacaatta  2520
gaatataacc tagagccttt gtttccatca tacttaaaag atgacatttt tatatagata  2580
aagtgtgcta ctcacaaggc ttactatata tgtgatgat acacacaaac tccacaaccc   2640
aaaactcttt caagttgtgt ggcccatcta tgctattaaa aagcccatt agcccatcca   2700
acatgagaaa ccctagggtt tttttcctat aaaagatacc taggttattg ttgcttttcc   2760
accccgcccg ccgccgctcc ctattcctat ttaatcccat ctctcttcct catcaccgct  2820
ctcctctctc caggcaagag gtacgcactt tttgtttcgg atttgaaatc tttgcttcgt  2880
tttactatca ttggtcataa gttctttttt gaagatgttt gagaataagt ttatcattga  2940
gattatcgtc acttgtgata ggaagtacgc aacctgcaag cggaacaagac gtgagcaaag  3000

SEQ ID NO: 255          moltype = DNA   length = 2023
FEATURE                 Location/Qualifiers
misc_feature            1..2023
                        note = Ceres Promoter pOsMEA
source                  1..2023
                        mol_type = unassigned DNA
                        organism = Oryza sativa
SEQUENCE: 255
gagagcagaa catagtagcc gctgttttct gggggtgcaa tttgtgcaag atcgctatcc       60
ttatggacca tgcaagcacc aagcaatatt aagccaggtc caacagcggt cttggggaat     120
tcagaaatga gcttaaaaac ctccttgagc tggccagctc agccaaggag gtccatcatg     180
catgtgcgta ctcaatactt ggaattattg caaaatgatc ggtcattgac tggaagactt     240
tgcgcccttc ctcagccaac cttatgtggc tgcatgcata gagtaccaac aggaaggtag    300
cgtttgttgg aataaggttt gcatccagca tgtccttgta gagcttcaaa gcctcagcac    360
cttgcccat gaaggccata tccagctaat tgcattccat gagaccacat tcttgctatc     420
catactgttg aagtgaagat gctccgagct tcggaaatgc ttccacacta tgcatacatg    480
tcaatgagca ctgtcatgac ataaacattg ggccccaagt cctcctcagc gataatccta    540
```

```
tgcagccact ttcccaggga caaagctcca agctgtgcac acgctgaaag agagctagaa  600
atgatgattg gatttggtca cacgctaagt accagcattt gctcaaagag ggcaattgcc  660
atctccgtcc agccattcta ggcatacct ggtattattg ctttccatga ttccgattcc  720
gtggtcttct atggcatcgc attgaaggcc ttccttgcag actccatatc atttaaccta  780
cagtacaata tggtaattgc tgtcgacact ggagaattca cagtaaatcc agacttgaga  840
ggaccatgta agcattgatc aagcagttca ttcccaaaca gactatacgg gatcagtgcc  900
agtgctcgag tttggcttca attccaaggc catcaaccca ataaacagat taactgatga  960
accaaccatg caattcgccg agcaaacata gattaagcat gtaggcaac caaatctgga 1020
ttctccatca agtcaaagag acgccatgca gaattccaca tccccgctgt atacaccgag 1080
atcaaccggt cagaacatgc tcatactccg ccaaccctct cttcagaaca tgctcatact 1140
ccgccaaccc tctcttctct gcaagaggca tcctccccaa ttcccattg ttatatctgt 1200
tgctggtaag accgttgcca gcgtggttgt gtcagaccga acagactctg cactcgccat 1260
cctcacgaac gactccaggg cctccgaacc aggaagcccg gccggccatc agcgtgttcc 1320
acataacggt atccggcgac tgcacagtgt cgaacatcct gcgtgcgtgg tcacctctgg 1380
acagcatgaa gcgtacaggc tacagcttgg ccaatgcgga cgccacgaac gtgtcggcgg 1440
cgtaacccgc gcgtacagcg cgccgcgcgc gggctgcgga gtcggttgga gacgacacgc 1500
cgccgccatg agagcaatga gcgaggtggc ggcgaaggcg aaggagaagt agtcgaggca 1560
agcggaagag aaggcggcag cggagaaagc gatcggggcg ggaggaggg tgggtgggag 1620
ggagggacgc gtagcggagg tcggaggagg agggagctga ggtttccggg gcggggggtcg 1680
agagggtagt gtacggaggc gagggacacg cgaggatct ggtcgaggta gcgcagtgtg 1740
aaggaaagcc cgatgaggcg gagggcgccg gcgaagagcg gcgcggcgga tagcgggagg 1800
aggcggcgcc ggcgggtct catccgattg gaaacagatt gggaagggg aggggtagg 1860
aatacgtggc gtcggcagta ttaggtagag agagaaaccc tttccatcct ttgtctctta 1920
gccccgaagg agagagaaaa atcagaaaaa aaaaccctc cgcgtgtggg ggaagcagag 1980
ctccggacgc tggcgccgct cgcgccaccg cacccgcacc gcc                    2023

SEQ ID NO: 256          moltype = DNA  length = 2034
FEATURE                 Location/Qualifiers
misc_feature            1..2034
                        note = Ceres Promoter pOsYp102
source                  1..2034
                        mol_type = unassigned DNA
                        organism = Oryza sativa
SEQUENCE: 256
gaacgaccca aacgcgtaaa tggtggtact ggtttccctg ctttgccgag taccagcagc   60
cacgaagaac gttacacaat cgagtacaaa atctataaga gcaagtttaa tagcatagcc  120
aaatactacc tctaaatcat ctatagccaa tttaatagtt catttattca ataattactt  180
ataacatat actacaatca ttaatatatg gtcttacttc ttatacacat aatattttgg  240
agtccgtgtt acagctggct ataaatataa gggattttgg ttggatgtgg tacatcctat  300
tataatgaat ctagacatga aacctgtcca aattcatcgt gctaggatac gcccacatcta  360
accaaaatct cttatctta gggatggaga gagtaataat taaatgaagc taggtagagt  420
ttcccggtca atacgcttgc gtgtgcttat aagagcatgg ccaacagttt cccgatactc  480
ttcccaatat cagttttgag gagttttgtt ggaaaaaatc gctccaacag tagacctaaa  540
tcaccctaa aagcttggcg tttcaaacc cgcatatttc gttctccact tgtagggaag  600
agactcggcg cccaatcctt caaccgcatg cacttcgcgc gcgctgtgtg aaaattttcc  660
taccaggttc ttctttgtgc gttcgtctac ctgtgagtca atccatcacg ccagcagcct  720
catcttcccc gcagctgtct gggaaagcag ccatggctcc cccaagcttc cccagcgttg  780
acatttttttt ctcagcggca gcgccagacc catctccaac ccaattggc ggaccttcgt  840
cggcgctccc ccagcaccac caccgactcg aatcggccgt cgcccctatt catctccaat  900
cgtccctcga ccctaccgca tcctgcagca cagcctgtct ctcgcgtcag actggcgctg  960
cgctccctcc ggtaatgtgc aggcgacaaa ggcccatgc gatgcgacca gcagccggcg 1020
acaaccggag gtgccagtc gctggccttc atcgaatcat cgtgcacctc ggtcggagtc 1080
gatttctgat tgttgctgct gctcaaatct ggagcttgct attgctgaga actgcttggt 1140
ggtggtactg gaaatttgtt gtttgctggc tgatgaaaac tgttgttctt tgctgctaaa 1200
aactgctgct tgctagtact gaaaagtact attgcagctg ctgaaatatc ttgctgcttg 1260
ctgctgaaaa cttcaagttg ttaacaccgt tcacactaaa aaagctgaaa ttttttttct 1320
gggctgaaaa ccccattgtt gatgattgca gaaccaatat ttttcatgt aaaatacagg 1380
agatcgtggt aataatcaag tgaaatatca ttttggggca aatactcaga tcgtacctga 1440
agccaatgga aacattgttc aatgcttaaa ctgtcagtta tgatgtcaaa gagattgatc 1500
actgaatgtc ctgaaaggag ccgtgaggag gatgcagcat tgcagcgtgc gcgagcgtga 1560
gtggaggaga ggaatgacga ttctgttggt agttgtcgat gtgcctact tttttttgttt 1620
tgaggattaa attttgggaa tctcttggag ataaaaggta ttctcatacc ttaaatcctt 1680
tttagagatc taaaaaaaat gatttagggg attgaatttt gggtggctgt tggtgatgct 1740
ctaagttgca catcctcggg aaaaacctcc ctaatccatc agcaaaccga tcaaccaccc 1800
acgacaagtc gacgccaccg tttttttttttt ctccctccta agtcctaacc ccacaaaaat 1860
cccgcgaact ttcgtctcac cacgcgccgc gtgccccta caaataccaa acaacaccca 1920
ccacgtccac tcaaaaccca cgcaggaaac ctcagaaaat caccgtacgc gacgcgggcc 1980
caagaaaacc ccgacagaaa ccgcgcagca gcaacaccac caccggcgtc ggag        2034

SEQ ID NO: 257          moltype = DNA  length = 1877
FEATURE                 Location/Qualifiers
misc_feature            1..1877
                        note = Ceres Promoter pOsYp285
source                  1..1877
                        mol_type = unassigned DNA
                        organism = Oryza sativa
SEQUENCE: 257
ggcccgagtt aaacgatctt ccacgtgtca gcgaatccta gtcgttcgat gaatctgaat   60
ctgacttgtg gtggttggac ggccacgtgt taaaaaggg aaacgtccgc atcacccgat  120
```

```
gctgggacat ttgcaatttc gatccagctg tagattgacc agttgttact ctctttttt   180
taacaccata caaacgtaat actccctctg tcccaaaata taagtatttt ttttaacctc   240
ggttcagtct tcgaggtgct actttgacca ataatattta taaaaataag atgttttaaa   300
taaagagagt tgcatattat gatagctcgt ttaatgataa caaagtacc atcaaattta    360
catgattaat ctttttaatt tatttgctat taatagttaa aatttaaaaa gtttgacttc   420
acactgttct aaaaatactt atattttggg acggagggag tacacattag agcaggtaca   480
atagcagact agtagccagc tataaacata ttttaatgag ataaaagatg agagagaaca   540
gcgggctaca gatctgtagc cagctgcagc acggactcca agacattgtg tgtgtatgac   600
aggtgggacc atatattaat agtacagtaa gtaactattg tatgaattgg ctattagatt   660
agctataggt gaattgtagc tagtagtggg ctatactatt gaacttactc ttatatctct   720
caatatctcc agaaaactag gacgatatat attgatatta acaaagtcat catagatatc   780
tcgctatcga catatatatt acctatcact gaaaaaataa ttaatcataa atgcaagcac   840
atatactacg ttcaacactg aatgtaggta gattggtaga cgggttccac cgcaagaaaa   900
gcattgcacc agtgaagaaa gaaacatcgg aatttgtatg tagtttgttg tttgatgaat   960
tcttttgatt aaaaaaaact aaaatcagag ttgattcagt taatggtgtt gcctacgata  1020
tacttccata tcatgatatc actgtagact atgaatcata tctttaatta aaactaaatc  1080
aagaaattaa gtatgagacc tcaactcaat gaagaatttc tagttgaaaa acattcctag  1140
tgtgcgttcg gatggaggta gggatcttct ctccgttcat ataaaaccgg atggttcatt  1200
agaacatgat taattaagca acagttaatc taaaaataaa ttaatatttt ttaagaaatt  1260
tttgtataga gatctttga aaaaaataca ttggttagaa agcatactaa taaaaagaga   1320
aaaataagaa catagtacta tagtagaaaa tgagaacttg gagtatttga gaggatggga  1380
aataagaaga ttaagaagat gcgtaaagtg aacggttaac gcatgattga ttaattaaat  1440
attaattatt ttaaatttgg aaaataaatt agtatgattt ttaagcaaca tatatatata  1500
tatatatata tatatagaaa aacatagttt tagaaaatat aagcgtgtaa aacgatatgc  1560
aggaacgaaa cgttgagcat tcaaaatttc aaattgaaca tatgaatcaa gagagaataa  1620
aaaaagaggc cttctaggct ggcatggaca atttgaccta ttttcaacta ggttttcaag  1680
cttcgagcat ccacttttgt ccttgcaaac tttatacggc aaggcccgtg aatctagccc  1740
cccacaccac cccacccgcc cgcgccgcgc ggccgcctcg cctccctcc cttctcctcc   1800
tctccgcccc cgccgccagg ccgtccacct ccgccgtctc ctcccccatt cgcacccaag  1860
gcgctggcgc ggaaggc                                                 1877

SEQ ID NO: 258         moltype = DNA  length = 1000
FEATURE                Location/Qualifiers
misc_feature           1..1000
                       note = Ceres Promoter PT0565
source                 1..1000
                       mol_type = unassigned DNA
                       organism = Arabidopsis thaliana
SEQUENCE: 258
caccaaatat agtgttattt caatactaaa atggtgttat ggttggagat gccctaaaga    60
taaacatgac gagacacgag atttattaat ttcttgatca accataactt aataacttaa   120
tattaatttc acttaataat ttccaattaa gtgaatcttt acttcaccaa aagttcctaa   180
cgaactctta ttttctagca tcaatattac catgaactag catcaatact atcatgaaaa   240
attcctactt cctatccaac tcttaataac aatgctagtc ttaacaatat tcatcaaaaa   300
cttgatatag accttctaac ttagccacga ctagtatcgg tgaataccaa aattaatgta   360
ttcatgagaa cttgagattt ctctaatgta ttcttgttac taaacaagta acaacactca   420
agaaatatca tgatcaaata tttttactcat aaactccata tttcacattt tgaaaatttt   480
aaacagcaaa tcacattgaa ttttcgtggt aaaagtattt aaaattgaaa aatagcagct   540
cctgatttca atgtataaat ttatcttat atggtttatg tctccaactt attttaaaaa   600
agagagaaag agcacccaaa aggtgaccgt ttgaaattcg aatttatttc cgtttgaaat   660
tcgaattcaa aaaaagtaaa ccgaaccgag tctcgttcga gactgtcaca cattgtttcc   720
ctaaaagcta attaacccat acgtggcgta atataacagg tcagtgatca atactaaata   780
acagacatac acctttaaaa ttcgtgcacg ctccaaaaca aaatctacac ttcaaaatca   840
acggtcacga tcattcctca aatttcaaaa aattattttaa cctcacttcc ttcgctttgt   900
ttttaaaacc tctctctctt tctctttctc tttgccatt aaaactctgt ttcctttttc    960
agagattctc agagaagatt cattttaccc taagaaaaaa                        1000

SEQ ID NO: 259         moltype = DNA  length = 999
FEATURE                Location/Qualifiers
misc_feature           1..999
                       note = Ceres Promoter YP0015
source                 1..999
                       mol_type = unassigned DNA
                       organism = Arabidopsis thaliana
SEQUENCE: 259
ttgagcctta ttgttgttat tgactttag ccaatagaaa gagatggaaa ttcaataatt      60
atccacaaaa ttccaaatca ttggtgtaca aaaagatcta aggctgttat attttcaaaa   120
aagaaagaaa agaaatgcaa caaatatgga ttaaactgtg gtttgtaaat tgagctttgc   180
atgaaaactt tatcactatg atttcactac tccatattta ttgactaaag tggcactaat   240
gaatttctta atcatgaaat cttgtatcaa aaagtactaa aataaacatg acattggcaa   300
ttaggaaaat tctaaattag aaattagtaa aaatgaaagg tgaagggaa agatgatgat    360
atgaattggt tggtgaccag gagaaatgta tcccgatttt tgcagacact ttcagtgtcc   420
ccattcatat aattatggcc cacctcgtta agattttca ttcaccacca taacaagatc    480
taagcttaga tttcatgtaa ttaaacatat aatattg ccaatactat ctaataagt       540
atacttaagc aaaaattatt actctagtgt aaggcgatga aatataagtt tagttgaaaa   600
tttatgtcga tataacaaag tataatgaat taagccttg gttttcgatt aacaaactaa    660
ttaaacacta gttttgccta ataaaaccgg gaatcgtatt caaaaccgaa cgacaaaaca   720
agggacaagt tgagagacaa aaccaaatca gcatctttct tccagaaatg tcatgaccac   780
atgacgtcat cttgacccct cttccattgt atatctgtgg ataaagcgca cgtgtttaat   840
```

```
tcacgaacct tcgtagtaac gaaaaatcca caactttcat atttttttaat tacccactaa   900
actaaaacaa atttggaaaa acatgaaaaa ctttttcttt ttttccaggt tcgtgaacct   960
cgtaccctct atataaacct cttaaccacc ttccacata                          999

SEQ ID NO: 260          moltype = DNA   length = 999
FEATURE                 Location/Qualifiers
misc_feature            1..999
                        note = Ceres Promoter YP0087
source                  1..999
                        mol_type = unassigned DNA
                        organism = Arabidopsis thaliana
SEQUENCE: 260
tgaattgagt aaaatgtgtt ttcaaacagt taggtggtag aaggtaaagg taataacatc   60
atgatcttac taaaagaatt gttgcatact aactatcaat attctcaaca acataatata   120
atgttttttt aggtaatttt ccattttaat tttttgtgat taaacaatta acaactcga    180
atgatgatga taaaaaaaaa aaattaacaa ctcgaataag ttaaagtagc aatacacatg   240
tcgttcaatt caaccaataa agtaagactt atattttaa gaagttgact aatagcttaa    300
taagttggaa aacttgtgta gtttcttaat tcccacgtgc agtaagaaat aaaaatgaaa   360
aaaattatta tatccttccc actctgcgac ttttctttta ttttatcaaa tattaaaaag   420
attcatatca cagtttacac attgaaatca taaacgataa ttatgtatt tgtaataaaa    480
agttagttct gaagctcata ctttggatag tcgctagtcg ctaatatgct ccttgtaata   540
attaaagtca ctacgacgca cgtcaaagcc gatatttaga ccttaattga tgcgtgtttt   600
tcttttcata taatagtaat ataaattagt actaataaag tatgatggat ggttgagaca   660
gaaaagaaaa aagatgactg tatggtcatc attacaaaga agaatgtatt cttcatgttc   720
ttaagaataa taaaatgtca cttgtaaatc aagttggtaa gcatttttgag aactttgttc   780
gatgcaacgt atgatgattt atgtagacaa aagataaac cgtatcttca actattgcca    840
agaaaagata aaacctaatc tagtcagtct ctcaacataa atacaaccca atagccaaac   900
tgtgtccaat tcggagagaa actaaactaa aacaaaacac aaaagcccaa cataagccca   960
ataaaaccca ttttataaac agaacattac taacactca                          999

SEQ ID NO: 261          moltype = DNA   length = 1000
FEATURE                 Location/Qualifiers
misc_feature            1..1000
                        note = Ceres Promoter YP0093
source                  1..1000
                        mol_type = unassigned DNA
                        organism = Arabidopsis thaliana
SEQUENCE: 261
atgatgaaca ttctacatat ataattatta tgtttaagca cttagacagc ataaattctt   60
tctaattata taaatctaac cttgttacat tgtacatcta taaattactt gaagaaataa   120
cgagttctat ttcttttta aaattaaaaa tactatacca tatctcagtg attaagttga    180
accaaaaggt acgaggaga aacaagcatt tgattcttcc ttatttttatt ttattcatct   240
ctcactaatg atggtggaga aaaaagaaa ataccaaca aacaaatata tattgtcata    300
caaaaatatt tctatatttt tagttaatta gtttatattc ctcactttc agggcttata    360
taagaaagtg agcaaacaca aatcaaaatg cagcagcaaa tactatcatc acccatctcc   420
ttagttctat tttataattc ctcttctttt tgttcatagc tttgtaatta tagtcttatt   480
tctctttaag gctcaataag aggaggtact attactacac ttctctctac ttttacttgt   540
attttagcat taaaatccta aaatccgttt taaattcaaa aataaactta gagatgttta   600
atctcgattc ggttttttcgg ctttaggaga ataattatat gaaattagta tggatatctt   660
tactagtttc cattcaaatg attctgattt caatctaata ctctcactct ttaattaaac   720
tatatgtagt gtaatttcac actgttaaat ttctaccatg tcatgtatat tagagtttga   780
tagaaaattg taaaacatcc atttgaattc gaatgaaaca aaatgtttta aaataaaatt   840
ttggtttta aagaaaaat ctaaaactga attatatcgt ttaaccaagt tgtaaaagtc     900
ataaaacgta gtatcttgta aatcgctctt ccacggtcca aatagacttc tagtaataaa   960
caagtaaaac taatttggt ttcttactaa ttttcacaga                         1000

SEQ ID NO: 262          moltype = DNA   length = 999
FEATURE                 Location/Qualifiers
misc_feature            1..999
                        note = Ceres Promoter YP0108
source                  1..999
                        mol_type = unassigned DNA
                        organism = Arabidopsis thaliana
SEQUENCE: 262
ttagctgaac caggaaattg atctcttata ccagtttccg ggtttagatt ggttgatgg    60
cgatttgatt aaaccccga aattttatgt cgtagttgtg catagtatta ttattctttg    120
cggacaatag acgtatcggg accaagttct gtagcaaaat tgtataagct taagtttgat   180
gaaatttaaa ggtaatcact aaaacccaaa tgggacaata aaccggtgaa gatttagagt   240
ttttaatttt gactcatgaa tctggagaaa gagccctcgt taaaaggagt gaatcaatcc   300
ataggggaaa aagttttgtc tttttaaaaa ctaaagaacc aaaccttaat agaagcagct   360
caatgtgtga caacttttcca ctggcactaa gataaagtga ctagcgatga gtgcaattat   420
tgaaatagta gatggtaaat attacataca agagtaaaaa tatctttatg tcaatgctta   480
attcagtgtt tctggttaac aagagaaact tctctaactt tcgtaattgg gtcttataaa   540
atttttatgca attatgattt taccctttta ctactttca ttagctttca cgaatctatt   600
ttgacaagag aaatcattag aggtaaacat gcttttttggt caagggcctt aacagttcca   660
ccaatcaagc tcaaagttg tacttaaccg acatcttctg tgaaaacata taattacatg   720
tacaaatcaa aactaccta tgaaatatt agaaatattg cagttcattt ctaatttaac    780
ctcttcaact tttaaaacta tttacatttc tttatgtcat ttcagtcat tttgatgcaa    840
attgtaccat ttatggatta tcttcacaaa ttttaagtt ggtgaaaaact ttttggtggg   900
```

```
tagttaaaac ttgaaataga aatttacttt accaaaataa actaatgaaa agtaatcact    960
ccactccta taataagatt tccaacgttc ccactaagc                             999

SEQ ID NO: 263           moltype = DNA   length = 999
FEATURE                  Location/Qualifiers
misc_feature             1..999
                         note = Ceres Promoter YP0022
source                   1..999
                         mol_type = unassigned DNA
                         organism = Arabidopsis thaliana
SEQUENCE: 263
tagttccatt acaatttcca aatgatttgt tacaaagcta caagattatt cgaaatagga    60
tttcatccat aagagagaat ggtgtggtcg acgctacaat gttgatttat tggttgtggt    120
ttgcatcttg gggatgtcaa atcctaagtt tcaagttctt gtaaaaacgt tttcaggttt    180
ctttaatata ttttaatatt aatgtaaaaa gaaaagatat agcttttgta caaaaaaatt    240
tgtttaatca ctatgtagga ggatgcgatc aaattcatgg aatgatgtat tattagcttt    300
tctatcctca ctctaaaaac aatactatag tgagttaaat aatttgatca tttcaatgta    360
gattaaaatt ttattaaaag aagaaaaatt taaaagccta taacaaaata aaaaaggagg    420
ctcgaggtat gatgggtgta gcagaagagc tggcaacagc tatcgactga gtgattacga    480
actcagtact cagtgttctc agctcacaca ctctttttt gttctctttc ttttggacag     540
cttttcatttt ctcttttctt ttttctattt tgtttcaaaa ttccatccat attaaaatag    600
gcctgatcat gagaataaag gaaatactaa tgatgagtt ctcaataagatg ataagaatg     660
caattattat gagctattta ctattgaaaa tgagcaaata aatgtcaaaa cacaatctgg    720
ttaagttaga gcaactccat tgtataggat tcatgtagtt tctaagaaaa caaaatgtat    780
taatatttta cttttacatc caaaaaacca acttatatga gtaatagaaa cgatcctaat    840
attaggaatt ttagagattt tctctcatct gtttcttact ttttcaatat tttttatttt    900
taaaattgta tgagttttcta ctaagaaact actgctggag ttggtcttag cttcccaatg    960
cttctccacc tatatatatg catatctcct tcttaaaac                            999

SEQ ID NO: 264           moltype = DNA   length = 999
FEATURE                  Location/Qualifiers
misc_feature             1..999
                         note = Ceres Promoter YP0080
source                   1..999
                         mol_type = unassigned DNA
                         organism = Arabidopsis thaliana
SEQUENCE: 264
aagcggcaat ttagtaagaa gtactcaaag tatcatttac caaaagtata tggttttggg    60
aagagttgtt agggatgtat tctttctaaa cagatgatat gacgatgttc ttgaaaacta    120
atgttaaaga cggaatctct ggcatcttca ctcgggagat atattaaacc gttgattgta    180
gttagccatg tacttagctt agtgcacaaa taatctgctg caagaaatct ttttctatta    240
taatatctct catttaaaca ttagaacata ttgttaact tgttcttcta gaaataaaac     300
tgctaatttc ttatggtaaa ctatttttcct ttagattgca caatcgaact cgaaaatca    360
gtggagacta tgtgactatg tttatatata tgaaacctaa atcaaattat cccaataatt    420
gggagacaca aagaaaaat tacgaaagaa aacaggaaat caaatcaaaa gataaagaga     480
aggtaaaaaa aggcaagaag cactaatgtt taatatttat agttttctcc attaaagaaa    540
aagcgatgat gtgtgttctc atcttttgtg aaagtatata tattgcttt gcttttctca     600
aaagcaaaag actcatccaa caagaacaaa aaaaaaaact aaagctcaat ccaaaagacg    660
aagaatgcat tggatactac aacttctttt tcacttttct ttcaaattta caattatgat    720
tttcacaata cagtttattc aaaataaat aaaaaaacga ggcatgaaaa taatgattat     780
cctcttcact tattaagcca ctcactataa gcagagcaat tccagaacat agtgagccct    840
caaaacatta aagcatgatg atgtctaatg atgatgatct tcttcgttcc atttctctaa    900
atttttggga tttctgcgaa gacccttctt ctctttctct tctctgaact tcaagattcg    960
tgtcggacaa attttgtttt ttattttct gatgttaca                            999

SEQ ID NO: 265           moltype = DNA   length = 3000
FEATURE                  Location/Qualifiers
misc_feature             1..3000
                         note = Ceres Promoter PR0924
source                   1..3000
                         mol_type = unassigned DNA
                         organism = Arabidopsis thaliana
SEQUENCE: 265
atctataacg agttaacatg ttgccagttt gaatcaagaa gcttggatga tgaatgaatg    60
gatcggtttg tggtacaatt cttaaaattg tagtagagga gacagagaaa aaacatgata    120
agactttggt atttacaact tgacggagac aagacagtaa gccaaatctg tcacaaaaac    180
actcaaactc ttttctcagt gttttgagtt taaagagaga cttattcact tcccctttcg    240
taacacttat ttgtctccca accaaacagt ttctgtcctt tcccttgtcc tcccacgtgc    300
atctttatat ctcatgactt ttcgtttcta gatcttgaat aatgtcttag tggattaggt    360
ttgttgtcgg taaattaggt gaccgttttt ttcttatatt tggaagatcg cgggatgaag    420
cagatactga gtttcaggc atacacacct aatttgaaaa tcattgttag tccaatttca    480
ctttaatctt gtttacaaaa aaattgatct gaaatgttg atgggataag taaaaatgta    540
agttttgcta gtagtcatga tataataata gcaaaccag atcaatttg agcaaaagga     600
agaaacaaaa aacagatcga tccacgagc aagactaagt gtaaagtggt tcccacaaga     660
gccatatgga tatggtcctt caactttaa agcccattac ttcagtggtc gacccgacat     720
tacgccacga gtagtcacgc acgcacgact ccgttcacgt gacattcacg ttgatatttc    780
ccctctact ctcttctgct tggttgatct aaaaacatg aagagaccaa cctaatttca     840
tattaatata tgatatagac ttcatactca acagtcactt tcgtaatcca aatccatatc    900
ttacgaaatt agttcttaat aaaggttgtg gattaagtta taatattgtg ttaagagtta    960
```

```
                                    -continued
agacacagca tataaccttg taccaacagt gctttattct taaatggaaa caaaacatat      1020
gtcaatgtca agcatacagc taaaatatca ttatctaata ttaagagtaa aacaagataa      1080
ttaaaaattg aaacaacacc atattttttat agctttactt atcgtatttt tctagtcttc     1140
atggtaattg tgttgcttta ttttgtttat aaatgaattt ggttcgacca gatagtctaa      1200
tatcagtttt taaacactgg ttttaataaa atcatatgtc ggcaattcaa cctgttacgt      1260
tgtatgattg tatcctagtc aaataggggga ggaggtacta gtcgtttcaa ttagtttacg    1320
taatcaatcc aaagaaacta taagctataa agatcctcaa tttgttggtt acaataaaaa      1380
caacagttgt caaaatttat gtttataaaa agtaataact atgttccttc ccatatagag      1440
caaagtacct caggataggc aaaccgtact taatagccct tattcataat ttgatccaac      1500
tcttccccac aaaattgcaa ctgatgaagt caatacttgt atagtgagtc aagctataaa      1560
tgtctagtga tagttttgtc tcttaaaagg ttaacaaaag ttatgacaag ctgaaaaatc      1620
agagtttgct aggagtatta cttacagtta tcagtttaag tatcacattt atagtattgt      1680
atacaatgat tcttaaattc cacctttttcc gtgcgaaacc aaattttcta ttggaaacat     1740
agaatgtaaa caaaaatatg ggacgttgtc cgttccaaca ttaaccaaac ttgtctatta      1800
ctaatattcg tgttggtttg atgttggatg tctaaattcg ttgaatcatg tgtctcttga      1860
cgaaatatgc atcttcttat ttcttagtat agatgcactt tatcattctt ttagtacatg      1920
cttaattttt tttttttaaaa tatgttgatt gtcatattgc caaaagtatg aattaaagac    1980
gcacatctaa cacaagttag cagccgtaaa tccttccata aatttattt gcaagttttg      2040
ctcattatat aatgagcgga atttatgata taatcgtttg taataatgtt atgtttttgat    2100
caaaatttga aattaaaagt aggtgagaac ttgttataca gtgtagataa ggtggatctt     2160
gaatataaaa ataaaattta taagatgtat ttaaagcaga aaagcataaa actttagata     2220
aaataatgta aaaatgtgtt agcatcaatg ttgggatatt ggccgacccg aacttaatca    2280
atgtcggaag ccattacttc tctcccaaaa gaccttttc cttcggagaa ctaggaactt      2340
cctcactacc tttcgcttaa cgtgaaagcc ataaatttca tatattcata aaaatcagaa     2400
aatctaaaac tgtttagtat cacctgtttt tggtatagac tattggtttt gtgttacttc    2460
ctaaactata tgatttcgta cttcattgga tcttataggga atgaatattc gtaaaaagat   2520
aagttatctg gtgaaacgtt acttcagtca tgttgggtct agatttacat actactatga    2580
aacatttttaa gataataatt atcctagcca actatatgtt ctatattatg ggccaagaag   2640
atatagaact aaaagttcag aatttaacga tataaattac tagtatattc taaatacttga  2700
atgattactg ttttagttgt ttagaataaa tagtagcgtg ttggttaaga taccatcgta   2760
ccacatctat atttgtgtgg gttacataaa atgtacataa tattatatac atatatatgt    2820
atattttga taaagccata tattactcct tgacctctgc ccccatttcc ttttactata     2880
aataggaata ctcatgatcc tctaattcag caatcaacac caacgaacac aacctttcc     2940
aaagccaata ataaaagaac aaaagctttt agtttcatca aagacgaagc tgccttagaa    3000

SEQ ID NO: 266         moltype = DNA  length = 1000
FEATURE                Location/Qualifiers
misc_feature           1..1000
                       note = Ceres Promoter YP0388
source                 1..1000
                       mol_type = unassigned DNA
                       organism = Arabidopsis thaliana
SEQUENCE: 266
agaagtattc acgcaccaag gttatatttg tagtgacata ttctacaatt atcacatttt      60
tctcttatgt ttcgtagtcg cagatggtca atttttttcta taataatttg tccttgaaca   120
caccaaaactt tagaaacgat gatatatacc gtattgtcac gctcacaatg aaacaaacgc    180
gatgaatcgt catcaccagc taaaagccta aaacaccatc ttagtttttca ttcagataaa   240
aagattattt gtttccaacc tttctattga attgattagc agtgatgacg taattagtga    300
tagtttatag taaaacaaat ggaagtggta ataaatttac acaacaaaat atggtaagaa    360
tctataaaat aagaggttaa gagatctcat gttatattaa atgattgaaa gaaaaacaaa    420
ctattggttg atttccatat gtaatagtaa gttgtgatga aagtgatgac gtaattgttt   480
gtatttatag taaaacaaat taaaatggta aggtaaattt ccacaacaaa acttggtaaa    540
aatcttaaaa aaaaaaaaag aggtttagag atcgcatgcg tgtcatcaaa ggttcttttt    600
cactttaggt ctgagtagtg ttagactttg attggtgcac gtaagtgttt cgtatcgcga    660
tttaggagaa gtacgtttta cacgtaggaca caatcaacgg tcaagatttc gtcgtccaga   720
tagaggagcg atacgtcacg ccattcaaca atctcctctt cttcattcct tcattttgat   780
tttgagttttt gatctgcccg ttcaaaagtc tcggtcatct gcccgtaaat ataaagatga   840
ttatatttat ttatatcttc tggtgaaaga agctaatata aagcttccat ggctaatctt    900
gtttaagctt ctcttcttct tctctctcct gtgtctcgtt cactagtttt ttttcggggg    960
agagtgatgg agtgtgtttg ttgaatagtt ttgacgatca                          1000

SEQ ID NO: 267         moltype = DNA  length = 283
FEATURE                Location/Qualifiers
misc_feature           1..283
                       note = Ceres Promoter PD0901
source                 1..283
                       mol_type = unassigned DNA
                       organism = Arabidopsis thaliana
SEQUENCE: 267
caaagtattt gacaagccat atggttttgg atcaaaaagt cggtccaaaa ttaatgtttt     60
atgtgcaaga accgacccat tgtacacacg tgttaacatc ttcaagactt tcatctctat    120
ttttcttttg gtcattaaga tacccattga tccgaatctg ttacattccc acctactttt    180
ttaattttta ctatccactc caaattaaac acaaccgatg attttaataa ttggaagctt    240
tttaaaatat ttctccacgt gcctctttgt gtttgtctat ata                      283

SEQ ID NO: 268         moltype = DNA  length = 1000
FEATURE                Location/Qualifiers
misc_feature           1..1000
                       note = Ceres Promoter PT0623
```

```
source                          1..1000
                                mol_type = unassigned DNA
                                organism = Arabidopsis thaliana
SEQUENCE: 268
aaagttattg acattttgaa aggaccgtaa atattaccaa aaaactgacg gagttaggat    60
cggccacgta gaaagggaca aagagagaac agtcacggac tcggccagac taagtatggg   120
cctgtctgaa tccaaactca gctaagttcc aaaagcataa agagagatgt gtaatgaaat   180
gaacgtattc tagaaacgaa agcaatgtta tgctttgttt ttgagccaca tgttttgggt   240
agatggagag aatcttttt acgttttaa cctaacccac ttggcacttg gccaaaaaag   300
tgagaagaaa ctgtggcgaa tgagtaggcc acgccatgga cttgttcct tgtccttcaa   360
aagttaaatt tatgttatgc gtggggacaa tctaagcaac gtggttcctt taaatatcgc   420
agcttcctct tttacacttt tggagcctac gtgttttgtt ttggaccggc caaatacacg   480
agtcagtcag tttagaaata atttggatgt ccaaaaatct tggagatcca aataaaataa   540
ttagcatgtt ttagttcata agaatatgaa atgtagataa acttgtctata ttaatttttc   600
catagaattg gcttttatc gaggtgatgt acttaatgac tttgttgatt actactcgta   660
taacaataaa gaatatgata ctatgtgaga cttataatga atttggtgtg tgttaattaa   720
tccagttgaa acagtttaat aacaaatcag aataaaaatt gtagtaagaa aatttgaacg   780
ctgatccttc aacctagata gtgaaccttt caaatactat atgattcacg tgtaatgttn   840
ttgaccgttg gttattttttg tgtgaactat attaacttat caatatcgaa aggctaaata   900
agtaaaataac taaagaaaag ttcaggaaac aactcgacct aatgacctat catttctgat   960
cacccgtcct ataaatacat acgtaagatc attcgttact                         1000

SEQ ID NO: 269                  moltype = DNA   length = 873
FEATURE                         Location/Qualifiers
misc_feature                    1..873
                                note = Ceres CLONE ID no.565421
misc_feature                    1..873
                                note = Encodes the peptide sequence at SEQ ID NO 270
source                          1..873
                                mol_type = unassigned DNA
                                organism = Glycine max
SEQUENCE: 269
tcaacataac tgttgttccc ttctttgcac tgcaaattcc ctgtgcatgt attagttttt    60
gattgatttt ttttctctg agggggggcac attaattgtg ctcaatactc atacattgcg   120
gttcctttat tatttgtaa ttcattacat tgatattgat taacatgtca tttgtcaaaa   180
agatctaat ttagttggtt gatcagagtg tgtgatagtc ttcgattcca cggattaaag   240
aaaaattaac atgtcatcaa agcttcaagt tcagcagctt aatcagttaa gggagatttt   300
cggtcgattt gacatggact cagatggaag cctaacaatg ctagagctag cagcacttct   360
taggtctctg gggctgaagc cctcgggtga ccaagtccaa gcactgttag ccaacatgga   420
ctcaaacgcc aatggcaaag tggagtttga tgaattgata agagccatat tacctgacat   480
aaatgcacag gttttgctga accaagaaca gctcctaggg gtgttcaagt gcttcgatcg   540
cgacggcaac ggttacatat cggccgcaga gttggccggg gcaatggcca aaatgggcca   600
gccactcacg taccgagagc tcacgggaga tgatcaaagag gctgacacgg atggggatgg   660
tgttattagc ttcactgagt ttgccactat catggctcgc tctgcttctg attttctagg   720
cctctcgttc tgctgaccgt ataacatata ttcatttcat ctaagttgta caatattctt   780
gatttttttt ccttttgaat gaatgaatca atcaaataat gatatttggt ttgtactggg   840
tattactaat actaattacc cacaattcct gcc                                873

SEQ ID NO: 270                  moltype = AA   length = 161
FEATURE                         Location/Qualifiers
REGION                          1..161
                                note = Ceres CLONE ID no. 565421
REGION                          1..161
                                note = Functional Homolog of Ceres Clone ID no. 29658 at
                                SEQ ID NO. 123
REGION                          87..115
                                note = Pfam Name: efhand Pfam Description: EF hand
VARIANT                         100
                                note = Xaa is any aa, unknown or other
VARIANT                         151
                                note = Xaa is any aa, unknown or other
source                          1..161
                                mol_type = protein
                                organism = Glycine max
SEQUENCE: 270
MSSKLQVQQL NQLREIFGRF DMDSDGSLTM LELAALLRSL GLKPSGDQVQ ALLANMDSNA    60
NGKVEFDELI RAILPDINAQ VLLNQEQLLG VFKCFDRDGX GYISAAELAG AMAKMGQPLT   120
YRELTEMIKE ADTDGDGVIS FTEFATIMAR XASDFLGLSF C                      161

SEQ ID NO: 271                  moltype = DNA   length = 842
FEATURE                         Location/Qualifiers
misc_feature                    1..842
                                note = Ceres CLONE ID no.3747
misc_feature                    1..842
                                note = Encodes the peptide sequence at SEQ ID NO 272
source                          1..842
                                mol_type = unassigned DNA
                                organism = Arabidopsis thaliana
SEQUENCE: 271
```

```
actttttctc caatggcttc tctgaagctt tcaccttctt ctccaatctc catttctaag    60
gttggtgtga ttccttcctc taagaaagga ctttcatttc ttgtaaaagc agagcaccat   120
tcctcgtctt cttcttctca tcttcaagat aaatgtcaga gacgtctgat tgtaacattt   180
ggtgttgttg ctccttggat ctcattgctt agtagagctc cattatcatt tgctgcagaa   240
agcaaaaaag gattccttgc tgtctctgac aataaagatg cttatgcgtt tctctatcca   300
tttggttggc aggaagttgt gattgaaggt caagataagg tatacaaaga tgtgattgag   360
cctttagaaa gtgttagtgt gaatttggtc ccaactagca aacagactat taaagaattt   420
ggccctccca agcagatagc tgaaacactg ataaagaaag ttttggcacc tccaaatcag   480
aaaacaaccc ttattgatgc atcagatcat gatgtcgatg ggaagactta ttatcagttt   540
gagttcactg ttcaagctag aaactacact cgccatgctc tgggtaccat cacggttttc   600
aacggaaact tctacacact gacgacggga gcgaatgaaa ggaggtggga gaagatgaaa   660
gataggcttc acactgtggt agattccttc aagatcactg tttgaaaata ctgtaatcaa   720
gtttgctttg gttgtctctt gttttgccca tttcttgtat ttttgtccat tcttcttctc   780
tctttccctt aacaatattc ttttcctgta agagagattc aataactctt gacttgcctc   840
cc                                                                  842

SEQ ID NO: 272         moltype = AA  length = 230
FEATURE                Location/Qualifiers
REGION                 1..230
                       note = Ceres CLONE ID no. 3747
REGION                 1..230
                       note = Functional Homolog of Ceres Clone ID no. 16403 at
                        SEQ ID NO. 146
REGION                 43..229
                       note = Pfam Name: PsbP Pfam Description: PsbP
source                 1..230
                       mol_type = protein
                       organism = Arabidopsis thaliana
SEQUENCE: 272
MASLKLSPSS PISISKVGVI PSSKKGLSFL VKAEHHSSSS SSHLQDKCQR RLIVTFGVVA    60
PWISLLSRAP LSFAAESKKG FLAVSDNKDA YAFLYPFGWQ EVVIEGQDKV YKDVIEPLES   120
VSVNLVPTSK QTIKEFGPPK QIAETLIKKV LAPPNQKTTL IDASEHDVDG KTYYQFEFTV   180
QARNYTRHAL GTITVFNGNF YTLTTGANER RWEKMKDRLH TVVDSFKITV              230

SEQ ID NO: 273         moltype = DNA  length = 1205
FEATURE                Location/Qualifiers
misc_feature           1..1205
                       note = Ceres CLONE ID no.34878
misc_feature           1..1205
                       note = Encodes the peptide sequence at SEQ ID NO 274
source                 1..1205
                       mol_type = unassigned DNA
                       organism = Arabidopsis thaliana
SEQUENCE: 273
acaacactcg acacagaagc aaaaacaaaa atgggtgaga agatatattcc aaggaacttg    60
aaggaagaag aagaaaacca aagtgaagat tccaaaagtt tgatctcttc acttcctcca   120
gacatagatt gctctgggac caagttgtac aagtatcaag gatgttggta cgataaagac   180
attctccaag caatcctcaa attcaacaaa atctttcagc cacaagaaac cgatatatt   240
gttgcttctt tccccaaatc aggtacgact tggctcaagg cactcacatt cgcactcgct   300
caaagatcaa aacatacttc agaaaatcat cctctgctaa ctcataatcc tcatgagcta   360
gtgccgtacc tcgagctcga tctttatctc aaaagctcga aaccggatat gtccaagtta   420
ccatcatcat ctccgagatt gttctcaacc cacatgtctt tcgatgcgct taaagtacca   480
atgaaggaga ctccttgcaa gatagtgtat gtgtgcagga acgtaaaaga cgtgttggta   540
tcactttggt gtttcgaaaa ctccattagt ggagaaaaca atttaagtct cgaggctttg   600
ttcgagtctt tatgtagcgg agttaactta tgccggtcct tgtgggaaaa tgtgttaggc   660
tattggagag gaagcttcgg agatcctaag catgtgctt ttcttgaggta cgaggagttg   720
aagacggagc ctcgtgtgca aatcaagaga cttcagagt tcttagattt tccattcaca   780
aaggaagaag aagatagtgg aggtgtagac aagatcttgg aactttgttc tctaagaaac   840
cttagcggtt tggagatcaa caaaacagga agcttgtcgg aaggagtaag tttcaagagt   900
tttttccgta aaggggaagt tggtgattgg aagagttta tgactcctga aatggaaaac   960
aaaatcgaca tgattgttga ggagaaactt caaggctctg gtttgatatt gtagagttca   1020
tatctctatg tatatgtgaa caggtttaat ctcaaaccta ataatgctgg tttgttcttt   1080
tcttgtatgc aatgtaataa aagttacttt gatgtaaggt taagagttta agattctgag   1140
cgatgtgtcg ttttttgttc ctttgataat caataaagct agcggctttt cttcttcgcc   1200
aaggc                                                               1205

SEQ ID NO: 274         moltype = AA  length = 327
FEATURE                Location/Qualifiers
REGION                 1..327
                       note = Ceres CLONE ID no. 34878
REGION                 1..327
                       note = Functional Homolog of Ceres Clone ID no. 3964 at SEQ
                        ID NO. 154
REGION                 66..324
                       note = Pfam Name: Sulfotransfer_1 Pfam Description:
                        Sulfotransferase domain
source                 1..327
                       mol_type = protein
                       organism = Arabidopsis thaliana
```

```
SEQUENCE: 274
MGEKDIPRNL KEEEENQSED SKSLISSLPS DIDCSGTKLY KYQGCWYDKD ILQAILKFNK    60
IFQPQETDII VASFPKSGTT WLKALTFALA QRSKHTSENH PLLTHNPHEL VPYLELDLYL   120
KSSKPDMSKL PSSSPRLFST HMSFDALKVP MKETPCKIVY VCRNVKDLV  SLWCFENSIS   180
GENNLSLEAL FESLCSGVNL CGPLWENVLG YWRGSLEDPK HVLFLRYEEL KTEPRVQIKR   240
LAEFLDFPFT KEEEDSGGVD KILELCSLRN LSGLEINKTG SLSEGVSFKS FFRKGEVGDW   300
KSYMTPEMEN KIDMIVEEKL QGSGLIL                                      327

SEQ ID NO: 275          moltype = DNA  length = 1459
FEATURE                 Location/Qualifiers
misc_feature            1..1459
                        note = Ceres CLONE ID no.295570
misc_feature            1..1459
                        note = Encodes the peptide sequence at SEQ ID NO 276
source                  1..1459
                        mol_type = unassigned DNA
                        organism = Zea mays
SEQUENCE: 275
acgcagggtg gctaggagtt gagtcgtgca gaagagacaa aggtcctcac ttggctaagc     60
tagacacgta cgagtgcagg aaacaagata agtcgcggtt tgcgacggcg agaagcgccg   120
gatgagtgtc cactgtccac aagtccgatc tccaattcca gtccgatcgt gagctcagct   180
cagctccgct agtcctctcc ccgcacgcac caccaccagc acagtccag  caccatgggc   240
ggcgccctgc tcctcacgct gctcctcgcg gccgtgcccc tctccktggg cggcggcggc   300
ggcgcgcacc cgggctactc cgacgacgac gagagcgcct gcacggtgga cgcgggcgcg   360
gagctgctgc ggcggatsga ggagcgcggg cccgacaggc gcatcatcga catcacgcac   420
gcggtcgtgc mggacctgcc ggcgttcgcc acggggcggg tcgcgggaat catgctgcgc   480
ctcaggagt  csatggcgga cgggtcgcga gtacaacctg tcggagctgc ggatggagtg   540
ccacaccggc acgcacgtcg acgcgcctgg ccacatcaac caggcccact tsgccgcctg   600
cctcgacgtc gacacgctcg acctccacgt cctcaacgga cctgcattgc tagttgatgt   660
gccaagaaac acaaatataa cagctgaagc gatggaattc ctaaacatcc cgagagggct   720
tcgccgagtt ctgttcagaa cactgaacac tgacaggaag ttgatgtgga ggaagggagg   780
tgacatgagc tacgttgggt ttacagagga tggcgcgcas tggttagtcg acaacaccga   840
cataaagcta gttggagttg acggtctgtc agwggcatca tttgatcacc tgatctctgc   900
ccacgtggtc ttttttcaaa aaccccggga tataatcct  gttgagagcc tsaatctgga   960
cgacatcgag gcgggggatat acatgctgca ctctgtctacct ctccaggctg tcggagccga  1020
gggtgcaccg accagatgca tcctcatcaa gtgatcgttc ctcggccggc ctgctcttgc  1080
tgccttgctg gaggtggcga cactggacca tgyccagctg agctggtgct ccgtcgtggg  1140
tcgcgtggcc aatatttggc tcgcatgcag tcgtcgatct atatggaaca gaacactgca  1200
tgcctatgta gatacgcttg tatggacaat aaaggaaccg cagtacttct gtcgawgaaa  1260
tastwkkggg tgrgmcggta atstaaaaca csaggcmtac twggttaagc tgggaggccc  1320
tgsmwaggct gaggmtrgmg gctggggatg gatccagagt tttwattcga atgstattttt  1380
tttttgggyc mtattttctt tgattgtara craataacat atatgatttt ctatatctct  1440
actaaaaaaa aaaaaaaaa                                               1459

SEQ ID NO: 276          moltype = AA  length = 271
FEATURE                 Location/Qualifiers
REGION                  1..271
                        note = Ceres CLONE ID no. 295570
REGION                  1..271
                        note = Functional Homolog of Ceres CLONE ID no. 8686 at SEQ
                         ID NO. 80
REGION                  57..257
                        note = Pfam Name: Cyclase Pfam Description: Putative cyclase
source                  1..271
                        mol_type = protein
                        organism = Zea mays
SEQUENCE: 276
MGGALLLTLL LAAVPLSLGG GGGAHPGYSD DDESACTVDA GAELLRRMEE RGPDRRIIDI    60
THAVVPDLPA FATGAVAGPM LRLRESMADG SEYNLSELRM ECHTGTHVDA PGHINQAHFA   120
ACLDVDTLDL HVLNGPALLV DVPRNTNITA EAMEFLNIPR GVRRVLFRTL NTDRKLMWRK   180
GGDMSYVGFT EDGAQWLVDN TDIKLVGVDG LSVASFDHLI SAHVVFFKTP DIIPVESLNL   240
DDIEAGIYML HCLPLRLVGA EGAPTRCILI K                                 271

SEQ ID NO: 277          moltype = DNA  length = 1212
FEATURE                 Location/Qualifiers
misc_feature            1..1212
                        note = Ceres CLONE ID no.150484
misc_feature            1..1212
                        note = Encodes the peptide sequence at SEQ ID NO 278
source                  1..1212
                        mol_type = unassigned DNA
                        organism = Arabidopsis thaliana
SEQUENCE: 277
acaacactcg acacaaaagc aaaaacaaaa atgggtgaga agatatattcc aaggaacttg     60
aaggaagaag aagaagaaga agaagaaaac caaagtgaag aaaccaaaag tttgatctct   120
tcacttcctt cagacataga ttgctcaggg accaagttgt acaagtacca aggatgttgg   180
tacgacaaag atattctcca agcaatcctc aatttcaaca aaaactttca gccacaagaa   240
acggatataa ttgttgcttc tttccccaaa tcgggtacga cttggctcaa ggcactcaca   300
ttcgcactcg cgcaaagatc aaaacacact tcagacaatc atcctctgct aactcataat   360
```

```
cctcatgagc tagtgccgta cctcgagctc gatctttatc tcaaaagctc gaaaccggat    420
ttgaccaagt tgccatcatc atctccgaga ttgttctcaa cccacatgtc ctttgatgcg    480
cttaaagtac cgttgaaaga gtctccttgc aagatcgtgt acgtgtgcag gaacgtgaat    540
gacgtattga tatcactttg gtgtttcgaa aactccatga gtggagaaaa caatttaagt    600
ctcgaggctt tgttcgagtc tttatgtagc ggagttaact tatgcggtcc cttatgggaa    660
aatgtgttag gctattggag aggaagcttg gaagatccta agcatgtgct tttcttgagg    720
tacgaggagt tgaagacgga gcctcgtgtg caaatcaaga gacttgcaga gttcttagat    780
tgtccattca caaggaaga agaagatagt ggaggtgtag acaagatctt ggaactttgt    840
tctctaagaa accttagcgg tttggagatc aacaaaacag gaagcttgtc ggaaggagta    900
agtttcaaga gtttttttccg taaaggggaa gttggtgatt ggaagagtta tgactcct     960
gaaatggaaa acaaaatcga catgattgtt gaggagaaac ttcaaggctc tggttttgaaa   1020
ttgtagagtt catatctcta tgtatatgtg tgggaacagg tttaatctca aacctaataa    1080
tgctggtttg ttcttttctt gtatgcaatg taataaaagt tactttgatg taaggttaag    1140
agtttaagat tcttagtgat gtgttgttgt ttttgtttcg tttgataacg aataaagcta    1200
gcggcttttc tc                                                       1212

SEQ ID NO: 278           moltype = AA   length = 331
FEATURE                  Location/Qualifiers
REGION                   1..331
                         note = Ceres CLONE ID no. 150484
REGION                   1..331
                         note = Functional Homolog of Ceres Clone ID no. 3964 at SEQ
                         ID NO. 154
REGION                   70..328
                         note = Pfam Name: Sulfotransfer_1 Pfam Description:
                         Sulfotransferase domain
source                   1..331
                         mol_type = protein
                         organism = Arabidopsis thaliana
SEQUENCE: 278
MGEKDIPRNL KEEEEEEEEN QSEETKSLIS SLPSDIDCSG TKLYKYQGCW YDKDILQAIL     60
NFNKNFQPQE TDIIVASFPK SGTTWLKALT FALAQRSKHT SDNHPLLTHN PHELVPYLEL    120
DLYLKSSKPD LTKLPSSSPR LFSTHMSFDA LKVPLKESPC KIVYVCRNVN DVLISLWCFE    180
NSMSGENNLS LEALFESLCS GVNLCGPLWE NVLGYWRGSL EDPKHVLFLR YEELKTEPRV    240
QIKRLAEFLD CPFTKEEEDS GGVDKILELC SLRNLSGLEI NKTGSLSEGV SFKSFFRKGE    300
VGDWKSYMTP EMENKIDMIV EEKLQGSGLK L                                   331

SEQ ID NO: 279           moltype = DNA   length = 1155
FEATURE                  Location/Qualifiers
misc_feature             1..1155
                         note = Ceres CLONE ID no.1368
misc_feature             1..1155
                         note = Encodes the peptide sequence at SEQ ID NO 280
source                   1..1155
                         mol_type = unassigned DNA
                         organism = Arabidopsis thaliana
SEQUENCE: 279
aaatcaccaa ccagtgacct aacaatggcc gttcctccat tattcttcct cctcacactc     60
ctctctctcc cttctcttct tatctccgcc ggtgcttcca atgccatcc ttctattccc    120
ggaaccgctc ctatcgacgg aggtttcacc gatgaactta aacccattcg ccgtgaagtc    180
tacgggaatg gcaaaatcta tgacatcagt caccgttaca ctccggagat gccgtcgtgg    240
gactcatcgg aaggaatcgg acggttccta tggttagctg cgagtatgaa gaacggatct    300
cttgctaata actctgaaat gaagattccc acgcacactg gtactcatgt tgattcacct    360
ggtcacgtct atgacaagta ttacgatgct ggctttgatg ttgactcgct tgatcttcaa    420
gtcctcaatg gtcttgcgtt gttggttgat gttccaaagg ataagaacat tactgctgaa    480
gtgatgaaat ctcttcacat tccaaaagga gttagtcgtg tgcttttcag aacattgaac    540
actgacaggc gtcttatgtt caagaaagaa tttgatacaa gctatgtcgg attcatgaag    600
gatggtgcgc aatggttggt agacaacaca gacatcaaac ttgttgggat tgattatcta    660
tcagtgactg catatgatga tcttattcca tcccacctag tattcctaaa agaccgggag    720
actatactcg tgragggggtt gaagctggat ggtgtgaagg caggactcta ctctgtccat    780
tgcttacctc taagactggt tggagcagaa gggtctccaa ttcgttgcat cctcatcgat    840
tgattctctc ccatcacaaa cctgccaaat ccgaaattgt ccgtaatcaa aagcttgctt    900
agcttatgaa ctgaatatca gtttgtgcta gatttatgca accaatatgg agattgaagt    960
aggaagaaat aagagagatg cagagaagca caagttgata ataatgaagc accgaagaaa   1020
aaagattttt catttctatg tatatgtcaa taaataaatt aaaaattctc ttaatctgtc   1080
aaggttgtac taattatcaa ataggggaaa gttcataaca tataaatcct tgttgaaata   1140
ggttttgtt ttccc                                                     1155

SEQ ID NO: 280           moltype = AA   length = 272
FEATURE                  Location/Qualifiers
REGION                   1..272
                         note = Ceres CLONE ID no. 1368
REGION                   1..272
                         note = Functional Homolog of Ceres CLONE ID no. 8686 at SEQ
                         ID NO. 80
REGION                   58..258
                         note = Pfam Name: Cyclase Pfam Description: Putative cyclase
source                   1..272
                         mol_type = protein
```

```
                          organism = Arabidopsis thaliana
SEQUENCE: 280
MAVPPLFFLL  TLLSLPSLLI  SAGASNAYPS  IPGTAPIDGG  FTDELKPIRR  EVYGNGKIYD   60
ISHRYTPEMP  SWDSSEGIGR  FLWLAASMKN  GSLANNSEMK  IPTHTGTHVD  SPGHVYDKYY  120
DAGFDVDSLD  LQVLNGLALL  VDVPKDKNIT  AEVMKSLHIP  KGVSRVLFRT  LNTDRRLMFK  180
KEFDTSYVGF  MKDGAQWLVD  NTDIKLVGID  YLSVAAYDDL  IPSHLVFLKD  RETILVEGLK  240
LDGVKAGLYS  VHCLPLRLVG  AEGSPIRCIL  ID                                  272

SEQ ID NO: 281          moltype = DNA  length = 1273
FEATURE                 Location/Qualifiers
misc_feature            1..1273
                        note = Ceres CLONE ID no.124067
misc_feature            1..1273
                        note = Encodes the peptide sequence at SEQ ID NO 282
source                  1..1273
                        mol_type = unassigned DNA
                        organism = Arabidopsis thaliana
SEQUENCE: 281
accaacacac aaagattcca ttacaaataa acaattttca tatatatcta taacaaaaaa   60
aaacaatggc gacctcaagc atgaagagca ttccaatggc gatcccaagt ttctccatgt  120
gtcacaagct cgagctcctt aaagaaggca aaactcgcga cgtcccgaaa gccgaagaag  180
atgagggct aagctgcgag ttccaagaga tgttggattc tcttcctaag gagagaggat   240
ggagaactcg ttacctttac ctattccaag ggttttggtg ccaagccaaa gagattcaag  300
ccatcatgtc tttccaaaaa catttccaat ccctcgaaaa cgacgtcgtt ctcgccacca  360
tacctaaatc cggtacaacc tggctaaaag ctttaacttt caccatcctt aaccgtcacc  420
ggtttgatcc ggttgcctcg agtaccaacc accctcttt cacttccaac cctcatgacc   480
ttgtaccttt cttcgagtac aagctttacg ccaacggaga tgttcccgat ctctcgggtc  540
tagccagtcc aagaacgttc gcaacccact taccgtcgg ttccttaaag gaaacgatcg    600
agaaacccgg tgtgaaggtc gtgtacttgt gccggaaccc gtttgacaca ttcatctctt  660
cgtggcatta caccaacaac atcaaatccg agtcagtgag cccagtcttg ctagaccaag  720
cttttgatct gtattgccgg ggagtgatcg ggtttggccg gttttgggaa cacatgttgg  780
gatactggag agagagcttg aagagaccag agaaagtctt ctttttaagg tacgaggatc  840
tcaaagacga catcgagacc aacttgaaga ggcttgcaac tttcttagag cttcctttca  900
ccgaagaaga ggaacgaaag ggagttgtga aggctatcgc cgagctgtgt agctcgaga   960
atctgaagaa gttggaggtg aacaagtcaa acaagtcgat caagaacttt gagaatcgat  1020
tcttgtttcg gaaaggagaa gtgagtgatt gggttaacta tttgtcacct tcacaagtgg  1080
aaagattgtc agccttagtg gatgacaagt taggtggatc tggtctcact ttcaggttga  1140
gctaaatata aggccacgtg cccccatttc tactcttgtt ctgagggcct actatatacg   1200
ttaagctaag ttaaggcagt tgtattgttg ttacagatag acatcgaagc aacgtaacgt  1260
ccataattaa gtc                                                       1273

SEQ ID NO: 282          moltype = AA  length = 359
FEATURE                 Location/Qualifiers
REGION                  1..359
                        note = Ceres CLONE ID no. 124067
REGION                  1..359
                        note = Functional Homolog of Ceres Clone ID no. 3964 at SEQ
                         ID NO. 154
REGION                  91..353
                        note = Pfam Name: Sulfotransfer_1 Pfam Description:
                         Sulfotransferase domain
source                  1..359
                        mol_type = protein
                        organism = Arabidopsis thaliana
SEQUENCE: 282
MATSSMKSIP  MAIPSFSMCH  KLELLKEGKT  RDVPKAEEDE  GLSCEFQEML  DSLPKERGWR   60
TRYLYLFQGF  WCQAKEIQAI  MSFQKHFQSL  ENDVVLATIP  KSGTTWLKAL  TFTILNRHRF  120
DPVASSTNHP  LFTSNPHDLV  PFFEYKLYAN  GDVPDLSGLA  SPRTFATHLP  FGSLKETIEK  180
PGVKVVYLCR  NPFDTFISSW  HYTNNIKSES  VSPVLLDQAF  YLCRGVIGF  GPFWEHMLGY  240
WRESLKRPEK  VFFLRYEDLK  DDIETNLKRL  ATFLELPFTE  EEERKGVVKA  IAELCSFENL  300
KKLEVNKSNK  SIKNFENRFL  FRKGEVSDWV  NYLSPSQVER  LSALVDDKLG  GSGLTFRLS   359

SEQ ID NO: 283          moltype = DNA  length = 845
FEATURE                 Location/Qualifiers
misc_feature            1..845
                        note = Ceres ANNOT ID no.870567
misc_feature            1..845
                        note = Encodes the peptide sequence at SEQ ID NO 284
source                  1..845
                        mol_type = unassigned DNA
                        organism = Arabidopsis thaliana
SEQUENCE: 283
aataagaaaa tcaaaatctt tactcgtttg aaatttgtaa tccattacct gtcatcgttg   60
acttgtcaag aagaaacaaa tcaactctaa aaagaaaaat gttgttcatc gaaatcgttc  120
cttgacagta ttcaaaatca gattcgagat gagctgcgac ggaggcaaac cggcgccggc  180
gaaactaggc gacgaacaac tagcggagct ccgggagata ttccgatcat ttgaccagaa   240
caaggatgga agtttgacgg agctgacgtt aggctcactt ctaagatctc tcggtctaaa  300
gccgagtcaa gaccaactcg acacattgat ccagaaagca gatcggaata caacggact   360
ggtcgagttc tccgagttcg tcgccctcgt cgagccagat ctggtcaagt gtccttacac  420
```

```
ggatgatcag cttaaagcca tctttagaat gtttgaccgc gatgaaacg gttacataac    480
ggcggcggag ttagcccatt cgatggcgaa gctaggtcac gcgttgacgg cggaggagtt    540
aacgggaatg atcaaagaag ctgatcgaga cggcgatggt tgtattgatt ccaagagtt     600
tgttcaagcg attacttcag ctgcgtttga taatgcttgg ggttgaagaa agaaaggtat    660
atatatacat agtttgaaat acttgtgttt tgttttttg gcttcatcct caaatcaaag     720
acatttggaa gtatatgtgt gtaggtgcga ttccatggaa aatgtgtgtt atttattgtt    780
tcatatattt ctttgatgaa attttgatag cttgaagaga aagctatcat tgttggtttt    840
agggc                                                                 845

SEQ ID NO: 284          moltype = AA  length = 165
FEATURE                 Location/Qualifiers
REGION                  1..165
                        note = Ceres ANNOT ID no. 870567
REGION                  1..165
                        note = Functional Homolog of Ceres Clone ID no. 29658 at
                         SEQ ID NO. 123
REGION                  56..84
                        note = Pfam Name: efhand Pfam Description: EF hand
source                  1..165
                        mol_type = protein
                        organism = Arabidopsis thaliana
SEQUENCE: 284
MSCDGGKPAP AKLGDEQLAE LREIFRSFDQ NKDGSLTELE LGSLLRSLGL KPSQDQLDTL     60
IQKADRNNNG LVEFSEFVAL VEPDLVKCPY TDDQLKAIFR MFDRDGNGYI TAAELAHSMA    120
KLGHALTAEE LTGMIKEADR DGDGCIDFQE FVQAITSAAF DNAWG                    165

SEQ ID NO: 285          moltype = DNA  length = 1248
FEATURE                 Location/Qualifiers
misc_feature            1..1248
                        note = Ceres ANNOT ID no.864284
misc_feature            1..1248
                        note = Encodes the peptide sequence at SEQ ID NO 286
source                  1..1248
                        mol_type = unassigned DNA
                        organism = Arabidopsis thaliana
SEQUENCE: 285
gttcacttaa caaacaaga accaaaaaaa atggatgaga aagatattct aaggaacttg     60
agggaagaag aagaagaaga agaagaaaat caaagcgaag aaaccaaaat tttgatctct    120
tcacttcctt gggagataga ttaccttggg aacaagctta tcaagtacca aggatattgg    180
tactacgaag acgttctcca atcaatcccc aatatacact cgagtttca gccacaagaa    240
accgatatag ttgttgcttc tttctacaaa tcgggcacga cttggctcaa agcactcaca    300
tttgcactcg ttcaacgatc aaaacactcg ttagaagatc atcatcatcc tctgctatct    360
cataaccctc atgagatagt accgtacctc gagctagatc tgtatctcaa cagctcaaaa    420
ccggacttga ccaagttctt atcatcatca tcatcatcat catctccgag attgttctca    480
actcatatgt ccttggacgc gcttaaacta cccttgaaga gtctcccttg caaggtagtg    540
tacgtgtgca ggaacgtgaa agacgtgttg gtgtcacttt ggtgtttcct caatgccaac    600
aagggagtag aatgggagga ttttagccaa aatgaaaaga tcattcgagc ggagaattat    660
tctttcaagg ctatatttga gtcattctgc aacggagtta ccctacacgg tcccttttgg    720
gaccatgcac agagctattg gcgaggcagc ttggaagatc ctaagcattt tcttttcatg    780
aggtacgagg agttgaaagc ggagcctcgt actcaggtca agagacttgc agagttcttg    840
gattgtccat tcactaagga agaggaagat agcggaactg tagacaagat cttggaactt    900
tgctctctaa gtaatttaag cagtttggag atcaacaaaa ctggatcctt gggtggagta    960
gattacaaga cttatttccg taaggacaa gttggtgact ggaagagtta tatgacctct    1020
gaaatgtaa ataaaatcga tatgatcgtc gaggagaaac tcaaaggttc cggtttgaaa    1080
ttctagaatt atgcgtgtgc tttgtgaaga actgcagaaa aagtgttctt gaatgcgtta    1140
tttaataata aaagttacat tgtcatatat ataactttga tgtatcatta caactgatgt    1200
gtggtttttg ttctctttga tgttgcaata aaaaccttct ttacttct                1248

SEQ ID NO: 286          moltype = AA  length = 351
FEATURE                 Location/Qualifiers
REGION                  1..351
                        note = Ceres ANNOT ID no. 864284
REGION                  1..351
                        note = Functional Homolog of Ceres Clone ID no. 3964 at SEQ
                         ID NO. 154
REGION                  70..348
                        note = Pfam Name: Sulfotransfer_1 Pfam Description:
                         Sulfotransferase domain
source                  1..351
                        mol_type = protein
                        organism = Arabidopsis thaliana
SEQUENCE: 286
MDEKDILRNL REEEEEEEEN QSEETKILIS SLPWEIDYLG NKLFKYQGYW YYEDVLQSIP     60
NIHSSFQPQE TDIVVASFYK SGTTWLKALT FAVVQRSKHS LEDHHHPLLS HNPHEIVPYL    120
ELDLYLNSSK PDLTKFLSSS SSSSPRLFS THMSLDALKL PLKKSPCKVV YVCRNVKDVL     180
VSLWCFLNAN KGVEWGDFSQ NEKIIRAENY SFKAIFESFC NGVTLHGPFW DHAQSYWRGS    240
LEDPKHFLFM RYEELKAEPR TQVKRLAEFL DCPFTKEEED SGTVDKILEL CSLSNLSSLE    300
INKTGSLGGV DYKTYFRKGQ VGDWKSYMTS EMVNKIDMIV EEKLKGSGLK F             351
```

| SEQ ID NO: 287 | moltype = DNA length = 1177 |
|---|---|
| FEATURE | Location/Qualifiers |
| misc_feature | 1..1177 |
| | note = Ceres ANNOT ID no.858178 |
| misc_feature | 1..1177 |
| | note = Encodes the peptide sequence at SEQ ID NO 288 |
| source | 1..1177 |
| | mol_type = unassigned DNA |
| | organism = Arabidopsis thaliana |

SEQUENCE: 287

```
atagagagct taagcaaaag atctcatact ttcaagattg atcgatctct caagtctcaa    60
caatgtcatc atcatcatca gttcctgctt acttgggaga tgaagatctg acacaagaaa   120
caagagctct gatctcttct cttcctaaag agaaaggttg gttagtgagt gaaatatatg   180
aattccaagg actttggcac acacaagcta ttttacaagg aatcttgatc tgccaaaaac   240
gctttgaagc taaagattcc gacattatcc tcgtcactaa tcctaaatca ggtaccactt   300
ggttaaaagc tcttgtcttt gctctcctta accgacacaa gtttccagtt tcttcttctg   360
gtaaccatcc tcttctggtc accaatccac accttcttgt gcccttcttg gaggagttt    420
actacgagtc cccagatttc gatttctcca gtttgccttc tccaagactg atgaacactg   480
acatatcgca tctttcgctc cccgagtctg ttaagagctc gtcttgtaag attgtgtatt   540
gttgtaggaa ccctaaggac atgtttgtgt cctatggca ttttgggaaa aagctagctc    600
ctgaggaaac cgcggattat cctatcgaaa agcggttga agcgttttgt gaagggaagt    660
ttataggtgg acccttttgg gatcatatat tggagtacgt gtatgcaagc cgtgagaatc   720
cgaacaaggt cttgtttgtt acttacgagg agctaaagca gcagaccgaa gttgagatga   780
agcggatcgc ggagttcttg aatgtggct tattgaaga agaagaagtg agagagattg     840
tgaagttgtg tagctttgag agtttaagta atttggaagt taacaaagaa gggaaattgc   900
caaatggaat agagactaaa actttctttta gaaaaggaga tggagagata                960
ctttgagtga gtcattggca gaggaaattg atagaaccat tgaagagaag tttaaaggtt   1020
ctggtcttaa attttcttct tgaatcaatc tttgaaactt gttctcatgt tcttgttttg   1080
cttcaattat gttatttctt gttttatata ttttctgct gttatgtttg tgtttgtgtt    1140
tatgaataaa atgaaataaa ttatgtttgt gtttttct                          1177
```

| SEQ ID NO: 288 | moltype = AA length = 326 |
|---|---|
| FEATURE | Location/Qualifiers |
| REGION | 1..326 |
| | note = Ceres ANNOT ID no. 858178 |
| REGION | 1..325 |
| | note = Functional Homolog of Ceres Clone ID no. 3964 at SEQ ID NO. 154 |
| REGION | 65..321 |
| | note = Pfam Name: Sulfotransfer_1 Pfam Description: Sulfotransferase domain |
| source | 1..326 |
| | mol_type = protein |
| | organism = Arabidopsis thaliana |

SEQUENCE: 288

```
MSSSSSVPAY LGDEDLTQET RALISSLPKE KGWLVSEIYE FQGLWHTQAI LQGILICQKR    60
FEAKDSDIIL VTNPKSGTTW LKALVFALLN RHKFPVSSSG NHPLLVTNPH LLVPFLEGVY   120
YESPDFDFSS LPSPRLMNTH ISHLSLPESV KSSSCKIVYC CRNPKDMFVS LWHFGKKLAP   180
EETADYPIEK AVEAFCEGKF IGGPFWDHIL EYWYASRENP NKVLFVTYEE LKKQTEVEMK   240
RIAEFLECGF IEEEVREIV KLCSFESLSN LEVNKEGKLP NGIETKTFFR KGEIGGWRDT    300
LSESLAEEID RTIEEKFKGS GLKFSS                                        326
```

| SEQ ID NO: 289 | moltype = DNA length = 486 |
|---|---|
| FEATURE | Location/Qualifiers |
| misc_feature | 1..486 |
| | note = Ceres ANNOT ID no.842118 |
| misc_feature | 1..486 |
| | note = Encodes the peptide sequence at SEQ ID NO 123 |
| source | 1..486 |
| | mol_type = unassigned DNA |
| | organism = Arabidopsis thaliana |

SEQUENCE: 289

```
atggcgtcaa caaaaccaac cgatcaaatc aaacaactca agatatcttt cgctcgtttc    60
gacatggaca aggacggaag cttaacgcag ctagaactcg ccgctcttct gcgttctctc   120
ggaatcaaac ctcgcagcga tcaaatctct cttctgttga accaaatcga ccgtaacggt   180
aacggatccg tagagttcga cgagctggtc gtggcgatat tgccggatat aaacgaagag   240
gtttttgataa atcaagaaca gttgatggag gttttccgtt cgtttgatcg tgacggaaac   300
ggttcaataa cggcggcgga acttgctggg tcaatggcta aaatgggaca tccgttgact   360
taccgtgaat taacggaaat gatgacggaa gctgattcta acggtgacgg tgttattagt   420
tttaatgttt tttctcatat tatggctaaa tcggctgctg attttcttgg attaaccgct   480
tcttga                                                              486
```

| SEQ ID NO: 290 | moltype = DNA length = 633 |
|---|---|
| FEATURE | Location/Qualifiers |
| misc_feature | 1..633 |
| | note = Ceres ANNOT ID no.566551 |
| misc_feature | 1..633 |
| | note = Encodes the peptide sequence at SEQ ID NO 291 |
| source | 1..633 |

```
                        mol_type = unassigned DNA
                        organism = Arabidopsis thaliana
SEQUENCE: 290
atggcggcga acgattcttc aaatgctatt gacatcgacg ggaatctcga ctccgattcg    60
aatcttaaca ctgacggtga cgaagcgacc gataatgatt cctcgaaggc attggttact   120
atccctgctc cagccgtttg tcttttccgg ttcgccggag atgctgctgg tgcgccgtt    180
atgggctcta tcttcggata tggttcagga ttgttcaaga agaaaggctt caaaggatca   240
tttgcagatg cagggcagtc tgctaagact tttgctgttt tatctggagt ccacagtttg   300
gttgtttgcc ttctgaagca aatccgaggc aaagatgacg ccattaatgt tggagtagca   360
gggtgttgca ctggtcttgc tcttagtttc cctggtgctc cacaggctct tctacagagt   420
tgtctcacgt ttggggcatt ctcttttatt cttgagggac tcaacaaaag acaaacagct   480
ttggcacact cggtctcgtt gagacaccaa accggactgt tccaagatca tcatcgtgct   540
ttaccactct ctcttgctct cccgatccct gaagaaatca aggagccttt tcttctttc    600
tgcaagtcct tagctaaacc aaggaagttc taa                                 633

SEQ ID NO: 291       moltype = AA   length = 210
FEATURE              Location/Qualifiers
REGION               1..210
                     note = Ceres ANNOT ID no. 566551
REGION               1..210
                     note = Functional Homolog of Ceres CLONE ID no. 965405 at
                            SEQ ID NO. 172
REGION               40..158
                     note = Pfam Name: Tim17 Pfam Description: Tim17/Tim22/Tim23
                            family
source               1..210
                     mol_type = protein
                     organism = Arabidopsis thaliana
SEQUENCE: 291
MAANDSSNAI DIDGNLDSDS NLNTDGDEAT DNDSSKALVT IPAPAVCLFR FAGDAAGGAV     60
MGSIFGYGSG LFKKKGFKGS FADAGQSAKT FAVLSGVHSL VVCLLKQIRG KDDAINVGVA    120
GCCTGLALSF PGAPQALLQS CLTFGAFSFI LEGLNKRQTA LAHSVSLRHQ TGLFQDHHRA    180
LPLSLALPIP EEIKGAFSSF CKSLAKPRKF                                     210

SEQ ID NO: 292       moltype = DNA   length = 1323
FEATURE              Location/Qualifiers
misc_feature         1..1323
                     note = Genomic Sequence Of Ceres ANNOT ID no. 566551
misc_feature         1..1323
                     note = Encodes the peptide sequence at SEQ ID NO 291
source               1..1323
                     mol_type = unassigned DNA
                     organism = Arabidopsis thaliana
SEQUENCE: 292
tggcggcgaa cgattcttca aatgctattg acatcgacgg gaatctcgac tccgattcga    60
atcttaacac tgacggtgac gaagcgaccg ataatgattc tcgaaggca ttggttacta    120
tccctgctcc agccgtttgt cttttccggt tcgccggaga tgctgctggt ggcgccgtta   180
tgggctctat cttcggatat ggtgctcttc ttctttctat tttgtttctt ctattgcttg   240
gttttatctg ctattgcttt actctctgat agtgaattga gaattactgg caaacaattg   300
agtttgtact ctttctctca tttaagttga tttcaaaaca tgtttcgtgg ataagggttt   360
gagaaatcat agttgtttta gcagactagc cttttgagtt attttcagga gtaatctaga   420
tttaggggat tcaacattcc tcaagtttgg ttatgttttg ctcctggaag ctatagaatt   480
gaattagctt agttttcatt aaagagcgtc aatgtgataa gattggctac tgatttgatt   540
acgatgatga aattgtgaaa tattatctca ctatataagt tggattcag gttcaggatt    600
gttcaagaag aaaggcttca aaggatcatt gcagatgcag gggcagtctg ctaaggtacc   660
cctcatcttt atgctatagc atatatatgc ttattgttcc aagaaactga gtaatttgct   720
aatttttgt tcaagacttt tgctgtttta tctggagtcc acagtttggt tgtttgcctt    780
ctgaagcaaa tccgaggcaa agatgacggt gagactcttc agattgcttc cttcttgtgt   840
aaatgattag tttttacatg aacttgtaat tctctctcca cttatattgc ttttgttctt   900
ttttacagc cattaatgtt ggagtagcag ggtgttgcac tggtcttgct cttagtttcc    960
ctggtaatcc aaatccatta tgctcattct gatttctact ttggcgttat gtatcatatc  1020
aaagatgcaa tcatcacaga gaggagagct aatagattct tcttatatg gcttttttta   1080
caggtgctcc acaggctctt ctacagagtt gtctcacgtt tggggcattc tcttttattc   1140
ttgagggact caacaaaaga caaacagctt tggcacactc ggtctcgttg agacaccaa    1200
ccggactgtt ccaagatcat catcgtgctt taccactctc tcttgctctc ccgatccctg   1260
aagaaatcaa ggagcctttt cttctttctg caagtccttt agctaaacca aggaagttct   1320
aat                                                                 1323

SEQ ID NO: 293       moltype = DNA   length = 486
FEATURE              Location/Qualifiers
misc_feature         1..486
                     note = Genomic Sequence Of Ceres ANNOT ID no. 842118
misc_feature         1..486
                     note = Encodes the peptide sequence at SEQ ID NO 123
source               1..486
                     mol_type = unassigned DNA
                     organism = Arabidopsis thaliana
SEQUENCE: 293
tggcgtcaac aaaaccaacc gatcaaatca aacaactcaa agatatcttc gctcgtttcg    60
```

-continued

```
acatggacaa ggacggaagc ttaacgcagc tagaactcgc cgctcttctg cgttctctcg   120
gaatcaaacc tcgcagcgat caaatctctc ttctgttgaa ccaaatcgac cgtaacggta   180
acggatccgt agagttcgac gagctggtcg tggcgatatt gccggatata aacgaagagg   240
ttttgataaa tcaagaacag ttgatggagg ttttccgttc gtttgatcgt gacggaaacg   300
gttcaataac ggcggcggaa cttgctgggt caatggacat ccgttgactt               360
accgtgaatt aacggaaatg atgacggaag ctgattctaa cggtgacggt gttattagtt   420
ttaatgagtt ttctcatatt atggctaaat cggctgctga ttttcttgga ttaaccgctt   480
cttgat                                                               486

SEQ ID NO: 294          moltype = DNA  length = 1177
FEATURE                 Location/Qualifiers
misc_feature            1..1177
                        note = Genomic Sequence Of Ceres ANNOT ID no. 858178
misc_feature            1..1177
                        note = Encodes the peptide sequence at SEQ ID NO 288
source                  1..1177
                        mol_type = unassigned DNA
                        organism = Arabidopsis thaliana
SEQUENCE: 294
catagagagc ttaagcaaaa gatctcatac tttcaagatt gatcgatctc tcaagtctca    60
acaatgtcat catcatcatc agttcctgct tacttgggag atgaagatct gacacaagaa   120
acaagagctc tgatctcttc tcttcctaaa gagaaaggtt ggttagtgga tgaaatatat   180
gaattccaag gactttggca cacacaagct attttacaag gaatcttgat ctgccaaaaa   240
cgctttgaag ctaaagattc cgacattatc ctcgtcacta atcctaaatc aggtaccact   300
tggttaaaag ctcttgtctt tgctctcctt aaccgacaca agtttccagt ttcttcttct   360
ggtaaccatc ctcttctggt caccaatcca caccttcttg tgcccttctt ggaaggagtt   420
tactacgagt ccccagattt cgatttctct agtttgcctt ctccaagact gatgaacacg   480
cacatatcgc atctttcgct ccccgagtct gttaagagct cgtcttgtaa gattgtgtat   540
tgttgtagga accctaagga catgtttgtg tccttatggc attttgggaa aaagctagct   600
cctgaggaaa ccgcggatta tcctatcgaa aaagcgtttg aagcgttttg tgaagggaag   660
tttataggtg gaccctttg ggatcatata ttggagtact ggtatgcaag ccgcgagaat   720
ccgaacaagg tcttgtttgt tacttacgag gagctaaaga agcagaccga agttgagatg   780
aagcggatcg cggagttctt ggaatgtggc tttattgaag aagaagaagt gagagagatt   840
gtgaagttgt gtagctttga gagtttaagt aatttggaag ttaacaaaga agggaaattg   900
ccaaatggaa tagagactaa aactttcttt agaaaaggag agattggagg atggagagat   960
actttgagtg agtcattggc agaggaaatt gatagaacca ttgaagagaa gtttaaaggt  1020
tctggtctta aattttcttc ttgaatcaat ctttgaaact tgtctcatg ttcttgtttt   1080
gcttcaatta tgttatttct tgttttatat attttttctgc tgttatgttt gtgtttgtgt  1140
ttatgaataa aatgaaataa attatgtttg tgttttc                             1177

SEQ ID NO: 295          moltype = DNA  length = 1248
FEATURE                 Location/Qualifiers
misc_feature            1..1248
                        note = Genomic Sequence Of Ceres ANNOT ID no. 864284
misc_feature            1..1248
                        note = Encodes the peptide sequence at SEQ ID NO 286
source                  1..1248
                        mol_type = unassigned DNA
                        organism = Arabidopsis thaliana
SEQUENCE: 295
ttcacttaac aaaacaagaa ccaaaaaaaa tggatgagaa agatattcta aggaacttga    60
gggaagaaga agaagaagaa gaagaaaatc aaagcgaaga aaccaaaatt ttgatctctt   120
cacttccttg ggagatagat taccttggga caagcttttt caagtaccaa ggatattggt   180
actacgaaga cgttctccaa tcaatcccca atatacactc gagttttcag ccacaagaaa   240
ccgatatagt tgttgcttct ttctacaaat cgggcacgac ttggctcaga gcactcacat   300
ttgcactcgt tcaacgatca aaacactcgt tagaagatca tcatcatcct ctgctatctc   360
ataaccctca tgagatagta ccgtacctcg agctagatct gtatctcaac agctcaaaac   420
cggacttgac caagttctta tcatcatcat catcatcatc atctccgaga ttgttctcaa   480
ctcatatgtc cttggacgcg cttaaactac ccttgaagaa gtctccttgc aaggtagtgt   540
acgtgtgcag gaacgtgaaa gacgtgttgg tgtcactttg gtgtttcctc aatgccaaca   600
agggagtaga atggggagat tttagccaaa atgaaaagat cattcgagcg gagaattatt   660
ctttcaaggc tatatttgag tcattctgca acggagttac cctacacggt ccctttgggg   720
accatgcaca gagctattgg cgaggcagct tggaagatcc taagcatttt cttttcatga   780
ggtacgagga gttgaaagcg gagcctcgta ctcaggtcaa gagacttgca gagttcttgg   840
attgtccatt cactaaggaa gaggaagata gcggaactgt agacaagatc ttggaacttt   900
gctctctaag taatttaagc agtttggaga tcaacaaaac tggatcctg ggtggagtag    960
attacaagac ttatttccgt aaaggacaag ttggtgactg gaagagttat atgacctctg  1020
aaatggtaaa taaaatcgat atgatcgtcg aggagaaact caaaggttcc ggtttgaaat  1080
tctagaatta tgcgtgtgct ttgtgaagaa ctgcagaaaa agtgttcttg aatgcgttat  1140
ttaataataa aagttacatt gtcatatata taactttgat gtatcattac aactgatgtg  1200
tggtttttgt tctctttgat gttgcaataa aaaccttctt tacttcta                1248

SEQ ID NO: 296          moltype = DNA  length = 845
FEATURE                 Location/Qualifiers
misc_feature            1..845
                        note = Genomic Sequence Of Ceres ANNOT ID no. 870567
misc_feature            1..845
                        note = Encodes the peptide sequence at SEQ ID NO 284
source                  1..845
```

```
                        mol_type = unassigned DNA
                        organism = Arabidopsis thaliana
SEQUENCE: 296
ataagaaaat caaaatcttt actcgtttga aatttgtaat ccattacctg tcatcgttga   60
cttgtcaaga agaaacaaat caactctaaa aagaaaaatg ttgttcatcg aaatcgaagc  120
ttgacagtat tcaaaatcag attcgagatg agctgcgacg gaggcaaacc ggcgccggcg  180
aaactaggcg acgaacaact agcggagctc cgggagatat tccgatcatt tgaccagaac  240
aaggatggaa gtttgacgga gctcgagtta ggctcacttc taagatctct cggtctaaag  300
ccgagtcaag accaactcga cacattgatc cagaaagcag atcggaataa caacggactg  360
gtcgagttct ccgagttcgt cgccctcgtc gagccagatc tggtcaagtg tccttcacag  420
gatgatcagc ttaaagccat ctttagaatg tttgaccgcg atggaaacgg ttacataacg  480
gcggcggagt tagcccattc gatggcgaag ctaggtcacg cgttgacggc ggaggagtta  540
acgggaatga tcaaagaagc tgatcgagac ggcgatggtt gtattgattt ccaagagttt  600
gttcaagcga ttacttcagc tgcgtttgat aatgcttggg gttgaagaaa gaaaggtata  660
tatatacata gtttgaaata cttgtgtttt gtttttttgg cttcatcctc aaatcaaaga  720
catttggaag tatatgtgtg taggtgcgat tccatggaaa atgtgtgtta tttattgttt  780
catattattc tttgatgaaa ttttgatagc ttgaagagaa agctatcatt gttggtttta  840
gggca                                                              845

SEQ ID NO: 297          moltype = DNA  length = 2020
FEATURE                 Location/Qualifiers
misc_feature            1..2020
                        note = Ceres CLONE ID no.1792902
misc_feature            1..2020
                        note = Encodes the peptide sequence at SEQ ID NO 298
source                  1..2020
                        mol_type = unassigned DNA
                        organism = Panicum virgatum
SEQUENCE: 297
gtcactctcg gcactgctcc cagctgttgc gacctccgaa catccaaggc tcctgcaccc   60
ctgtcagtcc tagctccagc caaaaatcgt tggctcccgc tgcctgctcc tccgccttgc  120
acctccatg accttccacg cgacatgatt gcattgcagg ccctgcgga gctcagctgt  180
cctcccacgc cgctgacgcc ttcttgttgc ctccacgctg ctgcgctcaa ccgaaagggc  240
cttcctctct ttgcttccgc ggaaggattt ggcgatttat tcatctacta aagttgcatc  300
tctcttgtgc gtggtgattg tttcgaggag cgtgggagcg agccatgggg aagaagggca  360
agtggttcgg cgcggtcaag aaagtgttca gccctgaatc caaggagaag aaggaggaga  420
ggcagaggag gaaatcagca gctagcaacc ctactccact agatctgacc ccgtcgacct  480
ccttggaagt caatgtttcg gtgccacccc ctccagctcc tccggctctt caccagatta  540
aggaggtcag gatccctgaa gctagcagg agcagagcaa gcacatcacc gtagaggagg  600
ccctgctgc ccctgcacag gcgtcggtgc ttccactctgg tgtgccaagt gaagagcttg  660
ctgcaatcaa gatccagact gccttccgag gttacctggc aaggagggca ctgcgagcgc  720
tgcgggcct tgttcgattg aagtcattgg ttgagggtga ttcagttagg cgtcaatctg  780
caagcactct gcgctgtatg cagactctat cgcgggtgca gtcacaaata cgttctagga  840
gagcaaagat gtctgaggag aaccaggccc tccagcgcca gctcctactg aagcaggaac  900
tggagaattt caggatgggt gagaactggg atgacagcac tcaatccaaa gagcaaatcg  960
aggcgagcct aataagcagg caagaggcag cgattagaaa gaaagagcg cttgcatatg 1020
cattttcaca tcagtggaag agcacgtcga ggtctgtcaa cccaatgttt gtagacccaa 1080
acaacttgca gtggggctgg agctggctgg agcgctggat ggctgcaaaa ccttgggagg 1140
gccgcaatgg gactgataag gagagcaatg ttgaccgtgg atccgttaag agcatgagct 1200
tgaaccttgg agagggtgag atcactaaag ctttcaaccg ccgggactca aagccagaaa 1260
agccatcccc gccaactcca aaactgaccc gtccagcctc caggcaatcc ccttcaacgc 1320
cctccgctaa agtagcgcca atacctgtga ggagaaaatc cgtcacgcca aagaatgggc 1380
tttcacatgt ggatgacgat gcgagaagtg tgttcagtgt gcagtctgag cgaccaagga 1440
ggcacagtat agccacctcg actgtgcggg acgatgagag tctcgcaagc tccccatcac 1500
tcccaagtta tatggttccc acagaatctg caagggcgaa gtctcgtctc cagggatcag 1560
cattgaataa tggtcagag acaccagaga aaggaagctc tgctggaccg gtcaagaaaa 1620
ggttgtcctt tcaaggtgga acagcggctg cctcaccaat gcgacggcat tctggtcctc 1680
ccaaggtggg gagtgcggtg aaggatattg ttgcccacc acagccagag gccttggtga 1740
tcaatggtgg aagcaagtga ctcatgacaa gtaccaggag ggtaaagcgg acaatgaata 1800
tatatttat ccatgaagaa aggttaacgt gatatcagct ctatgagtga tttgaattgt 1860
tttcagtta cgaccacatt gtttgctcta taagattcac agtacctgcc agttgattcc 1920
attcgttgtt tctgtaaaac aagtaccggt tcgtcactag aatcagtgat gtttgtatgt 1980
aaacaggtct tctatttatg taaaaaaaaa aaaaaaaaaa                       2020

SEQ ID NO: 298          moltype = AA  length = 471
FEATURE                 Location/Qualifiers
REGION                  1..471
                        note = Ceres CLONE ID no. 1792902
REGION                  104..124
                        note = Pfam Name: IQ Pfam Description: IQ
                        calmodulin-binding motif
REGION                  1..471
                        note = Functional Homolog of Ceres Ceres Clone ID no.
                        375578 at SEQ ID NO. 252 with e-value of 1.90e-67 and
                        BLAST sequence identity of 51.7
source                  1..471
                        mol_type = protein
                        organism = Panicum virgatum
SEQUENCE: 298
```

```
MGKKGKWFGA VKKVFSPESK EKKEERQRRK SAASNPTPLD LTPSTSLEVN VSVPPPPAPP    60
ALHQIKEVRI PEAEQEQSKH ITVEEAPAAP AQASVLPPGV PSEELAAIKI QTAFRGYLAR   120
RALRALRGLV RLKSLVEGDS VRRQSASTLR CMQTLSRVQS QIRSRRAKMS EENQALQRQL   180
LLKQELENFR MGENWDDSTQ SKEQIEASLI SRQEAAIRRE RALAYAFSHQ WKSTSRSVNP   240
MFVDPNNLQW GWSWLERWMA AKPWEGRNGT DKESNVDRGS VKSMSLNLGE GEITKAFNRR   300
DSKPEKPSPP TPKLTRPASR QSPSTPSAKV APIPVRRKSV TPKNGLSHVD DDARSVFSVQ   360
SERPRRHSIA TSTVRDDESL ASSPSLPSYM VPTESARAKS RLQGSALNNG AETPEKGSSA   420
GPVKKRLSFQ GGTAAASPMR RHSGPPKVGS AVKDIVAPPQ PEALVINGGS K            471

SEQ ID NO: 299           moltype = DNA  length = 1880
FEATURE                  Location/Qualifiers
misc_feature             1..1880
                         note = Ceres CLONE ID no.1919901
misc_feature             1..1880
                         note = Encodes the peptide sequence at SEQ ID NO 300
source                   1..1880
                         mol_type = unassigned DNA
                         organism = Gossypium hirsutum
SEQUENCE: 299
aactttctct tagttatcctc tgcaaatgcc aacctgttct tttattatta ttttccgcca    60
tttttgctct ctttcaagca ttttttttt gcctagatcc acttctctct ctttgatttt   120
taattactgc atttttgttt taatacacaa taagaacaac taagagatag aatgtgactt   180
atcaatcttt taactgagat ctgtgagaat ttttctatgt accaaggaat tatttacaga   240
tgggaaaaaa aggtggctgg cttcctattg tgaagaaagc tttgagccct gaatccaaga   300
aatctcagca ccaaactcca aagccaaaga aaaatggtt cggaaaaagc aaaaatttga   360
gccctgtgtc tgtgcctgaa gaaactgaag tgataactga agatgcaaag ctaaaagaag   420
ctgaaaacga acaaagcaaa catgcctact ctgtggctct tgccaccgct gtggcggccg   480
aggcagcggt ggcagctgct caggcggctg ctgaagttgt ccgtctcact tctcagccgc   540
gccatctggg gaagtcaaag gaggaaatag ctgctatcag gattcaaaca gcatttcgtg   600
gatatttggc taggagggca ctgcgagctt tgagagggct ggtaaggttg aaatcgttga   660
tcagagggca atccgtcaaa cgccaagcaa ctacaacgtt aagatgcatg cagactctag   720
ctcgtctgca gtctgagatt tctgcaagga ggattagaat gtcagaagag aaccaggctc   780
ttcagccgcca gcttcaacag aaatgccaga agagctcgaa gaagttgaga gctcccatga   840
gagaagactg gaacgatagt acacagtcga aggagcagat cgaagcaaga caacaaaata   900
agcaaggagc tactatgaaa agggaagag cattggctta tgcatactgt caccagcgat   960
cgtggaagaa ctgttctaga tcagtgaatc aaacatttat ggatccgagt aattcacact  1020
ggggttggag ttggttagag cgatggatgg cagcccgacc atgggaagtc caaagcacaa  1080
ctgataacaa tgaccgtggc tcagtcaaga gtatgggtgc ttgttcgata tctataagtg  1140
aaatcagcag agcttattct cgaagagatc ttaacaatga taacaaacca tctccaacac  1200
ctcagaagtc aagtcgagtt cctagccgcc agtctccatc gactccacct tcaaaggcac  1260
cttcgatttc atcggtttct ggtaaaacaa gactgccaag tccgagagga agtcaatggg  1320
gagggtatga agactcaagg agcatactca gtacccggtc tgatcgttat aggagacata  1380
gcattgcagg gtcctcaatg agagacgatg agagccttac aagctcacct ccagttccaa  1440
gttatatggc accaacacag tccacaaagg ccaggtccca catccagc cccttaggaa  1500
gtggcacacc agataggaga gtggcagggt ctgcaaagaa acggcttttg ttcccagcat  1560
ccccagccag tagtaggaga cattcagagc ctccaaagt ggacataagt gaggctagaa  1620
agaatcagca tgcaccaagc aatggaaggc aagtggcttg gtgaagagtg caacaaaagt  1680
tagattgaat aaacatggaa gggttatttc aacttgaagt tcttgtagtg tggttgtgat  1740
tatctttttc ttcctaggtt ttatgattat taattataaa agggttactt tttttctgggt  1800
gagatttagt ttattgtttg tggttgacaa acattcttaa aaatcttcaa gtttagtttc  1860
aattcatgaa atttgtaatt                                              1880

SEQ ID NO: 300           moltype = AA  length = 474
FEATURE                  Location/Qualifiers
REGION                   1..474
                         note = Ceres CLONE ID no. 1919901
REGION                   109..129
                         note = Pfam Name: IQ Pfam Description: IQ
                         calmodulin-binding motif
REGION                   1..474
                         note = Functional Homolog of Ceres Clone ID no. 375578 at
                          SEQ ID NO. 252 with e-value of 1.10e-62 and BLAST sequence
                          identity of 54.8
source                   1..474
                         mol_type = protein
                         organism = Gossypium hirsutum
SEQUENCE: 300
MGKKGGWLSI VKKALSPESK KSQHQTPKPK KWFGKSKNL SPVSVPEETE VITEDAKLKE    60
AENEQSKHAY SVALATAVAA EAAVAAAQAA AEVVRLTSQP RHLGKSKEEI AAIRIQTAFR   120
GYLARRALRA LRGLVRLKSL IRGQSVKRQA TTTLRCMQTL ARLQSEISAR RIRMSEENQA   180
LQRQLQQKCQ KELEKLRAPM REDWNDSTQS KEQIEARQQN KQGATMKRER ALAYAYCHQR   240
SWKNCSRSVN QTFMDPSNSH WGWSWLERWM AARPWEVQST TDNNDRGSVK SMGACSISIS   300
EISRAYSRRD LNNDNKPSPT PQKSSRVPSR QSPSTPPSKS PSISSVSGKT RLPSPRGSQW   360
GGYEDSRSIL STRSDRYRRH SIAGSSMRDD ESLTSSPAVP SYMAPTSSTK ARSHIPSPLG   420
SGTPDRRVAG SAKKRLLFPA SPASSRRHSE PPKVDISEAR KNQHAPSNGR QVAW         474

SEQ ID NO: 301           moltype = AA  length = 476
FEATURE                  Location/Qualifiers
REGION                   1..476
```

```
                        note = Ceres CLONE ID no. 228069
REGION                  1..476
                        note = Functional Homolog of Ceres Clone ID no. 375578 at
                         SEQ ID NO. 252
source                  1..476
                        mol_type = protein
                        note = Zea mays subsp. mays
                        organism = Zea mays
SEQUENCE: 301
MGKKGKWFGA VKKVFSPESK EKKEERLRRK SAASNPAPVD LTPSTSLEVN VSVPPPPAPP    60
PVPRQTDEVR VPEAEQEQSK HVTLEEAPAA AAAPAQASVL PPGAPTEELA AIKIQTAFRG   120
YLARRALRAL RGLVRLKSLV EGNSVKRQSA STLRCMQTLS RVQSQIRSRR AKMSEENQAL   180
QRQLLLKQEL ENFRMGENWD DSTQSKEQIE ASLISRQEAA IRRERALAYA FSHQWKSTSR   240
SANPMFVDPN NLQWGWSWLE RWMAAKPWEG RNGTDKESNI DRGSVKNMSL NLGVGEGEIT   300
KAFNRRDSKP EKPSPPTPKP ARPASRQSPS TPSARVAPIP ARRKSSTPKN GLSQVDDDVR   360
SVLSVQSERP RRHSIATTST MRDDESLASS PSLPSYMVPT ESARAKSRTA TANGAETPEK   420
GGSAGPVKKR LSFQGGAAAA SPMRRHSGPP KVESAVKDIA APPQPEALVA NGGGSK       476

SEQ ID NO: 302          moltype = AA  length = 217
FEATURE                 Location/Qualifiers
REGION                  1..217
                        note = Ceres CLONE ID no. 335348
REGION                  1..217
                        note = Ceres Seed Line ID no. ME10681
source                  1..217
                        mol_type = protein
                        note = Zea mays subsp. mays
                        organism = Zea mays
SEQUENCE: 302
MGKKGKWFGA VKKVFSPESK EKKEESNIDR GSVKSMSLNL GEGEITKAFN RRDSKLEKPS    60
PPTPRPARPT SRHSPLTPSA RVAPIPARRK SVTPKNGLSQ VDDDARSVLS VQSERPRRHS   120
IATSTVRDDE SLTSSPSLPS YMVPTESARA KSRLQGSAMA NGAETPEKGG STGPAKKRLS   180
FQGGTAAASP MRRHSGPPKV EIAPPQPEAL VVNGGSK                            217

SEQ ID NO: 303          moltype = AA  length = 474
FEATURE                 Location/Qualifiers
REGION                  1..474
                        note = Public GI ID no. 54306075
source                  1..474
                        mol_type = protein
                        organism = Oryza sativa
SEQUENCE: 303
MGKKGKWFGA VKKVFSPESK EKKEERLRRK LAASNPNPPD LTPSASLEVN VSVPPPPPPP    60
PVQQIEEVKV PEVEQEQSKH VTVEAVPEAV PVPAQTSSLP PGVSREEQAT IKIQTAFRGY   120
LARRALRALR GLVRLKSLVE GNSVKRQAAS TLRCMQTLAR VQSQIRSRRL KMSEENQALQ   180
RQLLLKQELE SLRMGEQWDD STQSKEQIEA SLISRQEAAV RRERALAYAF SHQWKSTSRS   240
VNPMFVDPNN PQWGWSWLER WMAAKPWEGR AGTDKESNLD RASAKSASLN LGEGEITKAF   300
NRRGSKPDKS SPTTPKLTRP ASRQSPSTPS AKVSPIFAKK KSATPKNGLS QVDDDAKSVF   360
SVQSERPRRH SIATSTVRDD ESLASSPSVP SYMAPTKSAR AKLRLQGSAV TDGAETPPEK   420
VASVGSVKKK LSFQAGMAPP SPMRRHSGPP KVEVVKDIAE PPQPEALVIN GGSK         474

SEQ ID NO: 304          moltype = AA  length = 193
FEATURE                 Location/Qualifiers
REGION                  1..193
                        note = Synthesized Sequence
REGION                  1..193
                        note = Fragment of Ceres CLONE ID no. 335348
source                  1..193
                        mol_type = protein
                        organism = synthetic construct
SEQUENCE: 304
ESNIDRGSVK SMSLNLGEGE ITKAFNRRDS KLEKPSPPTP RPARPTSRHS PLTPSARVAP    60
IPARRKSVTP KNGLSQVDDD ARSVLSVQSE RPRRHSIATS TVRDDESLTS SPSLPSYMVP   120
TESARAKSRL QGSAMANGAE TPEKGGSTGP AKKRLSFQGG TAAASPMRRH SGPPKVEIAP   180
PQPEALVVNG GSK                                                     193

SEQ ID NO: 305          moltype = AA  length = 200
FEATURE                 Location/Qualifiers
REGION                  1..200
                        note = Synthesized Sequence
REGION                  1..200
                        note = Fragment of Ceres CLONE ID no. 228069
source                  1..200
                        mol_type = protein
                        organism = synthetic construct
SEQUENCE: 305
ESNIDRGSVK NMSLNLGVGE GEITKAFNRR DSKPEKPSPP TPKPARPASR QSPSTPSARV    60
APIPARRKSS TPKNGLSQVD DDVRSVLSVQ SERPRRHSIA TTSTMRDDES LASSPSLPSY   120
MVPTESARAK SRTATANGAE TPEKGGSAGP VKKRLSFQGG AAAASPMRRH SGPPKVESAV   180
```

```
KDIAAPPQPE ALVANGGGSK                                                  200

SEQ ID NO: 306          moltype = AA  length = 189
FEATURE                 Location/Qualifiers
REGION                  1..189
                        note = Synthesized Sequence
REGION                  1..189
                        note = Fragment of Ceres CLONE ID no. 375578
source                  1..189
                        mol_type = protein
                        organism = synthetic construct
SEQUENCE: 306
DPKERAVTKN ASTSAVRVPV SRAISIQRPA TPNKSRPPS RQSLSTPPSK TPSASGKARP         60
ASPRNSWLYK EDDLRSITSI RSERPRRQST GGGSVRDDTS LTSTPPLPSY MQSTESARAK       120
SRYRSLLLTE KLEVPERAPL AHSVVKKRLS FPVVEKPSVV PTEKPRERVR RHSDPPKVDP       180
ATLKDAPAA                                                              189

SEQ ID NO: 307          moltype = AA  length = 193
FEATURE                 Location/Qualifiers
REGION                  1..193
                        note = Synthesized Sequence
REGION                  1..193
                        note = Fragment of Ceres CLONE ID no. 229668
source                  1..193
                        mol_type = protein
                        organism = synthetic construct
SEQUENCE: 307
ESNIDRGSVK SMSLNLGEGE ITKAFNRRDS KLEKPSPPTP RPARPTSRHS PLTPSARVAP        60
IPARRKSVTP KNGLSQVDDD ARSVLSVQSE RPRRHSIATS TVRDDESLTS SPSLPSYMVP       120
TESARAKSRL QGSAMANGAE TPEKGGSTGP AKKRLSFQGG TAAASPMRRH SGPPKVEIAP       180
PQPEALVVNG GSK                                                         193

SEQ ID NO: 308          moltype = AA  length = 199
FEATURE                 Location/Qualifiers
REGION                  1..199
                        note = Synthesized Sequence
REGION                  1..199
                        note = Fragment of Public GI ID no. 54306075
source                  1..199
                        mol_type = protein
                        organism = synthetic construct
SEQUENCE: 308
ESNLDRASAK SASLNLGEGE ITKAFNRRGS KPDKSSPTTP KLTRPASRQS PSTPSAKVSP        60
IFAKKKSATP KNGLSQVDDD AKSVFSVQSE RPRRHSIATS TVRDDESLAS SPSVPSYMAP       120
TKSARAKLRL QGSAVTDGAE TPPEKVASVG SVKKKLSFQA GMAPPSPMRR HSGPPKVEVV       180
KDIAEPPQPE ALVINGGSK                                                   199

SEQ ID NO: 309          moltype = AA  length = 188
FEATURE                 Location/Qualifiers
REGION                  1..188
                        note = Synthesized Sequence
REGION                  1..188
                        note = Fragment of Public GI ID no. 56202321
source                  1..188
                        mol_type = protein
                        organism = synthetic construct
SEQUENCE: 309
DPKDHYSTKN PSTSASRTYV PRAISIQRPA TPNKSSRPPS RQSPSTPPSR VPSVTGKIRP        60
ASPRDSWLYK EDDLRSITSI RSERPRRQST GGASVRDDAS LTSTPALPSY MQSTESARAK       120
SRYRSLLTDR FEVPERVPLV HSSIKKRLSF PVADKPNGEH ADKLMERGRR HSDPPKVDPA       180
SLKDVPVS                                                               188

SEQ ID NO: 310          moltype = AA  length = 199
FEATURE                 Location/Qualifiers
REGION                  1..199
                        note = Synthesized Sequence
REGION                  1..199
                        note = Fragment of Ceres CLONE ID. 1792902
source                  1..199
                        mol_type = protein
                        organism = synthetic construct
SEQUENCE: 310
ESNVDRGSVK SMSLNLGEGE ITKAFNRRDS KPEKPSPPTP KLTRPASRQS PSTPSAKVAP        60
IPVRRKSVTP KNGLSHVDDD ARSVFSVQSE RPRRHSIATS TVRDDESLAS SPSLPSYMVP       120
TESARAKSRL QGSALNNGAE TPEKGSSAGP VKKRLSFQGG TAAASPMRRH SGPPKVGSAV       180
KDIVAPPQPE ALVINGGSK                                                   199

SEQ ID NO: 311          moltype = AA  length = 200
FEATURE                 Location/Qualifiers
```

```
REGION              1..200
                    note = Synthesized Sequence
REGION              1..200
                    note = Fragment of Ceres CLONE ID no. 1727738
source              1..200
                    mol_type = protein
                    organism = synthetic construct
SEQUENCE: 311
KESNIDRGSV KSMSLNLGEG EITKAFNRRD SKPEKPSPPT PKLTRPASRQ SPSTPSAKVA     60
PIPARRKSAT PENGLSHVDD DARSVFSVQS ERPRRHSIAT STVQDNESLA SSPSLPSYMV    120
PTESARAKSR LQGSALTNGA ETPEKGSSAG PVKKRLSFQG GTAAASPMRR HSGPPKVDSA    180
VKDIVAPPQP EALVINGGSK                                                200

SEQ ID NO: 312      moltype = AA  length = 471
FEATURE             Location/Qualifiers
REGION              1..471
                    note = Ceres CLONE ID no. 1727738
REGION              1..471
                    note = Functional Homolog of Ceres Clone ID no. 375578 at
                     SEQ ID NO. 252
source              1..471
                    mol_type = protein
                    organism = Panicum virgatum
SEQUENCE: 312
MGKKGKWFGA VKKVFSPESK EKKEERQRRK SAASNPTPRD LTPSTSLEVN VSVPPPPAPP     60
ALHQIEEIRA PEAEQEQSKH VTVEEAPAAP AQASVLRPGV PSEELAAIKI QTAFRGYLAR    120
RALRALRGLV RLKSLVEGDS VRRQSASTLR CMQTLSRVQS QIRSRRAKMS EENQALQRQL    180
LLKQELENFR MGENWDDSTQ SKEQIEASLI SRQEAAIRRE RALAYAFSHQ WKSTSRSVNP    240
MFVDPNNLQW GWSWLERWMA AKPWEGCNGA DKESNIDRGS VKSMSLNLGE GEITKAFNRR    300
DSKPEKPSPP TPKLTRPASR QSPSTPSAKV APIPARRKSA TPENGLSHVD DDARSVFSVQ    360
SERPRRHSIA TSTVQDNESL ASSPSLPSYM VPTESARAKS RLQGSALTNG AETPEKGSSA    420
GPVKKRLSFQ GGTAAASPMR RHSGPPKVDS AVKDIVAPPQ PEALVINGGS K             471

SEQ ID NO: 313      moltype = DNA  length = 1806
FEATURE             Location/Qualifiers
misc_feature        1..1806
                    note = Ceres CLONE ID no. 228069
misc_feature        1..1806
                    note = Encodes the peptide sequence at SEQ ID NO 301
source              1..1806
                    mol_type = unassigned DNA
                    note = Zea mays subsp. mays
                    organism = Zea mays
SEQUENCE: 313
gagccgcgga ggagcagcgg cgcatcgcaa cactaaccaa agtcctcctc tccaggtgcc     60
gagccagggt gactgttccg aggagcgtgg cgtggaccca tggggaagaa gggcaagtgg    120
ttcggtgccg tcaagaaggt cttcagcccc gaatccgaag agaagaaaga ggagaggcta    180
aggaggaaat cagcagctag caacccagca ccggtagatc tgaccccatc tacctccctg    240
gaagtcaatg tttcggtgcc acccccctccg gctcctcctc cagttcctcg ccagaccgac    300
gaggtcaggg tccccgaagc cgagcaggag cagagcaagc atgtcaccct ggaggaggcc    360
cctgctgctg ctgctgcccc agcacaggcg tcggtgctgc cacctggtgc gccaaccgaa    420
gagctcgccg caatcaagat ccagaccgcc ttccgaggtt acctggcaag gagggcacta    480
agagcactac gaggccttgt acgattgaag tcattggttg agggtaattc agttaagcgt    540
caatctgcaa gcactctgcg ctgtatgcaa actctatcgc gggtgcagtc acaaatacga    600
tctaggagag caaagatgtc cgaggagaac caggcccctc aacgccagct cctacttaaa    660
caggaactgg agaatttcag aatgggtgag aactgggacg acagcactca atccaaggag    720
caaatcgagg caagcctaat aagcaggcaa gaggcagcga taagaagaga aagagctctt    780
gcatatgcat tttcacatca gtggaagagc acatcaagat ctgcgaaccc aatgtttgta    840
gacccaaata acttgcagtg gggctggagc tggttggagc gctgcaatgg agcaaaacct    900
tgggagggac gcaatgggac cgacaaggag agcaacattg atcgccggct cgtcaagaat    960
atgagcttga accttggagt tggagagggt gagatcacaa aagctttcaa ccgccgggac   1020
tcaaagccag agaagccatc accaccgact ccaaaaccgg cccgtccagc ttccaggcaa   1080
tcccctccga cgccctctgc tagagtggcc ccaatacctg cgaggaggaa atccagcacg   1140
ccaaagaatg ggcttcaca ggtggacgat gacgtgagtg gcgtgctcag tgctcgaacc   1200
gagcgaccaa ggaggcacag catagccacg acgtcgacca tgcgggacga tgagagcctc   1260
gcgagctccc cgtcgctccc gagctacatg gttcccacag aatctgcgag gccaaatct    1320
cgcacagcaa cggccaatgg cgcagagacg cctgagaaag gaggctctgc tggaccagtc   1380
aagaagaggt tgtctttcca aggtggagct gcggctgcct caccgatgcg acggcattct   1440
ggccctccca aggtggagag cgctgtgaag gacattgctg ccaccacca gcctgaggcc   1500
ttggtagcca atggtggtgg aagcaagtga cttgtattga caagttccag gatgggggag   1560
cgggtttatg tcttatggag ggacatgttt catccgtgaa cagaagttaa gagtggtgcc   1620
ggatctacga atggtttgaa ttgttttccc gttacaacca cattgtttgc tgtataagat   1680
tcactgtacc tgccagttgg ttccattgt tgttttctgt aaaacaaaca tcaatttgtc    1740
actagaaatct gtgatgcttg tatgtaaaca ggtcctctat ttatgtgagc catatatttc   1800
attttc                                                              1806

SEQ ID NO: 314      moltype = DNA  length = 1083
FEATURE             Location/Qualifiers
misc_feature        1..1083
```

```
                     note = Ceres CLONE ID no. 335348
misc_feature         1..1083
                     note = Encodes the peptide sequence at SEQ ID NO 302
source               1..1083
                     mol_type = unassigned DNA
                     note = Zea mays subsp. mays
                     organism = Zea mays
SEQUENCE: 314
aaccccgcc  gtatcggtct  tgttcgttgt  cctgccagat  acagataggt  ggctaccact   60
ggctcgcgtg  acctgttggc  ttgcttgctc  ctctccaggt  tcaggcaggg  gagagtgcct  120
gtttcgaggg  ggcgtggagc  ggagccggag  ccatggggaa  gaagggcaag  tggttcggcg  180
ccgtcaagaa  ggtcttcagc  cctgaatcca  aggagaagaa  agaggagagc  aacattgacc  240
ggggatccgt  taagagcatg  agcttgaacc  ttggagaggg  tgagatcaca  aaagctttca  300
accgccggga  ctcaaagcta  gaaaagccat  cgccgccaac  tccaagaccg  gcccgtccaa  360
cttccaggca  ttcccctttg  acgccctctg  ctagagtggc  accgatacct  gcgaggagaa  420
aatctgtcac  gcccaagaac  gggctttcac  aggtggacga  tgacgcgagg  agcgtgctca  480
gtgtgcagtc  tgagcggcca  aggaggcaca  gtatagccac  ctcgactgtg  cgggacgacg  540
agagcctcac  gagctccccg  tcgctcccaa  gctacatggt  tcccacagaa  tctgcaaggg  600
ccaaatctcg  cctccaggggt  tcagcaatgg  ccaatggcgc  agagcacct  gagaaaggag  660
gctcaactgg  accagccaag  aagaggttat  ccttccaggg  tggaactgcg  gctgcctcgc  720
caatgcgacg  acattctggt  cctcccaagg  tggagatcgc  gccaccacaa  ccagaggcct  780
tggtagtcaa  tggtggaagc  aagtgacaca  tatgtagtca  gccaggat  ggaaaacgga  840
ttatgaagat  attagtttca  ttttcatcca  tgaatagaag  ttaaaagtgg  tatcatatct  900
atgaatggtt  tcaattgttt  ttctgttaca  accacattat  ttgctatata  cgattcacag  960
tacctgccag  ttgattccat  tggttgtttc  tgtaaaacaa  atatcaattt  gtcactagaa  1020
tctgtgatgt  ttgtatgtaa  acagatcctc  tatttatgtg  agacatatat  ttctttctt  1080
tcg                                                                     1083

SEQ ID NO: 315       moltype = DNA  length = 2024
FEATURE              Location/Qualifiers
misc_feature         1..2024
                     note = Ceres CLONE ID no. 1727738
misc_feature         1..2024
                     note = Encodes the peptide sequence at SEQ ID NO 312
source               1..2024
                     mol_type = unassigned DNA
                     organism = Panicum virgatum
SEQUENCE: 315
gttctctctc  cctcgtcact  ctcgccactg  ctcccagctg  ttgcgacctc  cgatcatcca   60
aggctcctgc  acccctgtca  gtcctagctc  cagccaaaaa  tcgttggctt  ccgctgcctg  120
ctcctccgcc  ttgcacctcc  catgaccttc  cacgcgacat  gattgcattg  caggcccctg  180
cggagctcag  tgtcctccca  cgccgctgac  gccttcttgt  tgcctccccg  ctgctgcgca  240
caaccgaaag  gccttcctc  tcttcctttg  cttccgcgga  aagatttggc  gatttgttca  300
tctactaaag  ttgcatctct  cttggtgatt  gtttcgagga  gtgtggagtg  gagccatggg  360
gaagaagggc  aagtggttcg  gcgcggtcaa  gaaagtgttc  agccctgaat  ccaaggagaa  420
gaaggaggag  aggcagagga  ggaaatcagc  agctagcaac  cctactccac  gagatctgac  480
cccgtcgacc  tccttggaag  tcaatgtttc  ggtgccaccc  cctccagctc  ctccggccct  540
tcaccagatt  gaggaaatca  gggcccctga  agctgagcag  gagcagagca  agcacgtcac  600
cgtagaggag  gctcctgctg  ccctgcaca  ggcgtcggtg  ctgccacctg  tgtgccaag  660
tgaagagctt  gctgcaatca  agattcagac  tgccttccga  ggttacctgg  caaggagggc  720
actgcgagcg  ctgcggggcc  ttgttcgatt  gaaatcattg  gttgagggtg  attcagttag  780
gcgtcaatct  gcaagcactc  ttcgctgtat  gcagactcta  tcgcgggtgc  agtcacaaat  840
acgttctagg  agagcaaaga  tgtctgagga  gaaccaggcc  cttcagcgcc  agctcctact  900
gaagcaggaa  ctgagaaatt  tcaggatggg  tgagaactgg  gatgacagca  ctcaatccaa  960
agagcaaatc  gaggcaagcc  taataagcag  gcaagaggca  gcgattagaa  gagaaagagc  1020
gcttgcatat  gcattttcac  atcagtgaa  gagcacttcg  agatctgtca  acccaatgtt  1080
tgtagaccca  aacaacttgc  agtggggctg  gagctggttg  gagcgctgga  tggctgcaaa  1140
accttgggag  ggctgcaatg  gggctgataa  ggagagcaac  attgaccgtg  gatctgttaa  1200
gagcatgatga  ttgaaccttg  gagagggtga  gatcacaaaa  gctttcaacc  gccggatcg  1260
aaagccagaa  aagccatcac  cgccaactcc  aaaactaacc  cgtccagcct  ccaggcaatc  1320
cccttcgacg  ccctctgcta  aagtagcgcc  aatacctgct  aggagaaaat  ccgccacgcc  1380
agagaatggg  ctttcacatg  tggatgacga  tgcgagaagt  gtgttcagcg  tgcagtctga  1440
gcgaccaagg  aggcacagta  tagccacctc  gactgtgcag  gacaatgaga  gtctcgcaag  1500
ctccccatca  ctcccaagtt  acatggttcc  cacagaatct  gcaagggcga  agtctcgtct  1560
ccagggatca  gcattgacta  atggtgcaga  gacaccagag  aaaggaagct  ctgctggacc  1620
ggtcaagaaa  aggttgtcat  ttcaaggtgg  aacagcgct  gcctcaccaa  tgcgacggca  1680
ttctggtcct  cccaaggtgg  acagtgcggt  gaaggatatt  gttgcccac  cacagcagag  1740
ggccttggtg  atcaatggtg  gaagcaagta  actcatacca  ggaggggaaa  gcggattatg  1800
aatatatatt  ttatcgatga  agaaaggta  acgtgatatc  agctcaatga  gtgatttgaa  1860
ttgttttctt  acgaccacat  tgtttgctct  ataagattcg  cagtacctgc  cagttgattc  1920
cattcgttgt  ttctgtaaaa  caagtatcgg  ttcgtcacta  gaatcaatga  agtttgtatg  1980
taaacaggtc  ttctatttat  gtgagccata  tatttcttct  tctg                    2024
```

What is claimed is:

1. A method of increasing tolerance to salinity in a plant, said method comprising providing a plurality of transgenic plants comprising a promoter operably linked to a nucleic acid, wherein the promoter and the nucleic acid are heterologous to each other and whereby the nucleic acid is expressed, and said nucleic acid comprising a nucleotide sequence selected from the group consisting of:
   (a) a nucleotide sequence that encodes a protein comprising an amino acid sequence that has at least 95% amino acid sequence identity to the amino acid sequence of SEQ ID NO:172;
   (b) a nucleotide sequence that encodes a protein that comprises the amino acid sequence of SEQ ID NO:172;
   (c) a nucleotide sequence comprising the polynucleotide sequence of SEQ ID NO:171 that encodes a protein having the functional activity of the protein as set forth in SEQ ID NO: 172; and
   (d) a nucleotide sequence comprising a nucleotide sequence having at least 95% nucleotide sequence identity to the nucleotide sequence of SEQ ID NO: 171 and encoding a protein having the functional activity of the protein as set forth in SEQ ID NO: 172; and
   selecting from the plurality of said transgenic plants a transgenic plant that overexpresses said protein of (a), (b), (c) or (d) and exhibits increased tolerance to salinity as compared to a control plant of the same species lacking said nucleic acid and grown under identical growth conditions.

2. The method of claim 1, wherein said nucleotide sequence encodes a protein comprising an amino acid sequence that has at least 97% amino acid sequence identity to the amino acid sequence of SEQ ID NO:172.

3. The method of claim 1, wherein said nucleotide sequence encodes a protein that comprises the amino acid sequence of SEQ ID NO:172.

4. The method of claim 1, wherein said promoter is selected from the group consisting of YP0092 (SEQ ID NO: 38), PT0676 (SEQ ID NO: 12), PT0708 (SEQ ID NO: 17), PT0613 (SEQ ID NO: 5), PT0672 (SEQ ID NO: 11), PT0678 (SEQ ID NO: 13), PT0688 (SEQ ID NO: 15), PT0837 (SEQ ID NO: 24), a napin promoter, a Arcelin-5 promoter, a phaseolin gene promoter, a soybean trypsin inhibitor promoter, a ACP promoter, a stearoyl-ACP desaturase gene promoter, a soybean α' subunit of β-conglycinin promoter, a oleosin promoter, a 15 kD zein promoter, a 16 kD zein promoter, a 19 kD zein promoter, a 22 kD zein promoter, a 27 kD zein promoter, a Osgt-1 promoter, a beta-amylase gene promoter, and a barley hordein gene promoter.

5. The method of claim 1, wherein said promoter is selected from the group consisting of p326 (SEQ ID NO: 76), YP0144 (SEQ ID NO: 55), YP0190 (SEQ ID NO: 59), p13879 (SEQ ID NO: 75), YP0050 (SEQ ID NO: 35), p32449 (SEQ ID NO: 77), 21876 (SEQ ID NO: 1), YP0158 (SEQ ID NO: 57), YP0214 (SEQ ID NO: 61), YP0380 (SEQ ID NO: 70), PT0848 (SEQ ID NO: 26), and PT0633 (SEQ ID NO: 7), a cauliflower mosaic virus (CaMV) 35S promoter, a mannopine synthase (MAS) promoter, a 1' or 2' promoter derived from T-DNA of *Agrobacterium tumefaciens*, a figwort mosaic virus 34S promoter, an actin promoter, and an ubiquitin promoter.

6. The method of claim 1, wherein said promoter is selected from the group consisting of a ribulose-1,5-bisphosphate carboxylase (RbcS) promoter, a pine cab6 promoter, a Cab-1 gene promoter from wheat, a CAB-1 promoter from spinach, a cab1R promoter from rice, a pyruvate orthophosphate dikinase (PPDK) promoter from corn, a tobacco Lhcb1*2 promoter, an *Arabidopsis thaliana* SUC2 sucrose-H+symporter promoter, a thylakoid membrane protein promoter from spinach (SEQ ID NO: 3), PT0668 (SEQ ID NO: 2), PT0886 (SEQ ID NO: 29), PR0924 (SEQ ID NO: 265), YP0144 (SEQ ID NO: 55), YP0380 (SEQ ID NO: 70), and PT0585 (SEQ ID NO: 4).

7. The method of claim 1, wherein said nucleotide sequence encodes a protein comprising an amino acid sequence that has at least 99% amino acid sequence identity to the amino acid sequence of SEQ ID NO:172.

8. The method of claim 1, wherein said nucleotide sequence comprising the polynucleotide sequence of SEQ ID NO:171.

* * * * *